US012343401B2

(12) United States Patent
Santich et al.

(10) Patent No.: US 12,343,401 B2
(45) Date of Patent: Jul. 1, 2025

(54) MODULAR SELF ASSEMBLY DISASSEMBLY (SADA) TECHNOLOGIES

(71) Applicant: Memorial Sloan Kettering Cancer Center, New York, NY (US)

(72) Inventors: Brian H. Santich, New York, NY (US); Mahiuddin Ahmed, New York, NY (US); Nai-Kong V. Cheung, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 71 days.

(21) Appl. No.: 18/153,228

(22) Filed: Jan. 11, 2023

(65) Prior Publication Data

US 2023/0158162 A1 May 25, 2023

Related U.S. Application Data

(62) Division of application No. 16/609,401, filed as application No. PCT/US2018/031235 on May 4, 2018, now Pat. No. 11,583,588.

(60) Provisional application No. 62/502,151, filed on May 5, 2017.

(51) Int. Cl.
| | |
|---|---|
| A61K 47/64 | (2017.01) |
| A61K 47/54 | (2017.01) |
| A61K 51/04 | (2006.01) |
| A61K 51/10 | (2006.01) |
| C07K 14/47 | (2006.01) |
| C07K 14/715 | (2006.01) |
| C07K 16/30 | (2006.01) |
| C07K 16/44 | (2006.01) |

(52) U.S. Cl.
CPC .......... *A61K 47/641* (2017.08); *A61K 47/547* (2017.08); *A61K 51/0495* (2013.01); *A61K 51/10* (2013.01); *A61K 51/1096* (2013.01); *C07K 14/4746* (2013.01); *C07K 14/7155* (2013.01); *C07K 16/3084* (2013.01); *C07K 16/44* (2013.01); *C07K 2317/622* (2013.01); *C07K 2317/92* (2013.01); *C07K 2317/94* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 4,472,509 A | 9/1984 | Gansow et al. | |
| 4,938,948 A | 7/1990 | Ring et al. | |
| 5,021,236 A | 6/1991 | Gries et al. | |
| 5,641,870 A | 6/1997 | Rinderknecht et al. | |
| 5,670,356 A | 9/1997 | Sherf et al. | |
| 5,874,304 A | 2/1999 | Zolotukhin et al. | |
| 6,451,995 B1 | 9/2002 | Cheung et al. | |
| 11,583,588 B2 * | 2/2023 | Santich ................. | C07K 16/44 |
| 2004/0038339 A1 | 2/2004 | Kufer et al. | |
| 2005/0064509 A1 | 3/2005 | Bradbury et al. | |
| 2006/0228300 A1 | 10/2006 | Chang et al. | |
| 2023/0235087 A1 * | 7/2023 | Santich ............. | C07K 16/3084 424/1.65 |

OTHER PUBLICATIONS

Cheal et al., "Theranostic pretargeted radioimmunotherapy of colorectal cancer xenografts in mice using picomolar affinity 86Y-or 177Lu-DOTA-Bn binding scFv C825/GPA33 IgG bispecific immunoconjugates". Eur. J. Nucl Med Mol Imaging 43(5): 925-937 (Year: 2006).
Edwards et al., "The Remarkable Flexibility of the Human Antibody Repertoire; Isolation of Over One Thousand Different Antibodies to a Single Protein, BLyS". J Mol Biol. 334(1 ): 103-118 (Year: 2003).
International Search Report and Written Opinion, PCT/US2018/031235, Memorial Sloan Kettering Cancer Center (Sep. 19, 2018).
Lloyd et al., "Modelling the human immune response: performance of a $10^{11}$ human antibody repertoire against a broad panel of therapeutically relevant antigens". Protein Engineering, Design & Selection 22: 159-168 (Year: 2009).
Pluckthun et al., "New protein engineering approaches to multivalent and bispecific antibody fragments". Immunotechnology 3: 83-105 (Year: 1997).
Bhaskar et al., "Engineering protein nanocages as carriers for biomedical applications", NPG Asia Materials, vol. 9, No. 4, Apr. 7, 2017 (Apr. 7, 2017), p. e371, XP055427608, DOI: 10.1038/am.2016.128 * whole document, in particular p. 3, col. 1, par. 1; p. 12, col. 2, par. 1.
Thie et al., "Multimerization domains for antibody phage display and antibody production". New Biotechnology 26(6): 314-321 (Year: 2009).
UniProtKB—P56723, retrieved from: https://www.uniprot.org/uniprot/P56423>.
Wang et al., "Study on p53 tetramerization domain in improving functional affinity and biological activity of antibody". Zhonguha Yi Xue Za Zhi 85(7): 479-82, abstract only (Year: 2005).

* cited by examiner

*Primary Examiner* — Phuong Huynh
(74) *Attorney, Agent, or Firm* — Foley & Lardner LLP

(57) ABSTRACT

The present invention relates to compositions and methods employing conjugates that include a self-assembly and disassembly (SADA) polypeptide and a binding domain. The present invention encompasses the recognition that conjugates with a SADA polypeptide have certain improved biological properties. SADA-conjugates are described, along with uses thereof (e.g., as therapeutic or diagnostic agents) and methods of manufacture.

11 Claims, 33 Drawing Sheets

Specification includes a Sequence Listing.

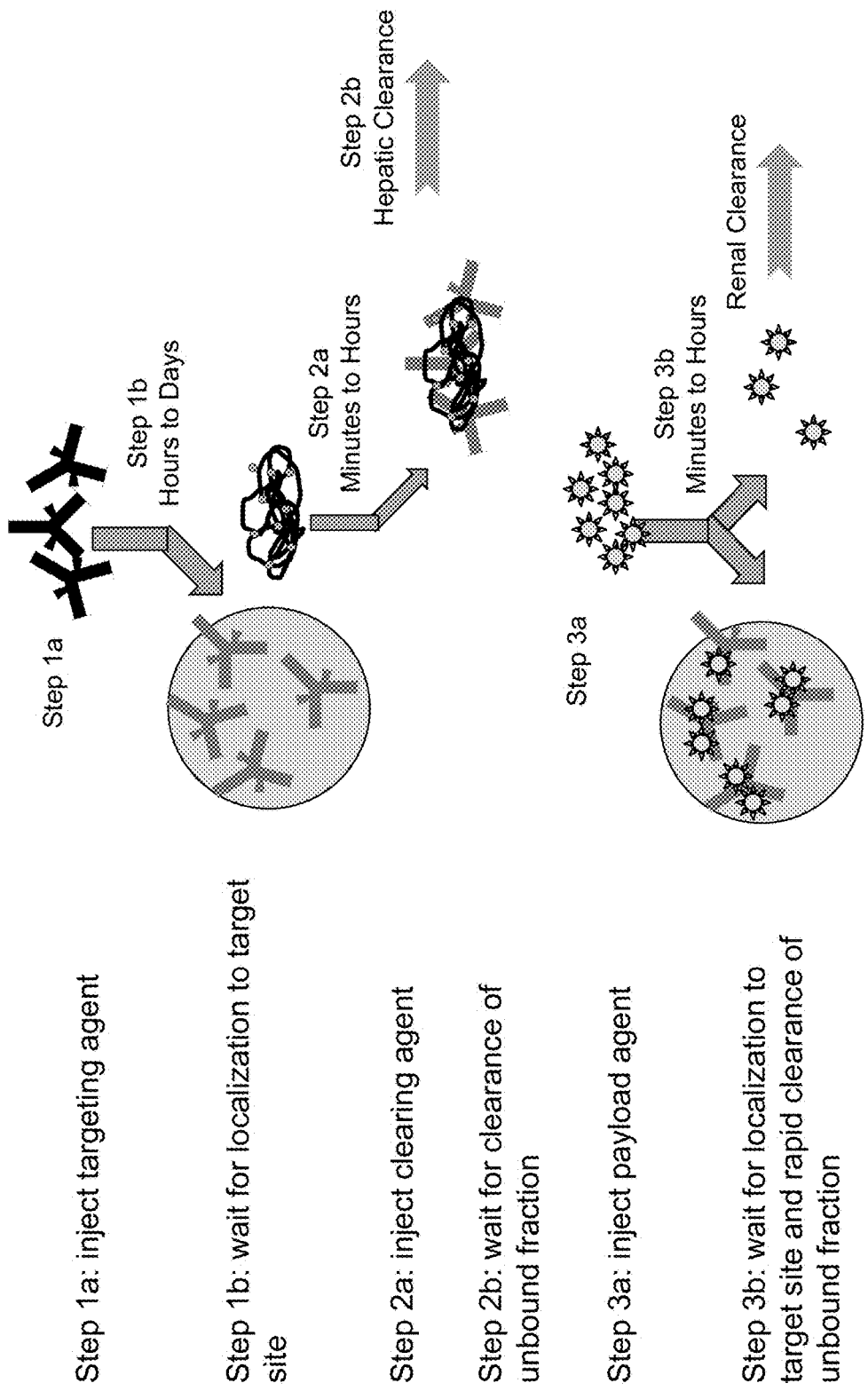

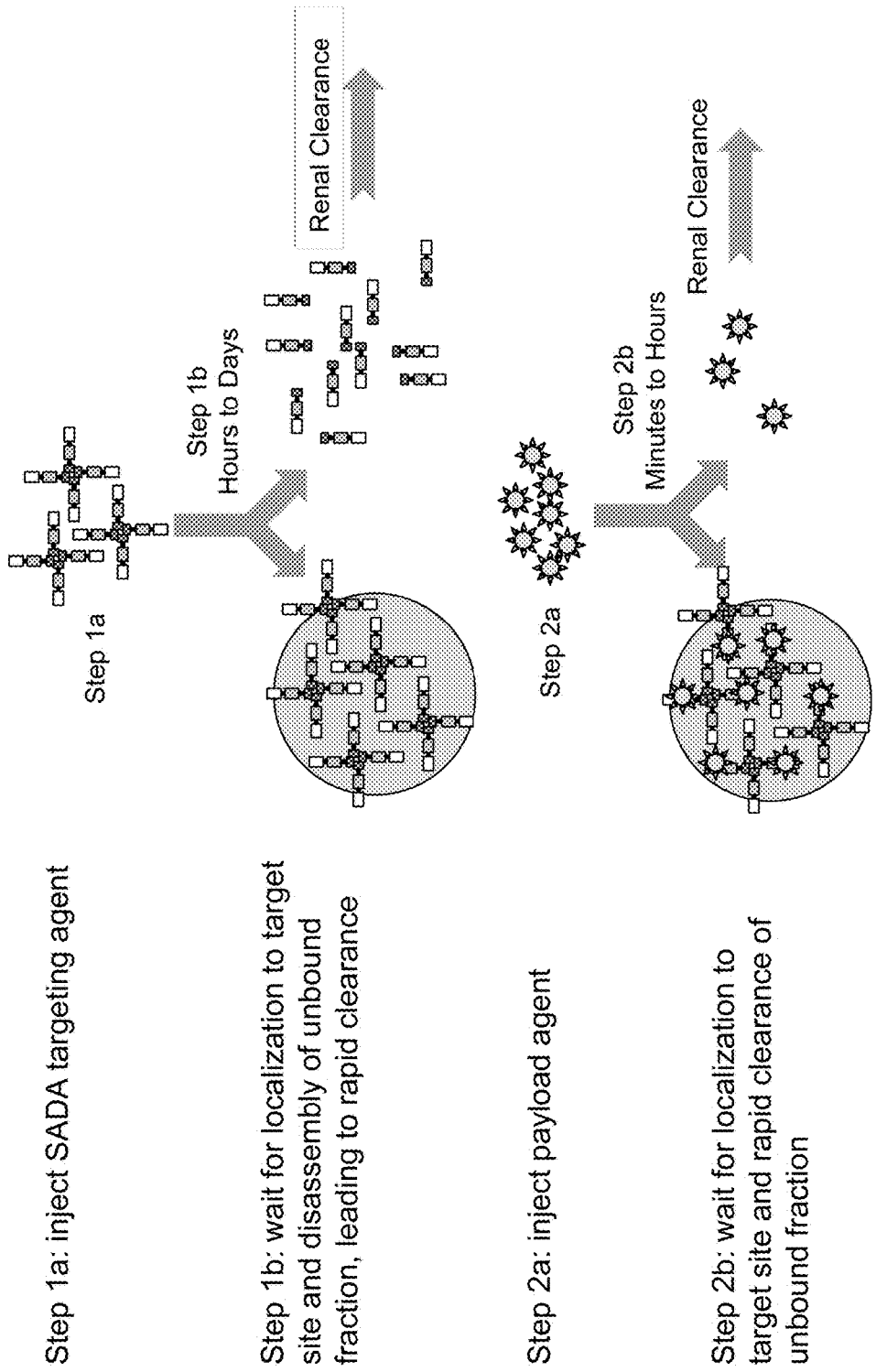

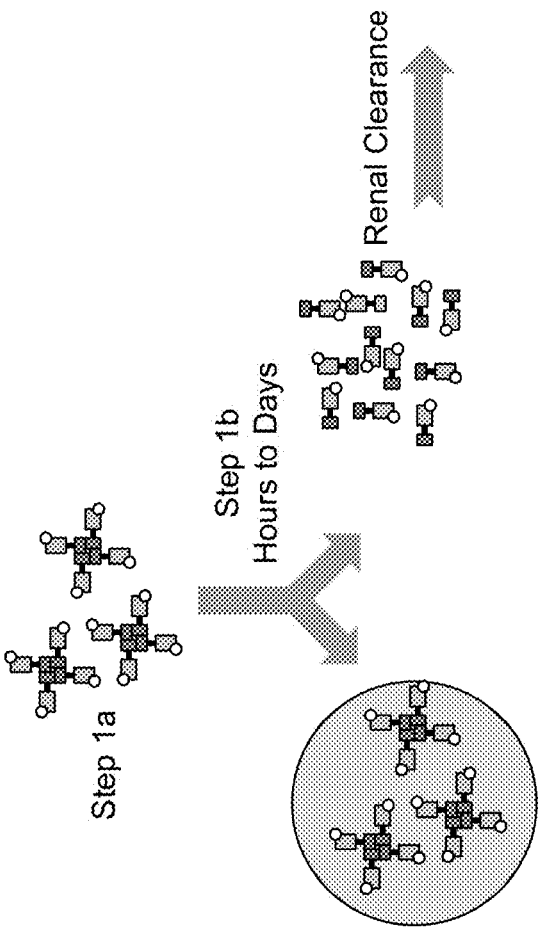

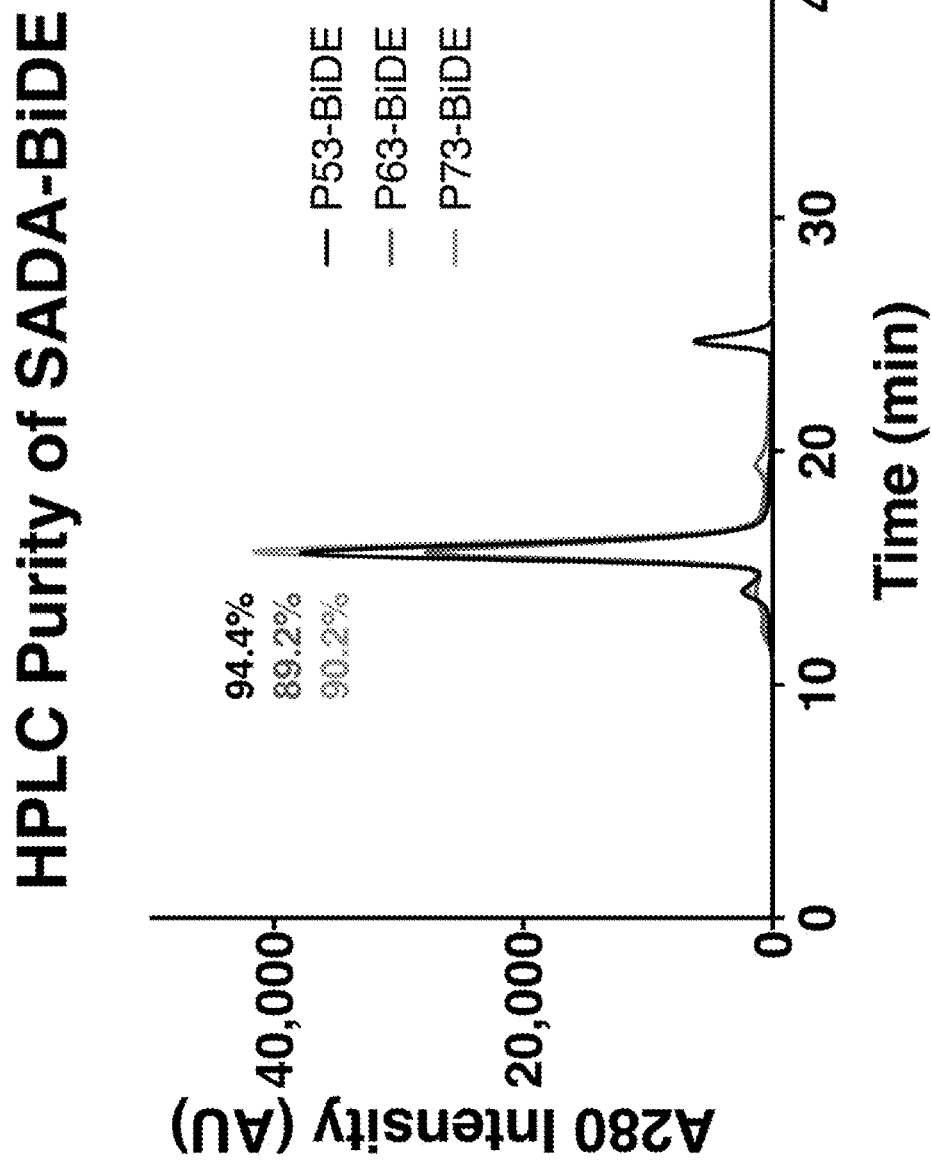

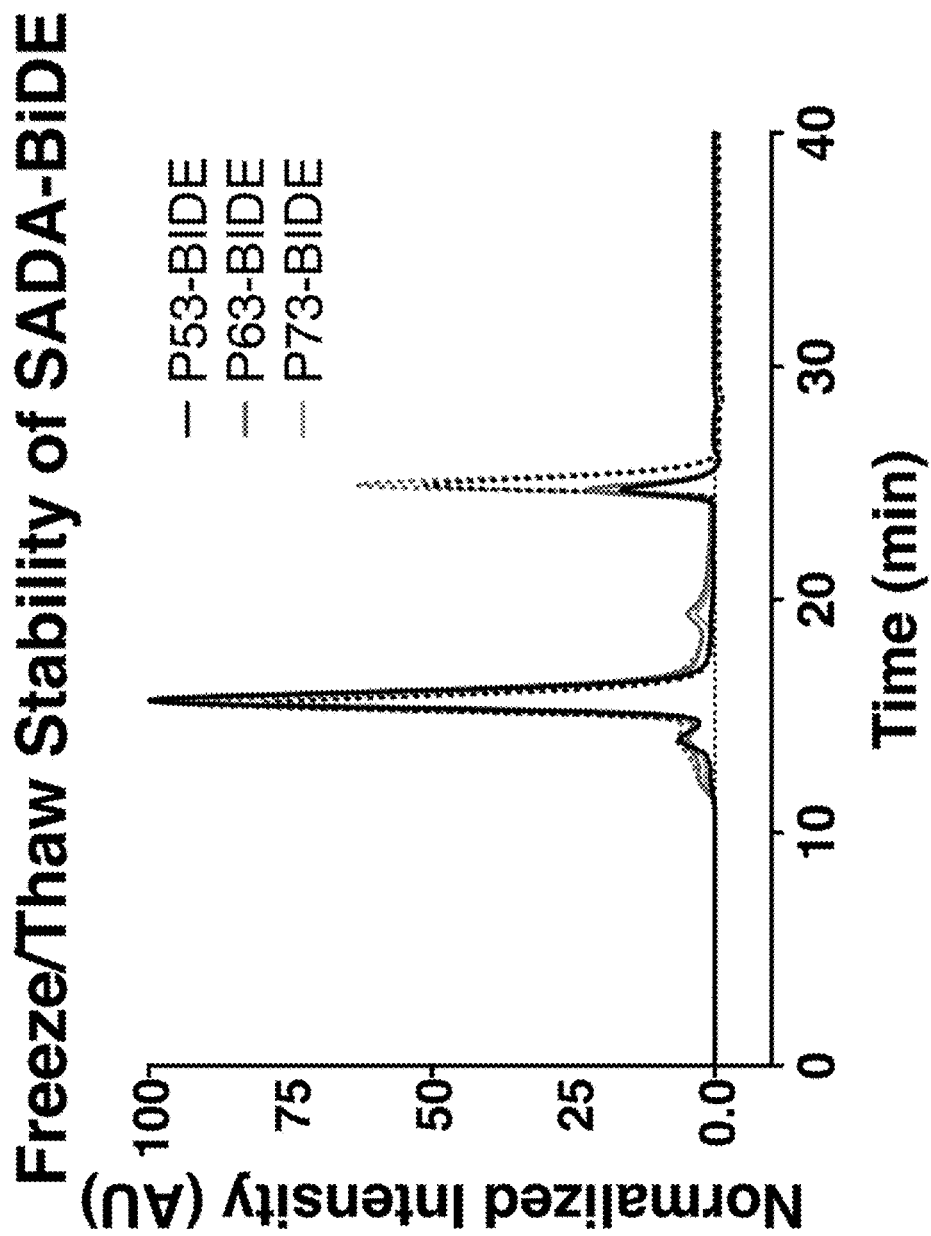

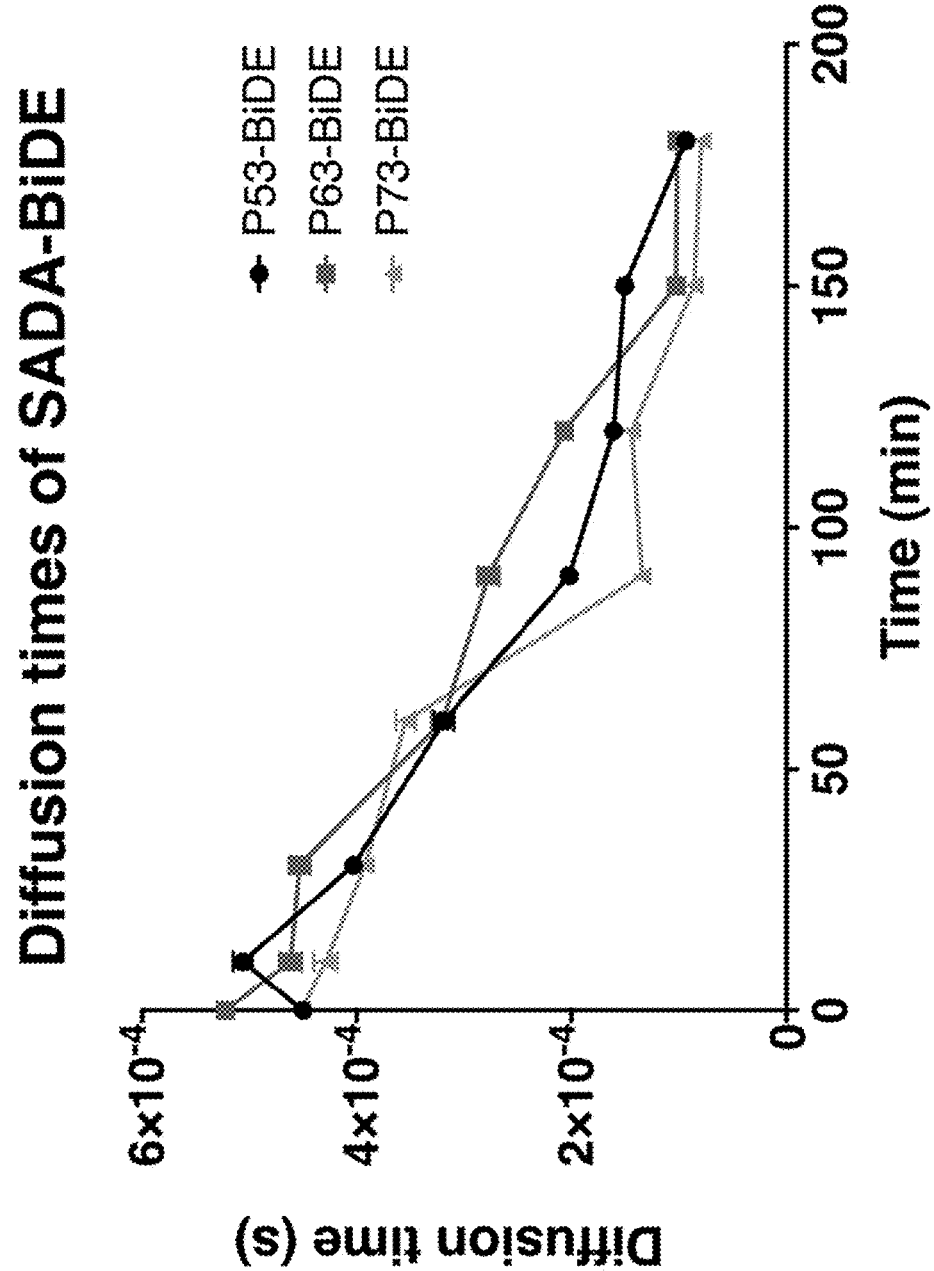

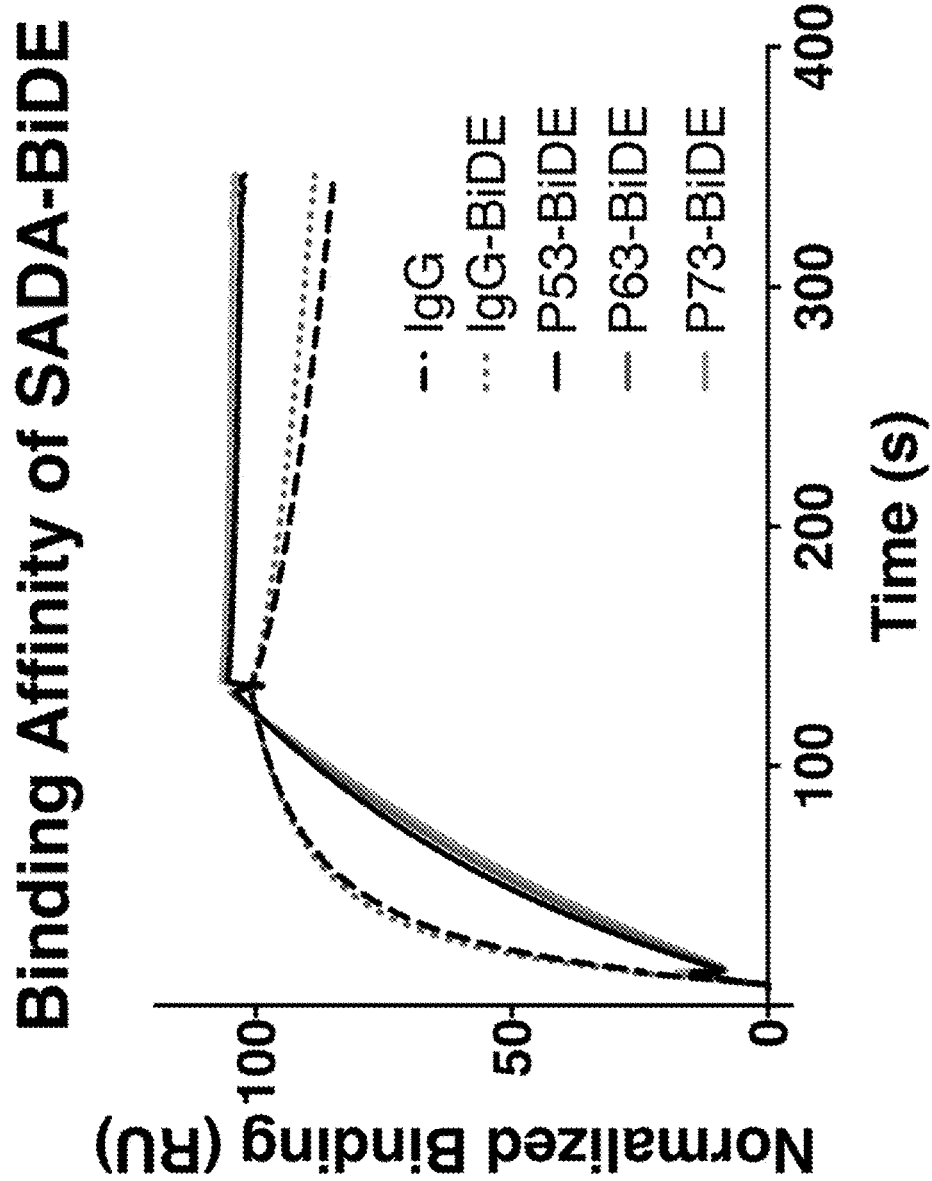

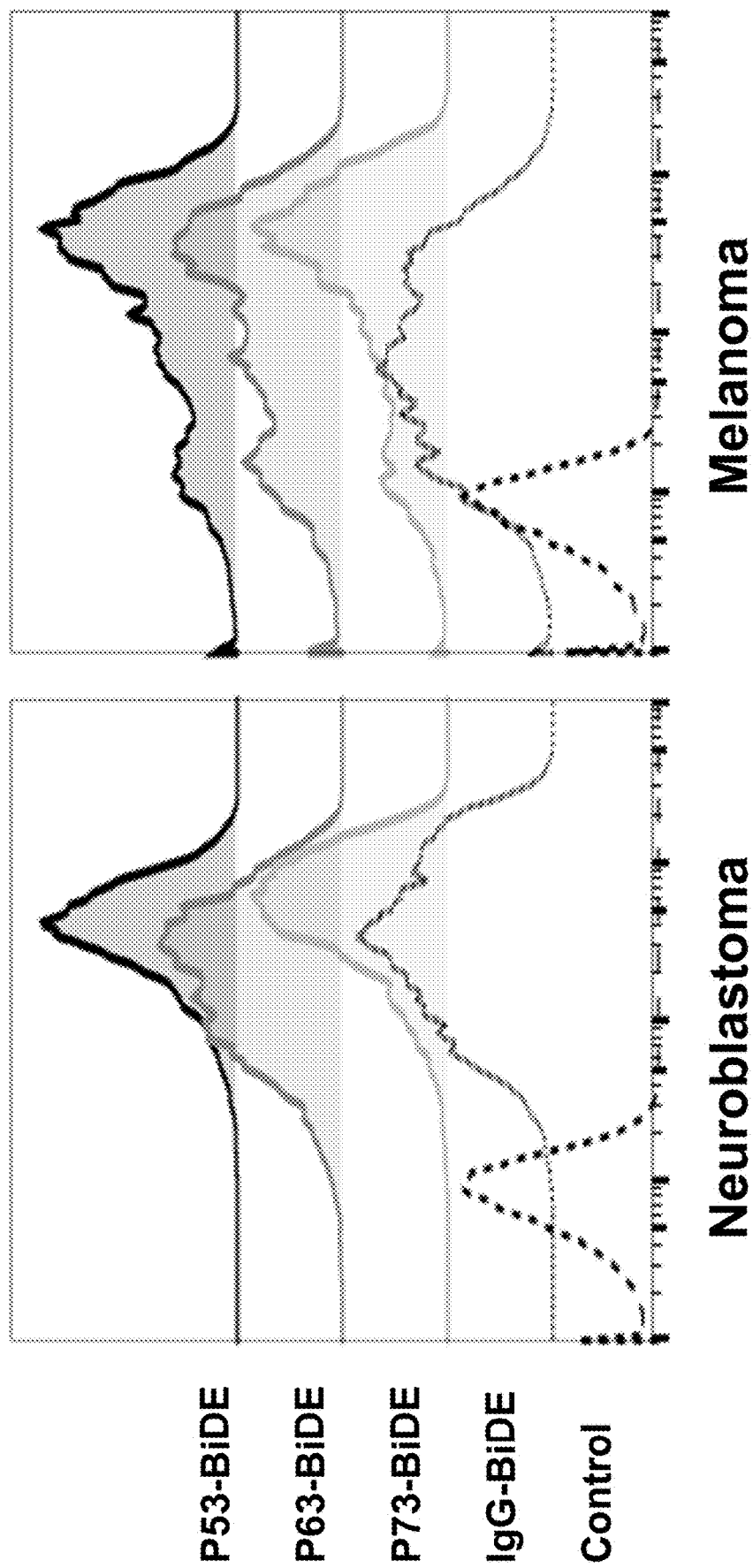

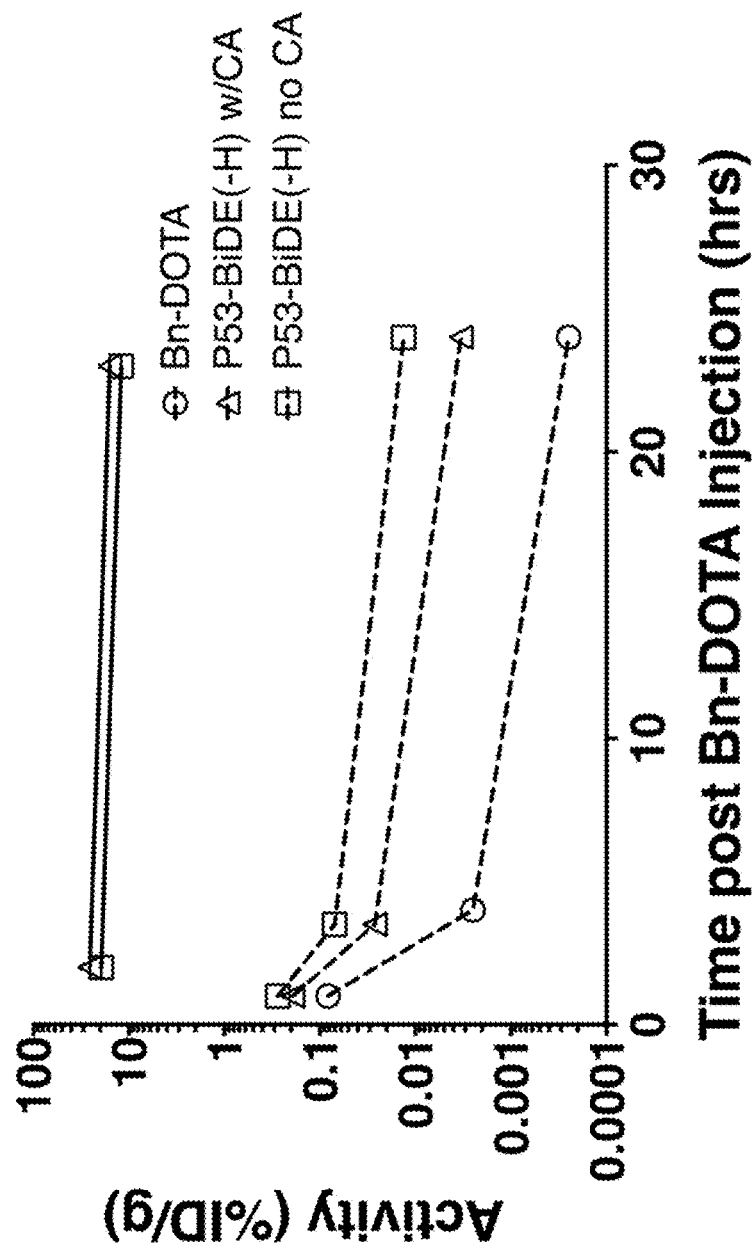

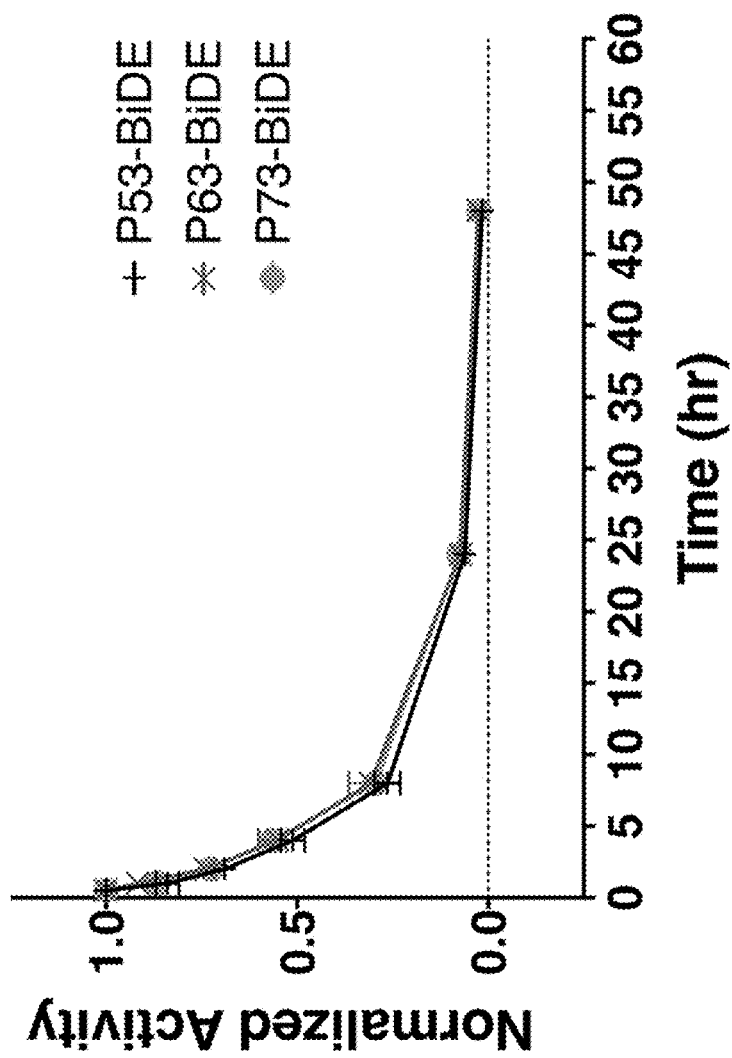

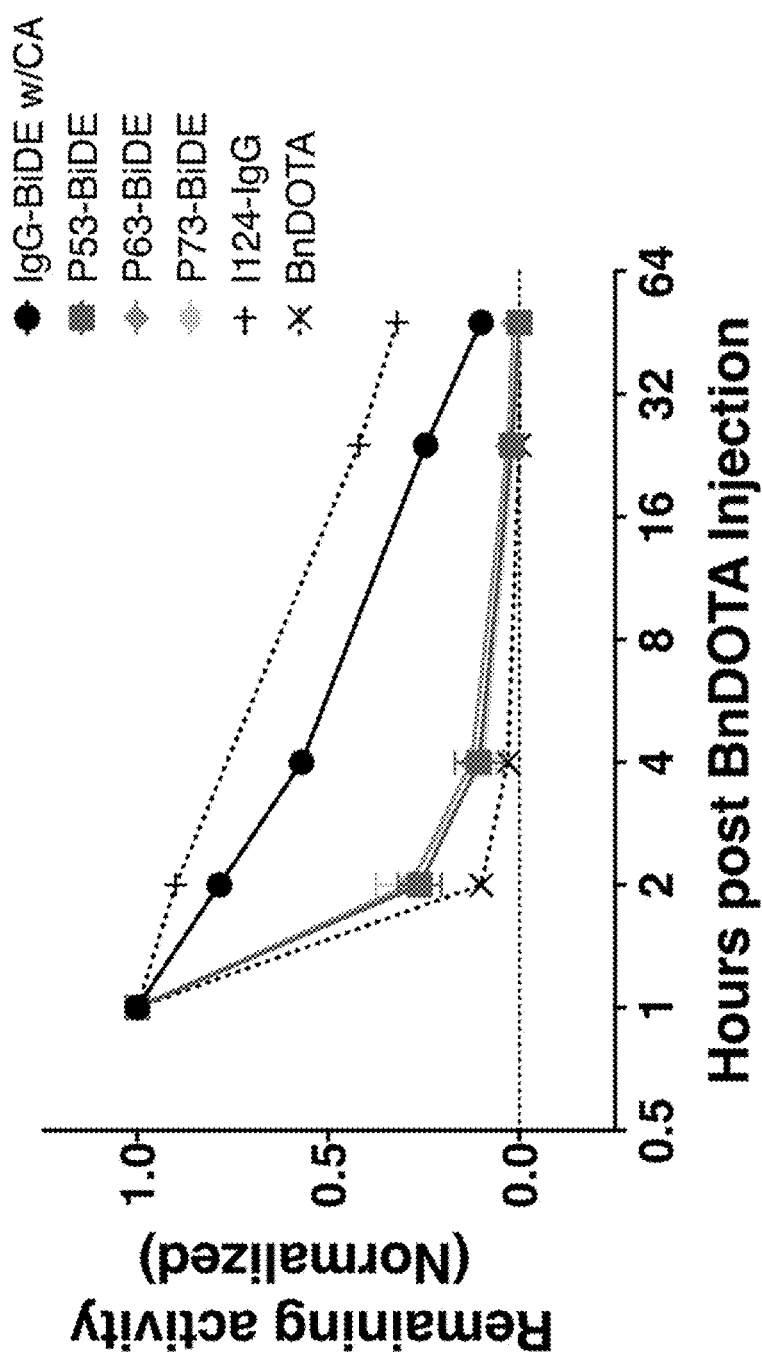

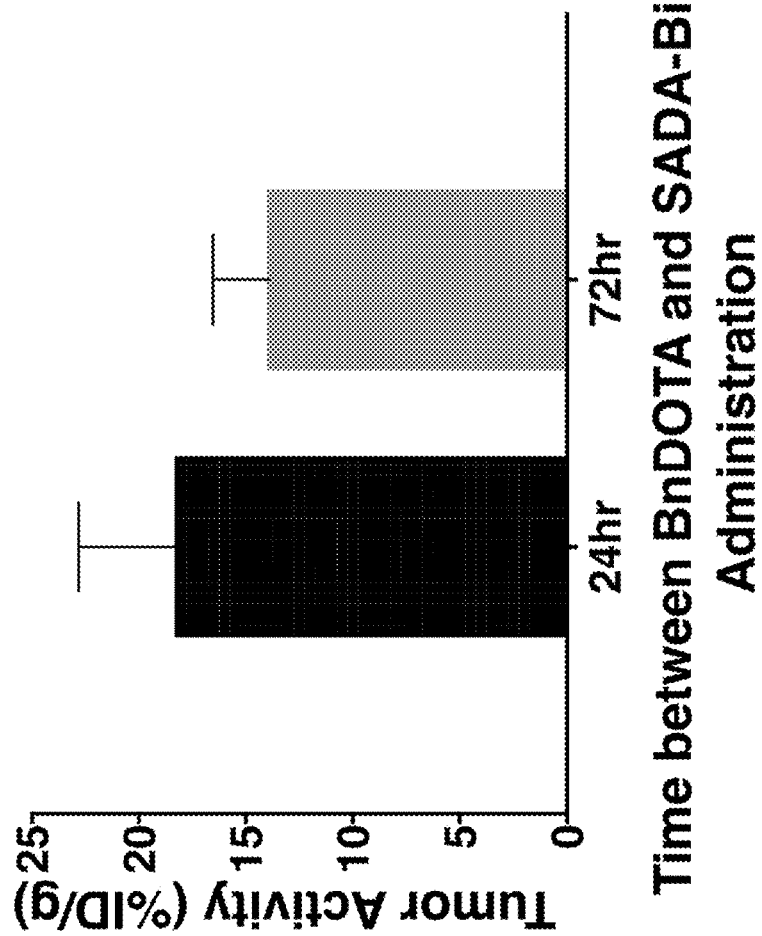

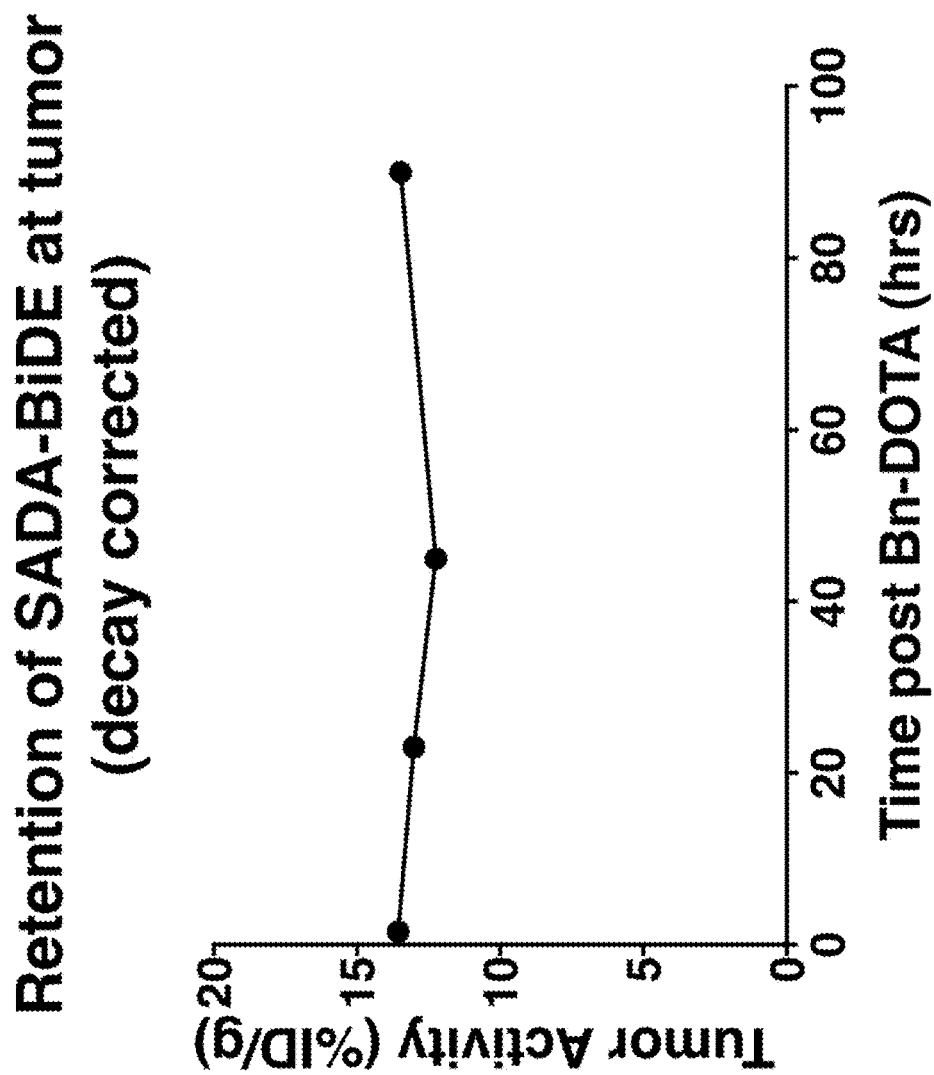

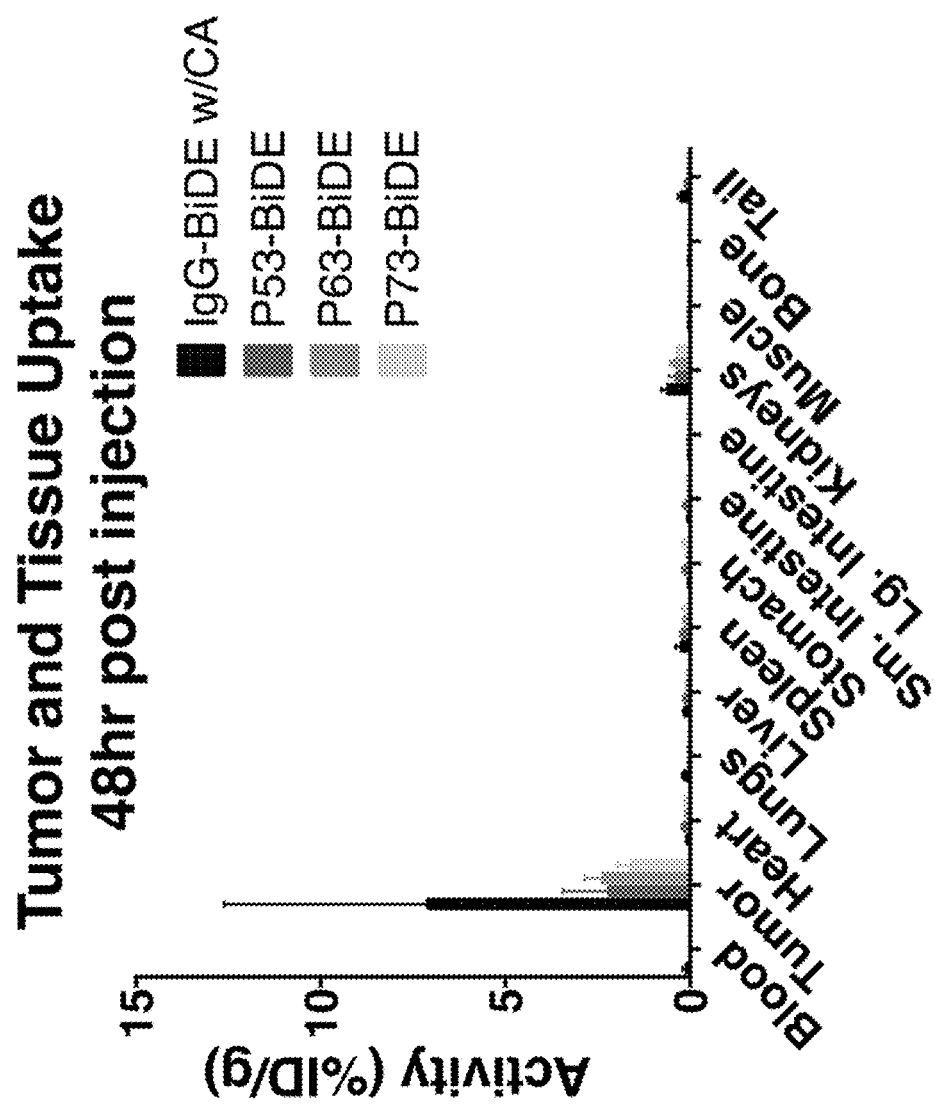

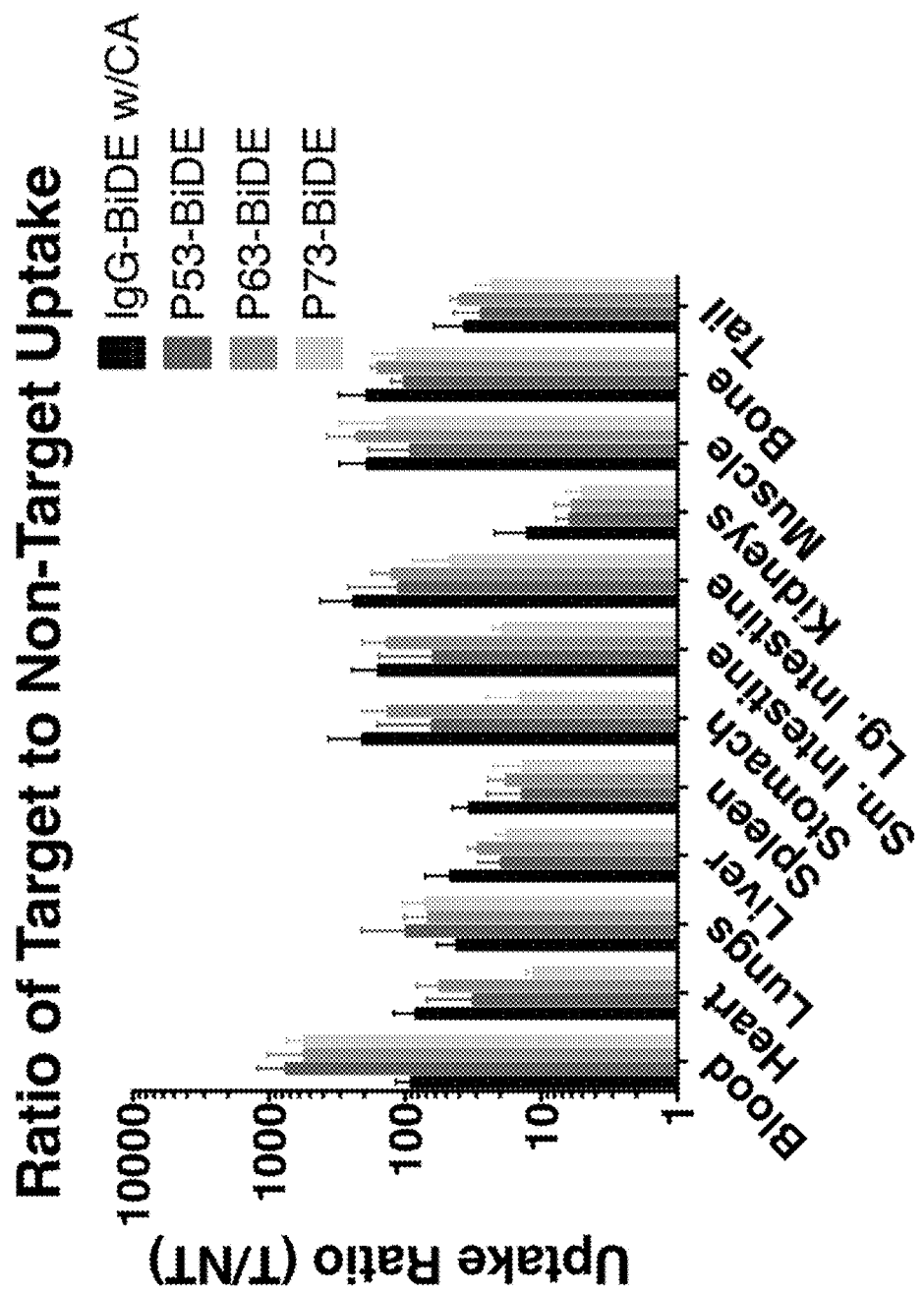

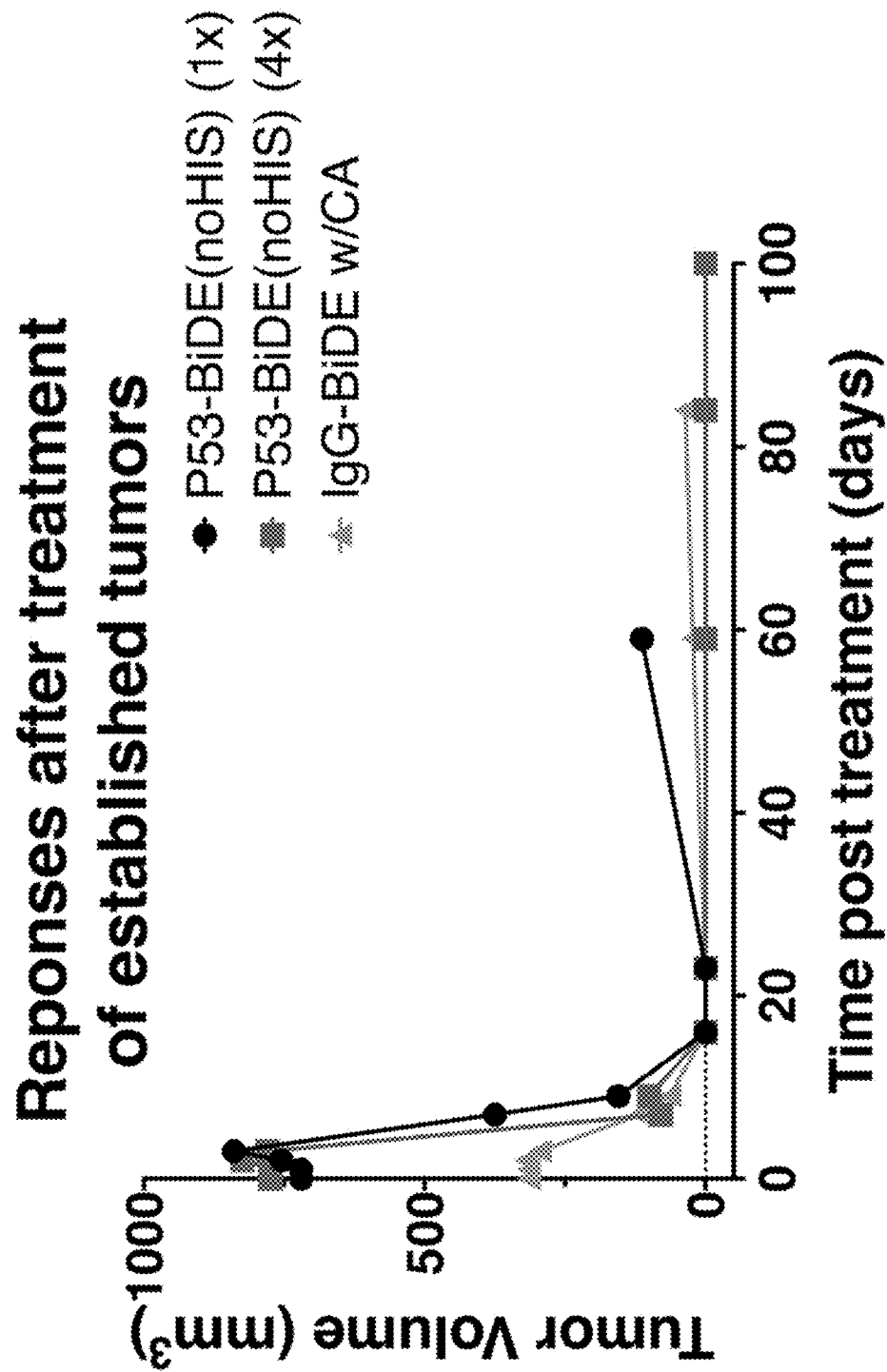

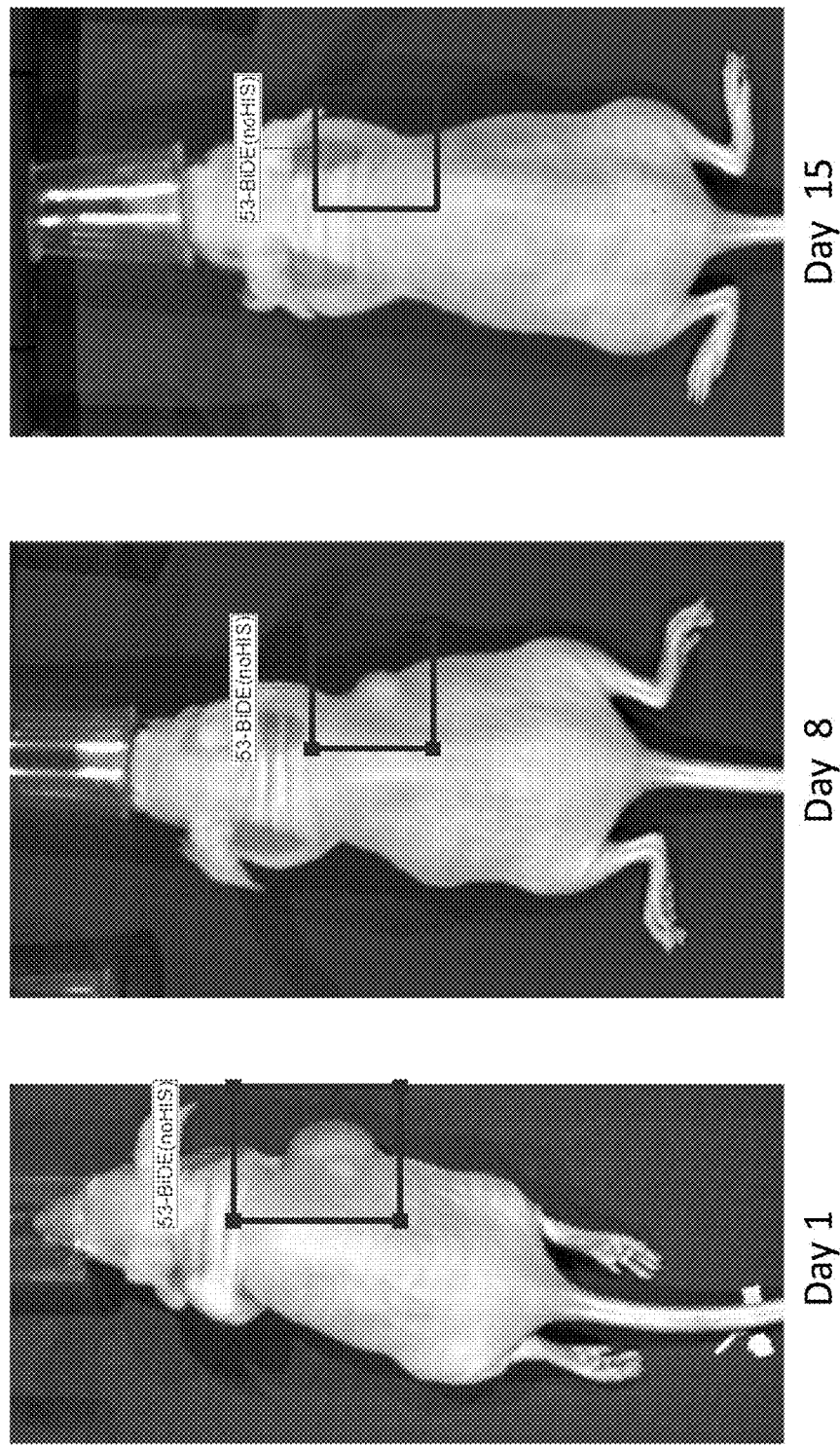

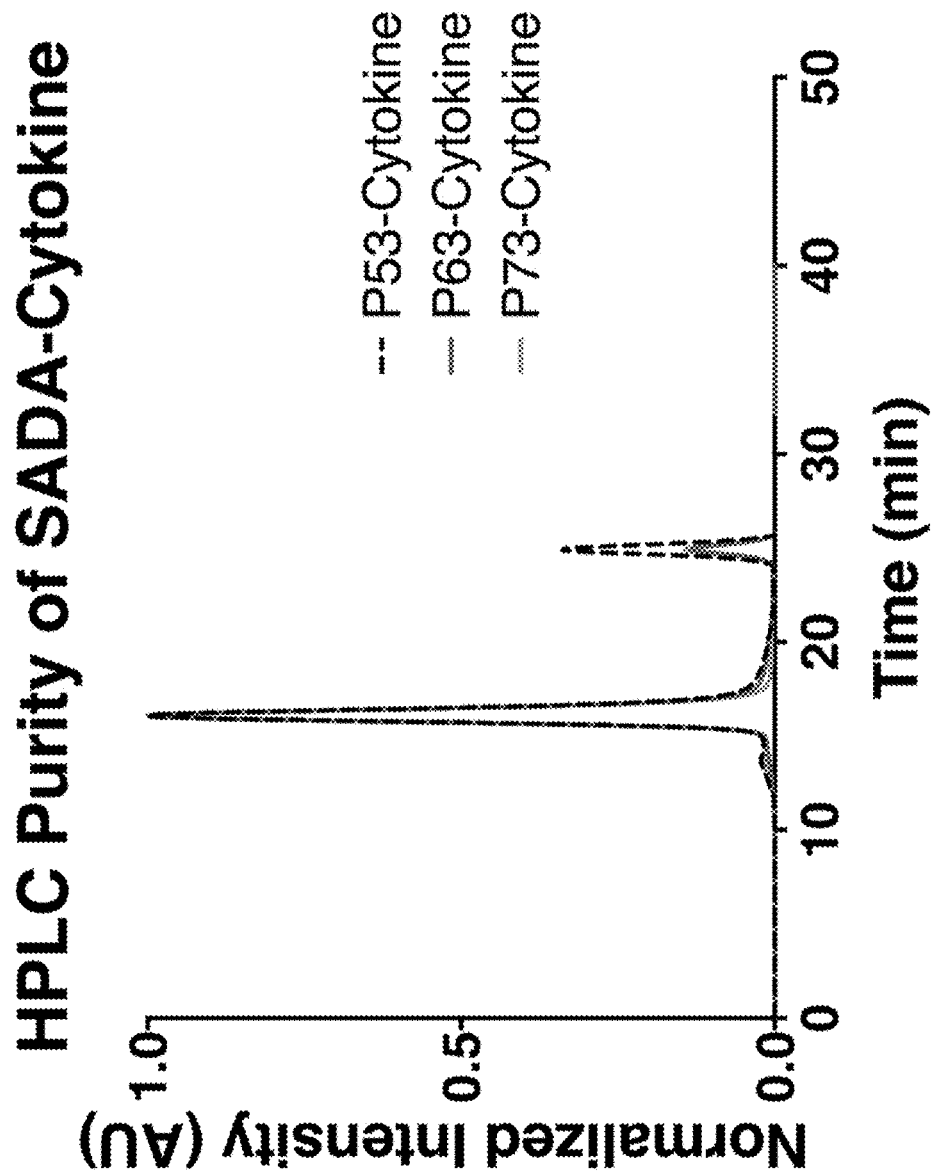

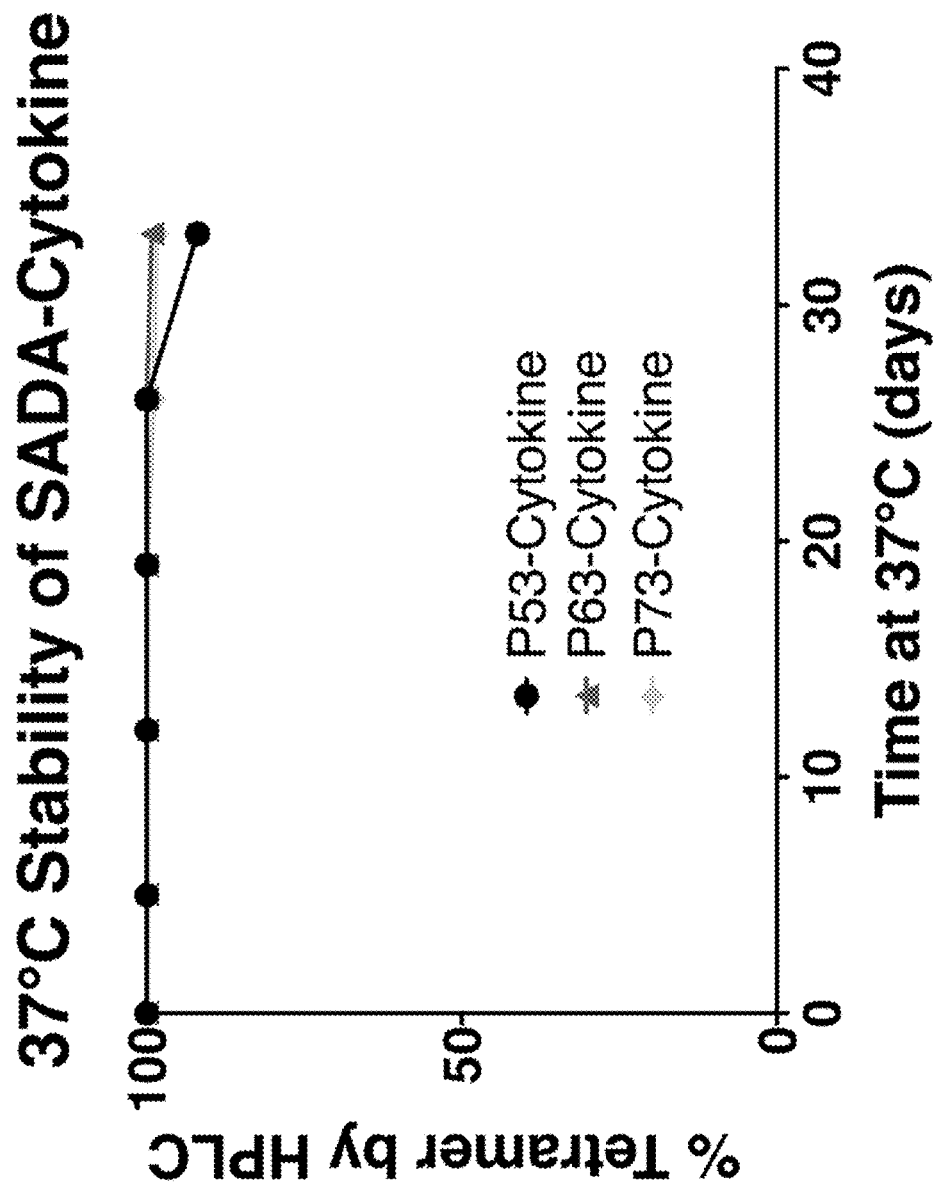

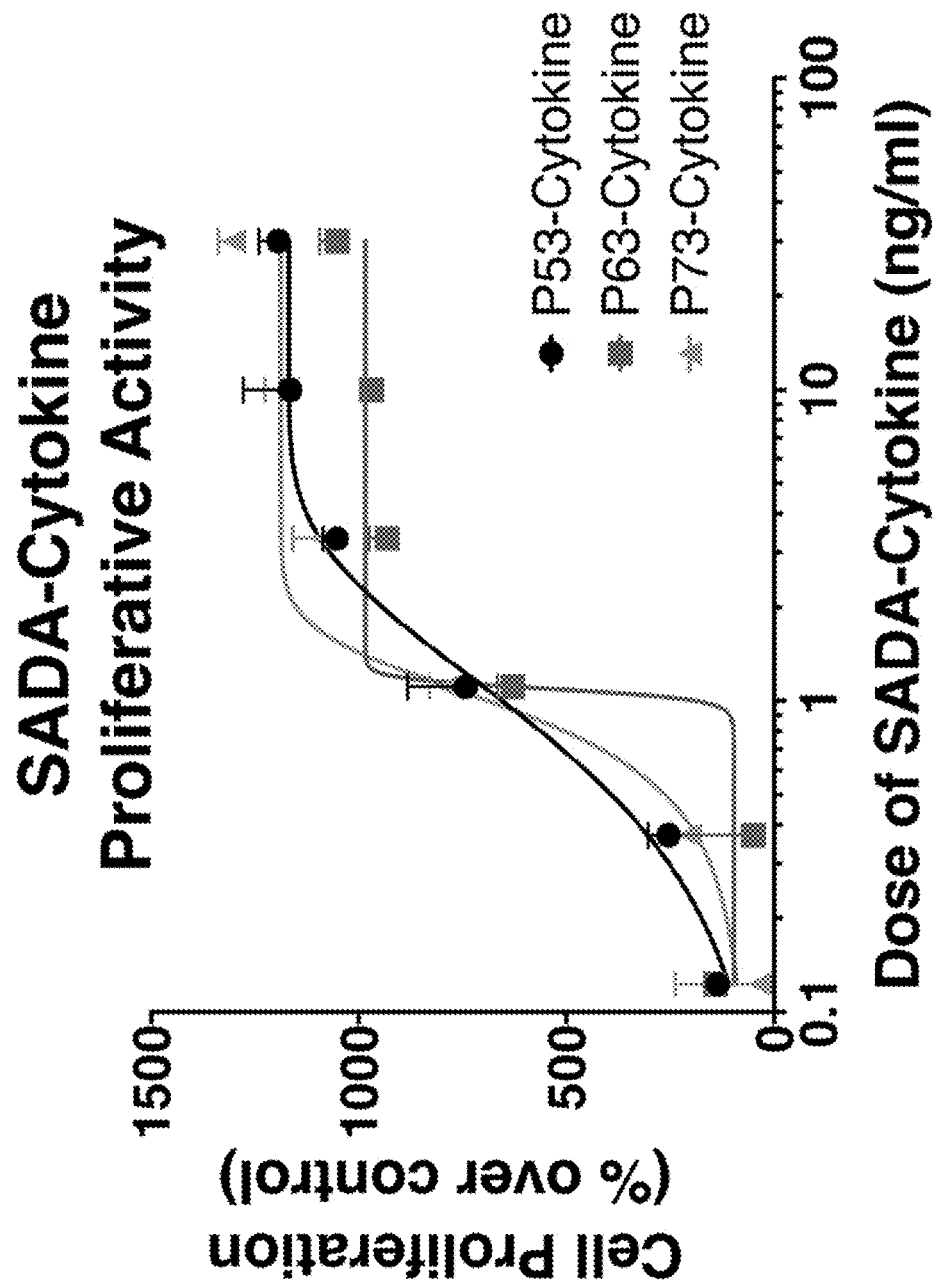

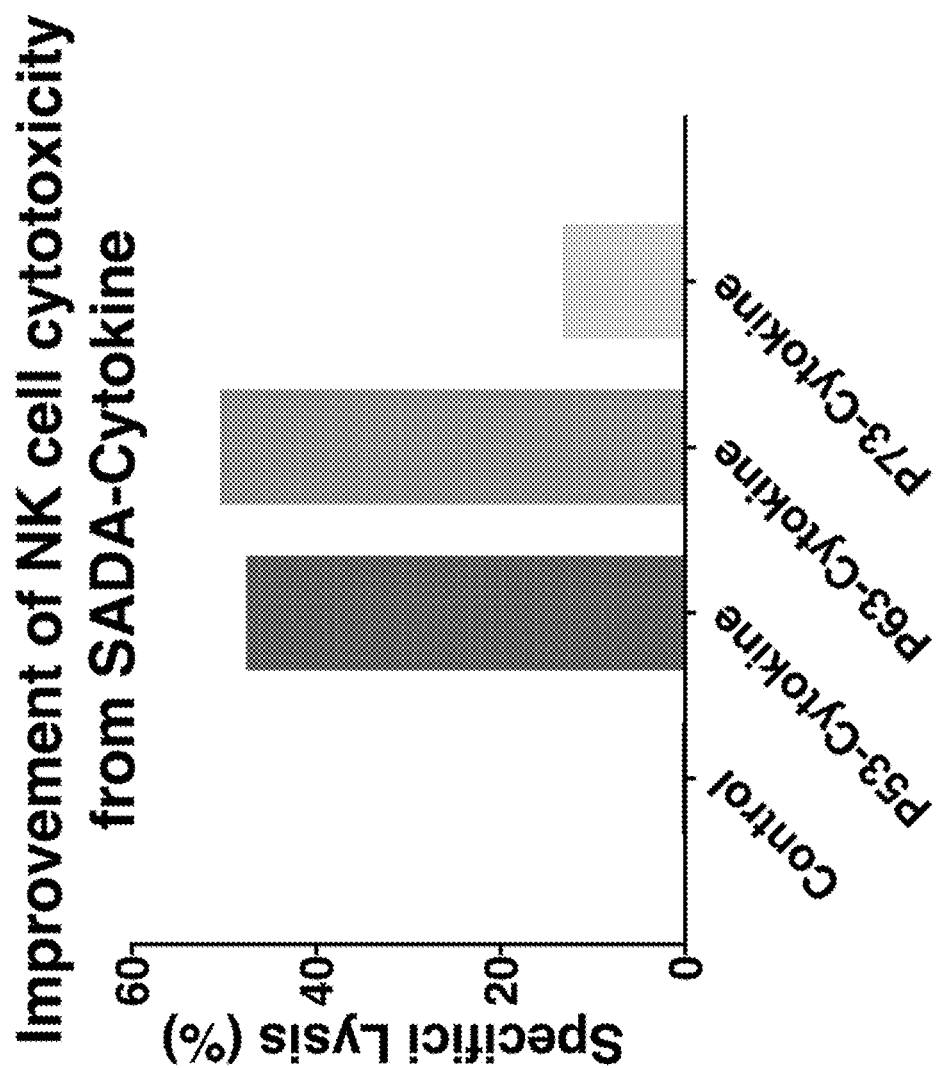

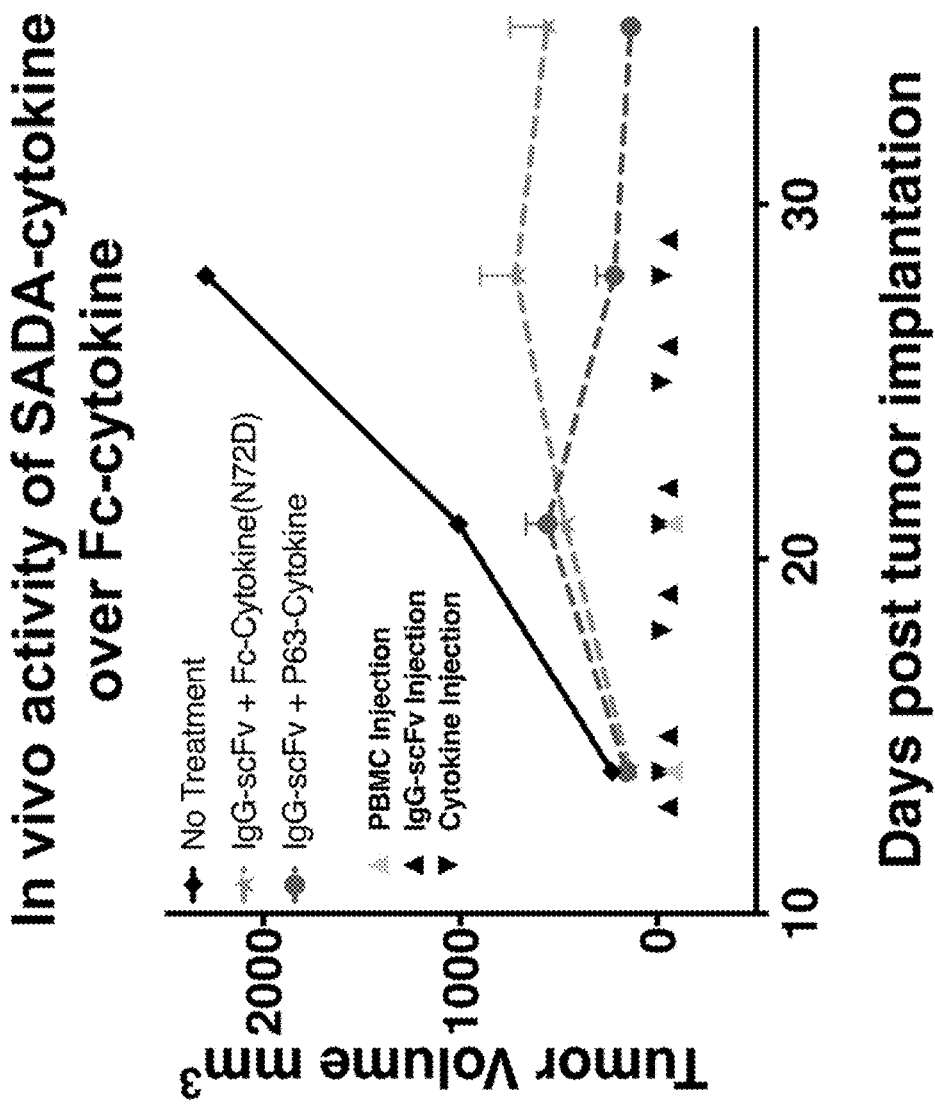

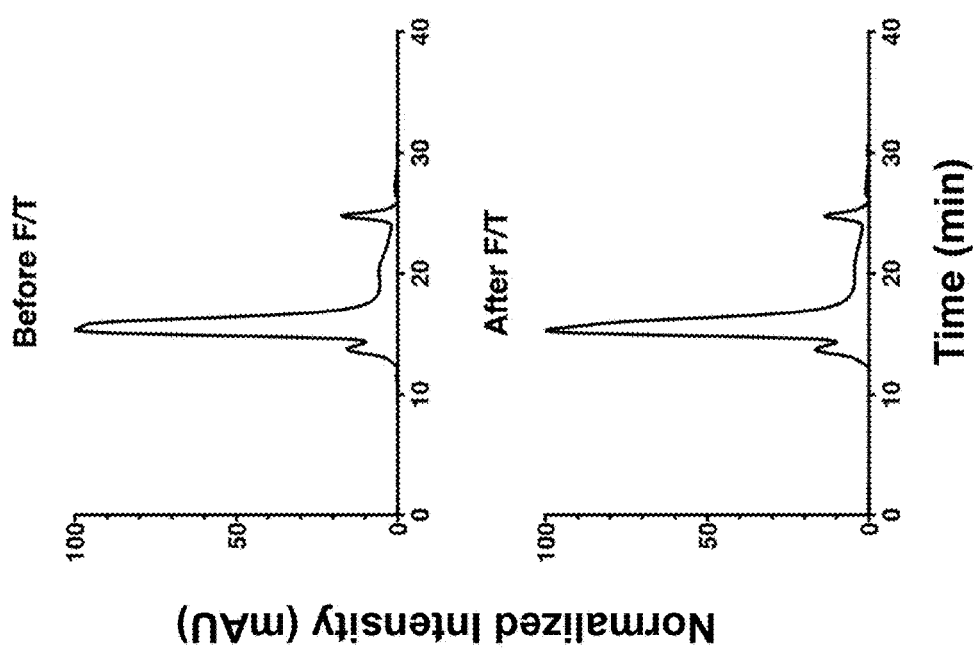

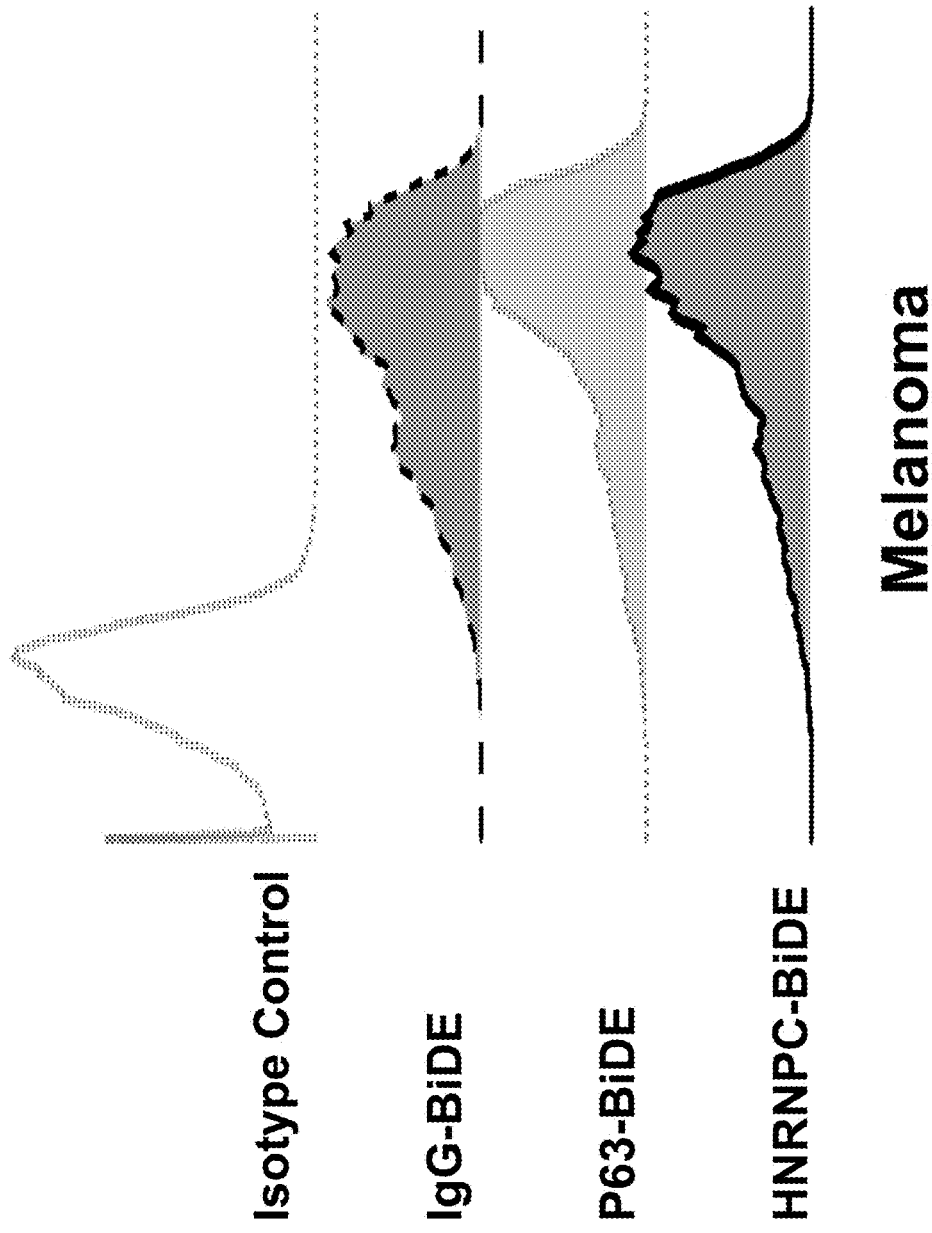

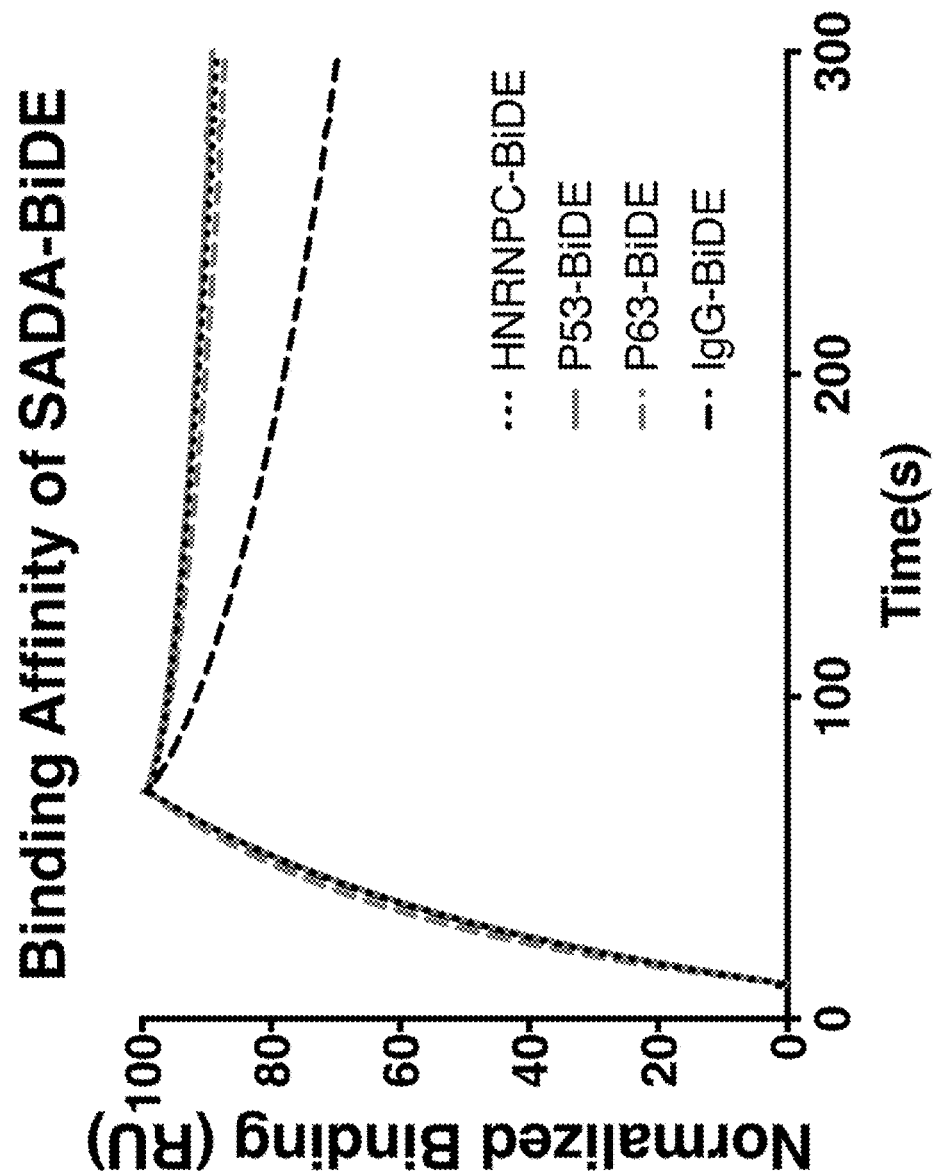

MODULAR SELF ASSEMBLY DISASSEMBLY (SADA) TECHNOLOGIES

CROSS-REFERENCE TO RELATED APPLICATIONS

This Application is a divisional of U.S. application Ser. No. 16/609,401, filed Oct. 29, 2019, now U.S. Pat. No. 11,583,588, which is a National Stage Application of PCT/US2018/031235, filed May 4, 2018, which claims the benefit of and priority to U.S. Provisional Application No. 62/502,151, filed May 5, 2017, each of which is incorporated herein by reference in its entirety.

STATEMENT OF GOVERNMENT SUPPORT

This invention was made with government support under CA008748 awarded by the National Institutes of Health. The government has certain rights in the invention.

SEQUENCE LISTING

The instant application contains a Sequence Listing which has been submitted electronically in XML file format and is hereby incorporated by reference in its entirety. Said XML copy, created on Dec. 13, 2024, is named 115872-2681_SL.xml and is 237,295 bytes in size.

BACKGROUND

Effective delivery of therapeutic and diagnostic agents to human and animal subjects can present significant challenges.

SUMMARY

The present disclosure provides, among other things, a novel platform technology using modular domains for self-assembly and disassembly (SADA). The present disclosure encompasses a recognition that SADA domains can impart certain desirable functional characteristics to a conjugate. For example, the present disclosure provides an insight that SADA domains can be designed and/or tailored to achieve environmentally-dependent multimerization with beneficial kinetic, thermodynamic, and/or pharmacologic properties. For example, it is recognized that SADA domains may be part of a conjugate that permit effective delivery of a payload to a target site of interest while minimizing risk of off-target interactions.

Among other things, the present disclosure provides various conjugates comprising a SADA domain linked to one or more binding domains. In some embodiments, such conjugates are characterized in that they multimerize to form a complex of a desired size under relevant conditions (e.g., in a solution in which the conjugate is present above a threshold concentration or pH and/or when present at a target site characterized by a relevant level or density of receptors for the payload), and disassemble to a smaller form under other conditions (e.g., absent the relevant environmental multimerization trigger).

The present disclosure provides an appreciation that assembly/disassembly through a SADA domain enables, at least in part, transition between a first multimeric state (e.g., monomeric or dimeric) and higher order multimeric states (e.g., tetrameric, pentameric, etc.) to occur with predictable kinetics. In some embodiments, a SADA conjugate is characterized in that it forms a higher order multimeric complex that is highly stable in solution at relevant conditions (e.g., sufficiently high concentration or relevant pH). In some embodiments, a SADA conjugate is characterized in that a higher order multimeric complex dissociates to smaller states (e.g., dimers, monomers) with predictable kinetics under conditions that do not meet a multimerization threshold (e.g., below a threshold concentration). In some embodiments, a SADA domain is selected and/or engineered for tunable delivery of a conjugate in vivo (e.g., selected for particular association and/or dissociation kinetics of a SADA domain).

The present disclosure provides, among other things, an appreciation that a SADA conjugate may have improved characteristics compared to a conjugate without a SADA domain. In some embodiments, a SADA conjugate includes a binding domain. In some embodiments, improved characteristics include that a multimeric conjugate has increased avidity/binding to a target, increased specificity for target cells or tissues, and/or extended initial serum half-life. In some embodiments, improved characteristics include that SADA conjugates exhibit reduced non-specific binding, decreased toxicity, and/or improved renal clearance, which may be due, at least in part, through dissociation to smaller states (e.g., dimeric or monomeric).

In some embodiments, a SADA conjugate further comprises a payload. In some embodiments, a SADA conjugate has improved characteristics when compared with a payload not conjugated to a SADA domain or with a payload conjugated to an alternative domain (e.g., an immunoglobulin domain).

In some embodiments, a multimeric SADA conjugate is highly stable in a solution in which the conjugate is present above a threshold concentration. In some embodiments a threshold concentration is 1 nM, 5 nM, 10 nM, 50 nM, 100 nM, 500 nM, 1 mM, 5 mM, 10 mM, 50 mM, 100 mM, 500 mM, 1 µM, 10 µM, 50 µM, 100 µM, 200 µM, 300 µM, 400 µM, 500 µM, 1 mM, etc. In some embodiments, a multimeric SADA conjugate is highly stable in a solution in which the conjugate is present above or below a threshold pH. In some embodiments, a multimeric SADA conjugate under relevant conditions is stable for at least a day, at least a week, at least two weeks, at least a month, at least two months, at least 3 months, at least 6 months, etc., when stored at −80° C., −20° C., 0° C., 20° C., 25° C. or 37° C. In some embodiments, a multimeric SADA conjugate is highly stable under in vivo conditions where the local environment (e.g., a target cell and/or a target tissue) meets multimerization threshold conditions (e.g., local concentration is above a threshold concentration, target density is above a threshold, or at a threshold pH).

In some embodiments, a multimeric SADA conjugate dissociates at a predictable rate under conditions that do not meet the multimerization threshold (e.g., below a threshold concentration). In some embodiments, a SADA conjugate multimer dissociates rapidly under conditions that do not meet the multimerization threshold (e.g., below a threshold concentration or an a pH above/below the relevant pH). In some embodiments, a SADA conjugate multimer dissociates at a relatively slow rate under conditions that do not meet the multimerization threshold. In some embodiments, a SADA conjugate multimer dissociates under conditions that do not meet the multimerization threshold with a koff rate in a range of about $1 \times 10^{-7}$ sec$^{-1}$ to $1 \times 10^{-3}$ sec$^{-1}$. In some embodiments, a SADA conjugate multimer dissociates under conditions that do not meet the multimerization threshold with a koff rate in a range of about $1 \times 10^{-6}$ sec$^{-1}$ to $5 \times 10^{-1}$. In some embodiments, a SADA conjugate multimer dissociates under conditions that do not meet the multimerization threshold with a half life of about 10 min, 20 min, 30 min, 40 min, 50 min, 60 min, 70 min, 80 min, 90 min, 100 min, 125 min, 150 min, 175 min, 200 min, 225 min, 250 min, 275 min, 300 min, 325 min, 350 min, 375 min, or 400 min.

In some embodiments, a SADA conjugate has predictable kinetics in vivo. In some embodiments, a multimerized SADA conjugate has an extended initial serum half-life. In some embodiments, such conjugates are characterized in that they multimerize to form a complex with a molecular weight greater than the threshold for renal clearance (i.e., greater than ~70 kDa). In some embodiments, a SADA conjugate multimer dissociates under in vivo conditions that do not meet a multimerization threshold (e.g., the do not meet a threshold concentration, such as at an off-target site). In some embodiments, dissociation of a multimerized SADA conjugate into a small units facilitates rapid clearance in vivo (e.g., through the renal clearance system). In some embodiments, a SADA conjugate monomer has a molecular weight less than the threshold for renal clearance (i.e., less than ~70 kDa). In some embodiments, a SADA conjugate dimer has a molecular weight less than the threshold for renal clearance (i.e., less than ~70 kDa).

In some embodiments, a multimerized SADA conjugate has a molecular weight greater than 150 kDa and rapidly dissociates to a smaller state (e.g., dimer or monomer of less than ~70 kDa) under in vivo conditions that do not meet the multimerization threshold (e.g., at off target sites in vivo). In some embodiments, a multimerized SADA conjugate has a molecular weight greater than 150 kDa and dissociates to a smaller state (e.g., dimer or monomer of less than ~70 kDa) under in vivo conditions that do not meet the multimerization threshold (e.g., at off target sites in vivo) over a discrete period.

In some embodiments, a SADA conjugate comprises (i) a self-assembly disassembly (SADA) polypeptide having an amino acid sequence that shows at least 75% identity (e.g., 75%, 80%, 85%, 90%, 95%, 96%, 97%, 98%, 99%, or 100% identity) with that of a human homo-multimerizing polypeptide and is characterized by one or more multimerization dissociation constants ($K_D$); and (ii) at least a first binding domain that binds to a first target and is covalently linked to the SADA polypeptide. In some embodiments, a SADA conjugate is constructed and arranged so that it adopts a first multimerization state and one or more higher-order multimerization states. In some embodiments, a first multimerization state is less than about ~70 kDa in size. In some embodiments, a first multimerization state is an unmultimerized state (e.g., a monomer or a dimer). In some embodiments, a first multimerization state is a monomer. In some embodiments, a first multimerization state is a dimer. In some embodiments, a first multimerization state is a multimerized state (e.g., a trimer or a tetramer). In some embodiments, a higher-order multimerization state is a homo-tetramer or higher-order homo-multimer greater than 150 kDa in size. In some embodiments, a higher-order homo-multimerized conjugate is stable in aqueous solution when the conjugate is present at a concentration above the SADA polypeptide $K_D$. In some embodiments, a SADA conjugate transitions from a higher-order multimerization state(s) to a first multimerization state under physiological conditions when the concentration of the conjugate is below the SADA polypeptide $K_D$.

In some embodiments, a higher-order homo-multimerized conjugate is stable for a period of at least 24 hours at a temperature from 25° C. to 37° C. in an aqueous buffer with a pH of about 6.8-7.2. In some embodiments, a higher-order homo-multimerized conjugate is stable for a period of at least 48 hours, 72 hours, 1 week, 2 weeks, 1 month, 2 months, 3 months, or more. In some embodiments, a higher-order homo-multimerized conjugate is stable over 3, 4, 5, or more freeze-thaw cycles.

In some embodiments, a conjugate transitions from a higher order multimerization state to a first multimerization state, and this transition is characterized by a $K_{off}$ within a range of $1 \times 10^{-6}$ to $1 \times 10^{-4}$ $(s^{-1})$.

In some embodiments, a SADA polypeptide has a total buried surface area of 900 Å2 to 4000 Å2. In some embodiments, a SADA polypeptide lacks unpaired cysteine residues. In some embodiments, a SADA polypeptide comprises a tetramerization, pentamerization or hexamerization domain.

In some embodiments, a SADA polypeptide is or comprises a tetramerization domain of p53, p63, p73, hnRNPC, SNAP-23, Stefin B, KCNQ4, or CBFA2T1. In some embodiments, a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 1, 3, 5, 7, 9, 11, 13, and 15.

In some certain embodiments, a conjugate comprising a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 17, 19, 21, 23, 25, 27, 29, 31, 33, 35, 37, 39, 41, 43, 45, 47, 49, 51, 53, 55, 57, 59, 61 and 63. In some certain embodiments, a conjugate comprising a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 17, 19, 21, 23, 25, 27, 29, 31, 33, 35, 37, 39, 41, 43, 45, 47, 49, 51, 53, 55, 57, 59, 61, 63, 67, 69, 71, 73, 75, 77, 79, 81, 83, 85, 87, 89, 91, 93, 95, and 97.

In some embodiments, a conjugate comprises a first binding domain that binds to a first target selected from the group consisting of an in situ target and a payload target. In some embodiments, a first target is an in situ target that is or comprises an entity selected from the group consisting of: a cell-surface moiety, a cytokine, a receptor ligand, a peptide, a hormone, a metabolite, and a hapten. In some embodiments, a first target is a therapeutic payload. In some embodiments, a first target is a diagnostic payload.

In some embodiments, a conjugate further comprises a second binding domain that binds to a second target, which is different from the first target. In some embodiments, a conjugate comprises at least two binding domains and wherein the conjugate in the second multimerization state is at least octavalent. In some embodiments, a second target is selected from the group consisting of an in situ target and a payload target. In some embodiments, a second target is an in situ target that is or comprises an entity selected from the group consisting of: a cell-surface moiety, a cytokine, a receptor ligand, a peptide, a hormone, a metabolite, and a hapten. In some embodiments, a second target is a therapeutic payload. In some embodiments, a second target is a diagnostic payload.

In some embodiments, a payload target is a drug, a polypeptide (such as a toxin, enzyme, cytokine, chemokine, receptor, or biologic), a chemical probe (such as a fluorescent dye or biotin tag), a radioactive isotope, or a nanoparticle. In some embodiments, a second target is a cell surface moiety. In some embodiments, a cell surface moiety is specifically expressed or enriched on a subset of cells in an organism. In some embodiments, a cell surface moiety is specifically expressed or enriched on tumor cells. In some embodiments, a cell surface moiety is a cell surface receptor. In some embodiments, a first and/or second binding domain is or comprises a ligand for a cell surface receptor. In some embodiments, a first and/or second binding domain is or comprises a cytokine receptor binding domain. In some embodiments, a conjugate is further complexed with a soluble cytokine polypeptide. In some embodiments, a cytokine receptor is IL15Rα and the soluble cytokine polypeptide is IL15.

In some embodiments, a first and/or second binding is or comprises an antibody component specific for a cell surface target. In some embodiments, a first and/or second binding domain may be any polypeptide whose amino acid sequence includes elements characteristic of an antibody-binding region. In some embodiments, a first and/or second binding domain is a VHH. In some embodiments, a first and/or second binding domain is a scFv. In some embodiments, a first and/or second binding domain is an anti-GD2, anti-Globo H, anti-GPA33, anti-PSMA, anti-polysialic acid, anti-Lew$^Y$, anti-L1CAM, anti-HER2, anti-B7H3, anti-CD33, anti-peptide/MHC, anti-glypican3, or anti-GD3 antibody component.

In some embodiments, a SADA conjugate is characterized in that it comprises a binding domain that binds a target at an in vivo site. In some embodiments, a target at an in vivo site is present at sufficient density such that a conjugate is substantially in the higher-order multimerization state at the target site. In some embodiments, a SADA conjugate is characterized in that it comprises a binding domain that binds a target, wherein the target is present at sufficient concentration such that higher order multimerization state of the SADA polypeptide is stabilized in vivo.

In some embodiments, a SADA conjugate further comprises a second multimerization domain (e.g., a dimerization domain, a trimerization domain, a tetramerization domain, or a second SADA domain). In some embodiments, a SADA conjugate can exist in one or more additional multimeric states.

In some embodiments, a SADA conjugate is substantially not immunogenic in a human subject.

In some embodiments, a payload is a therapeutic payload. In some embodiments, a payload is a diagnostic payload. In some embodiments a payload is or comprises a radioisotope, an antibody agent, a cytokine, a cytotoxic agent, a polypeptide, a protein toxin, a ligand binding domain, a peptide and/or a nanoparticle.

In some embodiments, a SADA conjugate comprises a first binding domain that is an antibody component (e.g., an antibody, a scFv, a VHH, etc.). In some embodiments, a SADA conjugate further comprises a second binding domain, wherein the second binding domain is an antibody component (e.g., an antibody, a scFv, a VHH, etc.). In some embodiments, a first and/or second binding domains are part of a bispecific antibody agent. In some embodiments, a bispecific antibody agent is a tandem scFv comprising a first binding domain that binds a tumor target and a second binding domain that binds a metal-Bn-DOTA. In some embodiments, a bispecific antibody agent is a tandem scFv comprising a first binding domain that binds a tumor target and a second binding domain that binds an immune-cell activating receptor. In some embodiments, a first binding domain that binds a tumor target is an anti-GD2, anti-Globo H, anti-GPA33, anti-PSMA, anti-polysialic acid, anti-Lew$^Y$, anti-L1CAM, anti-HER2, anti-B7H3, anti-CD33, anti-peptide/MHC, anti-glypican3, or anti-GD3 binding domain (e.g., an antibody component). In some embodiments, a first binding domain that binds a tumor target is an antibody component. In some embodiments, an antibody component is an scFv. In some embodiments, an antibody component is a VHH.

Also provided are nucleic acid sequences encoding SADA domains and SADA-domain containing conjugates, as well as vectors comprising such nucleic acid sequences. In some embodiments, a nucleotide sequence encoding a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 2, 4, 6, 8, 10, 12, 14 and 16. In some certain embodiments, a nucleotide sequence encoding a conjugate comprising a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 18, 20, 22, 24, 26, 28, 30, 32, 34, 36, 38, 40, 42, 44, 46, 48, 50, 52, 54, 56, 58, 60, 62 and 64. In some certain embodiments, a nucleotide sequence encoding a conjugate comprising a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 18, 20, 22, 24, 26, 28, 30, 32, 34, 36, 38, 40, 42, 44, 46, 48, 50, 52, 54, 56, 58, 60, 62, 64, 68, 70, 72, 74, 76, 78, 80, 82, 84, 86, 88, 90, 92, 94, 96, and 98.

Also provided are cells (e.g., host cells) comprising nucleic acids and/or vectors encoding SADA domains or SADA conjugates. In some embodiments, a host cell comprises a vector that comprises a nucleotide sequence encoding a SADA domain or a SADA conjugate. In some embodiments, a host cell is selected from the group consisting of a bacterial, yeast, insect or mammalian cell. In some embodiments, a host cell is selected from the group consisting of E. coli, Pichia pastoris, Sf9, COS, HEK293 and a CHO cell.

Also provided are compositions comprising one or more SADA conjugates. In some embodiments, a composition comprising a SADA conjugate is formulated for injection. In some embodiments, a SADA conjugate is formulated for injection so that stable binding between the conjugate and its target is detectable at its target tissue for a period of time at least 24 hours long, and wherein the conjugate is substantially undetectable in at least one non-target tissue within 72 hours post-injection without any extraneous drug or clearing agent. In some embodiments, a non-target tissue may be or include blood, gastrointestinal tissue, lymphoid tissue, nervous system tissue, renal tissue, hepatic tissue, muscle tissue, or any combinations thereof. In some embodiments, a non-target tissue is or comprises blood. In some certain embodiments, a target tissue is or comprises a tumor tissue. In some embodiments, a SADA conjugate is cleared from the blood serum of a subject within 30 minutes, within 1 hour, within 2 hours, within 3 hours, within 4 hours, within 5 hours, within 6 hours, within 12 hours, within 24 hours, within 36 hours, within 48 hours, within 72 hours, etc.

In some embodiments, a method is provided, said method comprising steps of (i) providing a liquid composition comprising a SADA conjugate in the higher-order multimeric state; and (ii) administering the composition to a subject. In some embodiments, a step of administering comprises delivering so that conjugate that is not bound to the target tissue disassembles into the first multimerization state or a monomeric state, whereas conjugate that is bound to the target is substantially in the higher-order multimeric state. In some embodiments, extent of a conjugate in a higher-order multimeric state may be or is assessed by measuring the retention of a conjugate at a target site. In some embodiments, extent of conjugate in a first multimerization state or monomeric state may be or is assessed by measuring an amount of conjugate in the blood of a subject. In some embodiments, extent of conjugate in a first multimerization state or monomeric state may be or is assessed by direct radiolabeling. In some embodiments, extent of conjugate in a first multimerization state or monomeric state may be or is assessed by measuring a rate of clearance of a conjugate into the urine of a subject. In some embodiments, a step of administering is to a subject suffering from or susceptible to cancer. In some embodiments, a SADA conjugate is cleared from the blood serum of a subject within 30 minutes, within 1 hour, within 2 hours, within 3 hours, within 4 hours, within 5 hours, within 6 hours, within 12 hours, within 24 hours, within 36 hours, within 48 hours, within 72 hours, etc.

In some embodiments, a method is provided, said method comprising steps of (i) providing a liquid composition comprising a SADA conjugate; and (ii) administering the composition to a subject that is suffering from cancer.

In some embodiments, a method of treating or diagnosing cancer in a subject is provided, said method comprising steps of (i) providing a liquid composition comprising a SADA conjugate in a concentration sufficient that greater than 90% of the conjugate is in the higher-order multimerization state; and (ii) administering the composition to a subject that is suffering from or susceptible to cancer. In some embodiments, a composition comprises a conjugate at a concentration within a range of about 100 nM to 10 mM.

In some embodiments, a method of pre-targeted radio immunotherapy is provided, said method comprising steps of (i) providing a liquid composition comprising a SADA conjugate in a higher order multimeric form; (ii) administering the composition to a subject that is suffering from or susceptible to cancer; and (ii) subsequently administering a radiolabeled Bn-DOTA to the subject. In some embodiments, such a method does not include administration of a clearing agent. In some embodiments, a SADA conjugate is cleared from the blood serum of a subject within 30 minutes, within 1 hour, within 2 hours, within 3 hours, within 4 hours, within 5 hours, within 6 hours, within 12 hours, within 24 hours, within 36 hours, within 48 hours, within 72 hours, etc.

In some certain embodiments, the present disclosure provides the insight that SADA-conjugate platform as described herein may be particularly useful, for example, in context of a pre-targeted therapy. In some embodiments, a method of pre-targeted radio immunotherapy is provided, said method comprising steps of (i) providing a liquid composition comprising a SADA conjugate in a concentration of at least 50 nM, 100 nM, 500 nM, 1 µM, 10 µM, 50 µM, 100 µM, 200 µM, 300 µM, 400 µM, 500 µM, or 1 mM; and (ii) administering the composition to a subject that is suffering from or susceptible to cancer. In some embodiments, a liquid composition comprises a conjugate, where at least 90% of the conjugate is in a higher order multimeric form (e.g., a tetramer, pentamer, hexamer, septamer, octamer, nonamer, decamer, etc.). In some embodiments, the conjugate is a SADA-Bispecific DOTA-engaging (SADA-BiDE) conjugate. In some embodiments, the conjugate further comprises a payload, such as Bn-DOTA. In some embodiments, a payload is or comprises Bn-DOTA or a variant thereof. In some embodiments, a Bn-DOTA variant may also comprise a biotin tag, a fluorescent tag, another DOTA tag, or a peptide tag, etc. In some embodiments, a Bn-DOTA or variant thereof is covalently attached to the conjugate. In some embodiments, a Bn-DOTA or variant thereof is non-covalently complexed with the conjugate. In some embodiments, a Bn-DOTA is radiolabeled. In some embodiments, a radiolabeled Bn-DOTA is covalently attached to the conjugate. In some embodiments, a radiolabeled Bn-DOTA is non-covalently complexed with the conjugate. In some embodiments, such a method does not include administration of a clearing agent. In some embodiments, a SADA conjugate is cleared from the blood serum of a subject within 30 minutes, within 1 hour, within 2 hours, within 3 hours, within 4 hours, within 5 hours, within 6 hours, within 12 hours, within 24 hours, within 36 hours, within 48 hours, within 72 hours, etc.

In some embodiments, a method is provided, said method comprising steps of (i) providing a liquid composition comprising a SADA conjugate, wherein at least 90% of the conjugate in the composition is in ae higher order multimeric form; and (ii) administering the composition to a subject from whom a target entity is to be removed, wherein the conjugate is capable of binding the target entity.

The present disclosure provides various technologies for identifying and/or characterizing such conjugates, compositions containing them, and/or useful components thereof. The present disclosure provides, among other things, a recognition of certain characteristics that may be used to select a polypeptide for use as SADA domain. In some embodiments, a SADA domain is a human polypeptide or a fragment and/or derivative thereof. In some embodiments, a SADA domain is substantially non-immunogenic in a human. In some embodiments, a SADA polypeptide is stable as a multimer. In some embodiments, a SADA polypeptide lacks unpaired cysteine residues. In some embodiments, a SADA polypeptide does not have large exposed hydrophobic surfaces. In some embodiments, a SADA domain has or is predicted to have a structure comprising helical bundles that can associate in a parallel or anti-parallel orientation. In some embodiments, a SADA polypeptide is capable of reversible multimerization. In some embodiments, a SADA domain is a tetramerization domain, a heptamerization domain, a hexamerization domain or an octamerization domain. In certain embodiments, a SADA domain is a tetramerization domain. In some embodiments, a SADA polypeptide comprises a multimerization domains from one of following human proteins: p53, p63, p73, heterogeneous nuclear Ribonucleoprotein C (hnRNPC), N-terminal domain of Synaptosomal-associated protein 23 (SNAP-23), Stefin B (Cystatin B), Potassium voltage-gated channel subfamily KQT member 4 (KCNQ4), or Cyclin-D-related protein (CBFA2T1).

In some embodiments, a SADA-conjugate may be identified or characterized by a method comprising steps of (i) providing a conjugate comprising a self-assembly disassembly (SADA) polypeptide and a binding domain, (ii) administering the composition to a subject and (iii) determining the affinity of the conjugate for a target. Any methods known in the art for determining the affinity of a conjugate for a target may be used. In some embodiments, affinity may be assessed as binding affinity. In some embodiments, affinity may be assessed by localization, using any techniques known in the art to visualize localization.

In some embodiments, a SADA-conjugate may be identified or characterized by a method that includes analysis of one or more conjugates in a plurality of conjugates. In some embodiments, a SADA-conjugate may be identified or characterized by a method comprising steps of (i) providing composition comprising a plurality of conjugates, each comprising a SADA polypeptide and a binding domain, (ii)

administering the composition to a subject and (iii) determining the affinity of one or more of the conjugates for a target. In some embodiments, a step of determining comprises determining the affinity for a target for each of the conjugates. In some embodiments, a method includes a step of determining the rate of clearance of one or more conjugates from blood. In some embodiments, a method includes a step of determining the rate of clearance of a conjugate from blood for each of a plurality of conjugates. In some embodiments, a plurality of conjugates includes SADA conjugates that comprise the same binding domain but differ in the SADA polypeptide.

In some embodiments, a SADA-conjugate may be identified or characterized as preferred relative to another conjugate in a plurality of conjugates when the preferred conjugate shows increased avidity for a target and/or when the preferred conjugate is more rapidly cleared from the blood.

In some embodiments, a SADA-conjugate may be identified or characterized by a method that includes steps of (i) providing a composition comprising a SADA conjugate, and (ii) formulating the conjugate with a pharmaceutically acceptable carrier or excipient to produce a composition in which the conjugate is present at a concentration sufficient for at least 90% of the conjugate to adopt the higher-order multimerized state. In some embodiments, a conjugate in the composition is at a concentration of about 50 nM, 100 nM, 500 nM, 1 µM, 10 µM, 50 µM, 100 µM, 200 µM, 300 µM, 400 µM, 500 µM, 1 mM, or more.

The present disclosure provides various technologies related to SADA-containing conjugates including, for example, technologies for making such conjugates and/or compositions containing them, technologies for using such conjugates and/or compositions containing them, and/or technologies related to the manufacture of preparations comprising such conjugates.

BRIEF DESCRIPTION OF THE DRAWING

The Drawing included herein, which is composed of the following Figures, is for illustration purposes only and not for limitation.

FIG. 1A to FIG. 1C illustrate different treatment strategies and exemplifies some unique properties of a SADA domain. FIG. 1A depicts a conventional three-step pretargeting treatment schematic (e.g. radioimmunotherapy, RIT) using an IgG-based targeting agent. Initially (1a) the targeting agent is delivered, followed by a waiting period (1b) where the targeting agent is allowed to bind to its target. After a period of time (e.g., several hours or days), a (2a) clearing agent is administered, which binds and (2b) clears excess targeting agent (e.g., in a matter of hours). Lastly a third step involves the (3a) administration of the payload agent, which is small and can rapidly permeate tissues and bind to a targeting agent. Excess payload agent is (3b) rapidly cleared through the kidneys in a matter of minutes to hours. FIG. 1B depicts a two-step pretargeting treatment strategy using a SADA therapeutic. Initially (1a) the SADA targeting agent is delivered followed by a waiting period where the SADA targeting agent either binds to its target, or disassembles into monomeric units that are rapidly cleared by the kidneys in a matter of hours to days. The second step involves the administration of (2a) the payload agent that is specific for the SADA targeting agent, which is very small and rapidly permeates the tissues to reach the SADA targeting agent. Excess payload agent is rapidly cleared (2b) through the kidneys (e.g., in a matter of minutes to hours). FIG. 1C depicts a one-step treatment strategy using a SADA therapeutic. Initially (1a) the SADA targeting agent is delivered followed by (1b) a waiting period where the SADA therapeutic agent either binds to its target, or disassembles into monomeric units that are rapidly cleared by the kidneys (e.g., in a matter of hours to days). No other steps are needed and the SADA therapeutic imparts it activity onto its target.

FIG. 3A to FIG. 3C depict experiments showing the purity and stability of a preparation of SADA-BiDEs. FIG. 3A depicts an HPLC chromatogram that shows the size and purity of a preparation of three SADA-BiDEs after single-step affinity purification. The main peak (~16 min) denotes the self-assembled tetramer, similar to an IgG-BiDE (Cheal, S. M. et al. (2014) *Mol Cancer Ther*), matching its calculated molecular weight of ~200 kDa. The earlier peak (~14 min) denotes some smaller aggregates of each SADA-BiDE (2-3 complexes). The last peak (~25 min) is a non-specific peak from the storage buffer (sodium citrate). Plots are normalized to the standard ran that same week. P53-BiDE is depicted in black. P63-BiDE is depicted in dark gray. P73-BiDE is depicted in light gray. The purity (percentage tetramer) of each SADA-BiDE is noted by the main peak. FIG. 3B depicts a summary of HPLC chromatograms of various SADA-BiDEs incubated at 37° C. for a 40 day period. Each line denotes the purity of the SADA-BiDE (fraction that is complete tetramer) over time. P53-BiDE is depicted in black. P63-BiDE is depicted in dark gray. P73-BiDE is depicted in light gray. FIG. 3C depicts a normalized HPLC chromatogram showing the purity of the original SADA-BiDE compared to the purity after the sample is repeatedly frozen and thawed (5 times from −80° C. to 25° C.). The main peak (~16 min) denotes the self-assembled tetramer. The earlier peak (~14 min) denotes a higher order aggregate (2-3 complexes). The last peak (~25 min) is from the storage buffer (sodium citrate). Plots are normalized to a standard ran that same week. P53-BiDE is depicted in black. P63-BiDE is depicted in dark gray. P73-BiDE is depicted in light gray. Solid lines refer to the original purity, dotted lies refer to the purity after the freeze/thaw cycles.

FIG. 4 depicts a summary of fluorescence correlation spectroscopy (FCS) experiment regarding the SADA domains used here. Specifically, P53-BiDE, P63-BiDE and P73-BiDE were labeled with a Cy3-labeled $^{175}$Lu-Bn-DOTA, quickly diluted down to low concentrations, and then fluctuations in fluorescent intensity were measure over the course of 2 hours. Measurements were taken with a Zeiss LSM 880 confocal microscope. Normalized autocorrelations functions G(T) were then plotted to determine the diffusion times for each SADA-BiDE over time. All samples were compared against a monomeric anti-GD2 BiDE. P53-BiDE is depicted in black. P63-BiDE is depicted in dark gray. P73-BiDE is depicted in light gray.

FIG. 5A and FIG. 5B depict target binding affinity and tumor cell binding activity of exemplary SADA constructs. FIG. 5A depicts normalized SPR curves (Biacore T100) for P53-BiDE (solid black line), P63-BiDE (solid dark gray line) and P73-BiDE (solid light gray line). A corresponding IgG-BiDE (Cheal, S. M. et al. (2014) Mol Cancer Ther) (dotted line) and an anti-GD2 IgG control (dashed line). Each construct was run in a concentration series (400 nM-0 nM) over a GD2-coated CMS chip. The plotted curves were normalized to both start and end of the binding phases for comparison. FIG. 5B depicts a histogram overlay of FACS plots of three SADA-BiDE relative to an IgG-BiDE (Cheal, S. M. et al. (2014) Mol Cancer Ther) binding against GD2(+) luciferase-transfected IMR32 and M14 tumor cell lines. 1 µg of either (top to bottom) P53-BIDE, P63-BIDE, P73-BIDE, IgG-BiDE (Cheal, S. M. et al. (2014) Mol Cancer Ther) a control protein was incubated with 1M cells at 4° C. for 30 min. A Cy5-labeled $^{175}$Lu-Bn-DOTA was used to detect and quantify the amount of bound complex.

FIG. 6A to FIG. 6E depict pharmacokinetics of exemplary SADA-BiDE constructs in vivo. FIG. 6A depicts activity over time after P53-BiDE(noHIS) and Bn-DOTA administration. Each line represents one group, with three mice per group. Triangles denote a group that received P53-BiDE (noHIS) followed by clearing agent (CA) 72 hours later. Squares denote a group that received P53-BiDE(noHIS) without any clearing agent before $^{177}$Lu-Bn-DOTA administration. Circles denote a group that only received $^{177}$Lu-Bn-DOTA but not any SADA-BiDE. Dashed lines correspond to the measured blood activity, while solid lines correspond to the activity measured in the tumor. For The Bn-DOTA alone, no tumor activity was detected. FIG. 6B depicts blood activity of radiolabeled SADA-BiDE in tumor-free mice. Activity measurements were normalized to the initial measurement for each group. Each line represents one group, with 4-5 mice per group. (+) symbols denote P53-BiDE, (X) symbols denote P63-BiDE and circles denote P73-BiDE. FIG. 6C depicts blood activity in tumor bearing mice treated with either IgG-BiDE (Cheal, S. M. et al. (2014) Mol Cancer Ther) or SADA-BiDE and then injected with $^{177}$Lu-Bn-DOTA. Each line represents one group, with 3-5 mice per group. Circles denote a group that received IgG-BiDE (Cheal, S. M. et al. (2014) Mol Cancer Ther) followed by clearing agent 48 hrs later. Squares denote a group that received P53-BiDE. Diamonds denote a group that received P63-BiDE. Hexagons denote a group that received P73-BiDE. No SADA-BiDE treated mice received any clearing agent. A representative anti-tumor IgG and $^{177}$Lu-Bn-DOTA alone clearance curves were added as a reference. (+) symbols with a dotted line denote the $^{124}$I-labeled anti-GD2 IgG, and (x) symbols with a dotted line denote $^{177}$Lu-Bn-DOTA alone. FIG. 6D depicts a graph showing tumor activity measurements from mice which received $^{177}$Lu-Bn-DOTA either 24 (black) or 72 (gray) hours after P53-BiDE(noHIS) administration. Measurements were made using SPECT. FIG. 6E depicts a graph showing decay corrected activity at the site of a tumor over a 96 hour time period from mice treated with P53-BiDE. Measurements were made using SPECT.

FIG. 7A and FIG. 7B depict results of biodistribution experiments with exemplary SADA-BiDE conjugates. FIG. 7A depicts a bar graph showing tissue biodistribution from mice treated with SADA-BiDE or IgG-BiDE (Cheal, S. M. et al. (2014) Mol Cancer Ther). Black bars denote measured activity in tissues from mice treated with IgG-BiDE (Cheal, S. M. et al. (2014) Mol Cancer Ther) and clearing agent. Gray bars denote measured activity in tissues from mice treated with P53-BIDE, P63-BiDE, or P73-BiDE (dark to light gray, respectively). Four or five mice were used per group. FIG. 7B depicts a bar graph showing the target to non-target uptake ratio from the biodistribution experimental data shown in FIG. 7A. Each organ had the percent injected dose per gram (% ID/g) calculated and then was divided in reference to the tumor activity. Black bars denote measured activity in tissues from mice treated with IgG-BiDE (Cheal, S. M. et al. (2014) Mol Cancer Ther) and clearing agent. Gray bars denote measured activity in tissues from mice treated with either P53-BIDE, P63-BIDE, or P73-BIDE SADA-BiDEs (dark to light gray, respectively)

FIG. 8A and FIG. 8B depict tumor responses after treatment with a SADA-BiDE construct P53-BIDE(NOHIS) in vivo. FIG. 8A depicts a graph showing the change in tumor volume after administration of 1 (circles) or 4 (squares) doses of P53-BiDE. As a reference other mice were also treated with IgG-BiDE (Cheal, S. M. et al. (2014) Mol Cancer Ther) and clearing agent (triangles). FIG. 8B provides images of an exemplary mouse treated with a single dose of P53-BIDE(NOHIS) from the experimental data shown in FIG. 8A. Images are shown of the mouse on days 1, 8 and 15 with a box around the site of the tumor.

FIG. 10A and FIG. 10B depict experiments showing purity and stability of preparations of P53-Cytokine, P63-Cytokine and P73-Cytokine SADA-Cytokines. FIG. 10A depicts an HPLC chromatogram that shows the size and purity of each SADA-Cytokine. All graphs are overlaid and normalized to their peak intensity. The main peak shows over 98% purity for all three versions. The last peak (~25 min) denotes a non-specific peak from the storage buffer (sodium citrate). P53-Cytokine is shown with a dashed black line, P63-Cytokine is shown with a dark gray line and P73-Cytokine is shown with a light gray line. FIG. 10B depicts a summary of HPLC chromatograms of preparations of P53-Cytokine (circles), P63-Cytokine (triangles) and P73-Cytokine (diamonds) incubated at 37° C. for a 30 day period. Percentage of correctly sized protein (~16 min) is plotted over each time point for all three versions.

FIG. 11A to FIG. 11D depict in vitro activity of P53-Cytokine, P63-Cytokine and P73-Cytokine SADA-Cytokines. FIG. 11A depicts a graph showing SADA-Cytokine dependent proliferation. The dose dependent proliferative response of TIB214 cells to each of P53-Cytokine (circles), P63-Cytokine (squares) and P73-Cytokine (triangles) is shown. FIG. 11B depicts a graph showing NK Cell cytotoxicity improvement from SADA-Cytokine stimulation. Bar graph summarizes peak cytotoxicity improvement from exposure of human NK cells to each SADA-Cytokine for 3 days. Cytotoxicity was assessed over a 4 hr period using a GD2(+) cell line that is sensitive to NK mediated killing and an anti-GD2 IgG (Ahmed, M. et al. (2015) *Oncolmmunology*). Control (black bar), P53-Cytokine (medium gray bar), P63-Cytokine (dark gray bar) and P73-Cytokine (light gray bar). FIG. 11C depicts a graph showing T Cell cytotoxicity improvement from SADA-Cytokine stimulation. Bar graph summarizes peak cytotoxicity improvement from exposure of human T cells to each SADA-Cytokine for 3 days. Cytotoxicity was assessed over a 4 hr period using a GD2(+) cell line and a T-cell engaging anti-GD2 IgG-scFv bispecific (Xu, H. et al. (2015) *Cancer immunology research*). Control (black bar), P53-Cytokine (medium gray bar), P63-Cytokine (dark gray bar) and P73-Cytokine (light gray bar). FIG. 11D depicts a graph showing tumor growth in DKO mice with GD2(+) tumors implanted subcutaneously. Each mouse was treated with PBMCs (gray triangles) and a low dose of an anti-tumor IgG-scFv (Xu, H. et al. (2015) *Cancer immunology research*) and additional cytokines. Untreated tumors grew out very quickly (black lines). Tumors treated with the IgG-scFv and an Fc-Cytokine (Liu et al. 2016 JBC, http://www.jbc.org/content/291/46/23859) with a mutation to improve binding (light gray line) shrunk tumors slower than mice treated with the IgG-scFv and SADA-Cytokine (dark gray line).

FIG. 12A depicts ribbon structures of SADA domains derived from human p53, p63, p73, hnRNPC, SNAP-23, Stefin B, KCNQ4, and CBFA2T1 proteins. FIG. 12B depicts ribbon structures of potential SADA domains derived from human SYCP3, UGP2 and TRIM33 proteins.

FIG. 13A shows SEC-HPLC chromatograms of two different variants of the anti-HER2 P53-BiDE (anti-HER2 scFv in the HL and LH orientations in upper and lower graphs, respectively). This exemplary anti-HER2 P53-BiDE is exceptionally pure after single-step affinity purification and retains a size of ~200 kDa (~16 min). FIG. 13B depicts a FACS analysis of an exemplary anti-HER2 P53-BiDE construct on a HER2(+) cell line HCC1954 (breast cancer) using a fluorescently labeled $^{175}$Lu-Bn-DOTA conjugate for detection. HER2/BnDOTA binding capacity of these anti-HER2 BiDEs (Black solid and dashed, filled) is similar to the comparable to the IgG-BiDE (grey dashed, filled).

FIG. 14A to FIG. 14C depict in vitro analysis of an exemplary HNRNPC—BiDE construct. FIG. 14A depicts an SEC-HPLC chromatogram and stability of an exemplary HNRNPC-BiDE after single-step affinity purification. As shown, an exemplary HNRNPC —BiDE construct forms a stable tetrameric multimer at the expected size of ~200 kDa (~16 min, upper graph) and can maintain its purity after five repeated freeze and thaw cycles (~16 min, lower graph). FIG. 14B shows FACS analysis of an exemplary HNRNPC—BiDE construct with a GD2(+) cell line M14-Luc (Melanoma) using a fluorescently labeled $^{175}$Lu-Bn-DOTA conjugate for detection. The GD2/BnDOTA binding capacity of the HNRNPC-BiDE (Solid Black, filled) is compared against an IgG-BiDE (Cheal, S. M. et al. (2014) *Mol Cancer Ther*) (Dashed black, filled) a P63-BiDE (dotted grey, filled) or an isotype control (dashed grey, empty). FIG. 14C depicts normalized binding kinetics of an exemplary HNRNPC-BiDE (dotted black) against the tumor antigen GD2 using SPR, compared with the P53-(solid grey), P63-(dashed grey), or IgG-BiDEs (dashed black). Each construct was run as a concentration series across a streptavidin chip coated with biotin-GD2. The highest concentrations of each were then plotted together on a normalized Y-axis to better show the differences in koff. Data was fitted using a two-state reaction model.

DEFINITIONS

Figure 2:
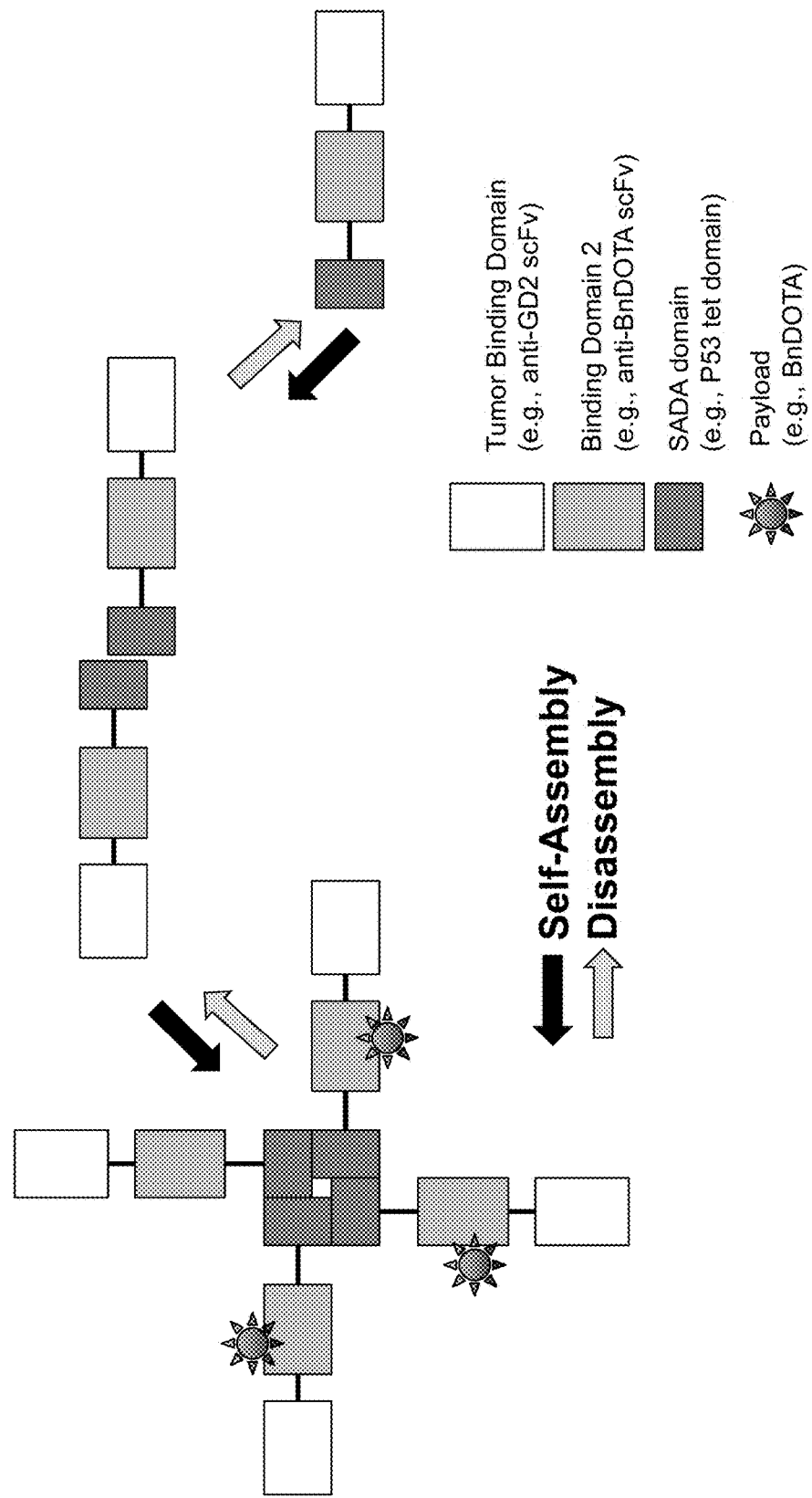
FIG. 2 depicts a schematic of an exemplary conjugate, SADA-Bispecific DOTA-engaging (BiDE), made up of a SADA domain and two binding domains, that may be useful for pre-targeted radioimmunotherapy (PRIT). The diagram illustrates self-assembly and disassembly of a SADA-BiDE into three states: Tetramer (full), Dimer (half), and Monomer (quarter). Black Stars represent bound or unbound payload (i.e. Bn-DOTA). Dark gray boxes represent a SADA domain (shown as the most inner/proximal domain when assembled) (i.e. a human p53-tetramerization domain for P53-BIDE; a human p63 tetramerization domain P63-BiDE and a p73 tetramerization domain for P73-BiDE). Light gray boxes represent first binding domain that binds a payload (i.e., a Bn-DOTA binding domain, such as huC825-scFv). White boxes represent a second binding domain (most distal domain when assembled) that binds a cellular component (e.g., the cell surface tumor cell marker GD2, such as hu3F8-scFv). Black arrows indicate self-assembly of the construct and gray arrows indicate disassembly of the construct.

The scope of present invention is defined by the claims appended hereto and is not limited by particular embodiments described herein; those skilled in the art, reading the present disclosure, will be aware of various modifications that may be equivalent to such described embodiments, or otherwise within the scope of the claims.

In general, terminology used herein is in accordance with its understood meaning in the art, unless clearly indicated otherwise. Explicit definitions of certain terms are provided below; meanings of these and other terms in particular instances throughout this specification will be clear to those skilled in the art from context.

References cited within this specification, or relevant portions thereof, are incorporated herein by reference.

In order that the present invention may be more readily understood, certain terms are first defined below. Additional definitions for the following terms and other terms are set forth throughout the specification.

"Affinity": As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

"Affinity matured" (or "affinity matured antibody"), as used herein, refers to an antibody with one or more alterations in one or more CDRs thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al. (1992) *BioTechnology* 10:779-783 describes affinity maturation by $V_H$ and $V_L$ domain shuffling. Random mutagenesis of CDR and/or framework residues is described by: Barbas et al. (1994) *Proc. Nat. Acad. Sci. U.S.A* 91:3809-3813; Schier et al. 1995, *Gene* 169: 147-155; Yelton et al. (1995) *J Immunol.* 155: 1994-2004; Jackson et al. (1995) *J Immunol.* 154(7): 3310-9; and Hawkins et al. (1992) *J. Mol. Biol.* 226:889-896.

"Amelioration", as used herein, refers to the prevention, reduction or palliation of a state, or improvement of the state of a subject. Amelioration includes, but does not require complete recovery or complete prevention of a disease, disorder or condition (e.g., radiation injury).

"Animal", as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by DV. In some embodiments, an animal may be a transgenic animal, genetically engineered animal, and/or a clone.

"Antibody", as used herein, has its art understood meaning and refers to an immunoglobulin (Ig) that binds specifically to a particular antigen. As is known by those of ordinary skill in the art, antibodies produced in nature are typically comprised of four polypeptide chains, two heavy (H) chains and two light (L) chains. Each heavy and light chain is comprised of a variable region (abbreviated herein as HCVR or $V_H$ and LCVR or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, $C_L$. The $V_H$ and $V_L$ regions further contain regions of hypervariability, termed complementarity determining regions (CDRs), interspersed with regions that are more conserved, which are termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgM, IgD, IgG, IgA and IgE), class (e.g., IgG1, IgG2, IgG3, IgG4, IgA1 and IgA2) or subclass.

Antibody agent: As used herein, the term "antibody agent" refers to an agent that specifically binds to a particular antigen. In some embodiments, the term encompasses any polypeptide with immunoglobulin structural elements sufficient to confer specific binding. In various embodiments, suitable antibody agents may include, but are not limited to, monoclonal antibodies, polyclonal antibodies, humanized antibodies, primatized antibodies, chimeric antibodies, human antibodies, bi-specific or multi-specific antibodies, single domain antibodies (e.g., shark single domain antibodies (e.g., IgNAR or fragments thereof)), conjugated antibodies (i.e., antibodies conjugated or fused to other proteins, radiolabels, cytotoxins), Small Modular Immuno-Pharmaceuticals ("SMIPsTM"), single chain antibodies, cameloid antibodies, antibody fragments, etc. In some embodiments, the term can refer to a stapled peptide. In some embodiments, the term can refer to an antibody-like binding peptidomimetic. In some embodiments, the term can refer to an antibody-like binding scaffold protein. In some embodiments, the term can refer to monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain, which is homologous or largely homologous to an immunoglobulin-binding domain. In some embodiments, an antibody agent is or comprises a polypeptide that includes all CDRs found in a particular reference antibody chain or chains (e.g., heavy chain and/or light chain).

"Antibody component", as used herein, refers to a polypeptide element (that may be a complete polypeptide, or a portion of a larger polypeptide, such as for example a fusion polypeptide as described herein) that specifically binds to an epitope or antigen and includes one or more immunoglobulin structural features. In general, an antibody component is any polypeptide whose amino acid sequence includes elements characteristic of an antibody-binding region (e.g., an antibody light chain or variable region or one or more complementarity determining regions ("CDRs") thereof, or an antibody heavy chain or variable region or one or more CDRs thereof, optionally in presence of one or more framework regions). In some embodiments, an antibody component is or comprises a full-length antibody. In some embodiments, an antibody component is less than full-length but includes at least one binding site (comprising at least one, and preferably at least two sequences with structure of known antibody "variable regions"). In some embodiments, the term "antibody component" encompasses any protein having a binding domain, which is homologous or largely homologous to an immunoglobulin-binding domain. In particular embodiments, an included "antibody component" encompasses polypeptides having a binding domain that shows at least 99% identity with an immunoglobulin binding domain. In some embodiments, an included "antibody component" is any polypeptide having a binding domain that shows at least 70%, 75%, 80%, 85%, 90%, 95% or 98% identity with an immunoglobulin binding domain, for example a reference immunoglobulin binding domain. An included "antibody component" may have an amino acid sequence identical to that of an antibody (or a portion thereof, e.g., an antigen-binding portion thereof) that is found in a natural source. An antibody component may be monospecific, bi-specific, or multi-specific. An antibody component may include structural elements characteristic of any immunoglobulin class, including any of the human classes: IgG, IgM, IgA, IgD, and IgE. It has been shown that the antigen-binding function of an antibody can be performed by fragments of a full-length antibody. Such antibody embodiments may also be bispecific, dual-specific, or multi-specific formats specifically binding to two or more different antigens. Examples of binding fragments encompassed within the term "antigen-binding portion" of an antibody include (i) a Fab fragment, a monovalent fragment consisting of the $V_H$, $V_L$, $C_H1$ and CL domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al. (1989) Nature 341:544-546), which comprises a single variable domain; and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). In some embodiments, an "antibody component", as described herein, is or comprises such a single chain antibody. In some embodiments, an "antibody component" is or comprises a diabody. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., (1993) *Proc. Natl. Acad. Sci. USA* 90:6444-6448; Poljak, R. J., (1994) *Structure* 2(12):1121-1123). Such antibody binding portions are known in the art (Kontermann and Dubel eds., Antibody Engineering (2001) Springer-Verlag. New York. 790 pp. (ISBN 3-540-41354-5). In some embodiments, an antibody component is or comprises a single chain "linear antibody" comprising a pair of tandem Fv segments ($V_H$-$C_H1$-$V_H$H-$C_H1$) which, together with complementary light chain polypeptides, form a pair of antigen binding regions (Zapata et al., 1995, Protein Eng. 8(10): 1057-1062; and U.S. Pat. No. 5,641,870). In some embodiments, an antibody component may have structural elements characteristic of chimeric or humanized antibodies. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some embodiments, an antibody component may have structural elements characteristic of a human antibody.

"Binding domain", as used herein, refers to a moiety or entity that specifically binds to a target moiety or entity. Typically, the interaction between a binding domain and its target is non-covalent. In some embodiments, a binding domain may be or comprise a moiety or entity of any chemical class including, for example, a carbohydrate, a lipid, a nucleic acid, a metal, a polypeptide, a small molecule. In some embodiments, a binding domain may be or comprise a polypeptide (or complex thereof). In some embodiments, a binding domain may be or comprise a target-binding portion of an antibody agent, a cytokine, a ligand (e.g., a receptor ligand), a receptor, a toxin, etc. In some embodiments, a binding domain may be or comprise an aptamer. In some embodiments, a binding domain may be or comprise a peptide nucleic acid (PNA).

"Biological activity", as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

"Bispecific binding agent", as used herein, refers a binding agent capable of binding to two antigens, which can be on the same molecule or on different molecules. Bispecific binding agents as described herein are, in some embodiments, engineered to have the two antigen binding sites, and are typically not naturally occurring proteins. Bispecific binding agents as described herein refer to binding agents capable of binding two or more related or unrelated targets. Bispecific binding agents as described herein are, in some embodiments, capable of binding simultaneously to two targets that are of different structure, e.g., two different antigens, two different epitopes on the same antigen, or a hapten and/or an antigen or epitope. In many embodiments, bispecific binding agents of the present invention are proteins engineered to have characteristics of bispecific binding agents as described herein.

"Bispecific antibody", as used herein, refers to a bispecific binding agent in which at least one, and typically both, of the binding moieties is or comprises an antibody component. A variety of different bi-specific antibody structures are known in the art. In some embodiments, each binding moiety in a bispecific antibody that is or comprises an antibody component includes $V_H$ and/or $V_L$ regions; in some such embodiments, the VH and/or $V_L$ regions are those found in a particular monoclonal antibody. In some embodiments, where the bispecific antibody contains two antibody component-binding moieties, each includes $V_H$ and/or $V_L$ regions from different monoclonal antibodies. In some embodiments, where the bispecific antibody contains two antibody component binding moieties, wherein one of the two antibody component binding moieties includes an immunoglobulin molecule having $V_H$ and/or $V_L$ regions that contain CDRs from a first monoclonal antibody, and one of the two antibody component binding moieties includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

"Bispecific binding agent", as used herein, refers to a polypeptide agent with two discrete binding moieties, each of which binds with a distinct target. In some embodiments, a bispecific binding agent is or comprises a single polypeptide; in some embodiments, a bispecific binding agent is or comprises a plurality of peptides which, in some such embodiments may be covalently associated with one another, for example by cross-linking. In some embodiments, the two binding moieties of a bispecific binding agent recognize different sites (e.g., epitopes) the same target (e.g., antigen); in some embodiments, they recognize different targets. In some embodiments, a bispecific binding agent is capable of binding simultaneously to two targets that are of different structure.

"Carrier", as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

"CDR", as used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

"CDR grafted antibody", as used herein, refers to an antibody whose amino acid sequence comprises heavy and light chain variable region sequences from one species but in which the sequences of one or more of the CDR regions of $V_H$ and/or $V_L$ are replaced with CDR sequences of another species, such as antibodies having murine $V_H$ and $V_L$ regions in which one or more of the murine CDRs (e.g., CDR3) has been replaced with human CDR sequences. Likewise, a "CDR grafted antibody" may also refer to antibodies having human $V_H$ and $V_L$ regions in which one or more of the human CDRs (e.g., CDR3) has been replaced with mouse CDR sequences.

"Combination therapy": As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

"Comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Corresponding to", as used herein designates the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

"Detection Agents", as described herein, refer to moieties or agents that are amenable to detection, for example, due to their specific structural and/or chemical characteristics, and/or their functional properties. Non-limiting examples of such agents include enzymes, radiolabel s, haptens, fluorescent labels, phosphorescent molecules, chemiluminescent molecules, chromophores, luminescent molecules, photoaffinity molecules, colored particles or ligands, such as biotin. Many detection agents are known in the art, as are systems for their attachment to antibodies (see, for e.g., U.S. Pat. Nos. 5,021,236; 4,938,948; and 4,472,509, each incorporated herein by reference). Particular examples may include paramagnetic ions, radioactive isotopes, fluorochromes, NMR-detectable substances, X-ray imaging agents, among others. In some embodiments of the present invention, the conjugated detection agent is a diagnostic or imaging agent.

"Dosage form" and "unit dosage form", as used herein, the term "dosage form" refers to physically discrete unit of a therapeutic agent for a subject (e.g., a human patient) to be treated. Each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage administered to any particular patient will be selected by a medical professional (e.g., a medical doctor) within the scope of sound medical judgment.

"Dosing regimen" (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously (e.g., by infusion) over a predetermined period. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

"Effector function" as used herein refers a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP), and complement-mediated cytotoxicity (CMC). In some embodiments, an effector function is one that operates after the binding of an antigen, one that operates independent of antigen binding, or both.

"Effector cell" as used herein refers to a cell of the immune system that expresses one or more Fc receptors and mediates one or more effector functions. In some embodiments, effector cells may include, but may not be limited to, one or more of monocytes, macrophages, neutrophils, dendritic cells, eosinophils, mast cells, platelets, large granular lymphocytes, Langerhans' cells, natural killer (NK) cells, T-lymphocytes, B-lymphocytes and may be from any organism including but not limited to humans, mice, rats, rabbits, and monkeys.

"Engineered" as used herein refers, in general, to the aspect of having been manipulated by the hand of man. For example, in some embodiments, a polynucleotide may be considered to be "engineered" when two or more sequences, that are not linked together in that order in nature, are manipulated by the hand of man to be directly linked to one another in the engineered polynucleotide. In some particular such embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by those in the art, progeny of an engineered polynucleotide or cell are typically still referred to as "engineered" even though the actual manipulation was performed on a prior entity. Furthermore, as will be appreciated by those skilled in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc. Alternatively or additionally, in some embodiments, "engineering" may involve use of in vitro chemical synthesis methodologies and/or recombinant nucleic acid technologies such as, for example, nucleic acid amplification (e.g., via the polymerase chain reaction), hybridization, mutation, transformation, transfection, etc. As will be appreciated by those skilled in the art, a variety of established such techniques (e.g., for recombinant DNA, oligonucleotide synthesis, and tissue culture and transformation [e.g., electroporation, lipofection, etc.]) are well known in the art and described in various general and more specific references that are cited and/or discussed throughout the present specification. See, e.g., Sambrook et al., Molecular Cloning: A Laboratory Manual (2nd ed., Cold Spring Harbor Laboratory Press, Cold Spring Harbor, N.Y. [1989]), which is incorporated herein by reference for any purpose.

"Epitope", as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

"Excipient", as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

"Fc ligand" as used herein refers to a molecule, preferably a polypeptide, from any organism that binds to the Fc region of an antibody to form an Fc-ligand complex. Fc ligands include but are not limited to FcγRIIA (CD32A), FcγRIIB (CD32B), FcγRIIIA (CD16A), FcγRIIIB (CD16B), FcγRI (CD64), FcεRII (CD23), FcRn, C1q, C3, staphylococcal protein A, streptococcal protein G, and viral FcγR. Fc ligands may include undiscovered molecules that bind Fc.

"Fluorescent Label", as is understood in the art, is a moiety or entity that has fluorescent character and, in some embodiments, may be detectable based on such fluorescence. In some embodiments, a fluorescent label may be or may comprise one or more of Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAN/IRA, TET, Tetramethylrhodamine, and/or Texas Red, among others.

"Framework" or "framework region", as used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

"Host cell", as used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO Kl, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Co10205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

"Human antibody", as used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

"Humanized", as is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

"Improve," "increase" or "reduce," as used herein or grammatical equivalents thereof, indicate values that are relative to a baseline or control measurement. In some embodiments, relative to a baseline or control may refer to a measurement in the same individual prior to initiation of a treatment described herein, or a measurement in a control individual (or multiple control individuals) in the absence of the treatment described herein. A "control individual" is an individual afflicted with the same form of disease or injury as the individual being treated. In some embodiments, values that are relative to a baseline or control may refer to may refer to a measurement in an experiment or animal or individual undergoing analogous treatment with a control or reference agent (e.g., with a therapeutic lacking a SADA domain and/or with a therapeutic with an alternative domain such as an Ig domain, or with no therapeutic agent).

"In vitro", as used herein refers to events that occur in an artificial environment, e.g., in a test tube or reaction vessel, in cell culture, etc., rather than within a multi-cellular organism.

"In vivo", as used herein refers to events that occur within a multi-cellular organism, such as a human and a non-human animal. In the context of cell-based systems, the term may be used to refer to events that occur within a living cell (as opposed to, for example, in vitro systems).

"Isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated"

polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

"$K_D$", as used herein, refers to the dissociation constant of a binding agent (e.g., a SADA domain, an antibody or binding component thereof) from a complex with its partner (e.g., a corresponding SADA domain or an epitope to which the antibody or binding component thereof binds).

"$k_{off}$", as used herein, refers to the off rate constant for dissociation of a binding agent (e.g., a SADA domain, an antibody or binding component thereof) from a complex with its partner (e.g., a corresponding SADA domain or an epitope to which the antibody or binding component thereof binds).

"$k_{on}$", as used herein, refers to the on rate constant for association of a binding agent (e.g., a SADA domain, an antibody or binding component thereof) with its partner (e.g., a corresponding SADA domain or an epitope to which the antibody or binding component thereof binds).

"Linker", as used herein, typically refers to a portion of a molecule or entity that connects two or more different regions of interest (e.g., particular structural and/or functional domains or moieties of interest). In some embodiments, a linker does not participate significantly in the relevant function of interest (e.g., so that presence or absence of the linker, in association with the relevant domain or moiety of interest does not materially alter the relevant function of the domain or moiety). In some embodiments, a linker in characterized by lack of defined or rigid structure. In some embodiments, particularly when one or more domains or moieties of interest is/are comprised of a polypeptide, a linker is or comprises a polypeptide. In some particular embodiments, a polypeptide (e.g., an engineered polypeptide) as described herein may have general structure S1-L-S2, wherein S1 and S2 are the moieties or domains of interest. In some embodiments, one or both of Si and S2 may be or comprise a binding element (e.g., an antibody component) as described herein. In some embodiments, a polypeptide linker may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids long. In some embodiments, a polypeptide linker may have an amino acid sequence that is or comprises a sequence as described in Holliger, P., et al. (1993) *Proc. Natl. Acad. Sci. USA* 90:6444-6448 or Poljak, R. J., et al. (1994) *Structure* 2: 1121-1123. In some embodiments, a polypeptide linker may have an amino acid sequence that is or comprises GGGGSGGGGSGGGGS (i.e., [G45]3) SEQ ID NO: 99 or GGGGSGGGGSGGGGSGGGGSGGGGSGGGGS (i.e., [G4S]6) SEQ ID NO: 100.

"Multimer", as used herein, refers to a complex of monomeric units. The term "multimer" as used herein excludes dimers, but includes trimers, and multimers of four monomers (tetramers), or of more than four monomers (pentamers, hexamers, septamers, octamers, nonamers, decamers, etc.). A domain that promotes association of monomeric units to form multimeric complexes is referred to herein as a "multimerization domain."

"Multivalent binding agent", as used herein, refers to a binding agent capable of binding to two or more targets, which can be on the same molecule or on different molecules. Multivalent binding agents as described herein are, in some embodiments, engineered to have the three or more target binding sites. In some embodiments, a multivalent binding agent is not a naturally occurring polypeptides. Multivalent binding agents as described herein refer to binding agents capable of binding two or more related or unrelated targets. In some embodiments, multivalent binding agents may be composed of multiple copies of a single antibody component or multiple copies of different antibody components. Such binding agents are capable of binding to two or more antigens and are tetravalent or multivalent binding agents. In some embodiments, multivalent binding agents may additionally or alternatively comprise a therapeutic agent, such as, for example, an immunomodulator, toxin or an RNase. Multivalent binding agents as described herein are, in some embodiments, capable of binding simultaneously to at least two targets that are of different structure, e.g., two different antigens, two different epitopes on the same antigen, a hapten, a small molecule, a cytokine, a receptor, or any combination thereof. In some embodiments, multivalent binding agents of the present disclosure are engineered polypeptides and/or fusion proteins. In some embodiments, multivalent binding agents of the present invention may include an antibody agent. In some embodiments, a multivalent binding agent includes an antibody agent that comprises a heavy chain variable domain and a light chain variable domain, which include six CDRs involved in antigen binding per antigen binding site.

"Nucleic acid", as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof).

In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

"Operably linked", as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

"Paramagnetic Ion", as is understood in the art, refers to an ion with paramagnetic character. In some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

"Payload", as used herein, refers to a moiety or entity that is delivered to a site of interest (e.g., to a cell, tissue, tumor, or organism) by association with another entity. In some embodiments, a payload is or comprises a detection agent. In some embodiments, a payload entity is or comprises a therapeutic agent. In some embodiments, a payload entity is or comprises a catalytic agent. Those of ordinary skill in the art will appreciate that a payload entity may be of any chemical class. For example, in some embodiments, a payload entity may be or comprise a carbohydrate, an isotope, a lipid, a nucleic acid, a metal, a nanoparticle (e.g., a ceramic or polymer nanoparticle), polypeptide, a small molecule, etc. To give but a few examples, in some embodiments, a therapeutic agent payload may be or comprise a toxin (e.g., a toxic peptide, small molecule, or isotope [e.g., radioisotope]); in some embodiments, a detection agent payload may be or comprise a fluorescent entity or agent, a radioactive entity or agent, an agent or entity detectable by binding (e.g., a tag, a hapten, a ligand, etc.), a catalytic agent, etc.

"Physiological conditions", as used herein, has its art-understood meaning referencing conditions under which cells or organisms live and/or reproduce. In some embodiments, the term refers to conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20° C. to 40° C., atmospheric pressure of 1, pH of 6 to 8, glucose concentration of 1 mM to 20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

"Polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modification of or covalent linkage to one or more amino acid side chains, the polypeptide's N-terminus, the polypeptide's C-terminus, or any combination thereof. In some embodiments, such pendant groups or modifications may be selected from acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30%, and is often greater than about 40%, 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least three to four and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice-versa, and/or fragments may be present in a different order in the polypeptide of interest than in the parent), so that the polypeptide of interest is a derivative of its parent polypeptide "Prevent" or "prevention", as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

"Pure": As used herein, an agent or entity is "pure" if it is substantially free of other components. For example, a preparation that contains more than about 80% of a particular agent or entity is typically considered to be a pure preparation. In some embodiments, an agent (or entity, therapeutic, etc.) is at least 85%, at least 90%, at least 91%, at least 92%, at least 93%, at least 94%, at least 95%, at least 96%, at least 97%, at least 98%, or at least 99% pure.

"Radioactive Isotope": The term "radioactive isotope" as used herein has its art-understood meaning referring to an isotope that undergoes radioactive decay. In some embodiments, a radioactive isotope may be or comprise one or more of actinium-225, astatine-211, bismuth-212, carbon-14, chromium-51, chlorine-36, cobalt-57, cobalt-58, copper-67, Europium-152, gallium-67, hydrogen-3, iodine-123, iodine-124, iodine-125, iodine-131, indium-111, iron-59, lead-212, lutetium-177, phosphorus-32, radium-223, radium-224, rhenium-186, rhenium-188, selenium-75, sulphur-35, technicium-99m, thorium-227, yttrium-90, and zirconium-89.

"Recombinant", as used herein, is intended to refer to polypeptides (e.g., protein therapeutics with a SADA domain) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R. (1997) *TIB Tech.* 15:62-70; Azzazy H., and Highsmith W. E. (2002) *Clin. Biochem.* 35:425-445; Gavilondo, J. V. and Larrick, J. W. (2002) *BioTechniques* 29: 128-145; Hoogenboom H., and Chames, P. (2000) *Immunology Today* 21:371-378), antibodies isolated from an animal (e.g., a mouse) that is transgenic for human immunoglobulin genes (see e.g., Taylor, L. D. et al. (1992) *Nucl. Acids Res.* 20:6287-6295; Little M. et al. (2000) *Immunology Today* 21:364-370; Kellermann S-A., and Green L. L. (2002) *Current Opinion in Biotechnology* 13:593-597; Murphy, A. J. et al. (2014) *Proc. Natl. Acad. Sci. U.S.A.* 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant antibody polypeptide is comprised of sequences found in the germline of a source organism of interest (e.g., human, mouse, etc.). In some embodiments, a recombinant antibody has an amino acid sequence that resulted from mutagenesis (e.g., in vitro or in vivo, for example in a transgenic animal), so that the amino acid sequences of the $V_H$ and $V_L$ regions of the recombinant antibodies are sequences that, while originating from and related to germline $V_H$ and $V_L$ sequences, may not naturally exist within the germline antibody repertoire in vivo.

"Recovering", as used herein, refers to the process of rendering an agent or entity substantially free of other previously-associated components, for example by isolation, e.g., using purification techniques known in the art. In some embodiments, an agent or entity is recovered from a natural source and/or a source comprising cells.

"Reference", as used herein describes a standard, control, or other appropriate reference against which a comparison is made as described herein. For example, in some embodiments, a reference is a standard or control agent, animal, individual, population, sample, sequence, series of steps, set of conditions, or value against which an agent, animal, individual, population, sample, sequence, series of steps, set of conditions, or value of interest is compared. In some embodiments, a reference is tested and/or determined substantially simultaneously with the testing or determination of interest. In some embodiments, a reference is a historical reference, optionally embodied in a tangible medium. Typically, as would be understood by those skilled in the art, a reference is determined or characterized under conditions comparable to those utilized in the assessment of interest.

"Risk", as will be understood from context, "risk" of a disease, disorder, and/or condition comprises likelihood that a particular individual will develop a disease, disorder, and/or condition (e.g., a radiation injury). In some embodiments, risk is expressed as a percentage. In some embodiments, risk is from 0, 1, 2, 3, 4, 5, 6, 7, 8, 9, 10, 20, 30, 40, 50, 60, 70, 80, 90 and up to 100%. In some embodiments, risk is expressed as a risk relative to a risk associated with a reference sample or group of reference samples. In some embodiments, a reference sample or group of reference samples have a known risk of a disease, disorder, condition and/or event (e.g., a radiation injury). In some embodiments a reference sample or group of reference samples are from individuals comparable to a particular individual. In some embodiments, relative risk is 0,1, 2, 3, 4, 5, 6, 7, 8, 9, 10 or more.

"Specific binding", as used herein, refers to a binding agent's ability to discriminate between possible partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

"Subject", as used herein, means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantial sequence homology", as used herein refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | Nonpolar | Neutral | 1.8 |
| Arginine | Arg | R | Polar | Positive | -4.5 |
| Asparagine | Asn | N | Polar | Neutral | -3.5 |
| Aspartic acid | Asp | D | Polar | Negative | -3.5 |
| Cysteine | Cys | C | Nonpolar | Neutral | 2.5 |
| Glutamic acid | Glu | E | Polar | Negative | -3.5 |
| Glutamine | Gln | Q | Polar | Neutral | -3.5 |
| Glycine | Gly | G | Nonpolar | Neutral | -0.4 |
| Histidine | His | H | Polar | Positive | -3.2 |

TABLE 1-continued

| Isoleucine | Ile | I | Nonpolar | Neutral | 4.5 |
| Leucine | Leu | L | Nonpolar | Neutral | 3.8 |
| Lysine | Lys | K | Polar | Positive | -3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | -1.6 |
| Serine | Ser | S | Polar | Neutral | -0.8 |
| Threonine | Thr | T | Polar | Neutral | -0.7 |
| Tryptophan | Trp | W | Nonpolar | Neutral | -0.9 |
| Tyrosine | Tyr | Y | Polar | Neutral | -1.3 |
| Valine | Val | V | Nonpolar | Neutral | 4.2 |

TABLE 2

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, *J. Mol. Biol.,* 215(3): 403-410; Altschul et al., 1996, *Methods in Enzymology* 266:460-80; Altschul et al., 1997, *Nucleic Acids Res.* 25:3389-3402; Baxevanis et al., 1998, *Bioinformatics: A Practical Guide to the Analysis of Genes and Proteins,* Wiley; and Misener et al., (eds.), *Bioinformatics Methods and Protocols (Methods in Molecular Biology,* Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

"Substantial identity", as used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., (1990) *J. Mol. Biol.,* 215(3): 403-410;

Altschul et al., (1996) *Methods in Enzymology* 266:460-80; Altschul et al., (1997) *Nucleic Acids Res.* 25:3389-3402; Baxevanis et al., (1998) *Bioinformatics: A Practical Guide to the Analysis of Genes and Proteins*, Wiley; and Misener et al., (eds.), Bioinformatics Methods and Protocols (*Methods in Molecular Biology*, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of a CDR, reference to "substantial identity" typically refers to a CDR having an amino acid sequence at least 80%, preferably at least 85%, at least 90%, at least 95%, at least 98% or at least 99% identical to that of a reference CDR.

"Surface plasmon resonance", as used herein, refers to an optical phenomenon that allows for the analysis of specific binding interactions in real-time, for example through detection of alterations in protein concentrations within a biosensor matrix, such as by using a BlAcore system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al., (1991) *Biotechniques* 11:620-627; Johnsson, B., et al., (1995) *J. Mol. Recognit.* 8:125-131; and Johnnson, B., et al., (1991) *Anal. Biochem.* 198:268-277.

"Therapeutically effective amount", as used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

"Transformation", as used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

"Vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

DETAILED DESCRIPTION OF CERTAIN EMBODIMENTS

One of the biggest hurdles in designing effective injectable therapeutics is balancing the benefits of extending the pharmacokinetic AUC (area under the curve of a drug over time) of the therapeutic with the increased risk of off-target toxicities as it gets slowly cleared from the system. (Matthay, K. K. et al. (2007) *J Clin Oncol* 25, 1054-1060). Blood and marrow toxicities are among the most common toxicities, but these may be reversible. In contrast, extramedullary toxicities, such as renal and hepatic toxicities, can be slow to recover and potentially serious and/or lethal to a subject. If a therapeutic is too small (<70 kDa) and filtered through the renal glomeruli, either larger doses or extended dosing regimens are necessary to overcome the short serum half-life, which is associated with the accompanying shortcomings of excessive cost, logistics, and increased risk of organ toxicity. Chemotherapeutic drugs, such as cisplatin (~300 Da) or microtubule poisons, are examples where extramedullary toxicities (renal) encountered during dose escalation is prohibitive. (Pinzani, V. et al. (1994) *Cancer Chemoth Pharm* 35, 1-9). Others chemotherapeutics, such as cyclophosphamide, where extramedullary toxicity is reduced but not absent, prolonged exposure will cause severe myelosuppression, myelodysplasia or even leukemia. For a small therapeutic protein, even one that is target-specific and extremely potent such as blinatumomab (CD19xCD3 bispecific antibody, ~50 kDa), quantitative delivery into the tumor is suboptimal, even with continuous infusion. (Topp, M. S. et al. (2014) *J Clin Oncol*; Topp, M. S. et al. (2015) *Lancet Oncol* 16, 57-66). On the other hand, when a therapeutic is too large (e.g. IgM, >1000 kDa), it may take many days to clear from the blood compartment, with difficulty penetrating tumor tissues or filtering through the kidney. For therapeutics in between this range (e.g., IgG, ~150 kDa), metabolism occurs through the retinculoendothelial system or liver and half-lives range from 1-4 weeks, where they recirculate in the blood/marrow, typically achieving a therapeutic index (ratio of AUC of tumor to AUC of blood/marrow) of <5:1. Such a low ratio is a setup for myelotoxicity, lymphotoxicity and major organ toxicities. An alternative approach is compartmental therapies, where the therapeutic is not given intravenously, but instead directly into the disease compartment (e.g., CSF or peritoneal cavity) to maximize drug level and efficacy. Parham, P. (2005) *Nat Rev Immunol* 5, 201-214; Kramer, K. et al. (2008) in ISPNO 2008; Kramer, K. et al. (2010) *J Neuro-Oncol* 97, 409-418). While this drug delivery strategy can be highly tumor-selective, its benefit is limited to those with localized disease in easily accessible body compartments. For human cancers where 90% of patients die from metastatic disease (Weigelt, B. et al. (2005) *Nat Rev Cancer* 5, 591-602) compartmental therapy is generally palliative but not curative.

Many groups are now focusing on pretargeted therapies, where targeting and payload steps are separated into two steps. Various pretargeting (multistep) platforms have been successfully built to improve the therapeutic index, in some cases 10-100 fold. (Pagel, J. M. et al. (2003) *Blood* 101, 2340-2348; Carr, W. H. et al. (2005) *J Immunol* 175, 5222-5229; Thomas, R. et al. (2008) *J Immunol* 180, 6743-6750; Cheal, S. M. et al. (2014) *Mol Cancer Ther* 13, 1803-1812; Cheung, N. K. et al. (2004) *J Nucl Med* 45, 867-877). But in order not to delay the critical last payload step, the excess unbound antibody from the first step must be removed from the circulation, necessitating a clearing agent, and therefore creating a three-step procedure (FIG. 1A): 1) pretargeting antibody, 2) clearing agent, and 3) payload. Whereas a two-step approach (FIG. 1b) in drug delivery is already laborious; a multistep (≥3) approach increases complexity substantially, a setup for reducing compliance. An equally important consideration is the immunogenicity of these antibody constructs (e.g., streptavidin), which prevents repeat dosing in patients. Furthermore, some designs (e.g., streptavidin) have created unwanted off-target retention in critical organs, such as the kidneys, reducing their clinical utility.

Thus, there is an on-going need for agents that have effective kinetic and/or pharmacological properties with reduced or without associated toxicities.

SADA Domains

The present disclosure encompasses a recognition that SADA domains can impart certain desirable functional characteristics to a conjugate. For example, the present disclosure provides an insight that SADA domains can be designed and/or tailored to achieve environmentally-dependent multimerization with beneficial kinetic, thermodynamic, and/or pharmacologic properties. For example, it is recognized that SADA domains may be part of a conjugate that permits effective delivery of a payload to a target site of interest while minimizing risk of off-target interactions.

The present disclosure also encompasses the recognition that most multimerization domains cannot be used for building a SADA domain. The present disclosure describes a number of beneficial characteristics and/or properties that may be used to select for an effective SADA domain. Example 11 describes a number of exemplary characteristics for selecting and/or designing an effective SADA domain. In some embodiments, a SADA domain may be selected for and/or designed to have certain beneficial properties. For example, in some embodiments, a SADA domain maintain a stable self-assembled multimeric state in vitro, to allow for manufacturability, but disassemble in vivo in a predictable way, such as, for example, to allow an initial prolonged serum half-life, followed by rapid clearance to reduce unwanted serum exposure. Additionally, a self-assembled multiunit SADA conjugate complex must be of sufficient size to ensure exceeding of the renal clearance threshold (~70 kDa), while falling below this cutoff when disassembled into monomeric subunits. Further beneficial properties of a SADA domain can include being non-immunogenic (e.g., of human origin), being of sufficient solubility and/or not being prone to aggregation or denaturation/instability during GMP manufacture.

Numerous multimerization domains would not meet the criteria of an effective SADA domain. For example, the most common multimerization domain, the human Fc domain derived from immunoglobulin IgG, would not qualify due to its covalent homodimerization with irreversible self-assembly. As a covalent dimer, it does not break into subunits in the serum for renal clearance. Even for IgG4-Fc, which undergoes Fab exchange, the stable format is still an intact IgG4 and not two Fab-Fc half molecules. Another example is streptavidin, which has been used previously to tetramerize single-chain fragments (scFv) for pre-targeted radioimmunotherapy (PRIT). Steptavidin was a clinical failure because of its high immunogenicity and intrinsic affinity for kidney tissues. (Pagel, J. M. et al. (2003) *Blood* 101, 2340-2348; Carr, W. H. et al. (2005) *J Immunol* 175, 5222-5229; Cheung, N. K. et al. (2004) *J Nucl Med* 45, 867-877; Parham, P. et al. (2011) *J Immunol* 187, 11-19; Zhang, M. L. et al. (2003) *Proc. Natl. Acad. Sci. U.S.A.* 100, 1891-1895; Oei, A. L. et al. (2008) *Int J Cancer* 123, 1848-1853). Other domains have not been successful partly due of their complexity, their size, or their instability during expression or purification, leading to difficulties during manufacturing and downstream processing.

The present disclosure encompasses the recognition that a SADA conjugate may have properties that permit a single-step (FIG. 1C) or two-step (FIG. 1B) targeting strategy. Further, it is recognized that these properties may improve antibody delivery, payload delivery, and their therapeutic indices for a targeted therapy (e.g., PRIT). As a proof of concept, we describe here design of a SADA domain derived from human p53, p63 and p73, and apply this to a Pretargeted Radio-Immuno-Therapy system (SADA-PRIT) as well as a cytokine therapy system (SADA-Cytokine). This modular self-clearing platform can be adapted to nearly any type of drug delivery: radioisotopes, cytokines, cytotoxic agents, protein toxins, peptides and nanoparticles, etc. It can also be used for trapping or sequestration of circulating ligands or receptors (e.g. drugs, toxins, venoms, growth factors, etc.) for hepatic or renal clearance, engaging immune cells to target cells (e.g. T-cell engagement, NK-cell engagement, etc.), or simply blocking receptor-ligand interactions.

The present disclosure encompasses the recognition that by modulating the self-association affinity of a SADA domain, including a combination of more than one independent SADA domain, one can regulate how quickly the multimeric complex disassembles into renally clearable subunits, therefore substantially influencing the pharmacokinetics of the therapeutic. In some embodiments, self-association affinity of a SADA domain allows for preferential self-assembly into a multimeric state at relatively high concentrations in vitro (>100 nM) but to prefer a disassembled lower order multimeric state (e.g., a monomeric state) at lower concentrations, which can allow for rapid renal clearance. The rate of disassembly of a SADA domain may be engineered to achieve a serum half-life that maximizes therapeutic index. In addition, the disassembly tendency (dissociation constant) of a SADA domain can be engineered to increase with decreasing pH or increasing temperature, whereby the multimeric forms will disassemble into monomeric units to enhance renal clearance. Therapeutics which benefit from extended half-lives can use more strongly associating domains in order to form larger complexes, while those that need a relatively short half-lives can use weaker associating domains. In some embodiments, a SADA domain is fused to a binding domain, wherein the binding domain binds a target in vivo, such that whenever target is present at sufficient concentration or density, this binding is strengthened by a multivalent avidity or cooperative binding to the target.

In some embodiments, by combining SADA domain, such as a tetramerizing SADA domain (e.g., p53, p63, p73, hnRNPC, SNAP-23, Stefin B, KCNQ4, CBFA2T1) with a dimerization domain such as a strong antiparallel dimerization domain (e.g., HNF1α) (Ahmed, M. et al. (2015) OncoImmunology 4, e989776) or a strong antiparallel dimerization domain or trap (e.g., IL15Rα)(Chirifu, M. et al. (2007) Nat Immunol 8, 1001-1007), a higher order multimerization platform can be built where the disassembly is sequential, from octamer to tetramer to dimer.

The present disclosure encompasses a recognition that association and disassociation rates of a SADA domain polypeptide can affect the pharmacokinetic properties of SADA conjugates (e.g., antibody-based SADA conjugates, SADA-Cytokine conjugates). In some embodiments, SADA domains are human derived multimerization domains that are sufficiently stable enough to multimerize tethered protein units in a non-covalent manner. In some embodiments, the present disclosure recognizes that it may be desirable to select a SADA domain that lacks unpaired cysteine residues. In some embodiments, it is recognized that it is beneficial to minimize exposed hydrophobic surfaces present in a SADA domain.

Exemplary SADA Domains

In some embodiments, a SADA domain is composed of a multimerization domains which are each composed of helical bundles that associate in a parallel or anti-parallel orientation. In some embodiments, a SADA domain is selected from the group of one of the following human proteins: p53, p63, p73, heterogeneous nuclear Ribonucleoprotein (hnRNPC) C, or N-terminal domain of Synaptosomal-associated protein 23 (SNAP-23), Stefin B (Cystatin B), Potassium voltage-gated channel subfamily KQT member 4 (KCNQ4), Cyclin-D-related protein (CBFA2T1), or variants or fragments thereof. Provided below are polypeptide and nucleic acid sequences for exemplary SADA domains.

Human p53 tetramerization domain amino acid
sequence (321-359)
SEQ ID NO: 1
KPLDGEYFTLQIRGRERFEMFRELNEALELKDAQAGKEP Human p53 tetramerization domain nucleotide
sequence
SEQ ID NO: 2
AAACCTCTGGATGGCGAGTACTTTACCCTGCAGATTAGAGGCCGCGAACG

ATTCGAGATGTTTCGCGAACTGAATGAGGCCCTGGAACTGAAGGATGCTC

AGGCAGGCAAGGAGCCA

Human p63 tetramerization domain amino acid
sequence (396-450)
SEQ ID NO: 3
RSPDDELLYLPVRGRETYEMLLKIKESLELMQYLPQHTIETYRQQQQQQH

QHLLQKQ

Human p63 tetramerization domain nucleotide
sequence
SEQ ID NO: 4
AGATCCCCCGACGATGAGCTGCTGTACCTGCCTGTGAGGGGCCGGGAGAC

CTATGAAATGCTGCTGAAGATCAAAGAGAGCCTGGAACTGATGCAGTACC

TGCCACAGCACACCATTGAAACATATAGGCAACAACAGCAGCAGCAGCAT

CAGCATCTGCTGCAGAAGCAG

Human p73 tetramerization domain amino acid
sequence (348-399)
SEQ ID NO: 5
RHGDEDTYYLQVRGRENFEILMKLKESLELMELVPQPLVDSYRQQQQLLQ

RP

Human p73 tetramerization domain nucleotide
sequence
SEQ ID NO: 6
AGGCACGGCGACGAAGATACCTACTATCTGCAGGTGAGGGGACGGGAGAA

CTTCGAAATCCTGATGAAGCTGAAAGAGTCCCTGGAACTGATGGAGCTGG

TGCCCCAGCCTCTGGTCGACAGCTACAGACAGCAGCAGCAGCTGCTGCAG

AGGCCA

Human HNRNPC tetramerization domain amino
acid sequence (194-220)
SEQ ID NO: 7
QAIKKELTQIKQKVDSLLENLEKIEKE Human HNRNPC tetramerization domain
nucleotide sequence
SEQ ID NO: 8
CAAGCTATAAAGAAGGAACTCACCCAGATTAAGCAAAAGGTTGACTCACT

GTTGGAAAATCTTGAGAAAATAGAAAAGGAA

Human SNAP-23 tetramerization domain amino
acid sequence (23-76)
SEQ ID NO: 9
STRRILGLAIESQDAGIKTITMLDEQKEQLNRIEEGLDQINKDMRETEKT

LTEL

Human SNAP-23 tetramerization domain
nucleotide sequence
SEQ ID NO: 10
TCTACCCGCAGGATCTTGGGACTTGCTATAGAGTCACAGGACGCCGGAAT

AAAAACTATCACTATGCTTGATGAACAGAAGGAACAACTGAATCGGATTG

AGGAAGGACTGGACCAGATTAACAAGGACATGCGAGAGACCGAAAAAACA

CTCACTGAGTTG

Human Stefin B tetramerizaiton domain amino
acid sequence (2-98)
SEQ ID NO: 11
MCGAPSATQPATAETQHIADQVRSQLEEKENKKFPVFKAVSFKSQVVAGT

NYFIKVHVGDEDFVHLRVFQSLPHENKPLTLSNYQTNKAKHDELTYF

Human Stefin B tetramerizaiton domain
nucleotide sequence
SEQ ID NO: 12
ATGTGCGGGGCGCCCTCCGCCACGCAGCCGGCCACCGCCGAGACCCAGCA

CATCGCCGACCAGGTGAGGTCCCAGCTTGAAGAGAAAGAAAACAAGAAGT

TCCCTGTGTTTAAGGCCGTGTCATTCAAGAGCCAGGTGGTCGCGGGGACA

AACTACTTCATCAAGGTGCACGTCGGCGACGAGGACTTCGTACACCTGCG

AGTGTTCCAATCTCTCCCTCATGAAAACAAGCCCTTGACCTTATCTAACT

ACCAGACCAACAAAGCCAAGCATGATGAGCTGACCTATTTC

-continued

KCNQ4 tetramerizaiton domain amino acid
sequence (611-640)
SEQ ID NO: 13
DEISMMGRVVKVEK<u>QVQ</u>SIEHKLDLLLGFY KCNQ4 tetramerizaiton domain nucleotide
sequence
SEQ ID NO: 14
GATGAAATCAGCATGATGGGACGCGTGGTCAAGGTGGAGAAGCAGGTGCA

GTCCATCGAGCACAAGCTGGACCTGCTGTTGGGCTTCTAT

CBFA2T1 tetramerizaiton domain amino acid
sequence (462-521)
SEQ ID NO: 15
TVAEAKRQAAEDALAVINQQEDSSESCWNCGRKASETCSGCNTARYCGSF

CQHKDWEKHH

CBFA2T1 tetramerizaiton domain nucleotide
sequence
SEQ ID NO: 16
ACGGTCGCCGAGGCCAAACGGCAGGCGGCGGAGGACGCACTGGCAGTTAT

CAATCAGCAGGAGGATTCAAGCGAGAGTTGCTGGAATTGTGGCCGTAAAG

CGAGTGAAACCTGCAGTGGCTGTAACACAGCCCGATACTGTGGCTCATTT

TGCCAGCACAAAGACTGGGAGAAGCACCAT

In some embodiments, a SADA polypeptide is or comprises a tetramerization domain of p53, p63, p73, hnRNPC, SNAP-23, Stefin B, KCNQ4, or CBFA2T1. In some embodiments, a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 1, 3, 5, 7, 9, 11, 13, and 15. In some embodiments, a SADA polypeptide is or comprises a sequence that is at least 75%, 80%, 85%, 90%, 91%, 92%, 93%, 94%, 95%, 96%, 97%, 98%, or 99% identical to a sequence as set forth in any one of SEQ ID NOs: 1, 3, 5, 7, 11, and 13, and wherein the underlined amino acid residues in these sequences above are conserved.

SADA Conjugates and Uses

The present disclosure encompasses a recognition that SADA domains can impart certain desirable functional characteristics to a conjugate. For example, the present disclosure provides an insight that SADA domains can be designed and/or tailored to achieve environmentally-dependent multimerization with beneficial kinetic, thermodynamic, and/or pharmacologic properties. For example, it is recognized that SADA domains may be part of a conjugate that permit effective delivery of a payload to a target site of interest while minimizing risk of off-target interactions.

Among other things, the present disclosure provides various conjugates comprising a SADA domain linked to one or more binding domains. In some embodiments, such conjugates are characterized in that they multimerize to form a complex of a desired size under relevant conditions (e.g., in a solution in which the conjugate is present above a threshold concentration or pH and/or when present at a target site characterized by a relevant level or density of receptors for the payload), and disassemble to a smaller form under other conditions (e.g., absent the relevant environmental multimerization trigger).

The present disclosure provides, among other things, an appreciation that a SADA conjugate may have improved characteristics compared to a conjugate without a SADA domain. In some embodiments, a SADA conjugate includes a binding domain. In some embodiments, improved characteristics include that a multimeric conjugate has increased avidity/binding to a target, increased specificity for target cells or tissues, and/or extended initial serum half-life. In some embodiments, improved characteristics include that through dissociation to smaller states (e.g. dimeric or monomeric) exhibit reduced non-specific binding, decreased toxicity, and/or improved renal clearance.

In some embodiments, a SADA conjugate comprises (i) a self-assembly disassembly (SADA) polypeptide having an amino acid sequence that shows at least 75% identity with that of a human homo-multimerizing polypeptide and is characterized by one or more multimerization dissociation constants ($K_D$); and (ii) at least a first binding domain that binds to a first target and is covalently linked to the SADA polypeptide. In some embodiments, a SADA conjugate is constructed and arranged so that it adopts a first multimerization state and one or more higher-order multimerization states. In some embodiments, a first multimerization state is less than about ~70 kDa in size. In some embodiments, a first multimerization state is an unmultimerized state (e.g., a monomer or a dimer). In some embodiments, a first multimerization state is a monomer. In some embodiments, a first multimerization state is a dimer. In some embodiments, a first multimerization state is a multimerized state (e.g., a trimer or a tetramer). In some embodiments, a higher-order multimerization states is a homo-tetramer or higher-order homo-multimer greater than 150 kDa in size. In some embodiments, a higher-order homo-multimerized conjugate is stable in aqueous solution when the conjugate is present at a concentration above the SADA polypeptide $K_D$. In some embodiments, a SADA conjugate transitions from a higher-order multimerization state(s) to a first multimerization state under physiological conditions when the concentration of the conjugate is below the SADA polypeptide $K_D$.

In some embodiments, a SADA polypeptide is covalently linked to a binding domain via a linker. Any suitable linker known in the art can be used. In some embodiments, a SADA polypeptide is linked to a binding domain via a polypeptide linker. In some embodiments, a polypeptide linker is a Gly-Ser linker. In some embodiments, a polypeptide linker is or comprises a sequence of (GGGGS)n, where n represents the number of repeating GGGGS units and is 1, 2, 3, 4, 5, 6, 7, 8, 9, 10, 11, 12, 13, 14, 15, 16, 17, 18, 19, 20, 25, 30 or more. In some embodiments, a binding domain is directly fused to a SADA polypeptide.

The present disclosure provides SADA conjugates as described herein that may be used in a method of treatment of the human or animal body, or in a method of diagnosis. In some embodiments, a SADA conjugate has a binding domain that can bind to a moiety associated with a target, such as target cells and/or tissues. In some embodiments a target cell is a tumor cell. In some embodiments, a SADA conjugate is capable of selectively binding a tumor that expresses moiety for which a binding domain has affinity. In some embodiments, a SADA conjugate may be suitable for therapeutic treatment of patients.

In some embodiments, as will be understood in the art, a SADA conjugate may be utilized without further modification. In some embodiments, a SADA conjugate may be incorporated into a composition or formulation. In some embodiments, a SADA conjugate comprises a binding domain that non-covalently binds to a therapeutic payload. In some embodiments, they may be chemically associated or linked (e.g., covalently linked) with one or more other agents or entities, e.g., with a therapeutic payload.

In some embodiments, a SADA conjugate may be used for targeted therapy and/or diagnostics. The present disclosure encompasses the recognition that a SADA conjugate may have properties that permit a single-step (FIG. 1C) or two-step (FIG. 1B) targeting strategy. Further, it is recognized that these properties may improve antibody delivery, payload delivery, and their therapeutic indices for a targeted therapy (e.g., PRIT). As a proof of concept, we describe here design of a SADA domain derived from human p53, p63 and p73, and apply this to a Pretargeted Radio-Immuno-Therapy system (SADA-PRIT) as well as a cytokine therapy system (SADA-Cytokine). This modular self-clearing platform can be adapted to nearly any type of drug delivery: radioisotopes, cytokines, cytotoxic agents, protein toxins, peptides and nanoparticles, etc. It can also be used for trapping or sequestration of circulating ligands or receptors (e.g. drugs, toxins, venoms, growth factors, etc.) for hepatic or renal clearance, engaging immune cells to target cells (e.g. T-cell engagement, NK-cell engagement, etc.), or simply blocking receptor-ligand interactions.

In some embodiments, a SADA-PRIT delivery system comprises: a multiunit antibody of (1) non-immunogenic human or humanized components, (2) sufficient initial self-assembled molecular size above the renal threshold to allow for continual blood circulation (e.g., range 12-96 hours) and quantitative uptake into tumors, (3) an inherent ability to disassemble into small units below the renal threshold, such that any remaining unbound protein will be excreted through the kidney (e.g. range 12-96 hours) without the requirement for any clearing agent, and thereby permitting (4) a final payload to be carried by a ligand small enough to efficiently penetrate tissues and bind with high affinity to the pretargeted antibody, while also allowing for any unbound payload to be excreted through the kidney, within minutes to hours after administration. Because multimeric self-assembly is in part a concentration dependent phenomenon, this system takes advantage of the fact that the SADA multimers will have an increased local concentration at their target sites (such as a tumor) where the multimer is stabilized by multivalent binding that favors self-assembly, while simultaneously having a decreased local concentration at non-target sites (e.g. blood) that favors disassembly followed by rapid renal clearance.

In some embodiments, a SADA conjugate (e.g., SADA-Cytokine or SADA-BiDE), a binding domain (e.g. antibody, cytokine, enzyme, fluorophore, small molecule inhibitor, etc.) can be covalently attached to a SADA polypeptide and be selectively delivered to the target. In some embodiments, a SADA conjugate can further comprise a payload. In some embodiments, a SADA conjugate may be covalently or non-covalently associated with a payload. In some embodiments, the payload may be or comprise a therapeutic agent payload (e.g., a toxic payload). In some embodiments the payload may be or comprise a detection agent payload. Without wishing to be bound by theory, it is envisions that selective delivery of a SADA conjugate and/or a SADA conjugate with a payload, may be due, at least in part, by virtue of the increased substrate avidity through multiunit assembly or enhanced endocytosis, allowing for maximal effect at the target sites (tumor, effector cells, etc.) while minimizing off target side effects due to the rapid clearance from non-targeted tissues.

In some embodiments, a SADA conjugate comprises a SADA domain and a binding domain that can bind to and sequester one or more target moieties or entities (e.g., a SADA-Trap conjugate). In some embodiments of the SADA platform soluble proteins or peptides (e.g. tumor factors, growth factors, inhibitory proteins, activation molecules, venoms, toxins, etc.), haptens, or chemicals can be sequestered by a SADA-Trap, and renally cleared. In a fully self-assembled state, the multimerized SADA-Trap can bind and capture relatively small soluble targets (<50 kDa) (in the blood, CSF, peritoneum, other body fluids or compartments, etc.) more effectively than classic Fab-based traps, by virtue of its enhanced avidity and its initial long serum half-life. After circulating for a specified period of time, the SADA-Trap will be disassembled into Trap:Target monomers and rapidly cleared renally. Similarly, when targeted to large soluble targets (>60 kDa), the SADA-Trap can bind and inhibit their function by blocking their active sites, or enhancing their metabolism by the liver.

In some embodiments, a SADA conjugate comprises a SADA domain and a binding domain that can bind to one or more targets that are associated with a white blood cell (e.g., a SADA-BiWE conjugate). In some embodiment of the SADA platform, a white blood cell engaging bispecific (BiWE), can be multimerized by the SADA domain (SADA-BiWE) to more effectively activate white blood cells against an antigen of interest. As opposed to classic bispecific engagers, such as blinatumomab, allowing for multivalent binding allows the targeted white blood cell to recognize low-density targets (such as low frequency peptide-HLA complexes) or classically difficult targets with low affinity antibodies (such as carbohydrate antigens). Furthermore, unlike IgG based bispecifics, the SADA domain allows for rapid clearance of unbound SADA-BiWE, limiting their off-target exposure. Additionally, their increased avidity should allow for better retention on both target and effector cell populations, providing a long period of activity without needing an excess of circulating mAb.

Conjugate Production

In some embodiments, conjugates comprising a SADA-domain as described herein may be produced from nucleic acid molecules using molecular biological methods known to the art. Nucleic acid molecules are inserted into a vector that is able to express the fusion proteins in when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element that are known in the art.

Nucleic acid constructs include sequences that encode SADA conjugates that include a SADA domain and a binding domain. In some embodiments, a binding domain of a SADA conjugate is an antibody or antibody component. Typically, such antibody components will be generated from $V_H$ and/or $V_L$ regions. After identification and selection of antibodies or antibody components exhibiting desired binding and/or functional properties, variable regions of each antibody are isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids. The antibodies and/or antibody components may be generated from human, humanized or chimeric antibodies.

Nucleic acid constructs of the present invention are inserted into an expression vector or viral vector by methods known to the art, and nucleic acid molecules are operatively linked to an expression control sequence.

Where appropriate, nucleic acid sequences that encode humanized antibodies and multi-specific binding agents as described herein may be modified to include codons that are optimized for expression in a particular cell type or organism (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, the coding sequence for a humanized heavy (or light) chain variable region as described herein may be optimized for expression in a bacterial cells. Alternatively, the coding sequence may be optimized for expression in a mammalian cell (e.g., a CHO). Such a sequence may be described as a codon-optimized sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS or CHO cell). Host cells transformed with an expression vector are grown under conditions permitting production of a SADA conjugate of the present invention followed by recovery of the SADA conjugate.

SADA conjugates of the present disclosure may be purified by any technique, which allows for the subsequent formation of a stable antibody or binding agent molecule. For example, not wishing to be bound by theory, SADA conjugates may be recovered from cells either as soluble polypeptides or as inclusion bodies, from which they may be extracted quantitatively by 8M guanidinium hydrochloride and dialysis. In order to further purify SADA conjugates of the present invention, conventional ion exchange chromatography, hydrophobic interaction chromatography, reverse phase chromatography or gel filtration may be used. SADA conjugates of the present invention may also be recovered from conditioned media following secretion from eukaryotic or prokaryotic cells.

A variety of technologies for conjugating agents, or components thereof, with other moieties or entities are well known in the art and may be utilized in accordance with the practice of the present disclosure. To give but one example, radioactively-labeled SADA conjugates may be produced according to well-known technologies in the art.

For instance, in some embodiments, SADA conjugates can be iodinated by contact with sodium and/or potassium iodide and a chemical oxidizing agent such as sodium hypochlorite, or an enzymatic oxidizing agent, such as lactoperoxidase. In some embodiments, SADA conjugates may be labeled with technetium-99m by ligand exchange process, for example, by reducing pertechnate with stannous solution, chelating the reduced technetium onto a Sephadex column and applying the antibody to this column. In some embodiments, provided SADA conjugates are labeled using direct labeling techniques, e.g., by incubating pertechnate, a reducing agent such as SNC12, a buffer solution such as sodium-potassium phthalate solution, and the antibody. Intermediary functional groups which are often used to bind radioisotopes which exist as metallic ions to antibody are diethylenetriaminepentaacetic acid (DTPA), or ethylene diaminetetracetic acid (EDTA), or 1,4,7,10-tetraazacyclododecane-1,4,7,10-tetraacetic acid (DOTA), or p-aminobenzyl-DOTA (Bn-DOTA). Radioactive isotopes may be detected by, for example, dosimetry.

Administration

The present disclosure provides methods of administering an effective amount of a conjugate comprising a SADA domain as described herein (e.g., antibody-based SADA conjugates, SADA-Cytokine conjugates) to a subject in need of treatment.

To give but a few examples, in some embodiments, a SADA conjugate as described herein is administered under conditions and for a period of time (e.g., according to a dosing regimen) sufficient for it to saturate a target or target cells (e.g., tumor cells). In some embodiments, unbound SADA conjugate clears from the blood stream after administration; in some such embodiments, such removal occurs (e.g., is permitted to occur) prior to administration of another agent.

In some particular embodiments, a SADA conjugate as described herein is administered in combination with another agent that targets Bn-DOTA. In some such embodiments, the another agent carries a payload. In some embodiments, the payload may be or comprise a therapeutic agent payload (e.g., a toxic payload). In some embodiments the payload may be or comprise a detection agent payload.

In some particular embodiments, a SADA domain as described herein (e.g., antibody-based SADA conjugates, SADA-Cytokine conjugates) as described herein is administered so that tumor cells are saturated, and subsequently a second agent, that targets Bn-DOTA (and may carry a payload) is administered. Optionally, at least one third agent that targets Bn-DOTA (e.g., and may carry a different payload) may be administered.

In some embodiments, additional agents are administered a period of time after administration of a SADA conjugate described herein, which period of time may be sufficient to permit clearance of unbound therapeutic agent. In some embodiments, additional agents are administered without further administration of the therapeutic agent. For example, in some embodiments, a SADA conjugate as described herein is administered according to a regimen that includes at least one cycle of: (i) administration of the SADA conjugate (optionally so that relevant tumor cells are saturated); (ii) administration of a second and, optionally at least one third agent (e.g., that targets Bn-DOTA, and may optionally carry a payload); (iii) optional additional administration of the second and/or third agents, without additional administration of the SADA conjugate. In some embodiments, a therapeutic regimen may comprise multiple such cycles; in some embodiments, a regimen may comprise 1, 2, 3, 4, 5, 6, 7, 8, 9, 10 or more cycles.

In some embodiments, a therapeutic regimen comprises only a single cycle that includes administration of a SADA conjugate; in some embodiments such a therapeutic regimen may comprise one or more cycles that include steps (ii) and, optionally, (iii) but do not include additional administrations of the SADA conjugate.

Those of ordinary skill in the art, reading the present disclosure, will readily appreciate that therapy with a SADA conjugate described herein (e.g., antibody-based SADA conjugates, SADA-Cytokine conjugates), may in certain embodiments be combined with other therapies, and particularly including other anti-tumor therapies. In some embodiments, such other anti-tumor therapies may be or comprise, for example administration of one or more chemotherapeutic agents, immunomodulatory agents, radiation therapy, high-frequency ultrasound therapy, surgery, etc.

In some embodiments, relative timing of administration of a SADA conjugate described herein (e.g., antibody-based SADA conjugates, SADA-Cytokine conjugates) and another therapy with which it is combined may be selected to optimize effect.

SADA conjugates as described herein may be administered through various methods known in the art for the therapeutic and/or diagnostic delivery of agents. For example, proteins or nucleic acids can be used for the therapeutic delivery of a SADA or a nucleic acid encoding a SADA conjugate of the present disclosure, e.g., cellular transfection, gene therapy, direct administration with a delivery vehicle or pharmaceutically acceptable carrier, indirect delivery by providing recombinant cells comprising a nucleic acid encoding a SADA conjugate of the present disclosure. In some embodiments, administration of a SADA conjugate induces killing of or inhibits growth of target cells in a subject.

Various delivery systems are known and can be used to administer a SADA conjugate of the present disclosure, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Routes of administration can be enteral or parenteral and include, but are not limited to, intravenous, subcutaneous, intramuscular, parenteral, transdermal, or transmucosal (e.g., oral or nasal). In some embodiments, SADA conjugates of the present disclosure are administered intravenously. In some embodiments, SADA conjugates of the present disclosure are administered subcutaneously. In some embodiments, SADA conjugates of the present disclosure are administered together with other biologically active agents.

In some embodiments, prior administration of a SADA conjugate as described herein permits combination therapy in which the agent with which the SADA conjugate is combined shows a broader therapeutic index than it does when administered alone (i.e., without the prior administration of a therapeutic agent as described herein). In some embodiments, such a broader therapeutic index is at least a logfold improved.

Formulation

The present disclosure further provides compositions comprising SADA conjugates of the present disclosure and a pharmaceutically acceptable carrier or excipient. The composition, if desired, can also contain one or more additional therapeutic and/or diagnostic agents.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

General considerations in the formulation and/or manufacture of pharmaceutical agents may be found, for example, in Remington: The Science and Practice of Pharmacy 21st ed., Lippincott Williams & Wilkins, 2005 (incorporated herein by reference).

The present disclosure further provides a pharmaceutical pack or kit comprising one or more containers filled with at least one SADA conjugate as described herein. Kits may be used in any applicable method, including, for example, therapeutically or diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Identification and/or Characterization of SADA Conjugates

In some embodiments, a SADA-conjugate may be identified or characterized by a method comprising steps of (i) providing a conjugate comprising a self-assembly disassembly (SADA) polypeptide and a binding domain and (ii) determining a threshold condition (e.g., concentration, pH/pOH, oxidation/reduction state) wherein the conjugate substantially adopts a multimeric form greater than about ~70 kDa. Any methods known in the art can be used to assess the multimeric form of an antibody agent, include chromatographic methods. In some embodiments, the step of providing comprises providing a conjugate in which the SADA polypeptide is a test polypeptide and the step of determining comprises identifying the multimerization domain as useful in the conjugate if the critical multimerization concentration is within a range of about 100 nM to 1 mM. In some embodiments, the step of providing comprises providing a plurality of conjugates, and the step of determining comprises determining the threshold for each of the conjugates. In some embodiments, each conjugate in the plurality comprises the same binding domain but differs in the SADA polypeptide.

In some embodiments, a SADA-conjugate may be identified or characterized by a method comprising steps of (i) providing a conjugate comprising a self-assembly disassembly (SADA) polypeptide and a binding domain, (ii) administering the composition to a subject and (iii) determining the affinity of the conjugate for a target. Any methods known in the art for determining the affinity of a conjugate for a target may be used in the art. In some embodiments, affinity may be assessed as binding affinity. In some embodiments, affinity by be assessed by localization, using any techniques known in the art to visualize localization.

In some embodiments, a SADA-conjugate may be identified or characterized by a method that includes analysis of one or more conjugates in a plurality of conjugates. In some embodiments, a SADA-conjugate may be identified or characterized by a method comprising steps of (i) providing composition comprising a plurality of conjugates, each comprising a SADA polypeptide and a binding domain, (ii) administering the composition to a subject and (iii) determining the affinity of one or more of the conjugates for a target. In some embodiments, a step of determining comprises determining the affinity for a target for each of the conjugates. In some embodiments, a method includes a step of determining the rate of clearance of one or more conjugate from blood. In some embodiments, a method includes a step of determining the rate of clearance of a conjugate from blood for each of a plurality of conjugates. In some embodiments, a plurality of conjugates includes SADA conjugates that comprise the same binding domain but differ in the SADA polypeptide.

In some embodiments, a SADA-conjugate may be identified or characterized as preferred relative to another conjugate in a plurality of conjugates when the preferred conjugate shows increased avidity for a target and/or when the preferred conjugate is more rapidly cleared from the blood.

In some embodiments, a SADA-conjugate may be identified or characterized by a method that includes steps of (i) providing a composition comprising a SADA conjugate, and (ii) formulating the conjugate with a pharmaceutically acceptable carrier or excipient to produce a composition in which the conjugate is present at a concentration sufficient for at least 90% of the conjugate to adopt the higher-order multimerized state. In some embodiments, a conjugate in the composition is at a concentration of 50 nM, 100 nM, 500 nM, 1 μM, 10 μM, 50 μM, 100 μM, 200 μM, 300 μM, 400 μM, 500 μM, or 1 mM.

Exemplary Embodiments

Exemplary embodiment 1. A polypeptide conjugate comprising: a self-assembly disassembly (SADA) polypeptide having an amino acid sequence that shows at least 75% identity with that of a human homo-multimerizing polypeptide and being characterized by one or more multimerization dissociation constants ($K_D$); and at least a first binding domain that binds to a first target and is covalently linked to the SADA polypeptide,
  the conjugate being constructed and arranged so that it adopts a first multimerization state and one or more higher-order multimerization states, where:
    the first multimerization state is less than about ~70 kDa in size,
    at least one of the higher-order multimerization states is a homo-tetramer or higher-order homo-multimer greater than 150 kDa in size,
    where the higher-order homo-multimerized conjugate is stable in aqueous solution when the conjugate is present at a concentration above the SADA polypeptide $K_D$, and
    the conjugate transitions from the higher-order multimerization state(s) to the first multimerization state under physiological conditions when the concentration of the conjugate is below the SADA polypeptide $K_D$.

Exemplary embodiment 2. The conjugate of exemplary embodiment 1, where the higher-order homo-multimerized conjugate is stable for a period of at least 24 hr at 37° C. in an aqueous buffer with a pH of about 7.

Exemplary embodiment 3. The conjugate of exemplary embodiment 2 or 3, where the higher-order homo-multimerized conjugate is stable for a period of at least 48 hours, 72 hours, 1 week, 2 weeks, 1 month, 2 months, 3 months, or more.

Exemplary embodiment 4. The conjugate of any one of exemplary embodiments 1-3, where the higher-order homo-multimerized conjugate is stable over 3 or more freeze-thaw cycles.

Exemplary embodiment 5. The conjugate of any one of exemplary embodiments 1-4, where the transition of the conjugate from the higher-order multimerization state to the first multimerization state is characterized by a $K_{off}$ within a range of $1 \times 10^{-6}$ to $1 \times 10^{-4}$ ($s^{-1}$).

Exemplary embodiment 6. The conjugate of any one of exemplary embodiments 1-5, where the SADA polypeptide has a total buried surface area of 900 Å2 to 4000 Å2.

Exemplary embodiment 7. The conjugate of any one of exemplary embodiments 1-6, where the SADA polypeptide lacks unpaired cysteine residues.

Exemplary embodiment 8. The conjugate of any one of exemplary embodiments 1-7, where the SADA polypeptide comprises a tetramerization, pentamerization or hexamerization domain.

Exemplary embodiment 9. The conjugate of any one of exemplary embodiments 1-8, where the SADA polypeptide is or comprises a tetramerization domain of any one of p53, p63, p73, hnRNPC, SNAP-23, Stefin B, KCNQ4, and CBFA2T1.

Exemplary embodiment 10. The conjugate of any one of exemplary embodiments 1-8, where the SADA polypeptide is or comprises a tetramerization domain of p53.

Exemplary embodiment 11. The conjugate of any one of exemplary embodiments 1-8, where the SADA polypeptide is or comprises a tetramerization domain of p63.

Exemplary embodiment 12. The conjugate of any one of exemplary embodiments 1-8, where the SADA polypeptide is or comprises a tetramerization domain of p73.

Exemplary embodiment 13. The conjugate of any one of exemplary embodiments 1-8, where the SADA polypeptide is or comprises a tetramerization domain of hnRNPC.

Exemplary embodiment 14. The conjugate of any one of exemplary embodiments 1-8, where the SADA polypeptide is or comprises a tetramerization domain of SNAP-23.

Exemplary embodiment 15. The conjugate of any one of exemplary embodiments 1-8, where the SADA polypeptide is or comprises a tetramerization domain of Stefin B.

Exemplary embodiment 16. The conjugate of any one of exemplary embodiments 1-8, where the SADA polypeptide is or comprises a tetramerization domain of KCNQ4.

Exemplary embodiment 17. The conjugate of any one of exemplary embodiments 1-8, where the SADA polypeptide is or comprises a tetramerization domain of CBFA2T1.

Exemplary embodiment 18. The conjugate of any one of exemplary embodiments 1-9, where the SADA polypeptide is or comprises a sequence that is at least 90%, at least 95%, at least 96%, at least 97%, at least 98%, at least 99% identical to a sequence as set forth in any one of SEQ ID NOs: 1, 3, 5, 7, 9, 11, 13, and 15.

Exemplary embodiment 19. The conjugate of any one of exemplary embodiments 1-18, where the first target is an in situ target.

Exemplary embodiment 20. The conjugate of exemplary embodiment 19, where the first target is an in situ target that is or comprises an entity selected from the group consisting of: a cell-surface moiety, a cytokine, a receptor ligand, a peptide, a hormone, a metabolite, and a hapten.

Exemplary embodiment 21. The conjugate of any one of exemplary embodiments 1-18, where the first target is a payload target.

Exemplary embodiment 22. The conjugate of exemplary embodiment 21, where the first target is a therapeutic payload.

Exemplary embodiment 23. The conjugate of exemplary embodiment 21, where the first target is a diagnostic payload.

Exemplary embodiment 24. The conjugate of any one of exemplary embodiments 21-23, where the payload target is a drug, a polypeptide (such as a toxin, enzyme, cytokine, chemokine, receptor, or biologic), a chemical probe (such as a fluorescent dye or biotin tag), a radioactive isotope, or a nanoparticle.

Exemplary embodiment 25. The conjugate of any one of exemplary embodiments 1-24, further comprising a second binding domain that binds to a second target, which is different from the first target.

Exemplary embodiment 26. The conjugate of exemplary embodiment 25, where the conjugate comprises at least two binding domains and wherein the conjugate in the second multimerization state is at least octavalent.

Exemplary embodiment 27. The conjugate of exemplary embodiment 25 or 26, where the second target is an in situ target.

Exemplary embodiment 28. The conjugate of exemplary embodiment 27, where the second target is an in situ target that is or comprises an entity selected from the group consisting of: a cell-surface moiety, a cytokine, a receptor ligand, a peptide, a hormone, a metabolite, and a hapten.

Exemplary embodiment 29. The conjugate of exemplary embodiment 25 or 26, where the second target is a payload target.

Exemplary embodiment 30. The conjugate of exemplary embodiment 29, where the second target is a therapeutic payload.

Exemplary embodiment 31. The conjugate of exemplary embodiment 29, where the second target is a diagnostic payload.

Exemplary embodiment 32. The conjugate of any one of exemplary embodiments 29-31, where the payload target is a drug, a polypeptide (such as a toxin, enzyme, cytokine, chemokine, receptor, or biologic), a chemical probe (such as a fluorescent dye or biotin tag), a radioactive isotope, or a nanoparticle.

Exemplary embodiment 33. The conjugate of of any one of exemplary embodiments 1-24, where the first target is a cell surface moiety.

Exemplary embodiment 34. The conjugate of exemplary embodiment 25 or 26, where the second target is a cell surface moiety.

Exemplary embodiment 35. The conjugate of exemplary embodiment 33 or 34, where the cell surface moiety is specifically expressed or enriched on a subset of cells in an organism.

Exemplary embodiment 36. The conjugate of exemplary embodiment 35, where the cell surface moiety is specifically expressed or enriched on tumor cells.

Exemplary embodiment 37. The conjugate of any one of exemplary embodiments 34-36, where the cell surface moiety is a cell surface receptor.

Exemplary embodiment 38. The conjugate of any one of exemplary embodiments 1-24, where the first binding domain is or comprises a ligand for a cell surface receptor.

Exemplary embodiment 39. The conjugate of any one of exemplary embodiments 25-36, where the first and/or second binding domain is or comprises a ligand for a cell surface receptor.

Exemplary embodiment 40. The conjugate of any one of exemplary embodiments 1-24, where the first binding domain is or comprises a cytokine receptor binding domain.

Exemplary embodiment 41. The conjugate of any one of exemplary embodiments 25-36, where the first and/or second binding domain is or comprises a cytokine receptor binding domain.

Exemplary embodiment 42. The conjugate of exemplary embodiment 40 or 41, where the conjugate is further complexed with a soluble cytokine polypeptide.

Exemplary embodiment 43. The conjugate of exemplary embodiment 42, where the cytokine receptor is IL15Rα and the soluble cytokine polypeptide is IL15.

Exemplary embodiment 44. The conjugate of any one of exemplary embodiments 1-24, where the first binding domain is or comprises an antibody, antibody component, or antigen-binding antibody fragment specific for a cell surface target.

Exemplary embodiment 45. The conjugate of any one of exemplary embodiments 25-36, where the first and/or second binding domain is or comprises an antibody, antibody component, or antigen-binding antibody fragment specific for a cell surface target.

Exemplary embodiment 46. The conjugate of exemplary embodiment 44 or 45, where the first and/or second binding domain is an antibody component.

Exemplary embodiment 47. The conjugate of exemplary embodiment 44 or 45, where the first and/or second binding domain is an antigen-binding antibody fragment.

Exemplary embodiment 48. The conjugate of exemplary embodiment 44 or 45, where the first and/or second binding domain is an scFv.

Exemplary embodiment 49. The conjugate of any one of exemplary embodiments 45-48, where the first binding domain is an anti-GD2, anti-Globo H, anti-GPA33, anti-PSMA, anti-polysialic acid, anti-Lew$^Y$, anti-L1CAM, anti-HER2, anti-B7H3, anti-CD33, anti-peptide/MHC, anti-glypican3, or anti-GD3 binding domain.

Exemplary embodiment 50. The conjugate of exemplary embodiment 49, where the first binding domain is an anti-GD2 antibody, antibody component, or antigen-binding antibody fragment.

Exemplary embodiment 51. The conjugate of exemplary embodiment 49, where the first binding domain is an anti-GD2 scFv.

Exemplary embodiment 52. The conjugate of exemplary embodiment 49, where the first binding domain is an anti-HER2 antibody, antibody component, or antigen-binding antibody fragment.

Exemplary embodiment 53. The conjugate of exemplary embodiment 49, where the first binding domain is an anti-HER2 scFv.

Exemplary embodiment 54. The conjugate of any one of exemplary embodiments 1-36, where the SADA polypeptide is or comprises a sequence as set forth in any one of SEQ ID NOs: 1, 3, 5, 7, 9, 11, 13, and 15.

Exemplary embodiment 55. The conjugate of any one of exemplary embodiments 1-36, where the conjugate comprises a polypeptide sequence that is at least 80% identical to a sequence as set forth in any one of SEQ ID NOs: 17, 19, 21, 23, 25, 27, 29, 31, 33, 35, 37, 39, 41, 43, 45, 47, 49, 51, 53, 55, 57, 59, 61, 63, 67, 69, 71, 73, 75, 77, 79, 81, 83, 85, 87, 89, 91, 93, 95, and 97.

Exemplary embodiment 56. The conjugate of any one of exemplary embodiments 1-36, where the conjugate comprises a polypeptide sequence that is at least 90% identical to a sequence as set forth in any one of SEQ ID NOs: 17, 19, 21, 23, 25, 27, 29, 31, 33, 35, 37, 39, 41, 43, 45, 47, 49, 51, 53, 55, 57, 59, 61, 63, 67, 69, 71, 73, 75, 77, 79, 81, 83, 85, 87, 89, 91, 93, 95, and 97.

Exemplary embodiment 57. The conjugate of any one of exemplary embodiments 1-36, where the conjugate comprises a polypeptide sequence that is at least 95% identical to a sequence as set forth in any one of SEQ ID NOs: 17, 19, 21, 23, 25, 27, 29, 31, 33, 35, 37, 39, 41, 43, 45, 47, 49, 51, 53, 55, 57, 59, 61, 63, 67, 69, 71, 73, 75, 77, 79, 81, 83, 85, 87, 89, 91, 93, 95, and 97.

Exemplary embodiment 58. The conjugate of any one of exemplary embodiments 1-36, where the conjugate comprises a polypeptide sequence that is 98% identical to a sequence as set forth in any one of SEQ ID NOs: 17, 19, 21, 23, 25, 27, 29, 31, 33, 35, 37, 39, 41, 43, 45, 47, 49, 51, 53, 55, 57, 59, 61, 63, 67, 69, 71, 73, 75, 77, 79, 81, 83, 85, 87, 89, 91, 93, 95, and 97.

Exemplary embodiment 59. The conjugate of any one of exemplary embodiments 1-58, further characterized in that the binding domain binds a target at an in vivo site, where the target is present at sufficient density such that the conjugate is substantially in the higher-order multimerization state at the site.

Exemplary embodiment 60. The conjugate of any one of exemplary embodiments 1-58, further characterized in that the binding domain binds a target, where the target is present at sufficient concentration such that higher order multimerization state of the SADA polypeptide is stabilized.

Exemplary embodiment 61. The conjugate of any one of exemplary embodiments 1-60, further comprising a dimerization domain or a second SADA domain.

Exemplary embodiment 62. The conjugate of any one of exemplary embodiments 1-61, where the conjugate can exist in one or more additional multimeric states.

Exemplary embodiment 63. The conjugate of exemplary embodiment 61, where the conjugate comprises a second SADA domain and can exist in one or more additional multimeric states.

Exemplary embodiment 64. The conjugate of exemplary embodiment 61, where the conjugate comprises a second SADA domain and can exist in two or more additional multimeric states.

Exemplary embodiment 65. The conjugate of any one of exemplary embodiments 1-64, where the conjugate is substantially not immunogenic in a human subject.

Exemplary embodiment 66. The conjugate of any one of exemplary embodiments 1-65, where the first binding domain is or comprises an antibody component.

Exemplary embodiment 67. The conjugate of any one of exemplary embodiments 1-66, where the first binding domain is or comprises a scFv.

Exemplary embodiment 68. The conjugate of exemplary embodiment 66 or 67, where the conjugate further comprises a second binding domain, wherein the second binding domain is or comprises an antibody component.

Exemplary embodiment 69. The conjugate of exemplary embodiment 68, where the second binding domain is or comprises a scFv.

Exemplary embodiment 70. The conjugate of exemplary embodiment 68 or 69, where the first and second binding domains are part of a bispecific antibody agent.

Exemplary embodiment 71. The conjugate of exemplary embodiment 70, where the bispecific antibody agent comprises a first binding domain that binds a tumor target and a second binding domain that binds a metal-Bn-DOTA.

Exemplary embodiment 72. The conjugate of exemplary embodiment 71, where the bispecific antibody agent comprises a first binding domain that binds a tumor target and a second binding domain that binds an immune-cell activating receptor.

Exemplary embodiment 73. The conjugate of exemplary embodiment 71 or 72, where the first binding domain that binds a tumor target is an anti-GD2, anti-Globo H, anti-GPA33, anti-PSMA, anti-polysialic acid, anti-Lew$^Y$, anti-L1CAM, anti-HER2, anti-B7H3, anti-CD33, anti-peptide/MHC, anti-glypican3, or anti-GD3 binding domain.

Exemplary embodiment 74. The conjugate of exemplary embodiment 73, where the first binding domain is an anti-GD2 scFv.

Exemplary embodiment 75. The conjugate of exemplary embodiment 73, where the first binding domain is an anti-HER2 scFv.

Exemplary embodiment 76. A nucleic acid sequence encoding a conjugate of any one of exemplary embodiments 1-75.

Exemplary embodiment 77. The nucleic acid sequence of exemplary embodiment 76, where the nucleic acid comprises a sequence that is at least 75%, 80%, 85%, 90%, 91%, 92%, 93%, 94%, 95%, 96%, 97%, 98%, or 99% identical to a sequence as set forth in any one of SEQ ID NOs: 2, 4, 6, 8, 10, 12, 14 and 16.

Exemplary embodiment 78. The nucleic acid sequence of exemplary embodiment 76, where the nucleic acid comprises a sequence as set forth in any one of SEQ ID NOs: 2, 4, 6, 8, 10, 12, 14 and 16.

Exemplary embodiment 79. The nucleic acid sequence of any one of exemplary embodiments 76-78, comprising a sequence that is at least 75%, 80%, 85%, 90%, 91%, 92%, 93%, 94%, 95%, 96%, 97%, 98%, or 99% identical to a sequence as set forth in any one of SEQ ID NOs: 18, 20, 22, 24, 26, 28, 30, 32, 34, 36, 38, 40, 42, 44, 46, 48, 50, 52, 54, 56, 58, 60, 62, 64, 68, 70, 72, 74, 76, 78, 80, 82, 84, 86, 88, 90, 92, 94, 96, and 98.

Exemplary embodiment 80. The nucleic acid sequence of any one of exemplary embodiments 76-78, comprising a sequence as set forth in any one of SEQ ID NOs: 18, 20, 22, 24, 26, 28, 30, 32, 34, 36, 38, 40, 42, 44, 46, 48, 50, 52, 54, 56, 58, 60, 62, 64, 68, 70, 72, 74, 76, 78, 80, 82, 84, 86, 88, 90, 92, 94, 96, and 98.

Exemplary embodiment 81. A vector comprising the nucleic acid sequence of any one of exemplary embodiments 76-80.

Exemplary embodiment 82. A host cell comprising the vector of exemplary embodiment 81.

Exemplary embodiment 83. The host cell of exemplary embodiment 82, where the host cell is selected from the group consisting of a bacterial, yeast, insect or mammalian cell.

Exemplary embodiment 84. The host cell of exemplary embodiment 83, where the host cell is selected from the group consisting of *E. coli, Pichia pastoris*, Sf9, COS, HEK293 and a CHO cell.

Exemplary embodiment 85. A composition comprising the conjugate of any one of exemplary embodiments 1-75.

Exemplary embodiment 86. The composition of exemplary embodiment 85, where the composition is formulated for injection so that stable binding between the conjugate and its target is detectable at its target tissue for a period of time at least 24 hours long, and wherein the conjugate is substantially undetectable in at least one non-target tissue within 72 hours post-injection without any extraneous drug or clearing agent.

Exemplary embodiment 87. The composition of exemplary embodiment 86, wherein the non-target tissue is selected from the group consisting of blood, gastrointestinal tissue, lymphoid tissue, nervous system tissue, renal tissue, hepatic tissue, and combinations thereof.

Exemplary embodiment 88. The composition of exemplary embodiment 86, where the non-target tissue is or comprises blood.

Exemplary embodiment 89. The composition of any one of exemplary embodiments 86-88, where the target tissue is or comprises a tumor tissue.

Exemplary embodiment 90. A composition comprising an isolated nucleic acid sequence of any one of exemplary embodiments 76-80.

Exemplary embodiment 91. A method comprising steps of providing a liquid composition comprising the conjugate of any one of exemplary embodiments 1-75 in the higher-order multimeric state; and administering the composition to a subject.

Exemplary embodiment 92. The method of exemplary embodiment 91, where the step of administering comprises delivering so that conjugate that is not bound to the target tissue disassembles into the first multimerization state or a monomeric state, whereas conjugate that is bound to the target is substantially in the higher-order multimeric state.

Exemplary embodiment 93. The method of exemplary embodiment 91 or 92, where the extent of the conjugate in the higher-order multimeric state may be or is assessed by measuring the retention of the conjugate at a target site.

Exemplary embodiment 94. The method of exemplary embodiment 91 or 92, where the extent of conjugate in the first multimerization state or monomeric state may be or is assessed by measuring the amount of conjugate in the blood of a subject.

Exemplary embodiment 95. The method of exemplary embodiment 91 or 92, where the extent of conjugate in the first multimerization state or monomeric state may be or is assessed by direct radiolabeling.

Exemplary embodiment 96. The method of exemplary embodiment 91 or 92, where the extent of conjugate in the first multimerization state or monomeric state may be or is assessed by measuring the rate of clearance of the conjugate into the urine.

Exemplary embodiment 97. The method of any one of exemplary embodiments 91-96, where the step of administering is to a subject suffering from or susceptible to cancer.

Exemplary embodiment 98. The method of exemplary embodiment 97, where the cancer is selected from a multiple myeloma, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, solid tumor, colorectal cancer, renal cancer, pancreatic cancer, prostate cancer, nasopharyngeal cancer, malignant histiocytosis, adenocarcinoma, sarcoma, hemangioma, sarcoma, cerebral tumor, bone tumor, breast cancer, squamous cell carcinoma, stomach cancer, melanoma and mesothelioma.

Exemplary embodiment 99. Use of a conjugate of any one of exemplary embodiments 1-75 in treating cancer.

Exemplary embodiment 100. A method comprising steps of: providing a liquid composition comprising the conjugate of any one of exemplary embodiments 71-75; and administering the composition to a subject that is suffering from cancer.

Exemplary embodiment 101. A method of treating or diagnosing cancer in a subject, the method comprising steps of: providing a liquid composition comprising the conjugate of any one of exemplary embodiments 71-75 in a concentration sufficient that greater than 90% of the conjugate is in the higher-order multimerization state; and administering the composition to a subject that is suffering from or susceptible to cancer.

Exemplary embodiment 102. The method of exemplary embodiment 101, where the concentration of conjugate is within a range of 50 nM to 1 mM.

Exemplary embodiment 103. The method of exemplary embodiment 101, where the concentration of conjugate is within a range of 100 nM to 10 µM.

Exemplary embodiment 104. The method of exemplary embodiment 101, where the concentration of conjugate is within a range of 100 nM to 100 µM.

Exemplary embodiment 105. The method of exemplary embodiment 101, where the concentration of conjugate is within a range of 500 nM to 500 µM.

Exemplary embodiment 106. The method of exemplary embodiment 101, where the concentration of conjugate is within a range of 1 µM to 1 mM.

Exemplary embodiment 107. The method of any one of exemplary embodiments 100-106, where the cancer is selected from a multiple myeloma, leukemia, acute leukemia, acute lymphoblastic leukemia (ALL), B-cell, T-cell or FAB ALL, acute myeloid leukemia (AML), chromic myelocytic leukemia (CIVIL), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, solid tumor, colorectal cancer, renal cancer, pancreatic cancer, prostate cancer, nasopharyngeal cancer, malignant histiocytosis, adenocarcinoma, sarcoma, hemangioma, sarcoma, cerebral tumor, bone tumor, breast cancer, squamous cell carcinoma, stomach cancer, melanoma and mesothelioma.

Exemplary embodiment 108. A method of pre-targeted radio immunotherapy, the method comprising steps of: providing a liquid composition comprising the conjugate of any one of exemplary embodiments 71-75 in the higher order multimeric form; administering the composition to a subject that is suffering from or susceptible to cancer; and subsequently administering a radiolabeled Bn-DOTA to the subject.

Exemplary embodiment 109. The method of exemplary embodiment 108, wherein the method does not include the administration of a clearing agent.

Exemplary embodiment 110. A method of pre-targeted radio immunotherapy, the method comprising steps of: providing a liquid composition comprising the conjugate of any one of exemplary embodiments 71-75 in a concentration of at least 50 nM, 100 nM, 500 nM, 1 µM, 10 µM, 50 µM, 100 µM, 200 µM, 300 µM, 400 µM, 500 µM, or 1 mM; administering the composition to a subject that is suffering from or susceptible to cancer.

Exemplary embodiment 111. The method of exemplary embodiment 110, where the concentration of conjugate is within a range of 50 nM to 1 mM.

Exemplary embodiment 112. The method of exemplary embodiment 110, where the concentration of conjugate is within a range of 100 nM to 10 0/1.

Exemplary embodiment 113. The method of exemplary embodiment 110, where the concentration of conjugate is within a range of 100 nM to 100 0/1.

Exemplary embodiment 114. The method of exemplary embodiment 110, where the concentration of conjugate is within a range of 500 nM to 500 0/1.

Exemplary embodiment 115. The method of exemplary embodiment 110, where the concentration of conjugate is within a range of 1 µM to 1 mM.

Exemplary embodiment 116. The method of any one of exemplary embodiments 110-115, where conjugate in the higher order multimeric form.

Exemplary embodiment 117. The method of any one of exemplary embodiments 110-116, where a radiolabeled agent comprising a Bn-DOTA is covalently attached to the conjugate.

Exemplary embodiment 118. The method of any one of exemplary embodiments 110-116, where a radiolabeled Bn-DOTA is non-covalently complexed with the conjugate.

Exemplary embodiment 119. The method of any one of exemplary embodiments 110-118, where the method does not include the administration of a clearing agent.

Exemplary embodiment 120. A method comprising steps of: providing a liquid composition comprising the conjugate of any one of exemplary embodiments 1-75, where at least 90% of the conjugate in the composition is in the higher order multimeric form; and administering the composition to a subject from whom a target entity is to be removed, wherein the conjugate is capable of binding the target entity.

Exemplary embodiment 121. A method of identifying or characterizing a conjugate, the method comprising steps of: providing a conjugate comprising a self-assembly disassembly (SADA) polypeptide and a binding domain; determining a threshold condition (concentration, pH/pOH, oxidation/reduction state) wherein the conjugate substantially adopts a multimeric form greater than about ~70 kDa.

Exemplary embodiment 122. The method of exemplary embodiment 121, where the step of providing comprises providing a conjugate in which the SADA polypeptide is a test polypeptide and the step of determining comprises identifying the multimerization domain as useful in the conjugate if the critical multimerization concentration is within a range of about 100 nM to 1 mM.

Exemplary embodiment 123. The method of exemplary embodiment 121 or 122, where the step of providing comprises providing a plurality of conjugates, and the step of determining comprises determining the threshold for each of the conjugates.

Exemplary embodiment 124. The method of any one of exemplary embodiments 121-123, where each conjugate in the plurality comprises the same binding domain but differs in the SADA polypeptide.

Exemplary embodiment 125. The method of any one of exemplary embodiments 121-124, where the SADA polypeptide is or comprises a tetramerization domain of any one of p53, p63, p73, hnRNPC, SNAP-23, Stefin B, KCNQ4, and CBFA2T1.

Exemplary embodiment 126. A method of identifying or characterizing a conjugate, the method comprising steps of: providing a conjugate comprising a self-assembly disassembly (SADA) polypeptide and a binding domain; administering the composition to a subject; and determining the affinity of the conjugate for a target.

Exemplary embodiment 127. The method of exemplary embodiment 126 where the step of providing comprises providing a plurality of conjugates, and the step of determining comprises determining the affinity for a target for each of the conjugates.

Exemplary embodiment 128. The method of exemplary embodiment 126 or 127, further comprising s step of determining the rate of clearance of the conjugate from blood.

Exemplary embodiment 129. The method of exemplary embodiment 128, where the step of determining the rate of clearance of the conjugate from blood is for each of the conjugates.

Exemplary embodiment 130. The method of any one of exemplary embodiments 126-129, where each conjugate in the plurality comprises the same binding domain but differs in the SADA polypeptide.

Exemplary embodiment 131. The method of any one of exemplary embodiments 126-130, further comprising a step of identifying one or more conjugates in the plurality as preferred relative to another conjugate in the plurality when the preferred conjugate shows increased avidity for a target and/or when the preferred conjugate is more rapidly cleared from the blood.

Exemplary embodiment 132. A method of producing a composition, the method comprising steps of: providing a composition comprising the conjugate of any one of exemplary embodiments 71-75; formulating the conjugate with a pharmaceutically acceptable carrier or excipient to produce a composition in which the conjugate is present at a concentration sufficient for at least 90% of the conjugate to adopt the higher-order multimerized state.

Exemplary embodiment 133. The method of exemplary embodiment 132, where the concentration of conjugate is within a range of 50 nM to 1 mM.

Exemplary embodiment 134. The method of exemplary embodiment 132, where the concentration of conjugate is within a range of 100 nM to 10 04.

Exemplary embodiment 135. The method of exemplary embodiment 132, where the concentration of conjugate is within a range of 100 nM to 100 04.

Exemplary embodiment 136. The method of exemplary embodiment 132, where the concentration of conjugate is within a range of 500 nM to 500 04.

Exemplary embodiment 136. The method of exemplary embodiment 132, where the concentration of conjugate is within a range of 1 µM to 1 mM.

Other features of the invention will become apparent in the course of the following descriptions of exemplary embodiments, which are given for illustration of the invention and are not intended to be limiting thereof.

EXEMPLIFICATION

Example 1—Production of an Exemplary Conjugate with a SADA Domain

This example demonstrates the production of exemplary SADA conjugates with a first binding domain that binds a payload (e.g., a molecular payload), a second domain that binds a cellular target (e.g., a cell surface target) and a SADA domain. Specifically, this example describes the production of exemplary bispecific antibody-based conjugates comprising a tandem-scFv bispecific antibody with two different scFv's linked by a G4S linker and followed by a tetrameric SADA tag. Three constructs were produced (P53-BIDE, P63-BIDE, P73-BIDE), each comprising a first scFv with specificity for tumor cells (a humanized anti-GD2 scFv) and a second scFv with specificity for a metal-chelate of Benzyl-1,4,7,10-tetraazacyclododecane-1,4,7,10-tetraacetic acid, [metal]-Bn-DOTA, which recognizes Bn-DOTA when chelating metal ions such as Lu-177, Y-86, Y-90, In-111, etc. The constructs, P53-BiDE and P53-BiDE (noHIS) (which lacks a terminal HIS tag) included a SADA domain that is derived from the human p53 tetramerization domain. The construct, P63-BiDE, included a SADA domain that is derived from the human p63 tetramerization domain. The construct, P73-BiDE included a SADA domain that is derived from the human p73 tetramerization domain. The amino acid sequences and the cDNA nucleotide sequences of these constructs are shown below.

```
P53-BIDE(noHIS) polypeptide (hu3F8-scFv, huC825-scFv,
huP53-tet, GS linker, (IgG3 spacer))
                                               SEQ ID NO: 17
EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSQVQLVE

SGPGVVQPGRSLRISCAVSGFSVTNYGVHWVRQPPGKCLEWLGVIWAGGITNYNSAFMSRLTI

SKDNSKNTVYLQMNSLRAEDTAMYYCASRGGHYGYALDYWGQGTLVTVSSGGGGSGGGGSGGG

GSGGGGSHVQLVESGGGLVQPGGSLRLSCAASGFSLTDYGVHWVRQAPGKGLEWLGVIWSGGG

TAYNTALISRFTISRDNSKNTLYLQMNSLRAEDTAVYYCARRGSYPYNYFDAWGCGTLVTVSS

GGGGSGGGGSGGGGSQAVVTQEPSLTVSPGGTVTLTCGSSTGAVTASNYANWVQQKPGQCPRG

LIGGHNNRPPGVPARFSGSLLGGKAALTLLGAQPEDEAEYYCALWYSDHWVIGGGTKLTVLG (TPLGDTTHT)SGKPLDGEYFTLQIRGRERFEMFRELNEALELKDAQAGKEPGGSGGA

P53-BIDE(noHIS) cDNA (hu3F8-scFv, huC825-scFv, huP53-
tet, GS linker, (IgG3 spacer))
                                               SEQ ID NO: 18
GAAATCGTCATGACTCAGACTCCCGCAACCCTGTCAGTGTCCGCTGGGGAACGTGTCACTATT

ACCTGCAAGGCATCTCAGAGCGTGAGCAACGACGTGACCTGGTATCAGCAGAAGCCTGGCCAG

GCTCCACGACTGCTGATCTATTCCGCAAGCAATCGCTACTCCGGAGTGCCCGCACGATTCTCT

GGAAGTGGGTACGGTACCGAGTTCACTTTTACCATTTCCAGCGTGCAGAGCGAAGACTTCGCT

GTCTATTTTTGCCAGCAGGATTACTCTAGTTTTGGCTGTGGAACAAAGCTGGAGATCAAAAGG

GGAGGAGGAGGTTCTGGCGGAGGAGGTAGTGGCGGAGGGGGTTCACAGGTGCAGCTGGTCGAA

TCTGGGCCAGGCGTGGTCCAGCCAGGACGTTCCCTGAGGATTAGCTGCGCCGTGAGCGGGTTC

TCTGTCACAAACTACGGAGTGCACTGGGTCCGTCAGCCACCTGGCAAATGTCTGGAGTGGCTG
```

-continued

GGAGTGATCTGGGCAGGAGGAATCACTAACTACAACTCTGCTTTTATGAGTCGCCTGACCATC

TCAAAGGACAACTCCAAAAATACAGTGTACCTGCAGATGAATTCACTGCGGGCAGAAGATACC

GCCATGTACTATTGCGCCTCCAGGGGGGTCATTACGGCTATGCCCTGGACTATTGGGCCAG

GGAACACTGGTGACTGTCTCATCCGGAGGAGGAGGATCCGGAGGAGGAGGTAGCGGCGGAGGG

GGTTCTGGCGGAGGGGGTAGTCACGTGCAGCTGGTCGAGTCCGGAGGAGGCTGGTGCAGCCT

GGTGGCAGCCTGCGACTGTCTTGTGCCGCTAGTGGCTTCTCACTGACAGATTACGGCGTGCAT

TGGGTCCGACAGGCTCCAGGGAAGGGTCTGGAATGGCTGGGAGTGATTTGGTCTGGAGGGGGT

ACAGCTTATAACACTGCACTGATCAGTCGGTTCACTATCAGTAGAGACAACTCAAAGAACACC

CTGTACCTGCAGATGAACTCTCTGCGGGCCGAGGATACCGCTGTGTACTATTGCGCTAGGCGG

GGCAGTTACCCTTATAATTACTTTGACGCATGGGGCTGTGGAACCCTGGTGACAGTCAGCTCT

GGCGGAGGGGGTTCAGGCGGCGGCGGTTCCGGCGGAGGAGGTAGCCAGGCCGTGGTCACTCAG

GAGCCTTCCCTGACCGTGAGCCCAGGAGGAACAGTCACTCTGACCTGCGGGAGTTCAACCGGT

GCCGTGACAGCCTCCAACTACGCTAATTGGGTCCAGCAGAAGCCCGGCAGTGTCCTAGAGGT

CTGATCGGGGGTCACAACAATCGTCCACCCGGAGTGCCAGCCAGGTTCTCAGGCTCCCTGCTG

GGCGGAAAAGCAGCACTGACTCTGCTGGGCGCTCAGCCAGAGGACGAAGCAGAGTACTATTGC

GCCCTGTGGTATTCTGATCACTGGGTCATCGGGGGTGGCACTAAGCTGACCGTGCTGGGC(AC

ACCCCTGGGAGACACCACACATACT)AGTGGCAAACCTCTGGATGGAGAGTACTTTACCCTGC

AGATTAGAGGCCGCGAACGATTCGAGATGTTTCGCGAACTGAATGAGGCCCTGGAACTGAAGG

ATGCTCAGGCAGGCAAGGAACCAGGCGGTAGCGGCGGCGCA

P53-BIDE polypeptide (hu3F8-scFv, *huC825-scFv*, **huP53-
tet**, <u>GS linker</u>, (IgG3 spacer))
SEQ ID NO: 19
EIVMTQTPATLSVSAGERVTITCKASQSVSNDVTWYQQKPGQAPRLLIYSASNRYSGVPARFS GSGYGTEFTFTISSVQSEDFAVYFCQQDYSSFGCGTKLEIKR<u>GGGGSGGGGSGGGGSGGGGSG</u>

<u>GGGSGGGGS</u>QVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SS<u>GGGGSGGGGSGGGGSGGGGS</u>*HVQLVESGGGLVQPGGSLRLSCAASGFSLTDYGVHWVRQAP*

*GKGLEWLGVIWSGGGTAYNTALISRFTISRDNSKNTLYLQMNSLRAEDTAVYYCARRGSYPYN*

*YFDAWGCGTLVTVSSGGGGSGGGGSGGGGSQAVVTQEPSLTVSPGGTVTLTCGSSTGAVTASN*

*YANWVQQKPGQCPRGLIGGHNNRPPGVPARFSGSLLGGKAALTLLGAQPEDEAEYYCALWYSD*

*HWVIGGGTKLTVLG*(TPLGDTTHT)SGKPLDGEYFTLQIRGRERFEMFRELNEALELKDAQAG

KEPGGSGGAPHHHHHH

P53-BIDE cDNA (hu3F8-scFv, *huC825-scFv*, huP53-tet,
<u>GS linker</u>, (IgG3 spacer))
SEQ ID NO: 20
GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAGG

GGAGGAGGAGGTAGTGGCGGAGGAGGTTCAGGCGGAGGGGGTAGCGGCGGAGGGGGTTCTGGC

GGCGGCGGTAGTGGCGGCGGAGGTAGCCAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

-continued

```
GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGGCAGGGTACCCTGGTGACAGTC

TCATCCGGCGGAGGGGGATCCGGAGGAGGAGGTAGCGGCGGAGGGGGTTCTGGCGGAGGGGGT

AGTCACGTGCAGCTGGTCGAGTCCGGAGGAGGGCTGGTGCAGCCTGGTGGCAGCCTGCGACTG

TCTTGTGCCGCTAGTGGCTTCTCACTGACAGATTACGGCGTGCATTGGGTCCGACAGGCTCCA

GGGAAGGGTCTGGAATGGCTGGGAGTGATTTGGTCTGGAGGGGGTACAGCTTATAACACTGCA

CTGATCAGTCGGTTCACTATCAGTAGAGACAACTCAAAGAACACCCTGTACCTGCAGATGAAC

TCTCTGCGGGCCGAGGATACCGCTGTGTACTATTGCGCTAGGCGGGGCAGTTACCCTTATAAT

TACTTTGACGCATGGGGCTGTGGAACCCTGGTGACAGTCAGCTCTGGCGGAGGGGGTTCAGGC

GGCGGCGGTTCCGGCGGAGGAGGTAGCCAGGCCGTGGTCACTCAGGAGCCTTCCCTGACCGTG

AGCCCAGGAGGAACAGTCACTCTGACCTGCGGAGTTCAACCGGTGCCGTGACAGCCTCCAAC

TACGCTAATTGGGTCCAGCAGAAGCCCGGGCAGTGTCCTAGAGGTCTGATCGGGGGTCACAAC

AAPCGTCCACCCGGAGTGCCAGCCAGGTTCTCAGGCTCCCTGCTGGGCGGAAAAGCAGCACTG

ACTCTGCTGGGCGCTCAGCCAGAGGACGAAGCAGAGTACTATTGCGCCCTGTGGTATTCTGAT

CACTGGGTCATCGGGGGTGGCACTAAGCTGACCGTGCTGGGC(ACACCCCTGGGAGACACCAC

ACATACT)AGTGGGAAACCTCTGGATGGCGAGTACTTTACCCTGCAGATTAGAGGCCGCGAAC

GATTCGAGATGTTTCGCGAACTGAATGAGGCCCTGGAACTGAAGGATGCTCAGGCAGGCAAGG

AGCCAGGAGGGTCAGGAGGAGCACCGCACCATCATCATCACCAT
```

P63- BIDE polypeptide (hu3F8-scFv, *huC825-scFv*,
huP63-tet, GS linker, (IgG3 spacer))

SEQ ID NO: 21

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSGGGGSG

GGGSGGGGSQVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SSGGGGSGGGGSGGGGSGGGGSHVQLVESGGGLVQPGGSLRLSCAASGFSLTDYGVHWVRQAP

*GKGLEWLGVIWSGGGTAYNTALISRFTISRDNSKNTLYLQMNSLRAEDTAVYYCARRGSYPYN*

*YFDAWGCGTLVTVS*SGGGGSGGGGSGGGGSQAVVTQEPSLTVSPGGTVTLTCGSSTGAVTASN

*YANWVQQKPGQCPRGLIGGHNNRPPGVPARFSGSLLGGKAALTLLGAQPEDEAEYYCALWYSD*

*HWVIGGGTKLTVLG*(TPLGDTTHT)SGRSPDDELLYLPVRGRETYEMLLKIKESLELMQYLPQ

HTIETYRQQQQQQHQHLLQKQGGSGGAPHHHHHH

P63- BIDE cDNA (hu3F8-scFv, *huC825-scFv*, **huP63-
tet**, GS linker, (IgG3 spacer))

SEQ ID NO: 22

```
GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAAGG

GGAGGAGGAGGTAGTGGCGGAGGAGGTTCAGGCGGAGGGGGTAGCGGCGGAGGGGGTTCTGGC

GGCGGCGGTAGTGGCGGCGAGGTAGCCAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA
```

-continued

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGCAGGGTACCCTGGTGACAGTC

TCATCC<u>GGAGGAGGAGGATCCGGAGGAGGAGGTAGCGGCGGAGGGGGTTCTGGCGGAGGGGGT

AGT</u>CACGTGCAGCTGGTCGAGTCCGGAGGAGGGCTGGTCAGCCTGGTGGCAGCCTGCGACTG

TCTTGTGCCGCTAGTGGCTTCTCACTGACAGATTACGGCGTGCATTGGGTCCGACAGGCTCCA

GGGAAGGGTCTGGAATGGCTGGGAGTGATTTGGTCTGGAGGGGGTACAGCTTATAACACTGCA

CTGATCAGTCGGTTCACTATCAGTAGAGACAACTCAAAGAACACCCTGTACCTGCAGATGAAC

TCTCTGCGGGCCGAGGATACCGCTGTGTACTATTGCGCTAGGCGGGGCAGTTACCCTTATAAT

TACTTTGACGCATGGGGCTGTGGAACCCTGGTGACAGTCAGCTCT<u>GGCGGAGGGGGTTCAGGC

GGCGGCGGTTCCGGCGGAGGAGGTAGC</u>CAGGCCGTGGTCACTCAGGAGCCTTCCCTGACCGTG

AGCCCAGGAGGAACAGTCACTCTGACCTGCGGGAGTTCAACCGGTGCCGTGACAGCCTCCAAC

TACGCTAATTGGGTCCAGCAGAAGCCCGGGCAGTGTCCTAGAGGTCTGATCGGGGGTCACAAC

AAPCGTCCACCCGGAGTGCCAGCCAGGTTCTCAGGCTCCCTGCTGGGCGGAAAAGCAGCACTG

ACTCTGCTGGGCGCTCAGCCAGAGGACGAAGCAGAGTACTATTGCGCCCTGTGGTATTCTGAT

CACTGGGTCATCGGGGTGGCACTAAGCTGACCGTGCTGGGC(ACACCCCTGGGAGACACCAC

ACATACT)AGTGGG**AGATCCCCCGACGATGAGCTGCTGTACCTGCCTGTGAGGGGCCGGGAGA

CCTATGAAATGCTGCTGAAGATCAAAGAGAGCCTGGAACTGATGCAGTACCTGCCACAGCACA

CCATTGAAACATATAGGCAACAACAGCAGCAGCAGCATCAGCATCTGCTGCAGAAGCAG**GGAG

GGTCAGGAGGAGCACCGCACCATCATCATCACCAT

**P73- BIDE polypeptide (hu3F8-scFv, *huC825-scFv*, huP73-
tet, <u>GS linker</u>, (IgG3 spacer))**
SEQ ID NO: 23
EIVMTQTPATLSVSAGERVTITCKASQSVSNDVTWYQQKPGQAPRLLIYSASNRYSGVPARFS GSGYGTEFTFTISSVQSEDFAVYFCQQDYSSFGCGTKLEIKR<u>GGGGSGGGGSGGGGSGGGGSG GGGSGGGGS</u>QVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SS<u>GGGGSGGGGSGGGGSGGGGS</u>*HVQLVESGGGLVQPGGSLRLSCAASGFSLTDYGVHWVRQAP

GKGLEWLGVIWSGGGTAYNTALISRFTISRDNSKNTLYLQMNSLRAEDTAVYYCARRGSYPYN

YFDAWGCGTLVTVSSGGGGSGGGGSGGGGS*QAVVTQEPSLTVSPGGTVTLTCGSSTGAVTASN

*YANWVQQKPGQCPRGLIGGHNNRPPGVPARFSGSLLGGKAALTLLGAQPEDEAEYYCALWYSD

HWVIGGGTKLTVLG*(TPLGDTTHT)SG**RHGDEDTYYLQVRGRENFEILMKLKESLELMELVPQ

PLVDSYRQQQQLLQRP**GGSGGAPHHHHHH

**P73- BIDE cDNA (hu3F8-scFv, *huC825-scFv*, huP73-
tet, <u>GS linker</u>, (IgG3 spacer))**
SEQ ID NO: 24
GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAGG

<u>GGAGGAGGAGGTAGTGGCGGAGGAGGTTCAGGCGGAGGGGGTAGCGGCGGAGGGGGTTCTGGC

GGCGGCGGTAGTGGCGGCGGAGGTAGC</u>CAGGTGCAGCTGGTCGAATCCGGCCCTGGAGTGGTC

-continued

```
CAGCCAGGCAGGTCTCTGCGGATCAGTTGCGCCGTGTCCGGATTCAGCGTCACCAACTACGGA
GTGCACTGGGTCAGACAGCCACCTGGCAAGTGTCTGGAGTGGCTGGGAGTGATCTGGGCAGGA
GGAATCACAAACTACAACTCAGCTTTTATGTCCCGCCTGACTATTAGCAAGGACAACTCTAAA
AATACCGTGTATCTGCAGATGAATTCTCTGCGAGCCGAAGATACCGCTATGTACTATTGTGCA
TCCCGTGGGGGTCATTACGGCTATGCCCTGGATTATTGGGGCAGGGTACCCTGGTGACAGTC
TCATCCGGAGGAGGAGGATCCGGAGGAGGAGGTAGCGGCGGAGGGGGTTCTGGCGGAGGGGGT
AGTCACGTGCAGCTGGTCGAGTCCGGAGGAGGGCTGGTGCAGCCTGGTGGCAGCCTGCGACTG
TCTTGTGCCGCTAGTGGCTTCTCACTGACAGATTACGGCGTGCATTGGGTCCGACAGGCTCCA
GGGAAGGGTCTGGAATGGCTGGGAGTGATTTGGTCTGGAGGGGGTACAGCTTATAACACTGCA
CTGATCAGTCGGTTCACTATCAGTAGAGACAACTCAAAGAACACCCTGTACCTGCAGATGAAC
TCTCTGCGGGCCGAGGATACCGCTGTGTACTATTGCGCTAGGCGGGCAGTTACCCTTATAAT
TACTTTGACGCATGGGGCTGTGGAACCCTGGTGACAGTCAGCTCTGGCGGAGGGGGTTCAGGC
GGCGGCGGTTCCGGCGGAGGAGGTAGCCAGGCCGTGGTCACTCAGGAGCCTTCCCTGACCGTG
AGCCCAGGAGGAACAGTCACTCTGACCTGCGGGAGTTCAACCGGTGCCGTGACAGCCTCCAAC
TACGCTAATTGGGTCCAGCAGAAGCCCGGGCAGTGTCCTAGAGGTCTGATCGGGGGTCACAAC
AAPCGTCCACCCGGAGTGCCAGCCAGGTTCTCAGGCTCCCTGCTGGGCGGAAAAGCAGCACTG
ACTCTGCTGGGCGCTCAGCCAGAGGACGAAGCAGAGTACTATTGCGCCCTGTGGTATTCTGAT
CACTGGGTCATCGGGGTGGCACTAAGCTGACCGTGCTGGGC(ACACCCCTGGGAGACACCAC
ACATACT)AGTGGGAGGCACGGCGACGAAGATACCTACTATCTGCAGGTGAGGGGACGGGAGA
ACTTCGAAATCCTGATGAAGCTGAAAGAGTCCCTGGAACTGATGGAGCTGGTGCCCCAGCCTC
TGGTCGACAGCTACAGACAGCAGCAGCAGCTGCTGCAGAGGCCAGGAGGGTCAGGAGGAGCAC
CGCACCATCATCATCACCAT
```

**P53- BIDE(SL) polypeptide (hu3F8-scFv, huC825scFv,  
huP53-tet, GS linker, (IgG3 spacer))**  
SEQ ID NO: 25

EIVMTQTPATLSVSAGERVTITCKASQSVSNDVTWYQQKPGQAPRLLIYSASNRYSGVPARFS  
GSGYGTEFTFTISSVQSEDFAVYFCQQDYSSFGCGTKLEIKRGGGGSGGGGSGGGGSQVQLVE  
SGPGVVQPGRSLRISCAVSGFSVTNYGVHWVRQPPGKCLEWLGVIWAGGITNYNSAFMSRLTI  
SKDNSKNTVYLQMNSLRAEDTAMYYCASRGGHYGYALDYWGQGTLVTVSSGGGGSGGGGSGGG  
GSGGGGSHVQLVESGGGLVQPGGSLRLSCAASGFSLTDYGVHWVRQAPGKGLEWLGVIWSGGG  
TAYNTALISRFTISRDNSKNTLYLQMNSLRAEDTAVYYCARRGSYPYNYFDAWGCGTLVTVSS  
GGGGSGGGGSGGGGSQAVVTQEPSLTVSPGGTVTLTCGSSTGAVTASNYANWVQQKPGQCPRG  
LIGGHNNRPPGVPARFSGSLLGGKAALTLLGAQPEDEAEYYCALWYSDHWVIGGGTKLTVLG  
(TPLGDYYHY)SGKPLDGEYFTLQIRGRERFEMFRELNEALELKDAQAGKEPGGSGGAPHHHH  
HH

**P53- BIDE(SL) cDNA (hu3F8-scFv, *huC825-scFv*, huP53-  
tet, GS linker, (IgG3 spacer))**  
SEQ ID NO: 26

GAAATCGTCATGACTCAGACTCCCGCAACCCTGTCAGTGTCCGCTGGGGAACGTGTCACTATT  
ACCTGCAAGGCATCTCAGAGCGTGAGCAACGACGTGACCTGGTATCAGCAGAAGCCTGGCCAG  
GCTCCACGACTGCTGATCTATTCCGCAAGCAATCGCTACTCCGGAGTGCCCGCACGATTCTCT  
GGAAGTGGGTACGGTACCGAGTTCACTTTTACCATTTCCAGCGTGCAGAGCGAAGACTTCGCT  
GTCTATTTTTGCCAGCAGGATTACTCTAGTTTTGGCTGTGGAACAAAGCTGGAGATCAAAGG

-continued

GGAGGAGGAGGTTCTGGCGGAGGAGGTAGTGGCGGAGGGGGTTCACAGGTGCAGCTGGTCGAA

TCTGGGCCAGGCGTGGTCCAGCCAGGACGTTCCCTGAGGATTAGCTGCGCCGTGAGCGGGTTC

TCTGTCACAAACTACGGAGTGCACTGGGTCCGTCAGCCACCTGGCAAATGTCTGGAGTGGCTG

GGAGTGATCTGGGCAGGAGGAATCACTAACTACAACTCTGCTTTTATGAGTCGCCTGACCATC

TCAAAGGACAACTCCAAAAATACAGTGTACCTGCAGATGAATTCACTGCGGGCAGAAGATACC

GCCATGTACTATTGCGCCTCCAGGGGGGGTCATTACGGCTATGCCCTGGACTATTGGGGCCAG

GGAACACTGGTGACTGTCTCATCCGGAGGAGGAGGATCCGGAGGAGGAGGTAGCGGCGGAGGG

GGTTCTGGCGGAGGGGGTAGTCACGTGCAGCTGGTCGAGTCCGGAGGAGGGCTGGTGCAGCCT

GGTGGCAGCCTGCGACTGTCTTGTGCCGCTAGTGGCTTCTCACTGACAGATTACGGCGTGCAT

TGGGTCCGACAGGCTCCAGGGAAGGGTCTGGAATGGCTGGGAGTGATTTGGTCTGGAGGGGGT

ACAGCTTATAACACTGCACTGATCAGTCGGTTCACTATCAGTAGAGACAACTCAAAGAACACC

CTGTACCTGCAGATGAACTCTCTGCGGGCCGAGGATACCGCTGTGTACTATTGCGCTAGGCGG

GGCAGTTACCCTTATAATTACTTTGACGCATGGGGCTGTGGAACCCTGGTGACAGTCAGCTCT

GGCGGAGGGGGTTCAGGCGGCGGCGGTTCCGGCGGAGGAGGTAGCCAGGCCGTGGTCACTCAG

GAGCCTTCCCTGACCGTGAGCCCAGGAGGAACAGTCACTCTGACCTGCGGGAGTTCAACCGGT

GCCGTGACAGCCTCCAACTACGCTAATTGGGTCCAGCAGAAGCCCGGGCAGTGTCCTAGAGGT

CTGATCGGGGGTCACAACAATCGTCCACCCGGAGTGCCAGCCAGGTTCTCAGGCTCCCTGCTG

GGCGGAAAAGCAGCACTGACTCTGCTGGGCGCTCAGCCAGAGGACGAAGCAGAGTACTATTGC

GCCCTGTGGTATTCTGATCACTGGGTCATCGGGGGTGGCACTAAGCTGACCGTGCTGGGC(AC

ACCCCTGGGAGACACCACACATACT)AGTGGGAAACCTCTGGATGGCGAGTACTTTACCCTGC

AGATTAGAGGCCGCGAACGATTCGAGATGTTTCGCGAACTGAATGAGGCCCTGGAACTGAAGG

ATGCTCAGGCAGGCAAGGAGCCAGGAGGGTCAGGAGGAGCACCGCACCATCATCATCACCAT

P63- BIDE(SL) polypeptide (hu3F8-scFv, *huC825-scFv*,
huP63-tet, GS linker, (IgG3 spacer))
SEQ ID NO: 27
EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSQVQLVE

SGPGVVQPGRSLRISCAVSGFSVTNYGVHWVRQPPGKCLEWLGVIWAGGITNYNSAFMSRLTI

SKDNSKNTVYLQMNSLRAEDTAMYYCASRGGHYGYALDYWGQGTLVTVSSGGGGSGGGGSGGG

GSGGGGSHVQLVESGGGLVQPGGSLRLSCAASGFSLTDYGVHWVRQAPGKGLEWLGVIWSGGG

*TAYNTALISRFTISRDNSKNTLYLQMNSLRAEDTAVYYCARRGSYPYNYFDAWGCGTLVTVSS*

*GGGGSGGGGSGGGGSQAVVTQEPSLTVSPGGTVTLTCGSSTGAVTASNYANWVQQKPGQCPRG*

*LIGGHNNRPPGVPARFSGSLLGGKAALTLLGAQPEDEAEYYCALWYSDHWVIGGGTKLTVLG*

(TPLGDTTHT)SGRSPDDELLYLPVRGRETYEMLLKIKESLELMQYLPQHTIETYRQQQQQQH

QHLLQKQGGSGGAPHHHHHH

P63- BIDE(SL) cDNA (hu3F8-scFv, *huC825-scFv*, **huP63-
tet**, GS linker, (IgG3 spacer))
SEQ ID NO: 28
GAAATCGTCATGACTCAGACTCCCGCAACCCTGTCAGTGTCCGCTGGGGAACGTGTCACTATT

ACCTGCAAGGCATCTCAGAGCGTGAGCAACGACGTGACCTGGTATCAGCAGAAGCCTGGCCAG

GCTCCACGACTGCTGATCTATTCCGCAAGCAATCGCTACTCCGGAGTGCCCGCACGATTCTCT

GGAAGTGGGTACGGTACCGAGTTCACTTTTACCATTTCCAGCGTGCAGAGCGAAGACTTCGCT

GTCTATTTTTGCCAGCAGGATTACTCTAGTTTTGGCTGTGGAACAAAGCTGGAGATCAAAAGG

GGAGGAGGAGGTTCTGGCGGAGGAGGTAGTGGCGGAGGGGGTTCACAGGTGCAGCTGGTCGAA

-continued

TCTGGGCCAGGCGTGGTCCAGCCAGGACGTTCCCTGAGGATTAGCTGCGCCGTGAGCGGGTTC

TCTGTCACAAACTACGGAGTGCACTGGGTCCGTCAGCCACCTGGCAAATGTCTGGAGTGGCTG

GGAGTGATCTGGGCAGGAGGAATCACTAACTACAACTCTGCTTTTATGAGTCGCCTGACCATC

TCAAAGGACAACTCCAAAAATACAGTGTACCTGCAGATGAATTCACTGCGGGCAGAAGATACC

GCCATGTACTATTGCGCCTCCAGGGGGGTCATTACGGCTATGCCCTGGACTATTGGGGCCAG

GGAACACTGGTGACTGTCTCATCC<u>GGAGGAGGAGGATCCGGAGGAGGAGGTAGCGGCGGAGGG</u>

<u>GGTTCTGGCGGAGGGGGTAGT</u>CACGTGCAGCTGGTCGAGTCCGGAGGAGGGCTGGTGCAGCCT

GGTGGCAGCCTGCGACTGTCTTGTGCCGCTAGTGGCTTCTCACTGACAGATTACGGCGTGCAT

TGGGTCCGACAGGCTCCAGGGAAGGGTCTGGAATGGCTGGGAGTGATTTGGTCTGGAGGGGT

ACAGCTTATAACACTGCACTGATCAGTCGGTTCACTATCAGTAGAGACAACTCAAAGAACACC

CTGTACCTGCAGATGAACTCTCTGCGGGCCGAGGATACCGCTGTGTACTATTGCGCTAGGCGG

GGCAGTTACCCTTATAATTACTTTGACGCATGGGGCTGTGGAACCCTGGTGACAGTCAGCTCT

<u>GGCGGAGGGGGTTCAGGCGGCGGCGGTTCCGGCGGAGGAGGTAGC</u>CAGGCCGTGGTCACTCAG

*GAGCCTTCCCTGACCGTGAGCCCAGGAGGAACAGTCACTCTGACCTGCGGGAGTTCAACCGGT*

*GCCGTGACAGCCTCCAACTACGCTAATTGGGTCCAGCAGAAGCCCGGGCAGTGTCCTAGAGGT*

*CTGATCGGGGGTCACAACAATCGTCCACCCGGAGTGCCAGCCAGGTTCTCAGGCTCCCTGCTG*

*GGCGGAAAAGCAGCACTGACTCTGCTGGGCGCTCAGCCAGAGGACGAAGCAGAGTACTATTGC*

*GCCCTGTGGTATTCTGATCACTGGGTCATCGGGGGTGGCACTAAGCTGACCGTGCTGGGC*(AC

ACCCCYGGGAGACACCACACAYACY)AGYGGGAGATCCCCCGACGATGAGCTGCTGTACCTGC

CTGTGAGGGCCGGGAGACCTATGAAATGCTGCTGAAGATCAAAGAGAGCCTGGAACTGATGC

AGTACCTGCCACAGCACACCATTGAAACATATAGGCAACAACAGCAGCAGCAGCATCAGCATC

TGCTGCAGAAGCAGGGAGGGTCAGGAGGAGCACCGCACCATCATCATCACCATT

P73- BIDE(SL) polypeptide (hu3F8-scFv, huC825scFv,
huP73-tet, <u>GS linker</u>, (IgG3 spacer))
SEQ ID NO: 29
EIVMTQTPATLSVSAGERVTITCKASQSVSNDVTWYQQKPGQAPRLLIYSASNRYSGVPARFS GSGYGTEFTFTISSVQSEDFAVYFCQQDYSSFGCGTKLEIKR<u>GGGGSGGGGSGGGGS</u>QVQLVE

SGPGVVQPGRSLRISCAVSGFSVTNYGVHWVRQPPGKCLEWLGVIWAGGITNYNSAFMSRLTI

SKDNSKNTVYLQMNSLRAEDTAMYYCASRGGHYGYALDYWGQGTLVTVSS<u>GGGGSGGGGSGGG</u>

<u>GSGGGGS</u>HVQLVESGGGLVQPGGSLRLSCAASGFSLTDYGVHWVRQAPGKGLEWLGVIWSGGG

*TAYNTALISRFTISRDNSKNTLYLQMNSLRAEDTAVYYCARRGSYPYNYFDAWGCGTLVTVSS*

*<u>GGGGSGGGGSGGGGS</u>QAVVTQEPSLTVSPGGTVTLTCGSSTGAVTASNYANWVQQKPGQCPRG*

*LIGGHNNRPPGVPARFSGSLLGGKAALTLLGAQPEDEAEYYCALWYSDHWVIGGGTKLTVLG*

(TTEGDTTHT)SGRHGDEDTYYLQVRGRENFEILMKLKESLELMELVPQPLVDSYRQQQQLLQ

RPGGSGGAPHHHHHH

P73- BIDE(SL) cDNA (hu3F8-scFv, *huC825-scFv*, **huP73-
tet**, <u>GS linker</u>, (IgG3 spacer))
SEQ ID NO: 30
GAAATCGTCATGACTCAGACTCCCGCAACCCTGTCAGTGTCCGCTGGGGAACGTGTCACTATT

ACCTGCAAGGCATCTCAGAGCGTGAGCAACGACGTGACCTGGTATCAGCAGAAGCCTGGCCAG

GCTCCACGACTGCTGATCTATTCCGCAAGCAATCGCTACTCCGGAGTGCCCGCACGATTCTCT

GGAAGTGGGTACGGTACCGAGTTCACTTTTACCATTTCCAGCGTGCAGAGCGAAGACTTCGCT

GTCTATTTTTGCCAGCAGGATTACTCTAGTTTTGGCTGTGGAACAAAGCTGGAGATCAAAGG

-continued

```
GGAGGAGGAGGTTCTGGCGGAGGAGGTAGTGGCGGAGGGGGTTCACAGGTGCAGCTGGTCGAA

TCTGGGCCAGGCGTGGTCCAGCCAGGACGTTCCCTGAGGATTAGCTGCGCCGTGAGCGGGTTC

TCTGTCACAAACTACGGAGTGCACTGGGTCCGTCAGCCACCTGGCAAATGTCTGGAGTGGCTG

GGAGTGATCTGGGCAGGAGGAATCACTAACTACAACTCTGCTTTTATGAGTCGCCTGACCATC

TCAAAGGACAACTCCAAAAATACAGTGTACCTGCAGATGAATTCACTGCGGGCAGAAGATACC

GCCATGTACTATTGCGCCTCCAGGGGGGGTCATTACGGCTATGCCCTGGACTATTGGGGCCAG

GGAACACTGGTGACTGTCTCATCCGGAGGAGGAGGATCCGGAGGAGGAGGTAGCGGCGGAGGG

GGTTCTGGCGGAGGGGGTAGTCACGTGCAGCTGGTCGAGTCCGGAGGAGGGCTGGTGCAGCCT

GGTGGCAGCCTGCGACTGTCTTGTGCCGCTAGTGGCTTCTCACTGACAGATTACGGCGTGCAT

TGGGTCCGACAGGCTCCAGGGAAGGGTCTGGAATGGCTGGGAGTGATTTGGTCTGGAGGGGGT

ACAGCTTATAACACTGCACTGATCAGTCGGTTCACTATCAGTAGAGACAACTCAAAGAACACC

CTGTACCTGCAGATGAACTCTCTGCGGGCCGAGGATACCGCTGTGTACTATTGCGCTAGGCGG

GGCAGTTACCCTTATAATTACTTTGACGCATGGGGCTGTGGAACCCTGGTGACAGTCAGCTCT

GGCGGAGGGGTTCAGGCGGCGGCGGTTCCGGCGGAGGAGGTAGCCAGGCCGTGGTCACTCAG

GAGCCTTCCCTGACCGTGAGCCCAGGAGGAACAGTCACTCTGACCTGCGGGAGTTCAACCGGT

GCCGTGACAGCCTCCAACTACGCTAATTGGGTCCAGCAGAAGCCCGGGCAGTGTCCTAGAGGT

CTGATCGGGGGTCACAACAATCGTCCACCCGGAGTGCCAGCCAGGTTCTCAGGCTCCCTGCTG

GGCGGAAAAGCAGCACTGACTCTGCTGGGCGCTCAGCCAGAGGACGAAGCAGAGTACTATTGC

GCCCTGTGGTATTCTGATCACTGGGTCATCGGGGGTGGCACTAAGCTGACCGTGCTGGGC(AC

ACCCCTGGGAGACACCACACATACT)AGTGGGAGGCACGGCGACGAAGATACCTACTATCTGC

AGGTGAGGGACGGGAGAACTTCGAAATCCTGATGAAGCTGAAAGAGTCCCTGGAACTGATGG

AGCTGGTGCCCCAGCCTCTGGTCGACAGCTACAGACAGCAGCAGCAGCTGCTGCAGAGGCCAG

GAGGGTCAGGAGGAGCACCGCACCATCATCATCACCAT
```

P53- BIDE(LL) polypeptide (hu3F8-scFv, *huC825-scFv*,
huP53-tet, <u>GS linker</u>, (IgG3 spacer))

SEQ ID NO: 31

```
EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSGGGGSG

GGGSGGGGSQVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SSGGGGSGGGGSGGGGSGGGGSHVQLVESGGGLVQPGGSLRLSCAASGFSLTDYGVHWVRQAP

GKGLEWLGVIWSGGGTAYNTALISRFTISRDNSKNTLYLQMNSLRAEDTAVYYCARRGSYPYN

YFDAWGCGTLVTVSSGGGGSGGGGSGGGGSGGGGSGGGGSGGGGSQAVVTQEPSLTVSPGGTV

TLTCGSSTGAVTASNYANWVQQKPGQCPRGLIGGHNNRPPGVPARFSGSLLGGKAALTLLGAQ

PEDEAEYYCALWYSDHWVIGGGTKLTVLG(TPLGDTTHT)SGKPLDGEYFTLQIRGRERFEMF

RELNEALELKDAQAGKEPGGSGGAPHHHHHH
```

P53- BIDE(LL) cDNA (hu3F8-scFv, *huC825-scFv*, huP53-tet, <u>GS linker</u>, (IgG3 spacer))

SEQ ID NO: 32

```
GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAGG
```

-continued

GGAGGAGGAGGTAGTGGCGGAGGAGGTTCAGGCGGAGGGGGTAGCGGCGGAGGGGGTTCTGGC

GGCGGCGGTAGTGGCGGCGGAGGTAGCCAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGCAGGGTACCCTGGTGACAGTC

TCATCCGGCGGAGGGGGATCCGGCGGCGGAGGATCTGGCGGAGGTGGAAGTGGGGGAGGCGGA

TCTCATGTGCAGCTGGTGGAAAGCGGAGGCGGCCTGGTGCAGCCTGGGGGATCTCTGAGACTG

TCTTGTGCCGCCAGCGGCTTCTCCCTGACCGATTATGGCGTGCACTGGGTGCGACAGGCCCCT

GGCAAAGGACTGGAATGGCTGGGAGTGATTTGGAGTGGCGGAGGCACCGCCTACAACACCGCC

CTGATCTCCCGGTTCACCATCAGCCGGGACAACTCCAAGAACACCCTGTACCTGCAGATGAAC

TCCCTGCGGGCCGAGGACACCGCTGTGTACTACTGCGCCAGACGGGGCTCCTACCCCTACAAC

TACTTCGACGCTTGGGGCTGCGGCACCCTCGTGACAGTGTCTAGCGGAGGGGGAGGTTCTGGG

GGCGGAGGTTCAGGTGGTGGTGGTTCCGGGGGTGGTGGCTCTGGTGGCGGTGGTTCTGGCGGT

GGCGGATCTCAGGCTGTCGTGACCCAGGAACCCAGCCTGACTGTGTCTCCTGGCGGAACCGTG

ACCCTGACCTGCGGATCTTCTACCGGCGCTGTGACCGCCAGCAACTACGCCAATTGGGTGCAG

CAGAAACCTGGACAGTGCCCTAGAGGCCTGATCGGCGGCCACAACAACAGACCTCCAGGCGTG

CCAGCCCGGTTCTCTGGATCTCTGCTGGGCGGAAAGGCCGCTCTGACACTGCTGGGTGCTCAG

CCTGAGGACGAGGCCGAGTACTACTGCCCCTGTGGTACTCCGACCACTGGGTCATCGGAGGC

GGGACCAAGCTGACCGTGCTGGGA(ACACCCCTGGGAGACACCACACATACT)AGTGGGAAAC

CTCTGGATGGCGAGTACTTTACCCTGCAGATTAGAGGCCGCGAACGATTCGAGATGTTTCGCG

AACTGAATGAGGCCCTGGAACTGAAGGATGCTCAGGCAGGCAAGGAGCCAGGAGGGTCAGGAG

GAGCACCGCACCATCATCATCACCAT

P63- BIDE(LL) polypeptide (hu3F8-scFv, *huC825-scFv*,
huP63-tet, GS linker, (IgG3 spacer))
SEQ ID NO: 33

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSGGGGSG

GGGSGGGGSQVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

*SSGGGGSGGGGSGGGGSGGGGSHVQLVESGGGLVQPGGSLRLSCAASGFSLTDYGVHWVRQAP*

*GKGLEWLGVIWSGGGTAYNTALISRFTISRDNSKNTLYLQMNSLRAEDTAVYYCARRGSYPYN*

*YFDAWGCGTLVTVSSGGGGSGGGGSGGGGSGGGGSGGGGSGGGGSQAVVTQEPSLTVSPGGTV*

*TLTCGSSTGAVTASNYANWVQQKPGQCPRGLIGGHNNRPPGVPARFSGSLLGGKAALTLLGAQ*

*PEDEAEYYCALWYSDHWVIGGGTKLTVLG*(TPLGDTTHT)SGRSPDDELLYLPVRGRETYEML

LKIKESLELMQYLPQHTIETYRQQQQQHQHLLQKQGGSGGAPHHHHHH

P63- BIDE(LL) cDNA (hu3F8-scFv, *huC825-scFv*, huP63-tet, GS linker, (IgG3 spacer))
SEQ ID NO: 34

GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

-continued

```
GGTTCAGGCTATGGAACTGAGTTCACCTTCACCATTTCCAGCGTGCAGTCCGAAGACTTCGCA
GTGTACTTTTGCCAGCAGGATTATTCTAGTTTTGGGTGTGGTACAAAGCTGGAGATCAAAAGG
GGAGGAGGAGGTAGTGGCGGAGGAGGTTCAGGCGGAGGGGGTAGCGGCGGAGGGGGTTCTGGC
GGCGGCGGTAGTGGCGGCGGAGGTAGCCAGGTGCAGCTGGTCGAATCCGGCCCTGGAGTGGTC
CAGCCAGGCAGGTCTCTGCGGATCAGTTGCGCCGTGTCCGGATTCAGCGTCACCAACTACGGA
GTGCACTGGGTCAGACAGCCACCTGGCAAGTGTCTGGAGTGGCTGGGAGTGATCTGGGCAGGA
GGAATCACAAACTACAACTCAGCTTTTATGTCCCGCCTGACTATTAGCAAGGACAACTCTAAA
AATACCGTGTATCTGCAGATGAATTCTCTGCGAGCCGAAGATACCGCTATGTACTATTGTGCA
TCCCGTGGGGGTCATTACGGCTATGCCCTGGATTATTGGGGCAGGGTACCCTGGTGACAGTC
TCATCCGGAGGAGGAGGATCCGGAGGAGGAGGTAGCGGCGGAGGGGGTTCTGGCGGAGGGGGT
AGTCATGTGCAGCTGGTGGAAAGCGGAGGCGGCCTGGTGCAGCCTGGGGGATCTCTGAGACTG
TCTTGTGCCGCCAGCGGCTTCTCCCTGACCGATTATGGCGTGCACTGGGTGCGACAGGCCCCT
GGCAAAGGACTGGAATGGCTGGGAGTGATTTGGAGTGGCGGAGGCACCGCCTACAACACCGCC
CTGATCTCCCGGTTCACCATCAGCCGGGACAACTCCAAGAACACCCTGTACCTGCAGATGAAC
TCCCTGCGGGCCGAGGACACCGCTGTGTACTACTGCGCCAGACGGGGCTCCTACCCCTACAAC
TACTTCGACGCTTGGGGCTGCGGCACCCTCGTGACAGTGTCTAGCGGAGGGGGAGGTTCTGGG
GGCGGAGGTTCAGGTGGTGGTGGTTCCGGGGGTGGTGGCTCTGGTGGCGGTGGTTCTGGCGGT
GGCGGATCTCAGGCTGTCGTGACCCAGGAACCCAGCCTGACTGTGTCTCCTGGCGGAACCGTG
ACCCTGACCTGCGGATCTTCTACCGGCGCTGTGACCGCCAGCAACTACGCCAATTGGGTGCAG
CAGAAACCTGGACAGTGCCCTAGAGGCCTGATCGGCGGCCACAACAACAGACCTCCAGGCGTG
CCAGCCCGGTTCTCTGGATCTCTGCTGGGCGGAAAGGCCGCTCTGACACTGCTGGGTGCTCAG
CCTGAGGACGAGGCCGAGTACTACTGTGCCCTGTGGTACTCCGACCACTGGGTCATCGGAGGC
GGGACCAAGCTGACCGTGCTGGGA(ACACCCTGGGAGACACCACACATACT)AGTGGGAGAT
CCCCCGACGATGAGCTGCTGTACCTGCCTGTGAGGGGCCGGGAGACCTATGAAATGCTGCTGA
AGATCAAAGAGAGCCTGGAACTGATGCAGTACCTGCCACAGCACACCATTGAAACATATAGGC
AACAACAGCAGCAGCAGCATCAGCATCTGCTGCAGAAGCAGGGAGGGTCAGGAGGAGCACCGC
ACCATCATCATCACCAT
```

P73- BIDE(LL) polypeptide (hu3F8-scFv, *huC825-scFv*,
huP73-tet, GS linker, (IgG3 spacer))

SEQ ID NO: 35

EIVMTQTPATLSVSAGERVTITCKASQSVSNDVTWYQQKPGQAPRLLIYSASNRYSGVPARFS
GSGYGTEFTFTISSVQSEDFAVYFCQQDYSSFGCGTKLEIKRGGGGSGGGGSGGGGSGGGGSG
GGGSGGGGSQVQLVESGPGVVQPGRSLRISCAVSGFSVTNYGVHWVRQPPGKCLEWLGVIWAG
GITNYNSAFMSRLTISKDNSKNTVYLQMNSLRAEDTAMYYCASRGGHYGYALDYWGQGTLVTV
SSGGGGSGGGGSGGGGSGGGGSHVQLVESGGGLVQPGGSLRLSCAASGFSLTDYGVHWVRQAP
GKGLEWLGVIWSGGGTAYNTALISRFTISRDNSKNTLYLQMNSLRAEDTAVYYCARRGSYPYN
YFDAWGCGTLVTVSSGGGGSGGGGSGGGGSGGGGSGGGGSGGGGSQAVVTQEPSLTVSPGGTV
TLTCGSSTGAVTASNYANWVQQKPGQCPRGLIGGHNNRPPGVPARFSGSLLGGKAALTLLGAQ
PEDEAEYYCALWYSDHWVIGGGTKLTVLG(TPLGDTTHT)SGRHGDEDTYYLQVRGRENFEIL
MKLKESLELMELVPQPLVDSYRQQQQLLQRPGGSGGAPHHHHHH

-continued

**P73- BIDE(LL) cDNA (hu3F8-scFv, *huC825-scFv*, huP73-tet, GS linker, (IgG3 spacer))**

SEQ ID NO: 36

GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAAGG

<u>GGAGGAGGAGGTAGTGGCGGAGGAGGTTCAGGCGGAGGGGGTAGCGGCGGAGGGGGTTCTGGC</u>

<u>GGCGGCGGTAGTGGCGGCGGAGGTAGC</u>CAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGGCAGGGTACCCTGGTGACAGTC

TCATCC<u>GGAGGAGGAGGATCCGGAGGAGGAGGTAGCGGCGGAGGGGGTTCTGGCGGAGGGGGT</u>

<u>AGT</u>CATGTGCAGCTGGTGGAAAGCGGAGGCGGCCTGGTGCAGCCTGGGGGATCTCTGAGACTG

*TCTTGTGCCGCCAGCGGCTTCTCCCTGACCGATTATGGCGTGCACTGGGTGCGACAGGCCCCT*

*GGCAAAGGACTGGAATGGCTGGGAGTGATTTGGAGTGGCGGAGGCACCGCCTACAACACCGCC*

*CTGATCTCCCGGTTCACCATCAGCCGGGACAACTCCAAGAACACCCTGTACCTGCAGATGAAC*

*TCCCTGCGGGCCGAGGACACCGCTGTGTACTACTGCGCCAGACGGGGCTCCTACCCCTACAAC*

*TACTTCGACGCTTGGGGCTGCGGCACCCTCGTGACAGTGTCTAGC<u>GGAGGGGGAGGTTCTGGG</u>*

<u>*GGCGGAGGTTCAGGTGGTGGTGGTTCCGGGGGTGGTGGCTCTGGTGGCGGTGGTTCTGGCGGT*</u>

<u>*GGCGGATCT*</u>*CAGGCTGTCGTGACCCAGGAACCCAGCCTGACTGTGTCTCCTGGCGGAACCGTG*

*ACCCTGACCTGCGGATCTTCTACCGGCGCTGTGACCGCCAGCAACTACGCCAATTGGGTGCAG*

*CAGAAACCTGGACAGTGCCCTAGAGGCCTGATCGGCGGCCACAACAACAGACCTCCAGGCGTG*

*CCAGCCCGGTTCTCTGGATCTCTGCTGGGCGGAAAGGCCGCTCTGACACTGCTGGGTGCTCAG*

*CCTGAGGACGAGGCCGAGTACTACTGTGCCCTGTGGTACTCCGACCACTGGGTCATCGGAGGC*

*GGGACCAAGCTGACCGTGCTGGGA*(ACACCCTGGGAGACACCACACATACT)AGTGGGAGGC

ACGGCGACGAAGATACCTACTATCTGCAGGTGAGGGGACGGGAGAACTTCGAAATCCTGATGA

AGCTGAAAGAGTCCCTGGAACTGATGGAGCTGGTGCCCCAGCCTCTGGTCGACAGCTACAGAC

AGCAGCAGCAGCTGCTGCAGAGGCCAGGAGGGTCAGGAGGAGCACCGCACCATCATCATCACC

AT

**P53- mBIDE(noHIS) polypeptide (hu3F8-scFv, *C825-scFv*, huP53-tet, GS linker, (IgG3 spacer))**

SEQ ID NO: 37

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKR<u>GGGGSGGGGSGGGGS</u>QVQLVE

SGPGVVQPGRSLRISCAVSGFSVTNYGVHWVRQPPGKCLEWLGVIWAGGITNYNSAFMSRLTI

SKDNSKNTVYLQMNSLRAEDTAMYYCASRGGHYGYALDYWGQGTLVTVSS<u>SGGGGSGGGGSGGG</u>

<u>GSGGGGS</u>*HVKLQESGPGLVQPSQSLSLTCTVSGFSLTDYGVHWVRQSPGKGLEWLGVIWSGGG*

*TAYNTALISRLNIYRDNSKNQVFLEMNSLQAEDTAMYYCARRGSYPYNYFDAWGCGTTVTVSS*

<u>*GGGGSGGGGSGGGGS*</u>*QAVVIQESALTTPPGETVTLTCGSSTGAVTASNYANWVQEKPDHCFTG*

-continued

*LIGGHNNRPPGVPARFSGSLIGDKAALTIAGTQTEDEAIYFCALWYSDHWVIGGGTRLTVLG*

(TPLGDTTHT)SGKPEDGEYFTLQIRGRERFEMFRELNEALELKDAQAGKEPGGSGGA

P53- mBIDE(noHIS) cDNA (hu3F8-scFv, *C825-scFv*,
huP53-tet, GS linker, (IgG3 spacer))
SEQ ID NO: 38

GAAATCGTCATGACTCAGACTCCCGCAACCCTGTCAGTGTCCGCTGGGGAACGTGTCACTATT

ACCTGCAAGGCATCTCAGAGCGTGAGCAACGACGTGACCTGGTATCAGCAGAAGCCTGGCCAG

GCTCCACGACTGCTGATCTATTCCGCAAGCAATCGCTACTCCGGAGTGCCCGCACGATTCTCT

GGAAGTGGGTACGGTACCGAGTTCACTTTTACCATTTCCAGCGTGCAGAGCGAAGACTTCGCT

GTCTATTTTTGCCAGCAGGATTACTCTAGTTTTGGCTGTGGAACAAAGCTGGAGATCAAAAGG

GGAGGAGGAGGTTCTGGCGGAGGAGGTAGTGGCGGAGGGGGTTCACAGGTGCAGCTGGTCGAA

TCTGGGCCAGGCGTGGTCCAGCCAGGACGTTCCCTGAGGATTAGCTGCGCCGTGAGCGGGTTC

TCTGTCACAAACTACGGAGTGCACTGGGTCCGTCAGCCACCTGGCAAATGTCTGGAGTGGCTG

GGAGTGATCTGGGCAGGAGGAATCACTAACTACAACTCTGCTTTTATGAGTCGCCTGACCATC

TCAAAGGACAACTCCAAAAATACAGTGTACCTGCAGATGAATTCACTGCGGGCAGAAGATACC

GCCATGTACTATTGCGCCTCCAGGGGGGTCATTACGGCTATGCCCTGGACTATTGGGGCCAG

GGAACACTGGTGACTGTCTCATCCGGAGGAGGAGGATCCGGAGGAGGAGGTAGCGGCGGAGGG

GGTTCTGGCGGAGGGGGTAGT*CACGTGAAGCTGCAGGAAAGCGGCCCTGGACTGGTGCAGCCT*

*TCCCAGTCTCTGTCCCTGACCTGCACCGTGTCCGGCTTCTCCCTGACCGATTACGGCGTGCAC*

*TGGGTGCGACAGTCTCCAGGCAAGGGCCTGGAATGGCTGGGAGTGATTTGGAGCGGTGGCGGA*

*ACCGCCTACAACACCGCCCTGATCTCCCGGCTGAACATCTACCGGGACAACTCCAAGAACCAG*

*GTGTTCCTGGAAATGAACTCCCTGCAGGCAGAGGACACCGCCATGTACTACTGCGCCAGACGG*

*GGCTCCTACCCCTACAACTACTTCGACGCTTGGGGCTGCGGCACCACCGTGACAGTGTCTAGC*

*GGAGGTGGTGGATCTGGGGGCGGAGGTAGCGGAGGGGGAGGTTCTCAGGCTGTCGTGATCCAG*

*GAATCTGCCCTGACCACCCCCCCTGGCGAGACAGTGACACTGACCTGCGGATCTTCCACCGGC*

*GCTGTGACCGCCTCCAACTACGCCAACTGGGTGCAGGAAAAGCCCGACCACTGCTTCACCGGC*

*CTGATCGGCGGCCACAACAACAGACCTCCAGGCGTGCCAGCCCGGTTCTCCGGCTCTCTGATC*

*GGAGATAAGGCCGCCCTGACAATCGCCGGCACCCAGACAGAGGACGAGGCTATCTACTTCTGC*

*GCCCTGTGGTACAGCGACCACTGGGTCATCGGCGAGGCACCAGACTGACCGTGCTGGGA*(AC

ACCCCTGGGAGACACCACACATACT)AGTGGCAAACCTCTGGATGGAGAGTACTTTACCCTGC

AGATTAGAGGCCGCGAACGATTCGAGATGTTTCGCGAACTGAATGAGGCCCTGGAACTGAAGG

ATGCTCAGGCAGGCAAGGAACCAGGCGGTAGCGGCGGCGCA

P53- mBIDE polypeptide (hu3F8-scFv, *C825-scFv,* **huP53-
tet,** GS linker. (IgG3 spacer))
SEQ ID NO: 39

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSGGGGSG

GGGSGGGGSQVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SSGGGGSGGGGSGGGGSGGGGSHVKLQESGPGLVQPSQSLSLTCTVSGFSLTDYGVHWVRQSP

GKGLEWLGVIWSGGGTAYNTALISRLNIYRDNSKNQVFLEMNSLQAEDTAMYYCARRGSYPYN

YFDAWGCGTTVTVSSGGGGSGGGGSGGGGSQAVVIQESALTTPPGETVTLTCGSSTGAVTASN

-continued

YANWVQEKPDHCFTGLIGGHNNRPPGVPARFSGSLIGDKAALTIAGTQTEDEAIYFCALWYSD

HWVIGGGTRLTVLG(TPLGDTTHT)SGKPLDGEYFTLQIRGRERFEMFRELNEALELKDAQAG

KEPGGSGGAPHHHHHH

P53- mBIDE cDNA (hu3F8-scFv, *C825-scFv*, huP53-tet,
<u>GS linker</u>, (IgG3 spacer))
SEQ ID NO: 40
GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAAGG

<u>GGAGGAGGAGGTAGTGGCGGAGGAGGTTCAGGCGGAGGGGGTAGCGGCGGAGGGGGTTCTGGC</u>

<u>GGCGGCGGTAGTGGCGGCGGAGGTAGC</u>CAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGCAGGGTACCCTGGTGACAGTC

TCATCC<u>GGCGGAGGGGGATCCGGAGGAGGAGGTAGCGGCGGAGGGGGTTCTGGCGGAGGGGT</u>

<u>AGT</u>CACGTGAAGCTGCAGGAAAGCGGCCCTGGACTGGTGCAGCCTTCCCAGTCTCTGTCCCTG

*ACCTGCACCGTGTCCGGCTTCTCCCTGACCGATTACGGCGTGCACTGGGTGCGACAGTCTCCA*

*GGCAAGGGCCTGGAATGGCTGGGAGTGATTTGGAGCGGTGGCGGAACCGCCTACAACACCGCC*

*CTGATCTCCCGGCTGAACATCTACCGGGACAACTCCAAGAACCAGGTGTTCCTGGAAATGAAC*

*TCCCTGCAGGCAGAGGACACCGCCATGTACTACTGCGCCAGACGGGGCTCCTACCCCTACAAC*

*TACTTCGACGCTTGGGGCTGCGGCACCACCGTGACAGTGTCTAGC<u>GGAGGTGGTGGATCTGGG</u>*

<u>*GGCGGAGGTAGCGGAGGGGGAGGTTCT*</u>*CAGGCTGTCGTGATCCAGGAATCTGCCCTGACCACC*

*CCCCCTGGCGAGACAGTGACACTGACCTGCGGATCTTCCACCGGCGCTGTGACCGCCTCCAAC*

*TACGCCAACTGGGTGCAGGAAAAGCCCGACCACTGCTTCACCGGCCTGATCGGCGGCCACAAC*

*AACAGACCTCCAGGCGTGCCAGCCCGGTTCTCCGGCTCTCTGATCGGAGATAAGGCCGCCCTG*

*ACAATCGCCGGCACCCAGACAGAGGACGAGGCTATCTACTTCTGCGCCCTGTGGTACAGCGAC*

*CACTGGGTCATCGGCGGAGGCACCAGACTGACCGTGCTGGGA*(ACACCCCTGGGAGACACCAC

ACATACT)AGTGGGAAACCTCTGGATGGCGAGTACTTTACCCTGCAGATTAGAGGCCGCGAAC

GATTCGAGATGTTTCGCGAACTGAATGAGGCCCTGGAACTGAAGGATGCTCAGGCAGGCAAGG

AGCCAGGAGGGTCAGGAGGAGCACCGCACCATCATCATCACCAT

P63- mBIDE polypeptide (hu3F8-scFv, *C825-scFv*,
huP63-tet, <u>GS linker</u>. (IgG3 spacer))
SEQ ID NO: 41
EIVMTQTPATLSVSAGERVTITCKASQSVSNDVTWYQQKPGQAPRLLIYSASNRYSGVPARFS GSGYGTEFTFTISSVQSEDFAVYFCQQDYSSFGCGTKLEIKR<u>GGGGSGGGGSGGGGS</u>ggggsg gggsggggsQVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SS<u>GGGGSGGGGSGGGGS</u>ggggsHVKLQESGPGLVQPSQSLSLTCTVSGFSLTDYGVHWVRQSP

GKGLEWLGVIWSGGGTAYNTALISRLNIYRDNSKNQVFLEMNSLQAEDTAMYYCARRGSYPYN

-continued

YFDAWGCGTTVTVSSGGGGSGGGGSGGGGSQAVVIQESALTTPPGETVTLTCGSSTGAVTASN

YANWVQEKPDHCFTGLIGGHNNRPPGVPARFSGSLIGDKAALTIAGTQTEDEAIYFCALWYSD

HWVIGGGTRLTVLG(TPLGDTTHT)SGRSPDDELLYLPVRGRETYEMLLKIKESLELMQYLPQ

HTIETYRQQQQQQHQHLLQKQGGSGGAPHHHHHH

P63- mBIDE cDNA (hu3F8-scFv, *C825-scFv*, huP63-tet, GS linker, (IgG3 spacer))
SEQ ID NO: 42

GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAGG

GGAGGAGGAGGTAGTGGCGGAGGAGGTTCAGGCGGAGGGGGTAGCGGCGGAGGGGGTTCTGGC

GGCGGCGGTAGTGGCGGCGGAGGTAGCCAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGCAGGGTACCCTGGTGACAGTC

TCATCCGGAGGAGGAGGATCCGGAGGAGGAGGTAGCGGCGGAGGGGGTTCTGGCGGAGGGGGT

AGTCACGTGAAGCTGCAGGAAAGCGGCCCTGGACTGGTGCAGCCTTCCCAGTCTCTGTCCCTG

*ACCTGCACCGTGTCCGGCTTCTCCCTGACCGATTACGGCGTGCACTGGGTGCGACAGTCTCCA*

*GGCAAGGGCCTGGAATGGCTGGGAGTGATTTGGAGCGGTGGCGGAACCGCCTACAACACCGCC*

*CTGATCTCCCGGCTGAACATCTACCGGGACAACTCCAAGAACCAGGTGTTCCTGGAAATGAAC*

*TCCCTGCAGGCAGAGGACACCGCCATGTACTACTGCGCCAGACGGGGCTCCTACCCCTACAAC*

*TACTTCGACGCTTGGGGCTGCGGCACCACCGTGACAGTGTCTAGC*GGAGGTGGTGGATCTGGG

GGCGGAGGTAGCGGAGGGGGAGGTTCTCAGGCTGTCGTGATCCAGGAATCTGCCCTGACCACC

CCCCCTGGCGAGACAGTGACACTGACCTGCGGATCTTCCACCGGCGCTGTGACCGCCTCCAAC

TACGCCAACTGGGTGCAGGAAAAGCCCGACCACTGCTTCACCGGCCTGATCGGCGGCCACAAC

AACAGACCTCCAGGCGTGCCAGCCCGGTTCTCCGGCTCTCTGATCGGAGATAAGGCCGCCCTG

ACAATCGCCGGCACCCAGACAGAGGACGAGGCTATCTACTTCTGCGCCCTGTGGTACAGCGAC

CACTGGGTCATCGGCGGAGGCACCAGACTGACCGTGCTGGGA(ACACCCCTGGGAGACACCAC

ACATACT)AGTGGGAGATCCCCCGACGATGAGCTGCTGTACCTGCCTGTGAGGGGCCGGGAGA

CCTATGAAATGCTGCTGAAGATCAAAGAGAGCCTGGAACTGATGCAGTACCTGCCACAGCACA

CCATTGAAACATATAGGCAACAACAGCAGCAGCAGCATCAGCATCTGCTGCAGAAGCAGGGAG

GGTCAGGAGGAGCACCGCACCATCATCATCACCATT

P73- mBIDE polypeptide (hu3F8-scFv, *C825-scFv*, huP73-tet, GS linker, (IgG3 spacer))
SEQ ID NO: 43

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSGGGGSG

GGGSGGGGSQVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SSGGGGSGGGGSGGGGSGGGGS*HVKLQESGPGLVQPSQSLSLTCTVSGFSLTDYGVHWVRQSP*

-continued

*GKGLEWLGVIWSGGGTAYNTALISRLNIYRDNSKNQVFLEMNSLQAEDTAMYYCARRGSYPYN*

*YFDAWGCGTTVTVSS*<u>*GGGGSGGGGSGGGGS*</u>*QAVVIQESALTTPPGETVTLTCGSSTGAVTASN*

*YANWVQEKPDHCFTGLIGGHNNRPPGVPARFSGSLIGDKAALTIAGTQTEDEAIYFCALWYSD*

*HWVIGGGTRLTVLG*(TPLGDTTHT)SGRHGDEDTYYLQVRGRENFEILMKLKESLELMELVPQ

PLVDSYRQQQQLLQRPGGSGGAPHHHHHH

P73- mBIDE cDNA (hu3F8-scFv, *C825-scFv,* **huP73-
tet,** <u>GS linker</u>, (IgG3 spacer))
SEQ ID NO: 44

GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAAGG

<u>GGAGGAGGAGGTAGTGGCGGAGGAGGTTCAGGCGGAGGGGGTAGCGGCGGAGGGGGTTCTGGC</u>

<u>GGCGGCGGTAGTGGCGGCGGAGGTAGC</u>CAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGCAGGGTACCCTGGTGACAGTC

TCATCC<u>GGAGGAGGAGGATCCGGAGGAGGAGGTAGCGGCGGAGGGGGTTCTGGCGGAGGGGGT</u>

<u>AGT</u>CACGTGAAGCTGCAGGAAAGCGGCCCTGGACTGGTGCAGCCTTCCCAGTCTCTGTCCCTG

ACCTGCACCGTGTCCGGCTTCTCCCTGACCGATTACGGCGTGCACTGGGTGCGACAGTCTCCA

GGCAAGGGCCTGGAATGGCTGGGAGTGATTTGGAGCGGTGGCGGAACCGCCTACAACACCGCC

CTGATCTCCCGGCTGAACATCTACCGGGACAACTCCAAGAACCAGGTGTTCCTGGAAATGAAC

TCCCTGCAGGCAGAGGACACCGCCATGTACTACTGCGCCAGACGGGGCTCCTACCCCTACAAC

TACTTCGACGCTTGGGGCTGCGGCACCACCGTGACAGTGTCTAGC<u>GGAGGTGGTGGATCTGGG</u>

<u>GGCGGAGGTAGCGGAGGGGGAGGTTCT</u>CAGGCTGTCGTGATCCAGGAATCTGCCCTGACCACC

CCCCCTGGCGAGACAGTGACACTGACCTGCGGATCTTCCACCGGCGCTGTGACCGCCTCCAAC

TACGCCAACTGGGTGCAGGAAAAGCCCGACCACTGCTTCACCGGCCTGATCGGCGGCCACAAC

AACAGACCTCCAGGCGTGCCAGCCCGGTTCTCCGGCTCTCTGATCGGAGATAAGGCCGCCCTG

ACAATCGCCGGCACCCAGACAGAGGACGAGGCTATCTACTTCTGCGCCCTGTGGTACAGCGAC

CACTGGGTCATCGGCGGAGGCACCAGACTGACCGTGCTGGGA(ACACCCCTGGGAGACACCAC

ACATACT)AGTGGGAGGCACGGCGACGAAGATACCTACTATCTGCAGGTGAGGGGACGGGAGA

ACTTCGAAATCCTGATGAAGCTGAAAGAGTCCCTGGAACTGATGGAGCTGGTGCCCCAGCCTC

TGGTCGACAGCTACAGACAGCAGCAGCAGCTGCTGCAGAGGCCAGGAGGGTCAGGAGGAGCAC

CGCACCATCATCATCACCAT

P73- mBIDE(SL) polypeptide (hu3F8-scFv, C825-
scFv, huP53-tet, <u>GS linker</u>, (IgG3 spacer))
SEQ ID NO: 45
EIVMTQTPATLSVSAGERVTITCKASQSVSNDVTWYQQKPGQAPRLLIYSASNRYSGVPARFS GSGYGTEFTFTISSVQSEDFAVYFCQQDYSSFGCGTKLEIKR<u>GGGGSGGGGSGGGGS</u>QVQLVE

SGPGVVQPGRSLRISCAVSGFSVTNYGVHWVRQPPGKCLEWLGVIWAGGITNYNSAFMSRLTI

-continued

SKDNSKNTVYLQMNSLRAEDTAMYYCASRGGHYGYALDYWGQTLVTVSS<u>GGGGSGGGGSGGG</u>

<u>GSGGGGS</u>HVKLQESGPGLVQPSQSLSLTCTVSGFSLTDYGVHWVRQSPGKGLEWLGVIWSGGG

TAYNTALISRLNIYRDNSKNQVFLEMNSLQAEDTAMYYCARRGSYPYNYFDAWGCGTTVTFSS

<u>GGGGSGGGGSGGGGS</u>QAVVIQESALTTPPGETVTLTCGSSTGAVTASNYANWVQEKPDHCFTG

LIGGHNNRPPGVPARFSGSLIGDKAALTIAGTQTEDEAIYFCALWYSDHWVIGGGTRLTVLG (TPLGDTTHT)SGKPLDGEYFTLQIRGRERFEMFRELNEALELKDAQAGKEPGGSGGAPHHHH

HH

P53- mBIDE(SL) cDNA (hu3F8-scFv, *C825-scFv*, huP53-tet, <u>GS linker</u>, (IgG3 spacer))
SEQ ID NO: 46

GAAATCGTCATGACTCAGACTCCCGCAACCCTGTCAGTGTCCGCTGGGGAACGTGTCACTATT

ACCTGCAAGGCATCTCAGAGCGTGAGCAACGACGTGACCTGGTATCAGCAGAAGCCTGGCCAG

GCTCCACGACTGCTGATCTATTCCGCAAGCAATCGCTACTCCGGAGTGCCCGCACGATTCTCT

GGAAGTGGGTACGGTACCGAGTTCACTTTTACCATTTCCAGCGTGCAGAGCGAAGACTTCGCT

GTCTATTTTTGCCAGCAGGATTACTCTAGTTTTGGCTGTGGAACAAAGCTGGAGATCAAAAGG

<u>GGAGGAGGAGGTTCTGGCGGAGGAGGTAGTGGCGGAGGGGGTTC</u>ACAGGTGCAGCTGGTCGAA

TCTGGGCCAGGCGTGGTCCAGCCAGGACGTTCCCTGAGGATTAGCTGCGCCGTGAGCGGGTTC

TCTGTCACAAACTACGGAGTGCACTGGGTCCGTCAGCCACCTGGCAAATGTCTGGAGTGGCTG

GGAGTGATCTGGGCAGGAGGAATCACTAACTACAACTCTGCTTTTATGAGTCGCCTGACCATC

TCAAAGGACAACTCCAAAAATACAGTGTACCTGCAGATGAATTCACTGCGGGCAGAAGATACC

GCCATGTACTATTGCGCCTCCAGGGGGGTCATTACGGCTATGCCCTGGACTATTGGGGCCAG

GGAACACTGGTGACTGTCTCATCC<u>GGAGGAGGAGGATCCGGAGGAGGAGGTAGCGGCGGAGGG</u>

<u>GGTTCTGGCGGAGGGGGTAGT</u>*CACGTGAAGCTGCAGGAAAGCGGCCCTGGACTGGTGCAGCCT*

*TCCCAGTCTCTGTCCCTGACCTGCACCGTGTCCGGCTTCTCCCTGACCGATTACGGCGTGCAC*

*TGGGTGCGACAGTCTCCAGGCAAGGGCCTGGAATGGCTGGGAGTGATTTGGAGCGGTGGCGGA*

*ACCGCCTACAACACCGCCCTGATCTCCCGGCTGAACATCTACCGGGACAACTCCAAGAACCAG*

*GTGTTCCTGGAAATGAACTCCCTGCAGGCAGAGGACACCGCCATGTACTACTGCGCCAGACGG*

*GGCTCCTACCCCTACAACTACTTCGACGCTTGGGGCTGCGGCACCACCGTGACAGTGTCTAGC*

<u>*GGAGGTGGTGGATCTGGGGGCGGAGGTAGCGGAGGGGGAGGTTCT*</u>*CAGGCTGTCGTGATCCAG*

*GAATCTGCCCTGACCACCCCCCCTGGCGAGACAGTGACACTGACCTGCGGATCTTCCACCGGC*

*GCTGTGACCGCCTCCAACTACGCCAACTGGGTGCAGGAAAAGCCCGACCACTGCTTCACCGGC*

*CTGATCGGCGGCCACAACAACAGACCTCCAGGCGTGCCAGCCCGGTTCTCCGGCTCTCTGATC*

*GGAGATAAGGCCGCCCTGACAATCGCCGGCACCCAGACAGAGGACGAGGCTATCTACTTCTGC*

*GCCCTGTGGTACAGCGACCACTGGGTCATCGGCGGAGGCACCAGACTGACCGTGCTGGGA*(AC

ACCCCTGGGAGACACCACACATACT)AGTGGGAAACCTCTGGATGGCGAGTACTTTACCCTGC

AGATTAGAGGCCGCGAACGATTCGAGATGTTTCGCGAACTGAATGAGGCCCTGGAACTGAAGG

ATGCTCAGGCAGGCAAGGAGCCAGGAGGGTCAGGAGGAGCACCGCACCATCATCATCACCAT

P63- mBIDE(SL) polypeptide (hu3F8-scFv, *C825-scFv*,
huP63-tet, <u>GS linker</u>, (IgG3 spacer))
SEQ ID NO: 47

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKR<u>GGGGSGGGGSGGGGS</u>QVQLVE

SGPGVVQPGRSLRISCAVSGFSVTNYGVHWVRQPPGKCLEWLGVIWAGGITNYNSAFMSRLTI

SKDNSKNTVYLQMNSLRAEDTAMYYCASRGGHYGYALDYWGQTLVTVSS<u>GGGGSGGGGSGGG</u>

-continued

GSGGGGS*HVKLQESGPGLVQPSQSLSLTCTVSGFSLTDYGVHWVRQSPGKGLEWLGVIWSGGG*

*TAYNTALISRLNIYRDNSKNQVFLEMNSLQAEDTAMYYCARRGSYPYNYFDAWGCGTTVTVSS*

*GGGGSGGGGSGGGGS*QAVVIQESALTTPPGETVTLTCGSSTGAVTASNYANWVQEKPDHCFTG

LIGGHNNRPPGVPARFSGSLIGDKAALTIAGTQTEDEAIYFCALWYSDHWVIGGGTRLTVLG (TPLGDTTHT)SGRSPDDELLYLPVRGRETYEMLLKIKESLELMQYLPQHTIETYRQQQQQQH

QHLLQKQGGSGGAPHHHHHH

P63- mBIDE(SL) cDNA (hu3F8-scFv, *C825-scFv*, huP63-tet, GS linker, (IgG3 spacer))
SEQ ID NO: 48

GAAATCGTCATGACTCAGACTCCCGCAACCCTGTCAGTGTCCGCTGGGGAACGTGTCACTATT

ACCTGCAAGGCATCTCAGAGCGTGAGCAACGACGTGACCTGGTATCAGCAGAAGCCTGGCCAG

GCTCCACGACTGCTGATCTATTCCGCAAGCAATCGCTACTCCGGAGTGCCCGCACGATTCTCT

GGAAGTGGGTACGGTACCGAGTTCACTTTTACCATTTCCAGCGTGCAGAGCGAAGACTTCGCT

GTCTATTTTTGCCAGCAGGATTACTCTAGTTTTGGCTGTGGAACAAAGCTGGAGATCAAAAGG

GGAGGAGGAGGTTCTGGCGGAGGAGGTAGTGGCGGAGGGGGTTCACAGGTGCAGCTGGTCGAA

TCTGGGCCAGGCGTGGTCCAGCCAGGACGTTCCCTGAGGATTAGCTGCGCCGTGAGCGGGTTC

TCTGTCACAAACTACGGAGTGCACTGGGTCCGTCAGCCACCTGGCAAATGTCTGGAGTGGCTG

GGAGTGATCTGGGCAGGAGGAATCACTAACTACAACTCTGCTTTTATGAGTCGCCTGACCATC

TCAAAGGACAACTCCAAAAATACAGTGTACCTGCAGATGAATTCACTGCGGGCAGAAGATACC

GCCATGTACTATTGCGCCTCCAGGGGGGTCATTACGGCTATGCCCTGGACTATTGGGGCCAG

GGAACACTGGTGACTGTCTCATCCGGAGGAGGAGGATCCGGAGGAGGAGGTAGCGGCGGAGGG

GGTTCTGGCGGAGGGGGTAGT*CACGTGAAGCTGCAGGAAAGCGGCCCTGGACTGGTGCAGCCT*

*TCCCAGTCTCTGTCCCTGACCTGCACCGTGTCCGGCTTCTCCCTGACCGATTACGGCGTGCAC*

*TGGGTGCGACAGTCTCCAGGCAAGGGCCTGGAATGGCTGGGAGTGATTTGGAGCGGTGGCGGA*

*ACCGCCTACAACACCGCCCTGATCTCCCGGCTGAACATCTACCGGGACAACTCCAAGAACCAG*

*GTGTTCCTGGAAATGAACTCCCTGCAGGCAGAGGACACCGCCATGTACTACTGCGCCAGACGG*

*GGCTCCTACCCCTACAACTACTTCGACGCTTGGGGCTGCGGCACCACCGTGACAGTGTCTAGC*

*GGAGGTGGTGGATCTGGGGGCGGAGGTAGCGGAGGGGGAGGTTCT*CAGGCTGTCGTGATCCAG

GAATCTGCCCTGACCACCCCCCCTGGCGAGACAGTGACACTGACCTGCGGATCTTCCACCGGC

GCTGTGACCGCCTCCAACTACGCCAACTGGGTGCAGGAAAAGCCCGACCACTGCTTCACCGGC

CTGATCGGCGGCCACAACAACAGACCTCCAGGCGTGCCAGCCCGGTTCTCCGGCTCTCTGATC

GGAGATAAGGCCGCCCTGACAATCGCCGGCACCCAGACAGAGGACGAGGCTATCTACTTCTGC

GCCCTGTGGTACAGCGACCACTGGGTCATCGGCGGAGGCACCAGACTGACCGTGCTGGGA(AC

ACCCCTGGGAGACACCACACATACT)AGTGGGAGATCCCCCGACGATGAGCTGCTGTACCTGC

CTGTGAGGGGCCGGGAGACCTATGAAATGCTGCTGAAGATCAAAGAGAGCCTGGAACTGATGC

AGTACCTGCCACAGCACACCATTGAAACATATAGGCAACAACAGCAGCAGCAGCATCAGCATC

TGCTGCAGAAGCAGGGAGGGTCAGGAGGAGCACCGCACCATCATCATCACCATT

P73- mBIDE(SL) polypeptide (hu3F8-scFv, *C825-scFv*,
huP73-tet, GS linker, (IgG3 spacer))
SEQ ID NO: 49

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKRGGGGSGGGGSGGGGSQVQLVE

SGPGVVQPGRSLRISCAVSGFSVTNYGVHWVRQPPGKCLEWLGVIWAGGITNYNSAFMSRLTI

-continued

SKDNSKNTVYLQMNSLRAEDTAMYYCASRGGHYGYALDYWGQTLVTVSS<u>GGGGSGGGGSGGG</u>
<u>GSGGGGS</u>HVKLQESGPGLVQPSQSLSLTCTVSGFSLTDYGVHWVRQSPGKGLEWLGVIWSGGG
TAYNTALISRLNIYRDNSKNQVFLEMNSLQAEDTAMYYCARRGSYPYNYFDAWGCGTTVTVSS
<u>GGGGSGGGGSGGGGS</u>QAVVIQESALTTPPGETVTLTCGSSTGAVTASNYANWVQEKPDHCFTG
LIGGHNNRPPGVPARFSGSLIGDKAALTIAGTQTEDEAIYFCALWYSDHWVIGGGTRLTVLG
(TPLGDTTHT)SGRHGDEDTYYLQVRGRENFEILMKLKESLELMELVPQPLVDSYRQQQQLLQ
RPGGSGGAPHHHHHH

**P73- mBIDE(SL) cDNA (hu3F8-scFv, *C825-scFv*, huP73-**
tet, <u>GS linker</u>, (IgG3 spacer))
                                                 SEQ ID NO: 50
GAAATCGTCATGACTCAGACTCCCGCAACCCTGTCAGTGTCCGCTGGGGAACGTGTCACTATT
ACCTGCAAGGCATCTCAGAGCGTGAGCAACGACGTGACCTGGTATCAGCAGAAGCCTGGCCAG
GCTCCACGACTGCTGATCTATTCCGCAAGCAATCGCTACTCCGGAGTGCCCGCACGATTCTCT
GGAAGTGGGTACGGTACCGAGTTCACTTTTACCATTTCCAGCGTGCAGAGCGAAGACTTCGCT
GTCTATTTTTGCCAGCAGGATTACTCTAGTTTTGGCTGTGGAACAAAGCTGGAGATCAAAAGG
<u>GGAGGAGGAGGTTCTGGCGGAGGAGGTAGTGGCGGAGGGGGTT</u>CACAGGTGCAGCTGGTCGAA
TCTGGGCCAGGCGTGGTCCAGCCAGGACGTTCCCTGAGGATTAGCTGCGCCGTGAGCGGGTTC
TCTGTCACAAACTACGGAGTGCACTGGGTCCGTCAGCCACCTGGCAAATGTCTGGAGTGGCTG
GGAGTGATCTGGGCAGGAGGAATCACTAACTACAACTCTGCTTTTATGAGTCGCCTGACCATC
TCAAAGGACAACTCCAAAAATACAGTGTACCTGCAGATGAATTCACTGCGGGCAGAAGATACC
GCCATGTACTATTGCGCCTCCAGGGGGGTCATTACGGCTATGCCCTGGACTATTGGGGCCAG
GGAACACTGGTGACTGTCTCATCC<u>GGAGGAGGAGGATCCGGAGGAGGAGGTAGCGGCGGAGGG</u>
<u>GGTTCTGGCGGAGGGGGTAGT</u>*CACGTGAAGCTGCAGGAAAGCGGCCCTGGACTGGTGCAGCCT*
*TCCCAGTCTCTGTCCCTGACCTGCACCGTGTCCGGCTTCTCCCTGACCGATTACGGCGTGCAC*
*TGGGTGCGACAGTCTCCAGGCAAGGGCCTGGAATGGCTGGGAGTGATTTGGAGCGGTGGCGGA*
*ACCGCCTACAACACCGCCCTGATCTCCCGGCTGAACATCTACCGGGACAACTCCAAGAACCAG*
*GTGTTCCTGGAAATGAACTCCCTGCAGGCAGAGGACACCGCCATGTACTACTGCGCCAGACGG*
*GGCTCCTACCCCTACAACTACTTCGACGCTTGGGGCTGCGGCACCACCGTGACAGTGTCTAGC*
<u>*GGAGGTGGTGGATCTGGGGGCGGAGGTAGCGGAGGGGGAGGTTCT*</u>*CAGGCTGTCGTGATCCAG*
*GAATCTGCCCTGACCACCCCCCCTGGCGAGACAGTGACACTGACCTGCGGATCTTCCACCGGC*
*GCTGTGACCGCCTCCAACTACGCCAACTGGGTGCAGGAAAAGCCCGACCACTGCTTCACCGGC*
*CTGATCGGCGGCCACAACAACAGACCTCCAGGCGTGCCAGCCCGGTTCTCCGGCTCTCTGATC*
*GGAGATAAGGCCGCCCTGACAATCGCCGGCACCCAGACAGAGGACGAGGCTATCTACTTCTGC*
*GCCCTGTGGTACAGCGACCACTGGGTCATCGGCGGAGGCACCAGACTGACCGTGCTGGGA*(AC
ACCCCTGGGAGACACCACACATACT)AGTGGGAGGCACGGCGACGAAGATACCTACTATCTGC
AGGTGAGGGGACGGGAGAACTTCGAAATCCTGATGAAGCTGAAAGAGTCCCTGGAACTGATGG
AGCTGGTGCCCCAGCCTCTGGTCGACAGCTACAGACAGCAGCAGCAGCTGCTGCAGAGGCCAG
GAGGGTCAGGAGGAGCACCGCACCATCATCATCACCAT P53- mBIDE(LL) polypeptide (hu3F8-scFv, C825-
scFv, huP53-tet, <u>GS linker</u>, (IgG3 spacer))
                                                 SEQ ID NO: 51
EIVMTQTPATLSVSAGERVTITCKASQSVSNDVTWYQQKPGQAPRLLIYSASNRYSGVPARFS
GSGYGTEFTFTISSVQSEDFAVYFCQQDYSSFGCGTKLEIKR<u>GGGGSGGGGSGGGGSGGGGSG</u>
<u>GGGSGGGGS</u>QVQLVESGPGVVQPGRSLRISCAVSGFSVTNYGVHWVRQPPGKCLEWLGVIWAG -continued GITNYNSAFMSRLTISKDNSKNTVYLQMNSLRAEDTAMYYCASRGGHYGYALDYWGQGTLVTV
SS<u>GGGGSGGGGSGGGGSGGGGS</u>HVKLQESGPGLVQPSQSLSLTCTVSGFSLTDYGVHWVRQSP
GKGLEWLGVIWSGGGTAYNTALISRLNIYRDNSKNQVFLEMNSLQAEDTAMYYCARRGSYPYN
YFDAWGCGTTVTVS<u>SGGGGSGGGGSGGGGSGGGGSGGGGSGGGGS</u>QAVVIQESALTTPPGETV
TLTCGSSTGAVTASNYANWVQEKPDHCFTGLIGGHNNRPPGVPARFSGSLIGDKAALTIAGTQ
TEDEAIYFCALWYSDHWVIGGGTRLTVLG(TPLGDTTHT)SGKPLDGEYFTLQIRGRERFEMF
RELNEALELKDAQAGKEPGGSGGAPHHHHHH P53- mBIDE(LL) cDNA (hu3F8-scFv, *C825-scFv*, **huP53-
tet**, <u>GS linker</u>, (IgG3 spacer))

SEQ ID NO: 52
GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAAGG

<u>GGAGGAGGAGGTAGTGGCGGAGGAGGTTCAGGCGGAGGGGGTAGCGGCGGAGGGGGTTCTGGC</u>

<u>GGCGGCGGTAGTGGCGGCGGAGGTAGC</u>CAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGCAGGGTACCCTGGTGACAGTC

TCATCC<u>GGCGGAGGGGGATCCGGCGGCGGAGGATCTGGCGGAGGTGGAAGTGGGGGAGGCGGA</u>

<u>TCT</u>CACGTGAAGCTGCAGGAAAGCGGCCCTGGACTGGTGCAGCCTTCCCAGTCTCTGTCCCTG

*ACCTGCACCGTGTCCGGCTTCTCCCTGACCGATTACGGCGTGCACTGGGTGCGACAGTCTCCA*

*GGCAAGGGCCTGGAATGGCTGGGAGTGATTTGGAGCGGTGGCGGAACCGCCTACAACACCGCC*

*CTGATCTCCCGGCTGAACATCTACCGGGACAACTCCAAGAACCAGGTGTTCCTGGAAATGAAC*

*TCCCTGCAGGCAGAGGACACCGCCATGTACTACTGCGCCAGACGGGGCTCCTACCCCTACAAC*

*TACTTCGACGCTTGGGGCTGCGGCACCACCGTGACAGTGTCTAGC<u>GGAGGTGGTGGATCTGGG</u>*

<u>GGCGGAGGTAGCGGAGGGGGAGGTTCTGGAGGTGGTGGATCTGGGGGCGGAGGTAGCGGAGGG</u>

<u>GGAGGTTCT</u>CAGGCTGTCGTGATCCAGGAATCTGCCCTGACCACCCCCCCTGGCGAGACAGTG

*ACACTGACCTGCGGATCTTCCACCGGCGCTGTGACCGCCTCCAACTACGCCAACTGGGTGCAG*

*GAAAAGCCCGACCACTGCTTCACCGGCCTGATCGGCGGCCACAACAACAGACCTCCAGGCGTG*

*CCAGCCCGGTTCTCCGGCTCTCTGATCGGAGATAAGGCCGCCCTGACAATCGCCGGCACCCAG*

*ACAGAGGACGAGGCTATCTACTTCTGCGCCCTGTGGTACAGCGACCACTGGGTCATCGGCGGA*

*GGCACCAGACTGACCGTGCTGGGA*(ACACCCCGGGAGACACCACACATACT)AGTGGGAAAC
CTCTGGATGGCGAGTACTTTACCCTGCAGATTAGAGGCCGCGAACGATTCGAGATGTTTCGC
AACTGAATGAGGCCCTGGAACTGAAGGATGCTCAGGCAGGCAAGGAGCCAGGAGGGTCAGGAG

GAGCACCGCACCATCATCATCACCAT

-continued

**P63- mBIDE(LL) polypeptide (hu3F8-scFv, *C825-scFv*, huP63-tet, GS linker, (IgG3 spacer))**

SEQ ID NO: 53

EIVMTQTPATLSVSAGERVTITCKASQSVSNDVTWYQQKPGQAPRLLIYSASNRYSGVPARFS
GSGYGTEFTFTISSVQSEDFAVYFCQQDYSSFGCGTKLEIKRGGGGSGGGGSGGGGSGGGGSG
GGGSGGGGSQVQLVESGPGVVQPGRSLRISCAVSGFSVTNYGVHWVRQPPGKCLEWLGVIWAG
GITNYNSAFMSRLTISKDNSKNTVYLQMNSLRAEDTAMYYCASRGGHYGYALDYWGQGTLVTV
SS*GGGGSGGGGSGGGGSGGGGSHVKLQESGPGLVQPSQSLSLTCTVSGFSLTDYGVHWVRQSP
GKGLEWLGVIWSGGGTAYNTALISRLNIYRDNSKNQVFLEMNSLQAEDTAMYYCARRGSYPYN
YFDAWGCGTTVTVSSGGGGSGGGGSGGGGSGGGGSGGGGSGGGGSQAVVIQESALTTPPGETV
TLTCGSSTGAVTASNYANWVQEKPDHCFTGLIGGHNNRPPGVPARFSGSLIGDKAALTIAGTQ
TEDEAIYFCALWYSDHWVIGGGTRLTVLG*(TPLGDTTHT)SG**RSPDDELLYLPVRGRETYEML
LKIKESLELMQYLPQHTIETYRQQQQQQHQHLLQKQ**GGSGGAPHHHHHH

**P63- mBIDE(LL) cDNA (hu3F8-scFv, *C825-scFv*, huP63-tet, GS linker, (IgG3 spacer))**

SEQ ID NO: 54

GAGATCGTGATGACCCAGACACCCGCAACACTGAGCGTGTCTGCCGGCGAAAGGGTCACTATT
ACCTGCAAGGCCAGTCAGTCAGTGTCCAACGACGTGACTTGGTACCAGCAGAAACCAGGCCAG
GCTCCCCGGCTGCTGATCTACAGCGCATCTAATAGATATAGCGGAGTGCCTGCTCGCTTCAGT
GGTTCAGGCTATGGAACTGAGTTCACCTTCACCATTTCCAGCGTGCAGTCCGAAGACTTCGCA
GTGTACTTTTGCCAGCAGGATTATTCTAGTTTTGGGTGTGGTACAAAGCTGGAGATCAAAGG
GGAGGAGGAGGTAGTGGCGGAGGAGGTTCAGGCGGAGGGGGTAGCGGCGGAGGGGGTTCTGGC
GGCGGCGGTAGTGGCGGCGAGGTAGCCAGGTGCAGCTGGTCGAATCCGGCCCTGGAGTGGTC
CAGCCAGGCAGGTCTCTGCGGATCAGTTGCGCCGTGTCCGGATTCAGCGTCACCAACTACGGA
GTGCACTGGGTCAGACAGCCACCTGGCAAGTGTCTGGAGTGGCTGGGAGTGATCTGGGCAGGA
GGAATCACAAACTACAACTCAGCTTTTATGTCCCGCCTGACTATTAGCAAGGACAACTCTAAA
AATACCGTGTATCTGCAGATGAATTCTCTGCGAGCCGAAGATACCGCTATGTACTATTGTGCA
TCCCGTGGGGGTCATTACGGCTATGCCCTGGATTATTGGGGCAGGGTACCCTGGTGACAGTC
TCATCC*GGAGGAGGAGGATCCGGAGGAGGAGGTAGCGGCGGAGGGGGTTCTGGCGGAGGGGT
AGT*CACGTGAAGCTGCAGGAAAGCGGCCCTGGACTGGTGCAGCCTTCCCAGTCTCTGTCCCTG
ACCTGCACCGTGTCCGGCTTCTCCCTGACCGATTACGGCGTGCACTGGGTGCGACAGTCTCCA
GGCAAGGGCCTGGAATGGCTGGGAGTGATTTGGAGCGGTGGCGGAACCGCCTACAACACCGCC
CTGATCTCCCGGCTGAACATCTACCGGGACAACTCCAAGAACCAGGTGTTCCTGGAAATGAAC
TCCCTGCAGGCAGAGGACACCGCCATGTACTACTGCGCCAGACGGGGCTCCTACCCCTACAAC
TACTTCGACGCTTGGGGCTGCGGCACCACCGTGACAGTGTCTAGCGGAGGTGGTGGATCTGGG
GGCGGAGGTAGCGGAGGGGGAGGTTCTGGAGGTGGTGGATCTGGGGCGGAGGTAGCGGAGGG
GGAGGTTCTCAGGCTGTCGTGATCCAGGAATCTGCCCTGACCACCCCCCCTGGCGAGACAGTG
ACACTGACCTGCGGATCTTCCACCGGCGCTGTGACCGCCTCCAACTACGCCAACTGGGTGCAG
GAAAAGCCCGACCACTGCTTCACCGGCCTGATCGGCGGCCACAACAACAGACCTCCAGGCGTG
CCAGCCCGGTTCTCCGGCTCTCTGATCGGAGATAAGGCCGCCCTGACAATCGCCGGCACCCAG
ACAGAGGACGAGGCTATCTACTTCTGCGCCCTGTGGTACAGCGACCACTGGGTCATCGGCGGA
GGCACCAGACTGACCGTGCTGGGA(ACACCCCGGGAGACACCACACATACT)AGTGGG**AGAT
CCCCCGACGATGAGCTGCTGTACCTGCCTGTGAGGGGCCGGGAGACCTATGAAATGCTGCTGA

-continued

AGATCAAAGAGAGCCTGGAACTGATGCAGTACCTGCCACAGCACACCATTGAAACATATAGGC

AACAACAGCAGCAGCAGCATCAGCATCTGCTGCAGAAGCAGGGAGGGTCAGGAGGAGCACCGC

ACCATCATCATCACCAT

P73- mBIDE(LL) polypeptide (hu3F8-scFv, *C825-scFv*,
huP73-tet, <u>GS linker</u>, (IgG3 spacer))
SEQ ID NO: 55

EIVMTQTPATLSVSAGERVTITCKASQSVSNDVTWYQQKPGQAPRLLIYSASNRYSGVPARFS

GSGYGTEFTFTISSVQSEDFAVYFCQQDYSSFGCGTKLEIKR<u>GGGGSGGGGSGGGGSGGGGSG</u>

<u>GGGSGGGGS</u>QVQLVESGPGVVQPGRSLRISCAVSGFSVTNYGVHWVRQPPGKCLEWLGVIWAG

GITNYNSAFMSRLTISKDNSKNTVYLQMNSLRAEDTAMYYCASRGGHYGYALDYWGQGTLVTV

SS<u>GGGGSGGGGSGGGGSGGGGS</u>HVKLQESGPGLVQPSQSLSLTCTVSGFSLTDYGVHWVRQSP

GKGLEWLGVIWSGGGTAYNTALISRLNIYRDNSKNQVFLEMNSLQAEDTAMYYCARRGSYPYN

YFDAWGCGTTVTVSs<u>GGGGSGGGGSGGGGSGGGGSGGGGSGGGGS</u>QAVVIQESALTTPPGETV

TLTCGSSTGAVTASNYANWVQEKPDHCFTGLIGGHNNRPPGVPARFSGSLIGDKAALTIAGTQ

TEDEAIYFCALWYSDHWVIGGGTRLTVLG(TPLGDTTHT)SGRHGDEDTYYLQVRGRENFEIL

MKLKESLELMELVPQPLVDSYRQQQQLLQRPGGSGGAPHHHHHH

P73- mBIDE(LL) cDNA (hu3F8-scFv, *C825-scFv*, **huP73-
tet**, <u>GS linker</u>, (IgG3 spacer))
SEQ ID NO: 56

GAGATCGTGATGACCCAGACACCCGCAACACTGAGCGTGTCTGCCGGCGAAAGGGTCACTATT

ACCTGCAAGGCCAGTCAGTCAGTGTCCAACGACGTGACTTGGTACCAGCAGAAACCAGGCCAG

GCTCCCCGGCTGCTGATCTACAGCGCATCTAATAGATATAGCGGAGTGCCTGCTCGCTTCAGT

GGTTCAGGCTATGGAACTGAGTTCACCTTCACCATTTCCAGCGTGCAGTCCGAAGACTTCGCA

GTGTACTTTTGCCAGCAGGATTATTCTAGTTTTGGGTGTGGTACAAAGCTGGAGATCAAAAGG

<u>GGAGGAGGAGGTAGTGGCGGAGGAGGTTCAGGCGGAGGGGGTAGCGGCGGAGGGGGTTCTGGC</u>

<u>GGCGGCGGTAGTGGCGGCGGAGGTAGC</u>CAGGTGCAGCTGGTCGAATCCGGCCCTGGAGTGGTC

CAGCCAGGCAGGTCTCTGCGGATCAGTTGCGCCGTGTCCGGATTCAGCGTCACCAACTACGGA

GTGCACTGGGTCAGACAGCCACCTGGCAAGTGTCTGGAGTGGCTGGGAGTGATCTGGGCAGGA

GGAATCACAAACTACAACTCAGCTTTTATGTCCCGCCTGACTATTAGCAAGGACAACTCTAAA

AATACCGTGTATCTGCAGATGAATTCTCTGCGAGCCGAAGATACCGCTATGTACTATTGTGCA

TCCCGTGGGGGTCATTACGGCTATGCCCTGGATTATTGGGGCAGGGTACCCTGGTGACAGTC

TCATCC<u>GGAGGAGGAGGATCCGGAGGAGGAGGTAGCGGCGGAGGGGGTTCTGGCGGAGGGGT</u>

<u>AGT</u>*CACGTGAAGCTGCAGGAAAGCGGCCCTGGACTGGTGCAGCCTTCCCAGTCTCTGTCCCTG*

*ACCTGCACCGTGTCCGGCTTCTCCCTGACCGATTACGGCGTGCACTGGGTGCGACAGTCTCCA*

*GGCAAGGGCCTGGAATGGCTGGGAGTGATTTGGAGCGGTGGCGGAACCGCCTACAACACCGCC*

*CTGATCTCCCGGCTGAACATCTACCGGGACAACTCCAAGAACCAGGTGTTCCTGGAAATGAAC*

*TCCCTGCAGGCAGAGGACACCGCCATGTACTACTGCGCCAGACGGGGCTCCTACCCCTACAAC*

*TACTTCGACGCTTGGGGCTGCGGCACCACCGTGACAGTGTCTAGC*<u>GGAGGTGGTGGATCTGGG</u>

<u>GGCGGAGGTAGCGGAGGGGGAGGTTCTGGAGGTGGTGGATCTGGGGGCGGAGGTAGCGGAGGG</u>

<u>GGAGGTTCT</u>*CAGGCTGTCGTGATCCAGGAATCTGCCCTGACCACCCCCCCTGGCGAGACAGTG*

*ACACTGACCTGCGGATCTTCCACCGGCGCTGTGACCGCCTCCAACTACGCCAACTGGGTGCAG*

*GAAAAGCCCGACCACTGCTTCACCGGCCTGATCGGCGGCCACAACAACAGACCTCCAGGCGTG*

*CCAGCCCGGTTCTCCGGCTCTCTGATCGGAGATAAGGCCGCCCTGACAATCGCCGGCACCCAG*

*ACAGAGGACGAGGCTATCTACTTCTGCGCCCTGTGGTACAGCGACCACTGGGTCATCGGCGGA*

-continued

```
GGCACCAGACTGACCGTGCTGGGA(ACACCCTGGGAGACACCACACATACT)AGTGGGAGGC

ACGGCGACGAAGATACCTACTATCTGCAGGTGAGGGGACGGGAGAACTTCGAAATCCTGATGA

AGCTGAAAGAGTCCCTGGAACTGATGGAGCTGGTGCCCCAGCCTCTGGTCGACAGCTACAGAC

AGCAGCAGCAGCTGCTGCAGAGGCCAGGAGGGTCAGGAGGAGCACCGCACCATCATCATCACC

AT
```

All constructs (including SADA-BiDEs) were cloned into standard IgG expression vectors using common molecular cloning techniques. Genes were either synthesized, PCR amplified or digested from other sources and ligated together using PCR or standard DNA ligases.

All constructs (including SADA-BiDEs) were expressed in either CHO-S, expiCHO or expi293 (HEK) suspension cell lines. Expression was either from a stable line (P53-BIDE(NOHIS)) or after transient expression (all others). P53-BIDE(NOHIS) was purified using one-step affinity purification using Protein-L resin (captoL). Briefly, supernatant from the host cells was harvested, filtered and run along the affinity column. The column was washed and bound protein was eluted by low pH elution. pH was neutralized and the buffer was dialyzed to a final storage buffer overnight. All other constructs followed the same basic protocol except used a nickel-NTA resin instead of protein, and elution was via high concentration imidazole instead of low pH.

It is envisioned that such an exemplary constructs (e.g., P53-BIDE(NOHIS), P53-BiDE, P63-BiDE, P73-BiDE) may be useful for pretargeted radioimmunotherapy (PRIT). Schematic diagrams for various 3-step, 2-step and 1-step PRIT methods are depicted in FIGS. 1A-C, respectively.

Example 2—Stability of an Exemplary Conjugate with a SADA Domain In Vitro

This Example demonstrates that an exemplary bispecific antibody-based conjugate with a SADA domain is highly stable in vitro. In particular, this Example describes biochemical purity analysis of a preparation of SADA conjugate as described in FIGS. 3A to 3C, P53-BIDE, P63-BiDE and P73-BiDE. Each SADA-BiDE self-assembles into a stable homo-tetramer through its SADA domain (i.e., p53, p63 or p73 tetramerization domains). Therefore, each can exist as an individual monomer (quarter), a dimer of monomers (half: dimer) or a dimer of dimers (full: tetramer). See schematic illustration of an exemplary SADA-BiDE conjugate in FIG. 2.

As shown in FIG. 3, P53-BIDE, P63-BiDE, and P73-BiDE show extremely high in vitro stability, comparable to that of an IgG. After single-step affinity purification, HPLC analysis of a preparation of all three SADA-BiDEs showed a major peak at ~16 min (~90%) with a calculated molecular weight of ~200 kDa (FIG. 3A). The expected and calculated size by HPLC standards, is ~200 kDa, similar to an IgG-scFv (Cheal, S. M. et al. (2014) *Mol Cancer Ther* 13, 1803-1812; Xu, H. et al. (2015) *Cancer immunology research* 3, 266-277). A small earlier peak (~14 min) denotes smaller aggregates of each SADA-BiDE (2-3 complexes) and a later peak (~25 min) is a non-specific peak from the storage buffer (sodium citrate). Therefore, P53-BiDE, P63-BiDE, and P73-BiDE exists in vitro predominantly as a tetramer.

Figure 3B:
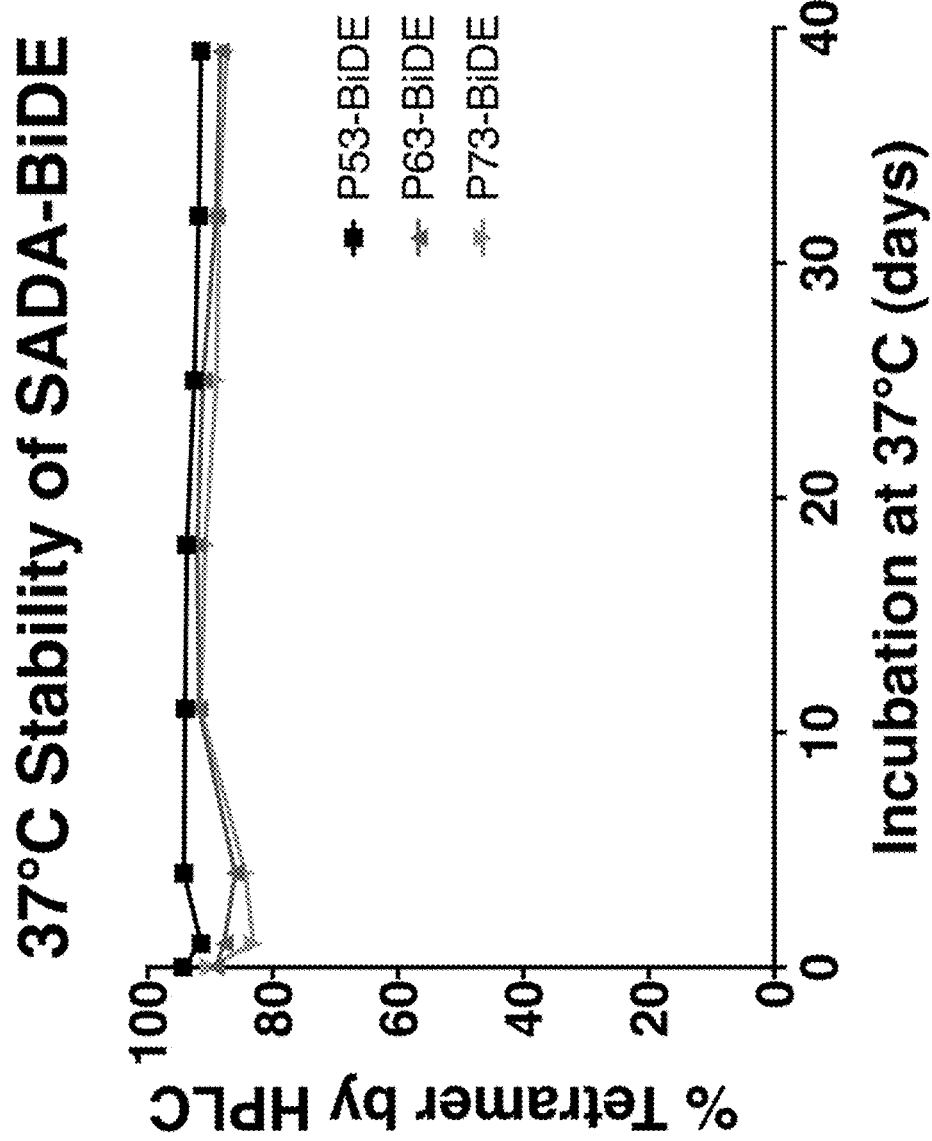

Moreover, all SADA-BiDEs were found to be highly stable, as shown in FIG. 3B. Preparations of P53-BIDE, P63-BiDE, and P73-BiDE remained stable for over four weeks at 37° C., with purity of the tetramer remaining unchanged over time. Additionally, all SADA-BiDEs remained tetrameric and did not show any loss in concentration or formations of aggregates/monomers after multiple freeze/thaw cycles (5 cycles; −80° C. to 25° C.) (FIG. 3C). Thus HPLC analysis provided herein documents the high in vitro stability of an exemplary tetrameric bispecific antibody-based conjugate with a SADA domain, which suggests a strong potential for manufacturability of these multimeric conjugates.

Analysis of the in vitro and in vivo functional activities of P53-BIDE, P63-BiDE, P73-BiDE and P53-BiDE(noHIS) is provided in the examples that follow. These examples demonstrate the potential of bispecific antibody-based conjugates with a SADA domain as effective agents for PRIT.

Example 3—Dissociation Kinetics of Exemplary SADA Conjugates In Vitro

This Example describes the dissociation kinetics of exemplary bispecific antibody-based conjugates with a SADA domain. In particular, this Example measures the rates of dissociation of exemplary p53, p63, and p73 SADA-BiDES. P53-BiDE, P63-BiDE and P73-BiDE, respectively, using fluorescence correlation spectroscopy (FCS). The samples were labeled with Cy3-labeled $^{175}$Lu-Bn-DOTA and prepared at a concentration of 500 nM, then rapidly diluted to 0.5 nM and then fluctuations in fluorescent intensity were measure over the course of 2 hours. Measurements were taken with a Zeiss LSM 880 confocal microscope. Normalized autocorrelations functions G(T) were then plotted to determine the diffusion times for each SADA-BiDE over time. All samples were compared against a monomeric GD2-BiDE To determine the dissociation rate $k_{off}$, the diffusion times were plotted as a function of time. A one-phase exponential decay curve fit model was utilized to determine $k_{off}$ and half-life ($R^2$ of 0.69-0.72). The results indicated that the P63-BiDE had the slowest dissociation rate.

TABLE 3

Dissociation kinetics of SADA-BiDEs (See also, e.g., FIG. 4)

|  | P53-BiDE | P63-BiDE | P73-BiDE |
|---|---|---|---|
| $k_{off}$ (sec$^{-1}$) | 11.2 ± 1.4 × 10$^{-5}$ | 6.3 ± 1.4 × 10$^{-5}$ | 9.5 ± 1.3 × 10$^{-5}$ |
| half-life (min) | 104 | 185 | 122 |

Example 4—Target Binding Affinity Exemplary Bispecific Antibody-Based SADA Conjugates with a SADA Domain This example documents the binding characteristics of an exemplary bispecific antibody-based conjugate with a SADA domain. In particular, this Example demonstrates that exemplary SADA-BiDE bispecific antibody-based conjugates with a SADA domain (P53-BIDE, P63-BiDE, P73-BiDE) effectively bind in vitro to their targets.

As shown in FIG. 5A, all three SADA-BiDEs exhibited improved binding to their tumor target (GD2), as measured by SPR, over both a standard IgG (hu3F8-IgG) (Cheung, N. K., et al. (2012) *OncoImmunology* 1, 477-486) and an IgG-scFv (hu3F8-IgG-scFv) (Cheal, S. M. et al. (2014) *Mol Cancer Ther* 13, 1803-1812). Table 4 shows SPR calculated affinity data, and fold increase over IgG and IgG-BiDE constructs. Data was fitted using a two-state reaction model. Strikingly, the off rate kinetics (koff) (FIG. 5A), which are thought to be critically important in determining the effectiveness of most receptor based therapeutics, had an improvement of 1e3-6e4 fold over hu3F8-IgG or IgG-BiDE, as well as a 3-10 fold improvement in $K_D$ (Table 4). Without being bound to theory, it is envisioned that, in at least some embodiments, multimerization through a SADA domain may stabilize and/or otherwise provide useful attributes to an antibody agent.

TABLE 4

SPR affinity data of SADA-BiDEs (See also, e.g., FIG. 5A)

| | ka1 (1/Ms) | kd1 (1/s) | ka2 (1/s) | kd2 (1/s) | $K_D$(M) | kd1 fold over IgG | KD fold over IgG |
|---|---|---|---|---|---|---|---|
| IgG | 1.1E+06 | 1.2E+00 | 1.5E−01 | 7.0E−04 | 5.0E−09 | 1 | 1 |
| IgG-BiDE | 2.8E+06 | 3.0E+00 | 1.6E−01 | 6.1E−04 | 4.0E−09 | 0.4 | 1 |
| P53-BiDE | 3.7E+04 | 3.4E−04 | 7.5E−03 | 3.9E−04 | 4.6E−10 | 3691 | 11 |
| P63-BiDE | 3.1E+04 | 6.2E−05 | 4.9E−04 | 2.1E−03 | 1.6E−09 | 20129 | 3 |
| P73-BiDE | 2.6E+04 | 2.0E−05 | 5.0E−03 | 1.3E−03 | 1.5E−10 | 62807 | 32 |

Further, preparations of various SADA-BiDEs (P53-BIDE, P63-BIDE, P73-BIDE) exhibited robust binding to two different GD2(+) tumor lines, IMR32-Luc (Neuroblastoma) and M14-Luc (Melanoma). FIG. 5B depicts a FACS analysis using a fluorescently labeled $^{175}$Lu-Bn-DOTA conjugate, thus demonstrating that each SADA-BiDE can bind both to the GD2 on the cell surface in the context of two different tumor cell lines and also simultaneously bind a second antigen (Bn-DOTA), which is critical for PRIT.

Example 5—Clearance of a Bispecific Antibody-Based Conjugate with a SADA Domain In Vivo This Example demonstrates in vivo clearance of an exemplary bispecific antibody-based conjugate with a SADA domain. In particular, this Example demonstrates that an exemplary tetrameric bispecific antibody-based conjugate with a SADA domain (P53-BIDE(NOHIS)) is rapidly cleared, even without the use of a clearing agent (CA). Thus, in vivo, using nude mice, use of a SADA technology eliminates the need for a CA.

In PRIT, an IgG-BiDE-based therapeutic has significant serum levels during the first 72 hours, necessitating the use of CA (Cheal, S. M. et al. (2014) *Mol Cancer Ther* 13, 1803-1812). In contrast, as illustrated in FIG. 6A, an exemplary bispecific antibody-based conjugates with a SADA domain (P53-BIDE(NOHIS)) is almost completely cleared on its own between 24 and 72 hours after injection without any CA. Administration of a CA had minimal effect on the clearance of an exemplary bispecific antibody-based conjugates with a SADA domain (P53-BIDE(NOHIS)), with detectable blood levels nearly identical to Bn-DOTA single treatment, suggesting almost all SADA-BiDE has cleared from the body before payload administration. As illustrated in FIG. 6A, clearance of P53-BIDE(NOHIS), even when CA was provided within this same window, had only a minor effect, decreasing residual blood activity by a negligible amount. Importantly, addition of a CA did not alter tumor uptake significantly. This Example confirms, among other things, that an exemplary bispecific antibody-based conjugates with a SADA domain (P53-BIDE(NOHIS)) is rapidly cleared from the blood without the use of a CA. Further, these data support that P53-BIDE(NOHIS) is capable of achieving high therapeutic indices even without a CA (low off target activity, high on target activity).

In a tumor free mouse, over 99% of unbound injected Bn-DOTA typically clears from the murine serum within four hours, with the vast majority of it being excreted in the urine within the first 30 minutes. In contrast, previous studies have shown that between 3 to 5% of directly labeled IgG will remain in the blood 48 hours after injection. (Azzopardi, N. et al. (2011) *Clin Cancer Res* 17, 6329-6337). As illustrated in FIG. 6B, over a 48 hours period, nearly 0.01% ID/g of directly labeled $^{131}$I-SADA-BiDE activity remains in the, indicating that P53-BiDE, P63-BiDE and P73-BiDE can all but completely cleared from the blood within 48 hours, without clearing agent.

Each dataset was analyzed using a two-phase decay model and the calculated values are presented here along with the integration of the curves (AUC), see Table 5. Here P53-BIDE and P63-BIDE stand out again, although the values are quite close. P53-BIDE has a longer portion of its decay during the slow component, but has a lower slow half-life. P63-BIDE has a greater portion in the fast component, but a substantially longer slow-half-life.

TABLE 5

Calculated values based on 2-phase decay model for P53-BIDE, P63-BIDE and P73-BIDE

| Normalized | P53-BIDE | P63-BIDE | P73-BIDE |
|---|---|---|---|
| Y0 | 1.50 | 1.11 | 1.48 |
| Plateau | 0.03 | 0.02 | 0.04 |
| PercentFast | 36.73 | 43.16 | 33.88 |
| KFast | 3.03 | 0.35 | 3.58 |
| KSlow | 0.17 | 0.11 | 0.16 |
| Half Life (Slow) | 4.15 | 6.42 | 4.43 |
| Half Life (Fast) | 0.23 | 1.99 | 0.19 |
| Tau (slow) | 5.98 | 9.26 | 6.40 |
| Tau (fast) | 0.33 | 2.87 | 0.28 |
| Rate constant ratio | 18.13 | 3.23 | 22.91 |
| Total Area (AUC) | 7.51 | 8.55 | 8.45 |
| Std. Error | 0.35 | 0.60 | 0.28 |
| 95% Confidence Interval | 6.83 to 8.19 | 7.37 to 9.73 | 7.90 to 8.99 |

In tumor bearing mice treated with either IgG-BiDE or SADA-BiDE (P53-BiDE, P63-BiDE, P73-BiDE), as shown in FIG. 6C, SADA-BiDE administration leads to minimal Bn-DOTA retention in the blood, as compared to the IgG-BiDE. Even while the IgG-BiDE received CA and the SADA-BiDE did not, the Bn-DOTA clears very rapidly, indicating very minimal SADA-BiDE remains in the blood 48 hours after pretargeting. This again highlights the exemplary pharmacokinetics of the SADA-BiDES for PRIT. Additionally it shows that the kinetics are similar between three different SADA domains in three different SADA-BiDE conjugates. Furthermore the representative overlays suggest that by the time of payload delivery SADA-BiDEs treated mice show a clearance of Bn-DOTA that almost exactly follows typical Bn-DOTA single administration, further proving that almost all SADA-BiDE has self cleared by this interval. By contrast, IgG-BiDE treated mice show a clearance curve similar to a directly labeled IgG, suggesting that while most excess IgG-BiDE has been removed from the serum via CA, the remaining amount binds the payload and clears slowly, exposing the blood to unwanted levels of payload activity.

Importantly, even though, as described in the previous examples, P53-BIDE(NOHIS), P53-BiDE, P63-BiDE and P73-BiDE is rapidly cleared from the serum, total tumor uptake of was not affected. With both 24 hours and 72 hours between P53-BIDE(NOHIS) and $^{177}$Lu-Bn-DOTA injections, significant activity (~15% ID/g) was measured at the tumor site (FIG. 6D)

Furthermore, SADA-BiDE P53-BIDE(NOHIS) is stably retained at the target site, even after 96 hours, as shown in FIG. 6E. This extended retention at the target contrasts the rapid clearance from all non-target tissues, such as the blood, displaying the exemplary in vivo activity of the SADA-BiDE.

These data demonstrate the surprising and contrasting in vivo behavior of exemplary SADA-based conjugates, P53-BiDE, P63-BiDE, P73-BiDE, which are rapidly cleared from blood and remains stably bound to a tumor site. Further, these data suggest, among other things, that there is substantial flexibility in the time interval between SADA-antibody conjugates and payload injections, which is an important consideration during clinical applications. Without wishing to be bound by theory, we propose that SADA-based conjugates have altered behavior based on target antigen density: in the presence of its cognate antigen, the self-assembled multimeric state demonstrates high avidity, thereby stabilizing its retention in the tumor site, while absence of the antigen (i.e. at off-target sites), the multimer disassembles into monomeric units which are then rapidly cleared renally.

Example 6—Pharmacokinetics and Tissue Biodistribution of Exemplary Antibody-Based SADA Conjugates This example describes the tissue biodistribution of exemplary bispecific antibody-based SADA conjugates. In particular, this Example demonstrates that exemplary bispecific antibody-based conjugates with three SADA domain (P53-BiDE, P63-BiD3, P73-BiDE) exhibit promising tissue biodistribution in vivo.

As illustrated in FIGS. 7A-7B and Tables 6a and 6b, all three SADA-BiDE conjugates have promising tissue biodistribution, even in comparison with a corresponding IgG-BiDE conjugate. Previously reported antibody-based therapeutics for PRIT, such as IgG-BiDE platforms (Cheal, S. M. et al. (2014) *Mol Cancer Ther* 13, 1803-1812), or biotin/streptavidin complexes (Cheung, N. K. et al. (2004) *J Nucl Med* 45, 867-877), are limited by biodistribution. For example, a clearing agent must be used with IgG-scFv platforms to remove excess unbound antibody. Streptavidin-based therapeutics, in addition issues related to immunogenicity of administering a bacterial protein, also have unwanted off-target effects resulting from the unusually high kidney uptake of these agents. In contrast, P53-BIDE, P63-BiDE and P73-BiDE had minimal kidney uptake, not significantly different from the uptake of Bn-DOTA alone (FIG. 7A and Table 6a). When compared to a IgG-BiDE platform, even with the additional benefit of clearing agents (CA), all three SADA-BiDEs were able to achieve remarkably low non-target uptake in nearly every tissue leading to very high therapeutic indices (FIG. 7B and Table 6b), despite no clearing agent being used. In particular, uptake was lower in the blood, spleen, liver and kidneys, all critically important tissues that are often damaged during conventional radio-immunotherapy.

TABLE 6a

Biodistribution (% ID/g uptake)
(See also, e.g., FIG. 7A)

| % ID/g uptake per tissue (Lower is Better) | IgG-BiDE w/CA | P53-BIDE | P63-BIDE | P73-BIDE |
|---|---|---|---|---|
| Blood | 0.099 | 0.003 | 0.006 | 0.003 |
| Tumor | 7.097 | 2.204 | 2.366 | 1.581 |
| Heart | 0.078 | 0.143 | 0.065 | 0.139 |
| Lungs | 0.156 | 0.036 | 0.042 | 0.024 |
| Liver | 0.143 | 0.122 | 0.081 | 0.089 |
| Spleen | 0.231 | 0.188 | 0.141 | 0.148 |
| Stomach | 0.043 | 0.130 | 0.042 | 0.142 |
| Sm. Intestine | 0.049 | 0.114 | 0.028 | 0.082 |
| Lg. Intestine | 0.031 | 0.051 | 0.025 | 0.052 |
| Kidneys | 0.602 | 0.369 | 0.422 | 0.321 |
| Muscle | 0.035 | 0.040 | 0.016 | 0.027 |
| Bone | 0.036 | 0.021 | 0.015 | 0.019 |
| Tail | 0.226 | 0.094 | 0.060 | 0.074 |

TABLE 6b

Biodistribution (Tumor:non-Tumor % ID/g ratio)
(See also, e.g., FIG. 7B)

| Tumor to Non-Tumor Uptake Ratio (Higher is better) | IgG-BiDE w/CA | P53-BIDE | P63-BIDE | P73-BIDE |
|---|---|---|---|---|
| Blood | 90 | 745 | 548 | 540 |
| Heart | 83 | 32 | 55 | 11 |
| Lungs | 42 | 98 | 67 | 70 |
| Liver | 46 | 20 | 29 | 18 |
| Spleen | 33 | 14 | 18 | 14 |
| Stomach | 205 | 63 | 133 | 14 |
| Sm. Intestine | 157 | 62 | 135 | 19 |
| Lg. Intestine | 237 | 112 | 125 | 46 |
| Kidneys | 13 | 6 | 6 | 5 |
| Muscle | 189 | 91 | 226 | 136 |
| Bone | 191 | 101 | 158 | 112 |
| Tail | 36 | 28 | 40 | 23 |

Example 7—Complete Tumor Ablation with a Bispecific Antibody-Based Conjugate with a SADA Domain This Example documents the in vivo efficacy of SADA-based antibody conjugates to mediate a reduction in tumor burden in mice. In particular, this Example demonstrates, among other things, that a two-step PRIT regimen using an exemplary tetrameric bispecific antibody-based conjugates with a SADA domain (P53-BIDE(NOHIS)) can relieve tumor burden, and even completely ablate tumors in vivo.

In mice with significant tumor burden (>500 mm³ tumor volumes) a single 250 µg (1.25 nmol) dose of P53-BIDE (NOHIS) was administered followed 24 hour later by administration of 2mCi of $^{177}$Lu-Bn-DOTA. As shown in FIGS. 8A and 8B, this two-step PRIT therapy with P53-BIDE(NOHIS) was able to completely ablate tumors in all four mice treated. Thus, two-step PRIT therapy using P53-BIDE(NOHIS), even with only 24 hours between administration of P53-BIDE(NOHIS) and $^{177}$Lu-Bn-DOTA, and importantly without the use of a CA, is a highly effective tumor therapy. Furthermore, even administration of up to four doses of P53-BIDE(NOHIS), totaling 2 mCi of $^{177}$Lu-Bn-DOTA, did not induce any clinical or histologic toxicity (data not shown). To date, no off-target toxicity was observed in any of the treated mice. This Example demonstrates, among other things, that two-step PRIT using a SADA-based antibody conjugate effectively reduces tumor burden in vivo and further suggests that such a therapy may be curative.

Example 8—Production of Exemplary SADA-Cytokine Multimers

This example demonstrates the production of exemplary cytokine-based conjugates with SADA domains. Specifically, this example describes the production of SADA-Cytokine multimers using three different exemplary SADA domains: p53, p63 and p73, as illustrated in FIG. 9.

Figure 9:
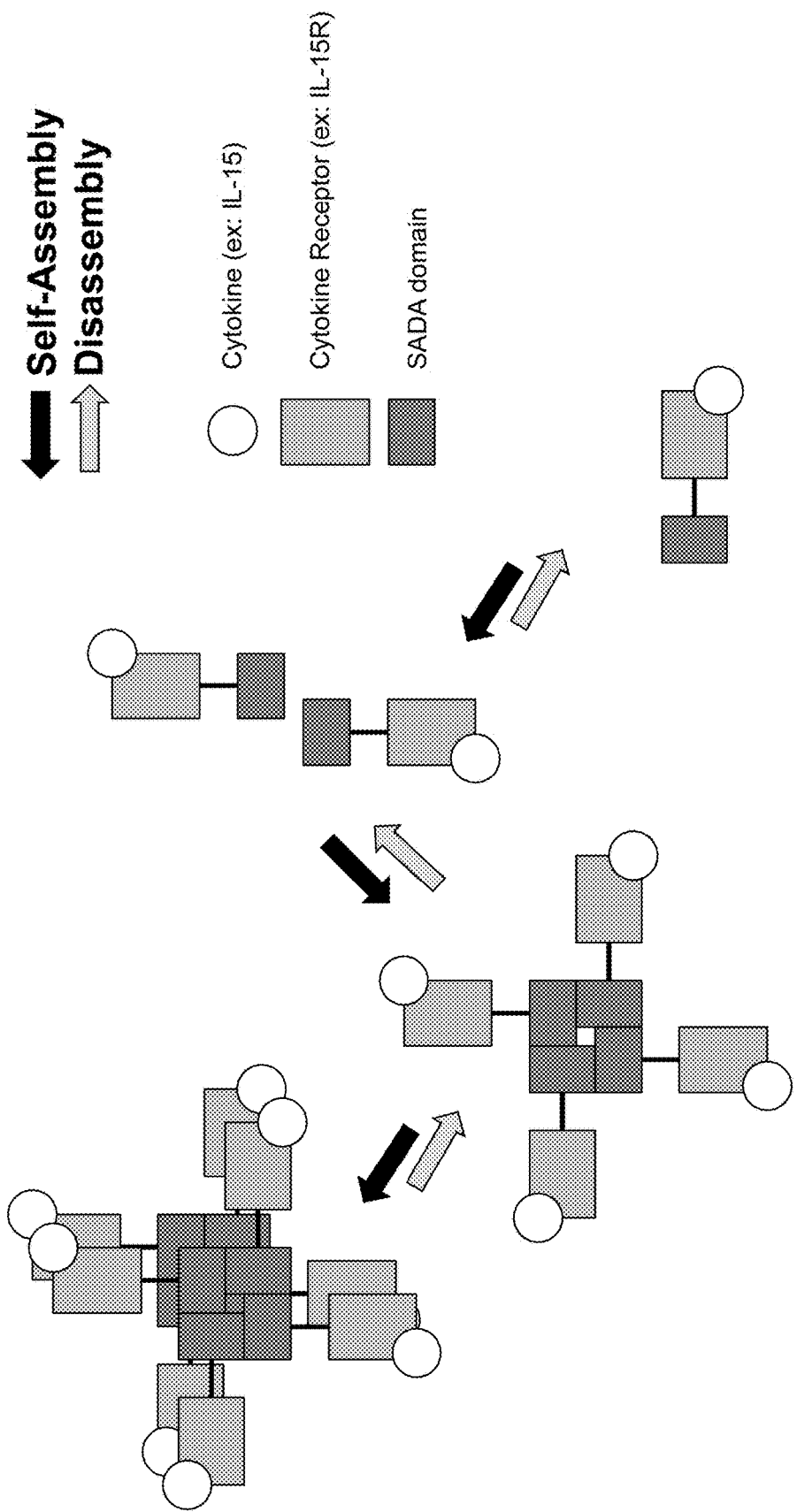
FIG. 9 depicts a schematic of an exemplary conjugate, SADA-Cytokine, made up of a SADA domain and one binding domain (e.g., IL15receptor alpha) which captures a soluble ligand (e.g., soluble IL15) during manufacture, that may be useful for immunotherapy. The circles denote the soluble IL15 (sIL15), which binds to the IL15receptor alpha domain (IL15Rα) (light gray boxes) during manufacture, such that it can be presented to its target as a complex. Dark gray boxes represent a SADA domain (shown as the most inner/proximal domain when assembled) (e.g. a human p53-tetramerization domain for P53-Cytokine; a human p63 tetramerization domain P63-Cytokine and a p73 tetramerization domain for P73-Cytokine). As illustrated, IL15Rα-sIL15 can dimerize, creating apparent octomers when fused with tetrameric SADA domains. Black arrows indicate self-assembly of the construct and gray arrows indicate disassembly of the construct.

In addition to these three exemplary SADA domains and, as a proof of concept for using multiple different SADA domains, we used a cytokine complex that can dimerize with itself, thus creating an additional layer of self-assembly and disassembly, resulting in an octameric complex when fully assembly (FIG. 9). Without wishing to be bound by theory, it is envisioned that, in at least some embodiments, use of both tetramerization and a dimerizable cytokine will result in hierarchical self-assembly and disassembly resulting in four distinct dates for the construct: octamer (full), tetramer (half), dimer (quarter), and monomer (eighth). Specifically, in this example a IL15Rα/IL15 cytokine complex was used, each monomer containing both a covalently linked polypeptide (IL15Rα) and a soluble polypeptide (IL15) that attaches non-covalently with subnanomolar affinity. Since the IL15Rα self-dimerizes through its built-in anti-parallel sequence (Azzopardi, N. et al. (2011) *Clin Cancer Res* 17, 6329-6337), the full complex is made up of 8 pairs of IL15Rα/IL15. With a molecular size of ~200 kDa, the octamer exceeds the renal threshold, but the unbound dimer or monomer of IL15Ra/IL15 is small enough to be cleared through the kidneys after disassembly. A schematic is shown in FIG. 9.

Three different SADA-Cytokine multimers were produced: P53-Cytokine (IL15Rα, huP53-tet), P63-Cytokine (IL15Rα, huP63-tet), P73-Cytokine IL15Rα, huP73-tet), each of associates non-covalently with a corresponding soluble cytokine polypeptide (sIL15) at high affinity to form a SADA-Cytokine dimer, which then self-assembles into a SADA-cytokine octomer. The amino acid sequences and cDNA nucleotide sequences of P53-Cytokine, P63-Cytokine, P73-Cytokine and sIL15 are shown below.

P53-Cytokine polypeptide (IL15Rα, huP53-tet, (IgG3 spacer))

SEQ ID NO: 57

ITCPPPMSVEHADIWVKSYSLYSRERYICNSGFKRKAGTSSLTECVLNK

ATNVAHWTTPSLKCIR(TPLGDTTHT)SGKPLDGEYFTLQIRGRERFEM

FRELNEALELKDAQAGKEPGGSGGAPHHHHHH

P53-Cytokine cDNA (IL15Rα, huP53-tet, (IgG3 spacer)))

SEQ ID NO: 58

ATCACCTGTCCTCCACCCATGTCTGTGGAACACGCCGACATCTGGGTCA

AGTCCTACTCCCTGTACTCCAGAGAGCGGTACATCTGCAACTCCGGCTT

CAAGCGGAAGGCCGGCACCTCTAGCCTGACCGAGTGCGTGCTGAACAAG

GCCACCAACGTGGCCCACTGGACCACCCCATCCCTGAAGTGCATCAGAA

CACCCCTGGGTGACACCACACATACTAGTGGGAAACCTCTGGATGGCGA

GTACTTTACCCTGCAGATTAGAGGCCGCGAACGATTCGAGATGTTTCGC

GAACTGAATGAGGCCCTGGAACTGAAGGATGCTCAGGCAGGCAAGGAGC

CAGGAGGGTCAGGAGGAGCACCGCACCATCATCATCACCAT

P63-Cytokine polypeptide (IL15Rα, huP63-tet, (IgG3 spacer)))

SEQ ID NO: 59

ITCPPPMSVEHADIWVKSYSLYSRERYICNSGFKRKAGTSSLTECVLNK

ATNVAHWTTPSLKCIR(TPLGDTTHT)SGRSPDDELLYLPVRGRETYEM

LLKIKESLELMQYLPQHTIETYRQQQQQHQHLLQKQGGSGGAPHHHHH

H

P63-Cytokine cDNA (IL15Rα, huP63-tet, (IgG3 spacer)))

SEQ ID NO: 60

ATCACCTGTCCTCCACCCATGTCTGTGGAACACGCCGACATCTGGGTCA

AGTCCTACTCCCTGTACTCCAGAGAGCGGTACATCTGCAACTCCGGCTT

CAAGCGGAAGGCCGGCACCTCTAGCCTGACCGAGTGCGTGCTGAACAAG

GCCACCAACGTGGCCCACTGGACCACCCCATCCCTGAAGTGCATCAGAA

CACCCCTGGGTGACACCACACATACTAGTGGGAGATCCCCCGACGATGA

GCTGCTGTACCTGCCTGTGAGGGGCCGGGAGACCTATGAAATGCTGCTG

AAGATCAAAGAGAGCCTGGAACTGATGCAGTACCTGCCACAGCACACCA

TTGAAACATATAGGCAACAACAGCAGCAGCAGCATCAGCATCTGCTGCA

GAAGCAGGGAGGGTCAGGAGGAGCACCGCACCATCATCATCACCAT

P73-Cytokine polypeptide (IL15Rα, huP73-tet, (IgG3 spacer))

SEQ ID NO: 61

ITCPPPMSVEHADIWVKSYSLYSRERYICNSGFKRKAGTSSLTECVLNK

ATNVAHWTTPSLKCIR(TPLGDTTHT)SGRHGDEDTYYLQVRGRENFEI

LMKLKESLELMELVPQPLVDSYRQQQQLLQRPGGSGGAPHHHHHH

P73-Cytokine cDNA (IL15Rα, huP73-tet, (IgG3 spacer))

SEQ ID NO: 62

ATCACCTGTCCTCCACCCATGTCTGTGGAACACGCCGACATCTGGGTCA

AGTCCTACTCCCTGTACTCCAGAGAGCGGTACATCTGCAACTCCGGCTT

CAAGCGGAAGGCCGGCACCTCTAGCCTGACCGAGTGCGTGCTGAACAAG

-continued

```
GCCACCAACGTGGCCCACTGGACCACCCCATCCCTGAAGTGCATCAGAA

CACCCCTGGGTGACACCACACATACTAGTGGGAGGCACGGCGACGAAGA

TACCTACTATCTGCAGGTGAGGGGACGGGAGAACTTCGAAATCCTGATG

AAGCTGAAAGAGTCCCTGGAACTGATGGAGCTGGTGCCCCAGCCTCTGG

TCGACAGCTACAGACAGCAGCAGCAGCTGCTGCAGAGGCCAGGAGGGTC

AGGAGGAGCACCGCACCATCATCATCACCAT
```

IL-15 polypeptide

SEQ ID NO: 63

```
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

IL-15 cDNA

SEQ ID NO: 64

```
ATGGGCTGGTCCTGCATCATCCTGTTTCTGGTGGCTACCGCCACCGGCA

ACTGGGTCAACGTGATCTCCGACCTGAAGAAGATCGAGGACCTGATCCA

GTCCATGCACATCGACGCCACCCTGTACACCGAGTCCGACGTGCACCCC

TCCTGCAAAGTGACCGCCATGAAGTGCTTTCTGCTGGAACTGCAAGTGA

TCTCCCTGGAATCCGGCGACGCCTCCATCCACGACACCGTGGAAAATCT

GATCATCCTGGCCAACAACTCCCTGTCCTCCAACGGCAACGTGACCGAG

AGCGGCTGCAAAGAGTGCGAGGAACTGGAAGAGAAGAACATCAAAGAGT

TTCTGCAGTCCTTCGTGCACATCGTGCAGATGTTCATCAACACCAGC
```

Example 9—Stability of Exemplary SADA-Cytokine Multimers

This Example demonstrates the stability of exemplary SADA-Cytokine multimers. In particular, this Example describes biochemical purity analysis of preparations of three different exemplary SADA-Cytokine multimers (P53-Cytokine, P63-Cytokine and P73-Cytokine), each of which employs a different SADA domain.

As illustrated in FIG. 10, each of the SADA-Cytokine multimers tested showed high in vitro stability. Preparations of P53-Cytokine, P63-Cytokine and P73-Cytokine were each able to form highly stable multimers of consistent size, as shown in HPLC chromatograms depicted in FIG. 10A, which have a major peak that corresponded with purity above 98%. Further, each of the constructs maintained their self-assembled multimeric state for over 30 days at 37° C. (FIG. 10B). Thus HPLC analysis provided herein demonstrates, among other things, the high in vitro stability of different SADA-Cytokine multimers that employ different SADA domains. These data demonstrate, among other things, the high stability of SADA-Cytokine complexes in vitro, and further suggests a strong potential for manufacturability.

Example 10—In Vitro Cell Toxicity/Activity of Exemplary SADA-Cytokine Multimers

Figure 11C:
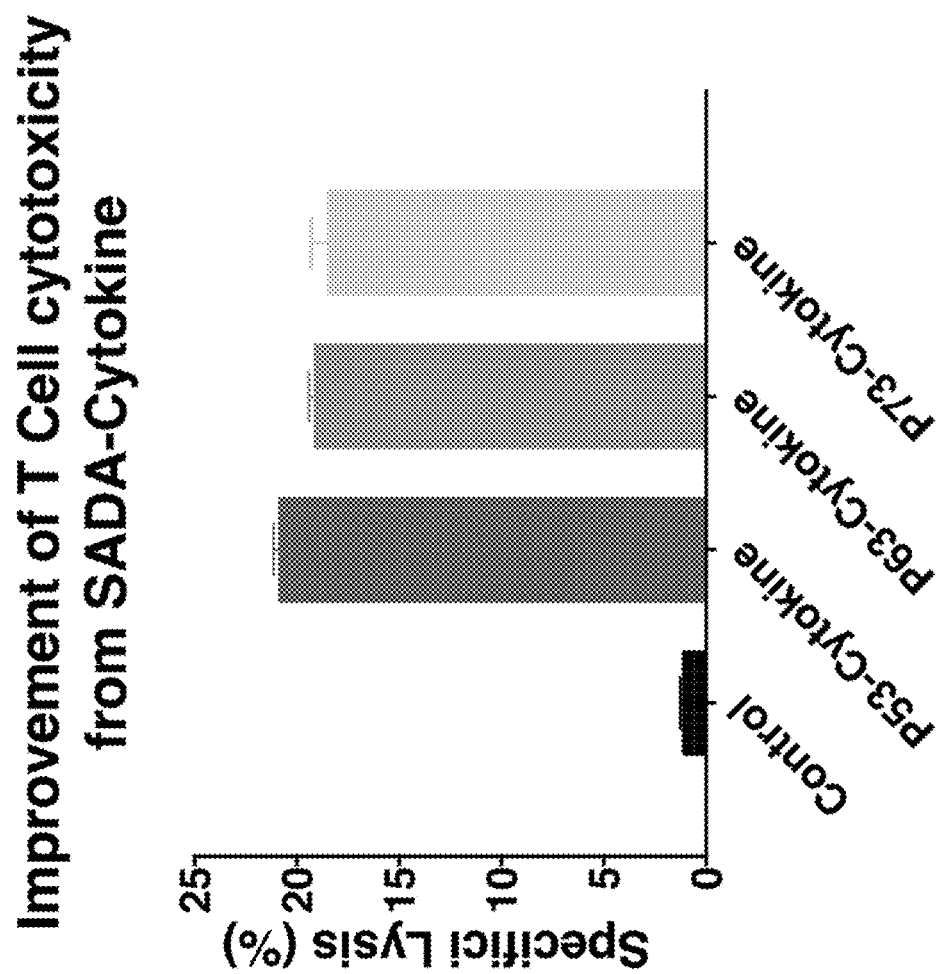

This example documents the in vitro activity of exemplary SADA-cytokine multimers. In particular, this Example demonstrates that preparations of three different exemplary SADA-cytokine multimers each have robust in vitro activity. Specifically, P53-Cytokine, P63-Cytokine and P73-Cytokine each exhibited strong IL15 signaling activity in vitro. As shown in FIG. 11A, P53-Cytokine, P63-Cytokine and P73-Cytokine each lead to robust proliferation of TIB214, an IL15 sensitive cell line relative to untreated control cells. Additionally, each complex could prime effector immune cells to kill more strongly. Human NK cells were incubated in 1 nM concentrations of P53-Cytokine, P63-Cytokine or P73-Cytokine for three days. As shown in FIG. 11B, each SADA-Cytokine multimeric complex increased antibody-independent cytotoxic response against a GD2(+) neuroblastoma cell line. Further, when incubated with human T cells for three days, each SADA-cytokine multimeric complex strongly increased IgG-scFv dependent killing of tumor cells (FIG. 11C) (Xu, H. et al. (2015) Cancer immunology research 3, 266-277). Importantly, these complexes showed improved functional activity over Fc dimerized versions (Liu et al. 2016 JBC.http://www.jbe.org/content/291/46/23809) in vivo, as shown in FIG. 11D, suggesting their self-assembled multimeric state improved their activity through 2+ multimeric binding.

Without being bound to theory, it is envisioned that, in at least some embodiments, hierarchical multimerization or increased valency of constructs may improve binding activity, functional activity, increased stability and/or otherwise provide useful attributes to an therapeutic polypeptide.

Example 11—Structural Analysis of SADA Domains

Figure 12A:
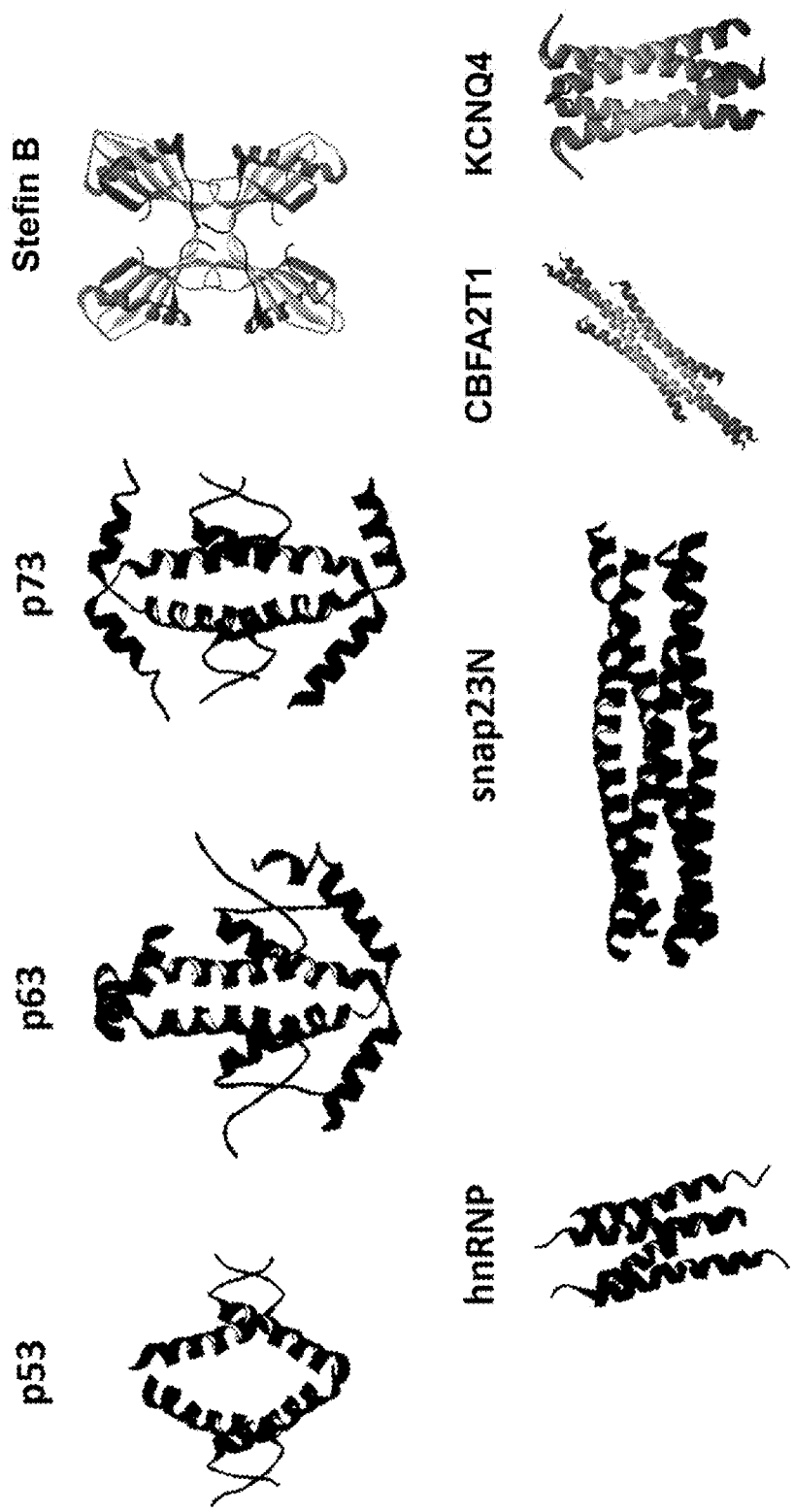
FIG. 12A and FIG. 12B depict ribbon structures of SADA domains and potential SADA domains.
Figure 12B:
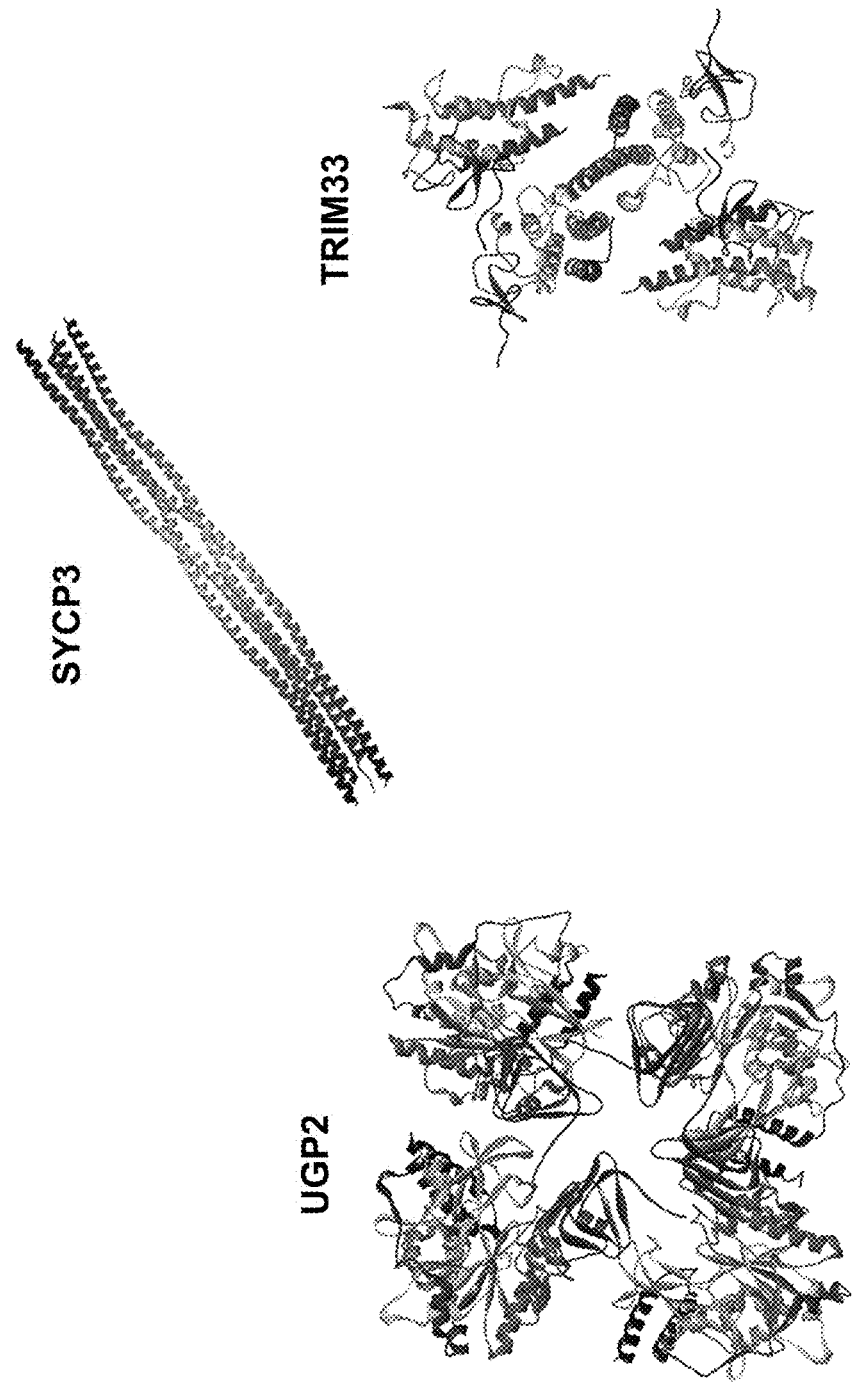

This example documents the characteristics of polypeptides for use as a SADA domain. Association and disassociation rates of a SADA domain polypeptide will affect the pharmacokinetic properties of SADA conjugates (e.g., antibody-based SADA conjugates, SADA-Cytokine conjugates). SADA domains are human derived multimerization domains that are sufficiently stable enough to multimerize tethered protein units in a non-covalent manner. In some embodiments, a SADA domain is composed of a multimerization domains from one of following human proteins: p53, p63, p73, heterogeneous nuclear Ribonucleoprotein C (hnRNPC), or N-terminal domain of Synaptosomal-associated protein 23 (SNAP-23), Stefin B (Cystatin B), Potassium voltage-gated channel subfamily KQT member 4 (KCNQ4), Cyclin-D-related protein (CBFA2T1), which are each composed of helical bundles that associate in a parallel or anti-parallel orientation (Table 7 and FIGS. 12A and 12B). Moreover, in some embodiments, a SADA domain lacks unpaired cysteine residues and/or large exposed hydrophobic surfaces, which without being bound by theory, are suggested to lead to aggregation. Each of the SADA domains described in Table 7a (i.e., p53, p63, p73, hnRNPC, SNAP-23, Stefin B, KCNQ4, and CBFA2T1) are absent of unpaired cysteine residues and large exposed hydrophobic surfaces.

TABLE 7a

Structural properties of SADA domains from analysis of crystal structures

| Protein Complex | Conformation | MW of monomer | PDB ID | Buried SA (dimer:dimer) (Å2) | No. H bonds (dimer:dimer) (Å2) | Buried SA (monomer:monomer) (Å2) | No. H bonds (monomer:monomer) (Å2) | Total buried surface area (Å2) |
|---|---|---|---|---|---|---|---|---|
| Tetramerization domain of p53 (residues 321-359) | Anti-parallel homotetramer | 3.8 kDa | 2J0Z | 242 | 3 | 478 | 20 | 1199 |
| Tetramerization domain of p73 (residues 348-399) | Anti-parallel homotetramer | 6.1 kDa | 2WQI | 1066 | 32 | 617 | 24 | 2301 |
| Tetramerization domain of p63 (residues 396-450) | Anti-parallel homotetramer | 7.3 kDa | 4A9Z | 1188 | 33 | 646 | 32 | 2480 |
| Oligomerization domain of hnRNP (residues 194-220) | Anti-parallel homotetramer | 3.3 kDa | 1TXP | 630 | 3 | 172 | 4 | 973 |
| Oligomerization domain of SNAP-23 (residues 23-76) | Parallel homotetramer | 6.2 kDa | 1NHL | 957 | 16 | 465 | 9 | 1887 |
| Oligomerization domain of Stefin B (residues 2-98) | domain swapped homotetramer | 11.1 kDa | 2OCT | 1520 | 70 | 1028 | 51 | 3576 |
| Oligomerization domain of KCNQ4 (residues 611-640) | parallel homotetramer | 3.5 kDa | 2OVC | 628 | 10 | 314 | 5 | 1256 |
| Oligomerization domain of CBFA2T1 (residues 462-521) | anti-parallel homotetramer | 7.5 kDa | 4JOL | 1207 | 18 | 514 | 15 | 2235 |

TABLE 7b

Structural properties of potential SADA domains from analysis of crystal structures

| | Conformation | MW of monomer | PDB ID | Protein Complex (Å2) | No. H bonds (dimer:dimer) (Å2) | Buried SA (monomer:monomer) (Å2) | No. H bonds (monomer:monomer) (Å2) | Total buried surface area (Å2) |
|---|---|---|---|---|---|---|---|---|
| Oligomerization domain of SYCP3 (residues 81-221) | anti-parallel homotetramer | 17.2 kDa | 4CPC | 3209 | 62 | 1052 | 23 | 5313 |
| Oligomerizaiton domain of UGP2 (residues 24-508) | large paralllel homotetramer | 54.3 kDa | 4R7P | 177 | 7 | 64 | 2 | 305 |
| Oligomerization domain of TRIM33 (residues 958-1055) | anti-parallel homotetramer | 11.0 kDa | 3U5O | 469 | 17 | 96 | 4 | 661 |

In some embodiments, a SADA domain is able to associate to form homo-tetramers, and further that can dissociate into dimers and monomers. The association and disassociation rates of a p53 tetramerization domain, was measured to have a dissociation constant (KD, which is equal to $k_{off}/k_{on}$) at 37° C. for tetramers dissociating into dimers of 150 nM (half-life of 2.5 minutes), and a dissociation constant of dimers into monomers of 1 nM (half-life of 13 min), based on fluorescence correlation spectroscopy (Matthay, K. K. et al. (2007) *J Clin Oncol* 25, 1054-1060). However accurate measurements of the association and disassociation rates of the other homo-tetramerization domains listed in Table 7a (i.e., p63, p73, hnRNPC, SNAP-23, Stefin B, KCNQ4, and CBFA2T1) have not been previously been reported. Since the crystal structures of each of the SADA domains listed in Table 7a (i.e., the tetramerization domains of p53, p63, p73, hnRNPC, SNAP-23, Stefin B, KCNQ4, and CBFA2T1) are known, the crystal structures were analyzed to determine the relative dissociation constants based on buried surface area of the complexes. Without wishing to be bound by theory, it has been suggested that the buried surface area of protein:protein complexes significantly correlate inversely to the log of the measured dissociation constants (Pinzani, V. et al. (1994) *Cancer Chemoth Pharm* 35, 1-9). Based on these observations, the crystal structures of the tetramerization domains of p53, p63, p73, hnRNPC, SNAP-23, Stefin B, KCNQ4, and CBFA2T1 were analyzed for buried surface area at the dimer:dimer and monomer:monomer interfaces, number of interface hydrogen bonds and the total buried surface area (Table 7a). The calculations were made using Biovia Discovery Studio (Dassault Systemes, San Diego Calif.). Based on these calculations, we extrapolated that the tetramerization domains of p63, p73, SNAP-23, Stefin B, and CBFA2T1 (957-1520 Å$^2$ of buried surface area of the dimer:dimer interfaces) will have a smaller dissociation constant in the tetramer-to-dimer transition than hnRNPC (630 Å$^2$), KCNQ4 (628 Å$^2$) or p53 (242 Å$^2$). Additionally, the dimer-to-monomer dissociations constants of p53, p63, p73, SNAP-23, Stefin B, KCNQ4, and CBFA2T1 (314-1028 Å$^2$ of buried surface area of monomer:monomer interface) will be significantly lower than hnRNPC (172 Å$^2$). Based on the total buried surface area, p63, p73, SNAP-23, Stefin B, and CBFA2T1 SADA domains (1887-3576 Å$^2$) will have smaller overall observed dissociation constants (tetramer-to-monomer) than p53 (1199 Å$^2$), hnRNPC (973 Å$^2$), KCNQ4 (1256 Å$^2$).

Additionally, three other potential SADA domains were analyzed (Table 7b) synaptonemal complex protein (SYCP3), UDP-glucose pyrophosphorylase (UGP2), and E3 ubiquitin-protein ligase (TRIM33). Based on these calculated buried surface area measurements, we extrapolate that UGP2 and TRIM33 would diassociate too quickly not bind to the target sufficiently. Furthermore the buried surface area measurements of SYCP3 suggest it it would diassociate too slowly and provide unwanted exposure to normal tissues.

Based on these calculated buried surface area measurements and the expected relative dissociation constants, a SADA domain can be selected for the specific type of application. In some applications a rapid clearance rate may be desirable (e.g., SADA-PRIT), and so a SADA domain that has a faster dissociation/disassembly rate (e.g., p53, hnRNPC, KCNQ4) may be preferred. In some applications a longer serum half-life may be desired (e.g., certain SADA-Cytokine, SADA-BiDE, or SADA-BiWE applications), and so a SADA domain that has a slower dissociation/disassembly rate (e.g., p63, p73, SNAP-23, Stefin B, or CBFA2T1) may be chosen. It is also envisioned that a SADA domain can be engineered (e.g., introduce amino acid mutations or post-translational modifications) to increase or decrease the dissociation constants for the different applications. A SADA domain can also be selected for having parallel (SNAP-23 or KCNQ4), anti-parallel orientation (p53, p63, p73, hnRNPC, or CBFA2T1) or domain swapped oriengation (Stefin B), which without being bound by theory, is suggested to affect the ability of the tethered therapeutic protein to cooperatively bind its target. Thus, it is contemplated by the present invention to alter or tune various elements of a SADA domain to optimize biochemical and/or functional properties of a multimeric protein therapeutic to for each specific application.

Example 12—Exemplary Tumor Binding Conjugates with SADA Domains

This example describes binding of tumor-targeted SADA conjugates to tumor antigens. Specifically, this example shows in vitro activity of an exemplary bispecific antibody based conjugate against the HER2 antigen using a P53 SADA domain, e.g., a HER2 P53-BiDE. This example confirms that SADA conjugates can be used to target different antigens (e.g., different tumor antigens) and different cell types (e.g. different tumor types). Provided below are polypeptide sequences and nucleotide sequences for various exemplary HER2-targeted SADA conjugates.

HER2 (HL DS) P53 BiDE (LL) polypeptide (hu4D5-scFv, huC825-scFv, huP53-tet, GS linker, (IgG3 spacer))
SEQ ID NO: 65
EVQLVESGGGLVQPGGSLRLSCAASGFNIKDTYIHWVRQAPGKCLEWVARIYPTNG

YTRYADSVKGRFTISADTSKNTAYLQMNSLRAEDTAVYYCSRWGGDGFYAMDYW

GQGTLVTVSSGGGGSGGGGSGGGGSGGGGSGGGGSGGGGSDIQMTQSPSSLSASVG

DRVTITCRASQDVNTAVAWYQQKPGKAPKLLIYSASFLYSGVPSRFSGSRSGTDFTLT

ISSLQPEDFATYYCQQHYTTPPTFGQCTKVEIKRGGGGSGGGGSGGGGSGGGGSHVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSSGGGGS

GGGGSGGGGSGGGGSGGGGSGGGGSQAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGKPLDGEYFTLQIRGRERFEMFRELNEA

LELKDAQAGKEPGGSGGAPHHHHHH

HER2 (HL DS) P53 BiDE (LL) cDNA (hu4D5-scFv, huC825-scFv, huP53-tet, GS linker, (IgG3 spacer))
SEQ ID NO: 66
GAAGTGCAGCTGGTCGAATCCGGGGGGGCCTGGTGCAGCCTGGAGGGTCACTGAG

ACTGTCCTGTGCCGCATCTGGGTTCAATATCAAGGACACCTACATCCACTGGGTGCGG

CAGGCACCTGGCAAGtGtCTGGAGTGGGTGGCAAGGATCTATCCAACCAACGGCTACA

CACGGTATGCCGACTCCGTGAAGGGCCGGTTCACCATCTCCGCCGATACCTCTAAGAA

CACAGCCTACCTGCAGATGAATTCTCTGAGGGCCGAGGATACAGCCGTGTACTATTGC

AGCCGCTGGGGAGGCGACGGCTTCTACGCTATGGACTATTGGGGCCAGGGCACCCTG

GTGACAGTGAGCTCTGGCGGCGGCGGATCCGGAGGAGGAGGCAGCGGCGGAGGA

GGCTCCGGAGGAGGCGGCTCTGGCGGCGGCGGCAGCGGCGGCGGCGGCTCCGAC

-continued

ATCCAGATGACCCAGTCCCCATCTAGCCTGAGCGCCTCCGTGGGCGACAGGGTGACC

ATCACATGCCGCGCCAGCCAGGATGTGAATACAGCCGTGGCCTGGTACCAGCAGAAG

CCAGGCAAGGCCCCCAAGCTGCTGATCTACTCTGCCAGCTTCCTGTATAGCGGAGTGC

CATCCCGGTTTTCCGGCAGCCGGAGCGGCACCGACTTCACCCTGACAATCTCCTCTCT

GCAGCCTGAGGATTTTGCCACATACTATTGTCAGCAGCACTATACCACACCCCCTACAT

TCGGACAGTGTACAAAGGTCGAGATCAAACGCGGCGGAGGGGGATCCGGCGGCGGA

GGATCTGGCGGAGGTGGAAGTGGGGGAGGCGGATCTCATGTGCAGCTGGTGGAAA

GCGGAGGCGGCCTGGTGCAGCCTGGGGGATCTCTGAGACTGTCTTGTGCCGCCAGC

GGCTTCTCCCTGACCGATTATGGCGTGCACTGGGTGCGACAGGCCCCTGGCAAGGA

CTGGAATGGCTGGGAGTGATTTGGAGTGGCGGAGGCACCGCCTACAACACCGCCCTG

ATCTCCCGGTTCACCATCAGCCGGGACAACTCCAAGAACACCCTGTACCTGCAGATGA

ACTCCCTGCGGGCCGAGGACACCGCTGTGTACTACTGCGCCAGACGGGGCTCCTACC

CCTACAACTACTTCGACGCTTGGGGCTGCGGCACCCTCGTGACAGTGTCTAGCGGAG

GGGGAGGTTCTGGGGGCGGAGGTTCAGGTGGTGGTGGTTCCGGGGGTGGTGGCTCT

GGTGGCGGTGGTTCTGGCGGTGGCGGATCTCAGGCTGTCGTGACCCAGGAACCCAG

CCTGACTGTGTCTCCTGGCGGAACCGTGACCCTGACCTGCGGATCTTCTACCGGCGC

TGTGACCGCCAGCAACTACGCCAATTGGGTGCAGCAGAAACCTGGACAGTGCCCTAG

AGGCCTGATCGGCGGCCACAACAACAGACCTCCAGGCGTGCCAGCCCGGTTCTCTGG

ATCTCTGCTGGGCGGAAAGGCCGCTCTGACACTGCTGGGTGCTCAGCCTGAGGACGA

GGCCGAGTACTACTGTGCCCTGTGGTACTCCGACCACTGGGTCATCGGAGGCGGGAC

CAAGCTGACCGTGCTGGGA(ACACCCCTGGGAGACACCACACATACT)AGTGGGAA

ACCTCTGGATGGCGAGTACTTTACCCTGCAGATTAGAGGCCGCGAACGATT

CGAGATGTTTCGCGAACTGAATGAGGCCCTGGAACTGAAGGATGCTCAGGC

AGGCAAGGAGCCAGGAGGGTCAGGAGGAGCACCGCACCATCATCATCACCAT

HER2 (HL) P53 BiDE (LL) polypeptide (hu4D5-scFv, huC825-scFv,
huP53-tet, <u>GS linker</u>, (IgG3 spacer))
SEQ ID NO: 67

EVQLVESGGGLVQPGGSLRLSCAASGFNIKDTYIHWVRQAPGKGLEWVARIYPTNG

YTRYADSVKGRFTISADTSKNTAYLQMNSLRAEDTAVYYCSRWGGDGFYAMDYW

GQGTLVTVSS<u>GGGGSGGGGSGGGGSGGGGSGGGGSGGGGS</u>DIQMTQSPSSLSASVG

DRVTITCRASQDVNTAVAWYQQKPGKAPKLLIYSASFLYSGVPSRFSGSRSGTDFTLT

ISSLQPEDFATYYCQQHYTTPPTFGQGTKVEIKR<u>GGGGSGGGGSGGGGSGGGGS</u>HVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSS<u>GGGGS</u>

<u>GGGGSGGGGSGGGGSGGGGSGGGGS</u>QAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGKPLDGEYFTLQIRGRERFEMFRELNEA

LELKDAQAGKEPGGSGGAPHHHHHH

HER2 (HL) P53 BiDE (LL) cDNA (hu4D5-scFv, huC825-scFv, huP53-tet,
<u>GS linker</u>, (IgG3 spacer))
SEQ ID NO: 68

GAAGTGCAGCTGGTCGAATCCGGGGGGGGCCTGGTGCAGCCTGGAGGGTCACTGAG

ACTGTCCTGTGCCGCATCTGGGTTCAATATCAAGGACACCTACATCCACTGGGTGCGG

-continued

```
CAGGCACCTGGCAAGGGACTGGAGTGGGTGGCAAGGATCTATCCAACCAACGGCTAC

ACACGGTATGCCGACTCCGTGAAGGGCCGGTTCACCATCTCCGCCGATACCTCTAAGA

ACACAGCCTACCTGCAGATGAATTCTCTGAGGGCCGAGGATACAGCCGTGTACTATTG

CAGCCGCTGGGGAGGCGACGGCTTCTACGCTATGGACTATTGGGGCCAGGGCACCCT

GGTGACAGTGAGCTCTGGCGGCGGCGGATCCGGAGGAGGAGGCAGCGGCGGAGG

AGGCTCCGGAGGAGGCGGCTCTGGCGGCGGCGGCAGCGGCGGCGGCGGCTCCGA

CATCCAGATGACCCAGTCCCCATCTAGCCTGAGCGCCTCCGTGGGCGACAGGGTGAC

CATCACATGCCGCGCCAGCCAGGATGTGAATACAGCCGTGGCCTGGTACCAGCAGAA

GCCAGGCAAGGCCCCCAAGCTGCTGATCTACTCTGCCAGCTTCCTGTATAGCGGAGTG

CCATCCCGGTTTTCCGGCAGCCGGAGCGGCACCGACTTCACCCTGACAATCTCCTCTC

TGCAGCCTGAGGATTTTGCCACATAGTATTGTCAGCAGCACTATACCACACCCCTACA

TTCGGACAGGGGACAAAGGTCGAGATCAAACGCGGCGGAGGGGGATCCGGCGGCG

GAGGATCTGGCGGAGGTGGAAGTGGGGGAGGCGGATCTCATGTGCAGCTGGTGG

AAAGCGGAGGCGGCCTGGTGCAGCCTGGGGATCTCTGAGACTGTCTTGTGCCGCCA

GCGGCTTCTCCCTGACCGATTATGGCGTGCACTGGGTGCGACAGGCCCCTGGCAAAG

GACTGGAATGGCTGGGAGTGATTTGGAGTGGCGGAGGCACCGCCTACAACACCGCCC

TGATCTCCCGGTTCACCATCAGCCGGGACAACTCCAAGAACACCCTGTACCTGCAGAT

GAACTCCCTGCGGGCCGAGGACACCGCTGTGTACTACTGCGCCAGACGGGGCTCCTA

CCCCTACAACTACTTCGACGCTTGGGGCTGCGGCACCCTCGTGACAGTGTCTAGCGG

AGGGGGAGGTTCTGGGGGCGGAGGTTCAGGTGGTGGTGGTTCCGGGGGTGGTGGCT

CTGGTGGCGGTGGTTCTGGCGGTGGCGGATCTCAGGCTGTCGTGACCCAGGAACCCA

GCCTGACTGTGTCTCCTGGCGGAACCGTGACCCTGACCTGCGGATCTTCTACCGGCG

CTGTGACCGCCAGCAACTACGCCAATTGGGTGCAGCAGAAACCTGGACAGTGCCCTA

GAGGCCTGATCGGCGGCCACAACAACAGACCTCCAGGCGTGCCAGCCCGGTTCTCTG

GATCTCTGCTGGGCGGAAAGGCCGCTCTGACACTGCTGGGTGCTCAGCCTGAGGACG

AGGCCGAGTACTACTGTGCCCTGTGGTACTCCGACCACTGGGTCATCGGAGGCGGGA

CCAAGCTGACCGTGCTGGGA(ACACCCCTGGGAGACACCACACATACT)AGTGGGA

AACCTCTGGATGGCGAGTACTTTACCCTGCAGATTAGAGGCCGCGAACGAT

TCGAGATGTTTCGCGAACTGAATGAGGCCCTGGAACTGAAGGATGCTCAGG

CAGGCAAGGAGCCAGGAGGGTCAGGAGGAGCACCGCACCATCATCATCACCAT
```

HER2 (LHDS) P53 BiDE (LL) polypeptide (hu4D5-scFv, huC825-scFv, huP53-tet, <u>GS linker</u>, (IgG3 spacer))
SEQ ID NO: 69

```
DIQMTQSPSSLSASVGDRVTITCRASQDVNTAVAWYQQKPGKAPKLLIYSASFLYSG

VPSRFSGSRSGTDFTLTISSLQPEDFATYYCQQHYTTPPTFGQCTKVEIKRGGGGSGG

GGSGGGGSGGGGSGGGGSGGGGSEVQLVESGGGLVQPGGSLRLSCAASGFNIKDTY

IHWVRQAPGKCLEWVARIYPTNGYTRYADSVKGRFTISADTSKNTAYLQMNSLRAE

DTAVYYCSRWGGDGFYAMDYWGQGTLVTVSSGGGGSGGGGSGGGGSGGGGSHVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSSGGGGS

GGGGSGGGGSGGGGSGGGGSGGGGSQAVVTQEPSLTVSPGGTVTLTCGSSTGAVTASNY

ANWVQQKPGQCPRGLIGGHNNRPPGVPARFSGSLLGGKAALTLLGAQPEDEAEYYCALW
```

-continued

YSDHWVIGGGTKLTVLG(TPLGDTTHT)SGKPLDGEYFTLQIRGRERFEMFRELNEA
LELKDAQAGKEPGGSGGAPHHHHHH

HER2 (LHDS) P53 BiDE (LL) cDNA (hu4D5-scFv, huC825-scFv,
huP53-tet, <u>GS linker</u>, (IgG3 spacer))

SEQ ID NO: 70

*GATATTCAGATGACTCAGTCCCCTAGTTCACTGTCTGCCTCAGTCGGAGATCGGGTCA*

*CTATCACTTGTCGGGCTTCTCAGGATGTGAACACCGCCGTGGCCTGGTACCAGCAGAA*

*GCCAGGCAAGGCCCCCAAGCTGCTGATCTACTCTGCCAGCTTCCTGTATTCCGGAGTG*

*CCATCTCGGTTTTCCGGCAGCCGGAGCGGCACCGACTTCACCCTGACAATCAGCTCC*

*CTGCAGCCTGAGGATTTTGCCACATACTATTGCCAGCAGCACTATACCACACCCCCTAC*

*CTTCGGCCAGtGCACAAAGGTGGAGATCAAGAGG*<u>GGAGGAGGAGGATCCGGAGGAG</u>

<u>GAGGCAGCGGAGGCGGCGGCTCCGGCGGCGGCGGCTCTGGCGGCGGCGGCAGC</u>

<u>GGAGGAGGCGGCTCC</u>*GAGGTGCAGCTGGTGGAGTCCGGCGGCGGCCTGGTGCAGC*

*CCGGCGGCAGCCTGCGGCTGTCCTGTGCCGCCTCTGGCTTTAACATCAAGGACACCT*

*ACATCCACTGGGTGAGGCAGGCACCTGGCAAGtGCCTGGAGTGGGTGGCAAGGATCT*

*ATCCAACCAATGGCTACACAAGATATGCCGACTCCGTGAAGGGCCGCTTTACCATCAG*

*CGCCGATACCTCCAAGAACACAGCCTACCTGCAGATGAATTCTCTGCGGGCCGAGGAT*

*ACAGCCGTGTACTATTGCTCCAGATGGGGCGGCGACGGCTTCTATGCTATGGACTATT*

*GGGGGCAGGGAACTCTGGTCACTGTCTCCTCT*<u>GGCGGAGGGGGATCCGGCGGCGG</u>

<u>AGGATCTGGCGGAGGTGGAAGTGGGGGAGGCGGATCT</u>*CATGTGCAGCTGGTGGAA*

*AGCGGAGGCGGCCTGGTGCAGCCTGGGGGATCTCTGAGACTGTCTTGTGCCGCCAG*

*CGGCTTCTCCCTGACCGATTATGGCGTGCACTGGGTGCGACAGGCCCCTGGCAAAGG*

*ACTGGAATGGCTGGGAGTGATTTGGAGTGGCGGAGGCACCGCCTACAACACCGCCCT*

*GATCTCCCGGTTCACCATCAGCCGGGACAACTCCAAGAACACCCTGTACCTGCAGATG*

*AACTCCCTGCGGGCCGAGGACACCGCTGTGTACTACTGCGCCAGACGGGGCTCCTAC*

*CCCTACAACTACTTCGACGCTTGGGGCTGCGGCACCCTCGTGACAGTGTCTAGC*<u>GGA</u>

<u>GGGGGAGGTTCTGGGGGCGGAGGTTCAGGTGGTGGTGGTTCCGGGGGTGGTGGCTC</u>

<u>TGGTGGCGGTGGTTCTGGCGGTGGCGGATCT</u>*CAGGCTGTCGTGACCCAGGAACCCAG*

*CCTGACTGTGTCTCCTGGCGGAACCGTGACCCTGACCTGCGGATCTTCTACCGGCGC*

*TGTGACCGCCAGCAACTACGCCAATTGGGTGCAGCAGAAACCTGGACAGTGCCCTAG*

*AGGCCTGATCGGCGGCACAACAACAGACCTCCAGGCGTGCCAGCCCGGTTCTCTGG*

*ATCTCTGCTGGGCGGAAAGGCCGCTCTGACACTGCTGGGTGCTCAGCCTGAGGACGA*

*GGCCGAGTACTACTGTGCCCTGTGGTACTCCGACCACTGGGTCATCGGAGGCGGGAC*

*CAAGCTGACCGTGCTGGGA*(ACACCCCTGGGAGACACCACACATACT)AGTGGGAA

ACCTCTGGATGGCGAGTACTTTACCCTGCAGATTAGAGGCCGCGAACGATT

CGAGATGTTTCGCGAACTGAATGAGGCCCTGGAACTGAAGGATGCTCAGGC

AGGCAAGGAGCCAGGAGGGTCAGGAGGAGCACCGCACCATCATCATCACCAT

HER2 (LH) P53 BiDE (LL) polypeptide (hu4D5-scFv, huC825-scFv,
huP53-tet, <u>GS linker</u>, (IgG3 spacer))

SEQ ID NO: 71

DIQMTQSPSSLSASVGDRVTITCRASQDVNTAVAWYQQKPGKAPKLLIYSASFLYSG

VPSRFSGSRSGTDFTLTISSLQPEDFATYYCQQHYTTPPTFGQGTKVEIKR<u>GGGGSGG</u>

<u>GGSGGGGSGGGGSGGGGSGGGGS</u>EVQLVESGGGLVQPGGSLRLSCAASGFNIKDTY

IHWVRQAPGKGLEWVARIYPTNGYTRYADSVKGRFTISADTSKNTAYLQMNSLRAE

DTAVYYCSRWGGDGFYAMDYWGQGTLVTVSS<u>GGGGSGGGGSGGGGSGGGGS</u>HVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSS<u>GGGGS</u>

<u>GGGGSGGGGSGGGGSGGGGSGGGGS</u>QAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGKPLDGEYFTLQIRGRERFEMFRELNEA

LELKDAQAGKEPGGSGGAPHHHHHH

HER2 (LH) P53 BiDE (LL) cDNA (hu4D5-scFv, huC825-scFv,
huP53-tet, <u>GS linker</u>, (IgG3 spacer))

SEQ ID NO: 72

GATATTCAGATGACTCAGTCCCCTAGTTCACTGTCTGCCTCAGTCGGAGATCGGTCA

CTATCACTTGTCGGGCTTCTCAGGATGTGAACACCGCCGTGGCCTGGTACCAGCAGAA

GCCAGGCAAGGCCCCCAAGCTGCTGATCTACTCTGCCAGCTTCCTGTATTCCGGAGTG

CCATCTCGGTTTTCCGGCAGCCGGAGCGGCACCGACTTCACCCTGACAATCAGCTCC

CTGCAGCCTGAGGATTTTGCCACATACTATTGCCAGCAGCACTATACCACACCCCTAC

CTTCGGCCAGGGCACAAAGGTGGAGATCAAGAGG<u>GGAGGAGGAGGATCCGGAGGA</u>

<u>GGAGGCAGCGGAGGCGGCGGCTCCGGCGGCGGCGGCTCTGGCGGCGGCGGCAG</u>

<u>CGGAGGAGGCGGCTCC</u>GAGGTGCAGCTGGTGGAGTCCGGCGGCGGCCTGGTGCAG

CCCGGCGGCAGCCTGCGGCTGTCCTGTGCCGCCTCTGGCTTTAACATCAAGGACACC

TACATCCACTGGGTGAGGCAGGCACCTGGCAAGGGCCTGGAGTGGGTGGCAAGGATC

TATCCAACCAATGGCTACACAAGATATGCCGACTCCGTGAAGGGCCGCTTTACCATCA

GCGCCGATACCTCCAAGAACACAGCCTACCTGCAGATGAATTCTCTGCGGGCCGAGG

ATACAGCCGTGTACTATTGCTCCAGATGGGGCGGCGACGGCTTCTATGCTATGGACTA

TTGGGGGCAGGGAACTCTGGTCACTGTCTCCTC<u>TGGCGGAGGGGGATCCGGCGGCG</u>

<u>GAGGATCTGGCGGAGGTGGAAGTGGGGGAGGCGGATCT</u>CATGTGCAGCTGGTGG

AAAGCGGAGGCGGCCTGGTGCAGCCTGGGGGATCTCTGAGACTGTCTTGTGCCGCCA

GCGGCTTCTCCCTGACCGATTATGGCGTGCACTGGGTGCGACAGGCCCCTGGCAAAG

GACTGGAATGGCTGGGAGTGATTTGGAGTGGCGGAGGCACCGCCTACAACACCGCCC

TGATCTCCCGGTTCACCATCAGCCGGGACAACTCCAAGAACACCCTGTACCTGCAGAT

GAACTCCCTGCGGGCCGAGGACACCGCTGTGTACTACTGCGCCAGCGGGGCTCCTA

CCCCTACAACTACTTCGACGCTTGGGGCTGCGGCACCCTCGTGACAGTGTCTAGC<u>GG</u>

<u>AGGGGGAGGTTCTGGGGGCGGAGGTTCAGGTGGTGGTGGTTCCGGGGGTGGTGGCT</u>

<u>CTGGTGGCGGTGGTTCTGGCGGTGGCGGATCT</u>CAGGCTGTCGTGACCCAGGAACCCA

GCCTGACTGTGTCTCCTGGCGGAACCGTGACCCTGACCTGCGGATCTTCTACCGGCG

CTGTGACCGCCAGCAACTACGCCAATTGGGTGCAGCAGAAACCTGGACAGTGCCCTA

GAGGCCTGATCGGCGGCCACAACAACAGACCTCCAGGCGTGCCAGCCCGGTTCTCTG

GATCTCTGCTGGGCGGAAAGGCCGCTCTGACACTGCTGGGTGCTCAGCCTGAGGACG

AGGCCGAGTACTACTGTGCCCTGTGGTACTCCGACCACTGGGTCATCGGAGGCGGGA

CCAAGCTGACCGTGCTGGGA(ACACCCCTGGGAGACACCACACATACT)AGTGGGA

AACCTCTGGATGGCGAGTACTTTACCCTGCAGATTAGAGGCCGCGAACGAT

TCGAGATGTTTCGCGAACTGAATGAGGCCCTGGAACTGAAGGATGCTCAGG

CAGGCAAGGAGCCAGGAGGGTCAGGAGGAGCACCGCACCATCATCATCACCAT

HER2 (HL DS) P63 BiDE (LL) polypeptide (hu4D5-scFv,
huC825-scFv, huP63-tet, GS linker, (IgG3 spacer))
SEQ ID NO: 73

EVQLVESGGGLVQPGGSLRLSCAASGFNIKDTYIHWVRQAPGKCLEWVARIYPTNG

YTRYADSVKGRFTISADTSKNTAYLQMNSLRAEDTAVYYCSRWGGDGFYAMDYW

GQGTLVTVSSGGGGSGGGGSGGGGSGGGGSGGGGSGGGGSDIQMTQSPSSLSASVG

DRVTITCRASQDVNTAVAWYQQKPGKAPKLLIYSASFLYSGVPSRFSGSRSGTDFTLT

ISSLQPEDFATYYCQQHYTTPPTFGQCTKVEIKRGGGGSGGGGSGGGGSGGGGSHVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSSGGGGS

GGGGSGGGGSGGGGSGGGGSGGGGSQAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGRSPDDELLYLPVRGRETYEMLLKIKESL

ELMQYLPQHTIETYRQQQQQQHQHLLQKQGGSGGAPHHHHHH

HER2 (HL DS) P63 BiDE (LL) cDNA (hu4D5-scFv, huC825-scFv,
huP63-tet, GS linker, (IgG3 spacer))
SEQ ID NO: 74

*GAAGTGCAGCTGGTCGAATCCGGGGGGGGCCTGGTGCAGCCTGGAGGGTCACTGAG*

*ACTGTCCTGTGCCGCATCTGGGTTCAATATCAAGGACACCTACATCCACTGGGTGCGG*

*CAGGCACCTGGCAAGtGtCTGGAGTGGGTGGCAAGGATCTATCCAACCAACGGCTACA*

*CACGGTATGCCGACTCCGTGAAGGGCCGGTTCACCATCTCCGCCGATACCTCTAAGAA*

*CACAGCCTACCTGCAGATGAATTCTCTGAGGGCCGAGGATACAGCCGTGTACTATTGC*

*AGCCGCTGGGGAGGCGACGGCTTCTACGCTATGGACTATTGGGGCCAGGGCACCCTG*

*GTGACAGTGAGCTCTGGCGGCGGCGGATCCGGAGGAGGAGGCAGCGGCGGAGGA*

*GGCTCCGGAGGAGGCGGCTCTGGCGGCGGCGGCAGCGGCGGCGGCGGCTCCGAC*

*ATCCAGATGACCCAGTCCCCATCTAGCCTGAGCGCCTCCGTGGGCGACAGGGTGACC*

*ATCACATGCCGCGCCAGCCAGGATGTGAATACAGCCGTGGCCTGGTACCAGCAGAAG*

*CCAGGCAAGGCCCCCAAGCTGCTGATCTACTCTGCCAGCTTCCTGTATAGCGGAGTGC*

*CATCCCGGTTTTCCGGCAGCCGGAGCGGCACCGACTTCACCCTGACAATCTCCTCTCT*

*GCAGCCTGAGGATTTTGCCACATACTATTGTCAGCAGCACTATACCACACCCCCTACAT*

*TCGGACAGTGTACAAAGGTCGAGATCAAACGCGGCGGAGGGGGATCCGGCGGCGGA*

*GGATCTGCGGAGGTGGAAGTGGGGGAGGCGGATCT*CATGTGCAGCTGGTGGAAA

GCGGAGGCGGCCTGGTGCAGCCTGGGGGATCTCTGAGACTGTCTTGTGCCGCCAGC

GGCTTCTCCCTGACCGATTATGGCGTGCACTGGGTGCGACAGGCCCCTGGCAAAGGA

CTGGAATGGCTGGGAGTGATTTGGAGTGGCGGAGGCACCGCCTACAACACCGCCCTG

ATCTCCCGGTTCACCATCAGCCGGGACAACTCCAAGAACACCCTGTACCTGCAGATGA

ACTCCCTGCGGGCCGAGGACACCGCTGTGTACTACTGCGCCAGACGGGGCTCCTACC

CCTACAACTACTTCGACGCTTGGGGCTGCGGCACCCTCGTGACAGTGTCTAGC*GGAG*

*GGGGAGGTTCTGGGGGCGGAGGTTCAGGTGGTGGTGGTTCCGGGGGTGGTGGCTCT*

*GGTGGCGGTGGTTCTGGCGGTGGCGGATCT*CAGGCTGTCGTGACCCAGGAACCCAG

CCTGACTGTGTCTCCTGGCGGAACCGTGACCCTGACCTGCGGATCTTCTACCGGCGC

TGTGACCGCCAGCAACTACGCCAATTGGGTGCAGCAGAAACCTGGACAGTGCCCTAG

AGGCCTGATCGGCGGCCACAACAACAGACCTCCAGGCGTGCCAGCCCGGTTCTCTGG

```
ATCTCTGCTGGGCGGAAAGGCCGCTCTGACACTGCTGGGTGCTCAGCCTGAGGACGA

GGCCGAGTACTACTGTGCCCTGTGGTACTCCGACCACTGGGTCATCGGAGGCGGGAC

CAAGCTGACCGTGCTGGGA(ACACCCTGGGAGACACCACACATACT)AGTGGGAG
```
ATCCCCCGACGATGAGCTGCTGTACCTGCCTGTGAGGGGCCGGGAGACCTA

TGAAATGCTGCTGAAGATCAAAGAGAGCCTGGAACTGATGCAGTACCTGCC

ACAGCACACCATTGAAACATATAGGCAACAACAGCAGCAGCAGCATCAGCA

TCTGCTGCAGAAGCAGGGAGGGTCAGGAGGAGCACCGCACCATCATCATCACCAT

HER2 (HL) P63 BiDE (LL) polypeptide (hu4D5-scFv,
huC825-scFv, huP63-tet, <u>GS linker</u>, (IgG3 spacer))

SEQ ID NO: 75

*EVQLVESGGGLVQPGGSLRLSCAASGFNIKDTYIHWVRQAPGKGLEWVARIYPTNG*

*YTRYADSVKGRFTISADTSKNTAYLQMNSLRAEDTAVYYCSRWGGDGFYAMDYW*

*GQGTLVTVSS<u>GGGGSGGGGSGGGGSGGGGSGGGGSGGGGS</u>DIQMTQSPSSLSASVG*

*DRVTITCRASQDVNTAVAWYQQKPGKAPKLLIYSASFLYSGVPSRFSGSRSGTDFTLT*

*ISSLQPEDFATYYCQQHYTTPPTFGQGTKVEIK<u>RGGGGSGGGGSGGGGSGGGGS</u>HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS<u>GGGGS</u>*

*<u>GGGGSGGGGSGGGGSGGGGSGGGGS</u>QAVVTQEPSLTVSPGGTVTLTCGSSTGAVTASNY*

*ANWVQQKPGQCPRGLIGGHNNRPPGVPARFSGSLLGGKAALTLLGAQPEDEAEYYCALW*

*YSDHWVIGGGTKLTVLG(TPLGDTTHT)SG*RSPDDELLYLPVRGRETYEMLLKIKESL*

*ELMQYLPQHTIETYRQQQQQQHQHLLQKQ**GGSGGAPHHHHHH*

HER2 (HL) P63 BiDE (LL) cDNA (hu4D5-scFv, huC825-scFv,
huP63-tet, <u>GS linker</u>, (IgG3 spacer))

SEQ ID NO: 76

*GAAGTGCAGCTGGTCGAATCCGGGGGGGGCCTGGTGCAGCCTGGAGGGTCACTGAG*

*ACTGTCCTGTGCCGCATCTGGGTTCAATATCAAGGACACCTACATCCACTGGGTGCGG*

*CAGGCACCTGGCAAGGGACTGGAGTGGGTGGCAAGGATCTATCCAACCAACGGCTAC*

*ACACGGTATGCCGACTCCGTGAAGGGCCGGTTCACCATCTCCGCCGATACCTCTAAGA*

*ACACAGCCTACCTGCAGATGAATTCTCTGAGGGCCGAGGATACAGCCGTGTACTATTG*

*CAGCCGCTGGGGAGGCGACGGCTTCTACGCTATGGACTATTGGGGCCAGGGCACCCT*

*GGTGACAGTGAGCTCT<u>GGCGGCGGCGGATCCGGAGGAGGAGGCAGCGGCGGAGG</u>*

*<u>AGGCTCCGGAGGAGGCGGCTCTGGCGGCGGCGGCAGCGGCGGCGGCGGCTCC</u>GA*

*CATCCAGATGACCCAGTCCCCATCTAGCCTGAGCGCCTCCGTGGGCGACAGGGTGAC*

*CATCACATGCCGCGCCAGCCAGGATGTGAATACAGCCGTGGCCTGGTACCAGCAGAA*

*GCCAGGCAAGGCCCCCAAGCTGCTGATCTACTCTGCCAGCTTCCTGTATAGCGGAGTG*

*CCATCCCGGTTTTCCGGCAGCCGGAGCGGCACCGACTTCACCCTGACAATCTCCTCTC*

*TGCAGCCTGAGGATTTTGCCACATAGTATTGTCAGCAGCACTATACCACACCCCCTACA*

*TTCGGACAGGGGACAAAGGTCGAGATCAAACGCGGC<u>GGAGGGGGATCCGGCGGCG</u>*

*<u>GAGGATCTGGCGGAGGTGGAAGTGGGGGAGGCGGATCT</u>CATGTGCAGCTGGTGG*

*AAAGCGGAGGCGGCCTGGTGCAGCCTGGGGGATCTCTGAGACTGTCTTGTGCCGCCA*

*GCGGCTTCTCCCTGACCGATTATGGCGTGCACTGGGTGCGACAGGCCCCTGGCAAAG*

*GACTGGAATGGCTGGGAGTGATTTGGAGTGGCGGAGGCACCGCCTACAACACCGCCC*

*TGATCTCCCGGTTCACCATCAGCCGGGACAACTCCAAGAACACCCTGTACCTGCAGAT*

*GAACTCCCTGCGGGCCGAGGACACCGCTGTGTACTACTGCGCCAGACGGGGCTCCTA*

-continued

CCCCTACAACTACTTCGACGCTTGGGGCTGCGGCACCCTCGTGACAGTGTCTAGC<u>GG</u>
<u>AGGGGGAGGTTCTGGGGGCGGAGGTTCAGGTGGTGGTGGTTCCGGGGGTGGTGGCT</u>
<u>CTGGTGGCGGTGGTTCTGGCGGTGGCGGATCT</u>CAGGCTGTCGTGACCCAGGAACCCA
GCCTGACTGTGTCTCCTGGCGGAACCGTGACCCTGACCTGCGGATCTTCTACCGGCG
CTGTGACCGCCAGCAACTACGCCAATTGGGTGCAGCAGAAACCTGGACAGTGCCCTA
GAGGCCTGATCGGCGGCCACAACAACAGACCTCCAGGCGTGCCAGCCCGGTTCTCTG
GATCTCTGCTGGGCGGAAAGGCCGCTCTGACACTGCTGGGTGCTCAGCCTGAGGACG
AGGCCGAGTACTACTGTGCCCTGTGGTACTCCGACCACTGGGTCATCGGAGGCGGGA
CCAAGCTGACCGTGCTGGGA(ACACCCCTGGGAGACACCACACATACT)AGTGGGA
GATCCCCCGACGATGAGCTGCTGTACCTGCCTGTGAGGGGCCGGGAGACCT
ATGAAATGCTGCTGAAGATCAAAGAGAGCCTGGAACTGATGCAGTACCTGC
CACAGCACACCATTGAAACATATAGGCAACAACAGCAGCAGCAGCATCAGC
ATCTGCTGCAGAAGCAGGGAGGGTCAGGAGGAGCACCGCACCATCATCATCAC
CAT

HER2 (LH DS) P63 BiDE (LL) polypeptide (hu4D5-scFv,
huC825-scFv, huP63-tet, <u>GS linker</u>, (IgG3 spacer))
SEQ ID NO: 77

DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQCTKVEIKR<u>GGGGSGG</u>
<u>GGSGGGGSGGGGSGGGGSGGGGS</u>EVQLVESGGGLVQPGGSLRLSCAASGFNIKDTY
IHWVRQAPGKCLEWVARIYPTNGYTRYADSVKGRFTISADTSKNTAYLQMNSLRAE
DTAVYYCSRWGGDGFYAMDYWGQGTLVTVS<u>SGGGGSGGGGSGGGGSGGGGS</u>HVQ
LVESGGGLVQPGGSLRLSCAASGFSLTDYGVHWVRQAPGKGLEWLGVIWSGGGTAYNTA
LISRFTISRDNSKNTLYLQMNSLRAEDTAVYYCARRGSYPYNYFDAWGCGTLVTVS<u>SGGGGS</u>
<u>GGGGSGGGGSGGGGSGGGGSGGGGS</u>QAVVTQEPSLTVSPGGTVTLTCGSSTGAVTASNY
ANWVQQKPGQCPRGLIGGHNNRPPGVPARFSGSLLGGKAALTLLGAQPEDEAEYYCALW
YSDHWVIGGGTKLTVLG(TPLGDTTHT)SGRSPDDELLYLPVRGRETYEMLLKIKESL
ELMQYLPQHTIETYRQQQQQHQHLLQKQGGSGGAPHHHHHH

HER2 (LHDS) P63 BiDE(LL) cDNA (hu4D5-scFv, huC825-scFv,
huP63-tet, <u>GS linker</u>, (IgG3 spacer))
SEQ ID NO: 78

CTATCACTTGTCGGGCTTCTCAGGATGTGAACACCGCCGTGGCCTGGTACCAGCAGAA
GCCAGGCAAGGCCCCCAAGCTGCTGATCTACTCTGCCAGCTTCCTGTATTCCGGAGTG
CCATCTCGGTTTTCCGGCAGCCGGAGCGGCACCGACTTCACCCTGACAATCAGCTCC
CTGCAGCCTGAGGATTTTGCCACATACTATTGCCAGCAGCACTATACCACACCCCCTAC
CTTCGGCCAGtGCACAAAGGTGGAGATCAAGAGG<u>GGAGGAGGAGGATCCGGAGGAG</u>
<u>GAGGCAGCGGAGGCGGCGGCTCCGGCGGCGGCGGCTCTGGCGGCGGCGGCAGC</u>
<u>GGAGGAGGCGGCTCC</u>GAGGTGCAGCTGGTGGAGTCCGGCGGCGGCCTGGTGCAGC
CCGGCGGCAGCCTGCGGCTGTCCTGTGCCGCCTCTGGCTTTAACATCAAGGACACCT
ACATCCACTGGGTGAGGCAGGCACCTGGCAAGtGCCTGGAGTGGGTGGCAAGGATCT
ATCCAACCAATGGCTACACAAGATATGCCGACTCCGTGAAGGGCCGCTTTACCATCAG
CGCCGATACCTCCAAGAACACAGCCTACCTGCAGATGAATTCTCTGCGGGCCGAGGAT
ACAGCCGTGTACTATTGCTCCAGATGGGGCGGCGACGGCTTCTATGCTATGGACTATT

-continued

```
GGGGGCAGGGAACTCTGGTCACTGTCTCCTCTGGCGGAGGGGGATCCGGCGGCGG

AGGATCTGGCGGAGGTGGAAGTGGGGGAGGCGGATCTCATGTGCAGCTGGTGGAA

AGCGGAGGCGGCCTGGTGCAGCCTGGGGGATCTCTGAGACTGTCTTGTGCCGCCAG

CGGCTTCTCCCTGACCGATTATGGCGTGCACTGGGTGCGACAGGCCCCTGGCAAGG

ACTGGAATGGCTGGGAGTGATTTGGAGTGGCGGAGGCACCGCCTACAACACCGCCCT

GATCTCCCGGTTCACCATCAGCCGGGACAACTCCAAGAACACCCTGTACCTGCAGATG

AACTCCCTGCGGGCCGAGGACACCGCTGTGTACTACTGCGCCAGACGGGGCTCCTAC

CCCTACAACTACTTCGACGCTTGGGGCTGCGGCACCCTCGTGACAGTGTCTAGCGGA

GGGGGAGGTTCTGGGGGCGGAGGTTCAGGTGGTGGTGGTTCCGGGGGTGGTGGCTC

TGGTGGCGGTGGTTCTGGCGGTGGCGGATCTCAGGCTGTCGTGACCCAGGAACCCAG

CCTGACTGTGTCTCCTGGCGGAACCGTGACCCTGACCTGCGGATCTTCTACCGGCGC

TGTGACCGCCAGCAACTACGCCAATTGGGTGCAGCAGAAACCTGGACAGTGCCCTAG

AGGCCTGATCGGCGGCCACAACAACAGACCTCCAGGCGTGCCAGCCCGGTTCTCTGG

ATCTCTGCTGGGCGGAAAGGCCGCTCTGACACTGCTGGGTGCTCAGCCTGAGGACGA

GGCCGAGTACTACTGTGCCCTGTGGTACTCCGACCACTGGGTCATCGGAGGCGGGAC

CAAGCTGACCGTGCTGGGA(ACACCCCTGGGAGACACCACACATACT)AGTGGGAG

ATCCCCCGACGATGAGCTGCTGTACCTGCCTGTGAGGGGCCGGGAGACCTA

TGAAATGCTGCTGAAGATCAAAGAGAGCCTGGAACTGATGCAGTACCTGCC

ACAGCACACCATTGAAACATATAGGCAACAACAGCAGCAGCAGCATCAGCA

TCTGCTGCAGAAGCAGGGAGGGTCAGGAGGAGCACCGCACCATCATCATCACCAT
```

HER2 (LH) P63 BiDE(LL) polypeptide (hu4D5-scFv, huC825-scFv,
huP63-tet, GS linker, (IgG3 spacer))

SEQ ID NO: 79

```
DIQMTQSPSSLSASVGDRVTITCRASQDVNTAVAWYQQKPGKAPKLLIYSASFLYSG

VPSRFSGSRSGTDFTLTISSLQPEDFATYYCQQHYTTPPTFGQGTKVEIKRGGGGSGG

GGSGGGGSGGGGSGGGGSGGGGSEVQLVESGGGLVQPGGSLRLSCAASGFNIKDTY

IHWVRQAPGKGLEWVARIYPTNGYTRYADSVKGRFTISADTSKNTAYLQMNSLRAE

DTAVYYCSRWGGDGFYAMDYWGQGTLVTVSSGGGGSGGGGSGGGGSGGGGSHVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSSGGGGS

GGGGSGGGGSGGGGSGGGGSGGGGSQAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGRSPDDELLYLPVRGRETYEMLLKIKESL
```

ELMQYLPQHTIETYRQQQQQQHQHLLQKQGGSGGAPHHHHHH

HER2 (LH) P63 BiDE(LL) cDNA (hu4D5-scFv, huC825-scFv,
huP63-tet, GS linker, (IgG3 spacer))

SEQ ID NO: 80

```
GATATTCAGATGACTCAGTCCCCTAGTTCACTGTCTGCCTCAGTCGGAGATCGGGTCA

CTATCACTTGTCGGGCTTCTCAGGATGTGAACACCGCCGTGGCCTGGTACCAGCAGAA

GCCAGGCAAGGCCCCCAAGCTGCTGATCTACTCTGCCAGCTTCCTGTATTCCGGAGTG

CCATCTCGGTTTTCCGGCAGCCGGAGCGGCACCGACTTCACCCTGACAATCAGCTCC

CTGCAGCCTGAGGATTTTGCCACATACTATTGCCAGCAGCACTATACCACACCCCCTAC

CTTCGGCCAGGGCACAAAGGTGGAGATCAAGAGGGGAGGAGGAGGATCCGGAGGA
```

-continued

<u>GGAGGCAGCGGAGGCGGCGGCTCCGGCGGCGGCGGCTCTGGCGGCGGCGGCAG</u>

<u>CGGAGGAGGCGGCTCC</u>GAGGTGCAGCTGGTGGAGTCCGGCGGCGGCCTGGTGCAG

*CCCGGCGGCAGCCTGCGGCTGTCCTGTGCCGCCTCTGGCTTTAACATCAAGGACACC*

*TACATCCACTGGGTGAGGCAGGCACCTGGCAAGGGCCTGGAGTGGGTGGCAAGGATC*

*TATCCAACCAATGGCTACACAAGATATGCCGACTCCGTGAAGGGCCGCTTTACCATCA*

*GCGCCGATACCTCCAAGAACACAGCCTACCTGCAGATGAATTCTCTGCGGGCCGAGG*

*ATACAGCCGTGTACTATTGCTCCAGATGGGGCGGCGACGGCTTCTATGCTATGGACTA*

*TTGGGGGCAGGGAACTCTGGTCACTGTCTCCTCT*<u>GGCGGAGGGGGATCCGGCGGCG</u>

<u>GAGGATCTGGCGGAGGTGGAAGTGGGGGAGGCGGATCT</u>CATGTGCAGCTGGTGG

AAAGCGGAGGCGGCCTGGTGCAGCCTGGGGGATCTCTGAGACTGTCTTGTGCCGCCA

GCGGCTTCTCCCTGACCGATTATGGCGTGCACTGGGTGCGACAGGCCCCTGGCAAAG

GACTGGAATGGCTGGGAGTGATTTGGAGTGGCGGAGGCACCGCCTACAACACCGCCC

TGATCTCCCGGTTCACCATCAGCCGGGACAACTCCAAGAACACCCTGTACCTGCAGAT

GAACTCCCTGCGGGCCGAGGACACCGCTGTGTACTACTGCGCCAGACGGGGCTCCTA

CCCCTACAACTACTTCGACGCTTGGGGCTGCGGCACCCTCGTGACAGTGTCTAGC<u>GG</u>

<u>AGGGGGAGGTTCTGGGGGCGGAGGTTCAGGTGGTGGTGGTTCCGGGGGTGGTGGCT</u>

<u>CTGGTGGCGGTGGTTCTGGCGGTGGCGGATCT</u>CAGGCTGTCGTGACCCAGGAACCCA

GCCTGACTGTGTCTCCTGGCGGAACCGTGACCCTGACCTGCGGATCTTCTACCGGCG

CTGTGACCGCCAGCAACTACGCCAATTGGGTGCAGCAGAAACCTGGACAGTGCCCTA

GAGGCCTGATCGGCGGCCACAACAACAGACCTCCAGGCGTGCCAGCCCGGTTCTCTG

GATCTCTGCTGGGCGGAAAGGCCGCTCTGACACTGCTGGGTGCTCAGCCTGAGGACG

AGGCCGAGTACTACTGCCCTGTGGTACTCCGACCACTGGGTCATCGGAGGCGGGA

CCAAGCTGACCGTGCTGGGA(ACACCCCTGGGAGACACCACACACTACT)AGTGGGA

GATCCCCCGACGATGAGCTGCTGTACCTGCCTGTGAGGGGCCGGGAGACCT

ATGAAATGCTGCTGAAGATCAAAGAGAGCCTGGAACTGATGCAGTACCTGC

CACAGCACACCATTGAAACATATAGGCAACAACAGCAGCAGCATCAGC

ATCTGCTGCAGAAGCAGGGAGGGTCAGGAGGAGCACCGCACCATCATCATCAC

CAT

HER2 (HL DS) P73 BiDE(LL) polypeptide (hu4D5-scFv,
huC825-scFv, huP73-tet, <u>GS linker</u>, (IgG3 spacer))
                     SEQ ID NO: 81

EVQLVESGGGLVQPGGSLRLSCAASGFNIKDTYIHWVRQAPGKCLEWVARIYPTNG

YTRYADSVKGRFTISADTSKNTAYLQMNSLRAEDTAVYYCSRWGGDGFYAMDYW

GQGTLVTVSS<u>GGGGSGGGGSGGGGSGGGGSGGGGSGGGGS</u>DIQMTQSPSSLSASVG

*DRVTITCRASQDVNTAVAWYQQKPGKAPKLLIYSASFLYSGVPSRFSGSRSGTDFTLT*

*ISSLQPEDFATYYCQQHYTTPPTFGQCTKVEIK*<u>RGGGGSGGGGSGGGGSGGGGS</u>*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*<u>GGGGS</u>

<u>GGGGSGGGGSGGGGSGGGGSGGGGS</u>*QAVVTQEPSLTVSPGGTVTLTCGSSTGAVTASNY*

*ANWVQQKPGQCPRGLIGGHNNRPPGVPARFSGSLLGGKAALTLLGAQPEDEAEYYCALW*

*YSDHWVIGGGTKLTVLG*(TPLGDTTHT)SGRHGDEDTYYLQVRGRENFEILMKLKES

LELMELVPQPLVDSYRQQQQLLQRPGGSGGAPHHHHHH

HER2 (HL DS) P73 BiDE(LL) cDNA (hu4D5-scFv, huC825-scFv, huP73-tet, <u>GS linker</u>, (IgG3 spacer))
SEQ ID NO: 82

*GAAGTGCAGCTGGTCGAATCCGGGGGGGCCTGGTGCAGCCTGGAGGGTCACTGAG*

*ACTGTCCTGTGCCGCATCTGGGTTCAATATCAAGGACACCTACATCCACTGGGTGCGG*

*CAGGCACCTGGCAAGtGtCTGGAGTGGGTGGCAAGGATCTATCCAACCAACGGCTACA*

*CACGGTATGCCGACTCCGTGAAGGGCCGGTTCACCATCTCCGCCGATACCTCTAAGAA*

*CACAGCCTACCTGCAGATGAATTCTCTGAGGGCCGAGGATACAGCCGTGTACTATTGC*

*AGCCGCTGGGGAGGCGACGGCTTCTACGCTATGGACTATTGGGGCCAGGGCACCCTG*

*GTGACAGTGAGCTCT*<u>GGCGGCGGCGGATCCGGAGGAGGAGGCAGCGGCGGAGGA</u>

<u>GGCTCCGGAGGAGGCGGCTCTGGCGGCGGCGGCAGCGGCGGCGGCGGCTCC</u>*GAC*

*ATCCAGATGACCCAGTCCCCATCTAGCCTGAGCGCCTCCGTGGGCGACAGGGTGACC*

*ATCACATGCCGCGCCAGCCAGGATGTGAATACAGCCGTGGCCTGGTACCAGCAGAAG*

*CCAGGCAAGGCCCCCAAGCTGCTGATCTACTCTGCCAGCTTCCTGTATAGCGGAGTGC*

*CATCCCGGTTTTCCGGCAGCCGGAGCGGCACCGACTTCACCCTGACAATCTCCTCTCT*

*GCAGCCTGAGGATTTTGCCACATACTATTGTCAGCAGCACTATACCACACCCCCTACAT*

*TCGGACAGTGTACAAAGGTCGAGATCAAACGC*<u>GGCGGAGGGGGATCCGGCGGCGGA</u>

<u>GGATCTGGCGGAGGTGGAAGTGGGGGAGGCGGATCT</u>*CATGTGCAGCTGGTGGAAA*

*GCGGAGGCGGCCTGGTGCAGCCTGGGGGATCTCTGAGACTGTCTTGTGCCGCCAGC*

*GGCTTCTCCCTGACCGATTATGGCGTGCACTGGGTGCGACAGGCCCCTGGCAAAGGA*

*CTGGAATGGCTGGGAGTGATTTGGAGTGGCGGAGGCACCGCCTACAACACCGCCCTG*

*ATCTCCCGGTTCACCATCAGCCGGGACAACTCCAAGAACACCCTGTACCTGCAGATGA*

*ACTCCCTGCGGGCCGAGGACACCGCTGTGTACTACTGCGCCAGACGGGGCTCCTACC*

*CCTACAACTACTTCGACGCTTGGGGCTGCGGCACCCTCGTGACAGTGTCTAGC*<u>GGAG</u>

<u>GGGGAGGTTCTGGGGGCGGAGGTTCAGGTGGTGGTGGTTCCGGGGGTGGTGGCTCT</u>

<u>GGTGGCGGTGGTTCTGGCGGTGGCGGATCT</u>*CAGGCTGTCGTGACCCAGGAACCCAG*

*CCTGACTGTGTCTCCTGGCGGAACCGTGACCCTGACCTGCGGATCTTCTACCGGCGC*

*TGTGACCGCCAGCAACTACGCCAATTGGGTGCAGCAGAAACCTGGACAGTGCCCTAG*

*AGGCCTGATCGGCGGCCACAACAACAGACCTCCAGGCGTGCCAGCCCGGTTCTCTGG*

*ATCTCTGCTGGGCGGAAAGGCCGCTCTGACACTGCTGGGTGCTCAGCCTGAGGACGA*

*GGCCGAGTACTACTGTGCCCTGTGGTACTCCGACCACTGGGTCATCGGAGGCGGGAC*

*CAAGCTGACCGTGCTGGGA*(ACACCCCTGGGAGACACCACACATACT)*AGTGGG*AG

GCACGGCGACGAAGATACCTACTATCTGCAGGTGAGGGGACGGGAGAACTT

CGAAATCCTGATGAAGCTGAAAGAGTCCCTGGAACTGATGGAGCTGGTGCC

CCAGCCTCTGGTCGACAGCTACAGACAGCAGCAGCAGCTGCTGCAGAGGCC

AGGAGGGTCAGGAGGAGCACCGCACCATCATCATCACCAT

HER2 (HL) P73 BiDE(LL) polypeptide (hu4D5-scFv, huC825-scFv, huP73-tet, <u>GS linker</u>, (IgG3 spacer))
SEQ ID NO: 83

EVQLVESGGGLVQPGGSLRLSCAASGFNIKDTYIHWVRQAPGKGLEWVARIYPTNG

YTRYADSVKGRFTISADTSKNTAYLQMNSLRAEDTAVYYCSRWGGDGFYAMDYW

GQGTLVTVSS<u>GGGGSGGGGSGGGGSGGGGSGGGGSGGGGS</u>DIQMTQSPSSLSASVG

DRVTITCRASQDVNTAVAWYQQKPGKAPKLLIYSASFLYSGVPSRFSGSRSGTDFTLT

ISSLQPEDFATYYCQQHYTTPPTFGQGTKVEIKR<u>GGGGSGGGGSGGGGSGGGGS</u>*HVQ*

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSS<u>GGGGS</u>

<u>GGGGSGGGGSGGGGSGGGGSGGGGS</u>QAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGRHGDEDTYYLQVRGRENFEILMKLKES

LELMELVPQPLVDSYRQQQQLLQRPGGSGGAPHHHHHH

HER2 (HL) P73 BiDE(LL) cDNA (hu4D5-scFv, huC825-scFv,
huP73-tet, <u>GS linker</u>, (IgG3 spacer))

SEQ ID NO: 84

GAAGTGCAGCTGGTCGAATCCGGGGGGGGCCTGGTGCAGCCTGGAGGGTCACTGAG

ACTGTCCTGTGCCGCATCTGGGTTCAATATCAAGGACACCTACATCCACTGGGTGCGG

CAGGCACCTGGCAAGGGACTGGAGTGGGTGGCAAGGATCTATCCAACCAACGGCTAC

ACACGGTATGCCGACTCCGTGAAGGGCCGGTTCACCATCTCCGCCGATACCTCTAAGA

ACACAGCCTACCTGCAGATGAATTCTCTGAGGGCCGAGGATACAGCCGTGTACTATTG

CAGCCGCTGGGGAGGCGACGGCTTCTACGCTATGGACTATTGGGGCCAGGGCACCCT

GGTGACAGTGAGCTCT<u>GGCGGCGGCGGATCCGGAGGAGGAGGCAGCGGCGGAGG</u>

<u>AGGCTCCGGAGGAGGCGGCTCTGGCGGCGGCGGCAGCGGCGGCGGCGGCTCCGA</u>

CATCCAGATGACCCAGTCCCCATCTAGCCTGAGCGCCTCCGTGGGCGACAGGGTGAC

CATCACATGCCGCGCCAGCCAGGATGTGAATACAGCCGTGGCCTGGTACCAGCAGAA

GCCAGGCAAGGCCCCCAAGCTGCTGATCTACTCTGCCAGCTTCCTGTATAGCGGAGTG

CCATCCCGGTTTTCCGGCAGCCGGAGCGGCACCGACTTCACCCTGACAATCTCCTCTC

TGCAGCCTGAGGATTTTGCCACATACTATTGTCAGCAGCACTATACCACACCCCCTACA

TTCGGACAGGGGACAAAGGTCGAGATCAAACG<u>CGGCGGAGGGGGATCCGGCGGCG</u>

<u>GAGGATCTGGCGGAGGTGGAAGTGGGGGAGGCGGATCT</u>CATGTGCAGCTGGTGG

AAAGCGGAGGCGGCCTGGTGCAGCCTGGGGGATCTCTGAGACTGTCTTGTGCCGCCA

GCGGCTTCTCCCTGACCGATTATGGCGTGCACTGGGTGCGACAGGCCCCTGGCAAAG

GACTGGAATGGCTGGGAGTGATTTGGAGTGGCGGAGGCACCGCCTACAACACCGCCC

TGATCTCCCGGTTCACCATCAGCCGGGACAACTCCAAGAACACCCTGTACCTGCAGAT

GAACTCCCTGCGGGCCGAGGACACCGCTGTGTACTACTGCGCCAGACGGGGCTCCTA

CCCCTACAACTACTTCGACGCTTGGGGCTGCGGCACCCTCGTGACAGTGTCTAGC<u>GG</u>

<u>AGGGGGAGGTTCTGGGGGCGGAGGTTCAGGTGGTGGTGGTTCCGGGGGTGGTGGCT</u>

<u>CTGGTGGCGGTGGTTCTGGCGGTGGCGGATCT</u>CAGGCTGTCGTGACCCAGGAACCCA

GCCTGACTGTGTCTCCTGGCGGAACCGTGACCCTGACCTGCGGATCTTCTACCGGCG

CTGTGACCGCCAGCAACTACGCCAATTGGGTGCAGCAGAAACCTGGACAGTGCCCTA

GAGGCCTGATCGGCGGCCACAACAACAGACCTCCAGGCGTGCCAGCCCGGTTCTCTG

GATCTCTGCTGGGCGGAAAGGCCGCTCTGACACTGCTGGGTGCTCAGCCTGAGGACG

AGGCCGAGTACTACTGTGCCCTGTGGTACTCCGACCACTGGGTCATCGGAGGCGGGA

CCAAGCTGACCGTGCTGGGA(ACACCCCTGGGAGACACCACACATACT)AGTGGGA

GGCACGGCGACGAAGATACCTACTATCTGCAGGTGAGGGGACGGGAGAACT

TCGAAATCCTGATGAAGCTGAAAGAGTCCCTGGAACTGATGGAGCTGGTGC

CCCAGCCTCTGGTCGACAGCTACAGACAGCAGCAGCAGCTGCTGCAGAGGC

CAGGAGGGTCAGGAGGAGCACCGCACCATCATCATCACCAT

HER2 (LH DS) P73 BiDE(LL) polypeptide (hu4D5-scFv,
huC825-scFv, huP73-tet, GS linker, (IgG3 spacer))
SEQ ID NO: 85

DIQMTQSPSSLSASVGDRVTITCRASQDVNTAVAWYQQKPGKAPKLLIYSASFLYSG

VPSRFSGSRSGTDFTLTISSLQPEDFATYYCQQHYTTPPTFGQCTKVEIKRGGGSGG

GGSGGGGSGGGGSGGGGSGGGGSEVQLVESGGGLVQPGGSLRLSCAASGFNIKDTY

IHWVRQAPGKCLEWVARIYPTNGYTRYADSVKGRFTISADTSKNTAYLQMNSLRAE

DTAVYYCSRWGGDGFYAMDYWGQGTLVTVSSGGGGSGGGGSGGGGSGGGGSHVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSSGGGGS

GGGGSGGGGSGGGGSGGGGSGGGGSQAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGRHGDEDTYYLQVRGRENFEILMKLKES

LELMELVPQPLVDSYRQQQQLLQRPGGSGGAPHHHHHH

HER2 (LHDS) P73 BiDE(LL) cDNA (hu4D5-scFv, huC825-scFv,
huP73-tet, GS linker, (IgG3 spacer))
SEQ ID NO: 86

GATATTCAGATGACTCAGTCCCCTAGTTCACTGTCTGCCTCAGTCGGAGATCGGGTCA

CTATCACTTGTCGGGCTTCTCAGGATGTGAACACCGCCGTGGCCTGGTACCAGCAGAA

GCCAGGCAAGGCCCCCAAGCTGCTGATCTACTCTGCCAGCTTCCTGTATTCCGGAGTG

CCATCTCGGTTTTCCGGCAGCCGGAGCGGCACCGACTTCACCCTGACAATCAGCTCC

CTGCAGCCTGAGGATTTTGCCACATACTATTGCCAGCAGCACTATACCACACCCCCTAC

CTTCGGCCAGtGCACAAAGGTGGAGATCAAGAGGGGAGGAGGAGGATCCGGAGGAG

GAGGCAGCGGAGGCGGCGGCTCCGGCGGCGGCGGCTCTGGCGGCGGCGGCAGC

GGAGGAGGCGGCTCCGAGGTGCAGCTGGTGGAGTCCGGCGGCGGCCTGGTGCAGC

CCGGCGGCAGCCTGCGCTGTCCTGTGCCGCCTCTGGCTTTAACATCAAGGACACCT

ACATCCACTGGGTGAGGCAGGCACCTGGCAAGtGCCTGGAGTGGGTGGCAAGGATCT

ATCCAACCAATGGCTACACAAGATATGCCGACTCCGTGAAGGGCCGCTTTACCATCAG

CGCCGATACCTCCAAGAACACAGCCTACCTGCAGATGAATTCTCTGCGGGCCGAGGAT

ACAGCCGTGTACTATTGCTCCAGATGGGGCGGCGACGGCTTCTATGCTATGGACTATT

GGGGGCAGGGAACTCTGGTCACTGTCTCCTCTGGCGGAGGGGGATCCGGCGGCGG

AGGATGTGGCGGAGGTGGAAGTGGGGGAGGCGGATCTCATGTGCAGCTGGTGGAA

AGCGGAGGCGGCCTGGTGCAGCCTGGGGGATCTCTGAGACTGTCTTGTGCCGCCAG

CGGCTTCTCCCTGACCGATTATGGCGTGCACTGGGTGCGACAGGCCCCTGGCAAAGG

ACTGGAATGGCTGGGAGTGATTTGGAGTGGCGGAGGCACCGCCTACAACACCGCCCT

GATCTCCCGGTTCACCATCAGCCGGGACAACTCCAAGAACACCCTGTACCTGCAGATG

AACTCCCTGCGGGCCGAGGACACCGCTGTGTACTACTGCGCCAGACGGGGCTCCTAC

CCCTACAACTACTTCGACGCTTGGGGCTGCGGCACCCTCGTGACAGTGTCTAGCGGA

GGGGGAGGTTCTGGGGGCGGAGGTTCAGGTGGTGGTGGTTCCGGGGGTGGTGGCTC

TGGTGGCGGTGGTTCTGGCGGTGGCGGATCTCAGGCTGTCGTGACCCAGGAACCCAG

CCTGACTGTGTCTCCTGGCGGAACCGTGACCCTGACCTGCGGATCTTCTACCGGCGC

TGTGACCGCCAGCAACTACGCCAATTGGGTGCAGCAGAAACCTGGACAGTGCCCTAG

AGGCCTGATCGGCGGCCACAACAACAGACCTCCAGGCGTGCCAGCCCGGTTCTCTGG

-continued

ATCTCTGCTGGGCGGAAAGGCCGCTCTGACACTGCTGGGTGCTCAGCCTGAGGACGA

GGCCGAGTACTACTGTGCCCTGTGGTACTCCGACCACTGGGTCATCGGAGGCGGGAC

CAAGCTGACCGTGCTGGGA(ACACCCTGGGAGACACCACACATACT)AGTGGGAG

GCACGGCGACGAAGATACCTACTATCTGCAGGTGAGGGGACGGGAGAACTT

CGAAATCCTGATGAAGCTGAAAGAGTCCCTGGAACTGATGGAGCTGGTGCC

CCAGCCTCTGGTCGACAGCTACAGACAGCAGCAGCAGCTGCTGCAGAGGCC

AGGAGGGTCAGGAGGAGCACCGCACCATCATCATCACCAT

HER2 (LH) P73 BiDE(LL) polypeptide (hu4D5-scFv, huC825-
scFv, huP73-tet, <u>GS linker</u>, (IgG3 spacer))
SEQ ID NO: 87

DIQMTQSPSSLSASVGDRVTITCRASQDVNTAVAWYQQKPGKAPKLLIYSASFLYSG

VPSRFSGSRSGTDFTLTISSLQPEDFATYYCQQHYTTPPTFGQGTKVEIKR<u>GGGGSGG</u>

<u>GGSGGGGSGGGGSGGGGSGGGGS</u>EVQLVESGGGLVQPGGSLRLSCAASGFNIKDTY

IHWVRQAPGKGLEWVARIYPTNGYTRYADSVKGRFTISADTSKNTAYLQMNSLRAE

DTAVYYCSRWGGDGFYAMDYWGQGTLVTVSS<u>GGGGSGGGGSGGGGSGGGGS</u>HVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSS<u>GGGGS</u>

<u>GGGGSGGGGSGGGGSGGGGSGGGGS</u>QVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGRHGDEDTYYLQVRGRENFEILMKLKES

LELMELVPQPLVDSYRQQQQLLQRPGGSGGAPHHHHHH

HER2 (LH) P73 BiDE(LL) cDNA (hu4D5-scFv, huC825-scFv,
huP73-tet, <u>GS linker</u>, (IgG3 spacer))
SEQ ID NO: 88

GATATTCAGATGACTCAGTCCCCTAGTTCACTGTCTGCCTCAGTCGGAGATCGGGTCA

CTATCACTTGTCGGGCTTCTCAGGATGTGAACACCGCCGTGGCCTGGTACCAGCAGAA

GCCAGGCAAGGCCCCCAAGCTGCTGATCTACTCTGCCAGCTTCCTGTATTCCGGAGTG

CCATCTCGGTTTTCCGGCAGCCGGAGCGGCACCGACTTCACCCTGACAATCAGCTCC

CTGCAGCCTGAGGATTTTGCCACATACTATTGCCAGCAGCACTATACCACACCCCCTAC

CTTCGGCCAGGGCACAAAGGTGGAGATCAAGAGG<u>GGAGGAGGAGGATCCGGAGGA</u>

<u>GGAGGCAGCGGAGGCGGCGGCTCCGGCGGCGGCGGCTCTGGCGGCGGCGGCAG</u>

<u>CGGAGGAGGCGGCTCC</u>GAGGTGCAGCTGGTGGAGTCCGGCGGCGGCCTGGTGCAG

CCCGGCGGCAGCCTGCGGCTGTCCTGTGCCGCCTCTGGCTTTAACATCAAGGACACC

TACATCCACTGGGTGAGGCAGGCACCTGGCAAGGGCCTGGAGTGGGTGGCAAGGATC

TATCCAACCAATGGCTACACAAGATATGCCGACTCCGTGAAGGGCCGCTTTACCATCA

GCGCCGATACCTCCAAGAACACAGCCTACCTGCAGATGAATTCTCTGCGGGCCGAGG

ATACAGCCGTGTACTATTGCTCCAGATGGGGCGGCGACGGCTTCTATGCTATGGACTA

TTGGGGGCAGGGAACTCTGGTCACTGTCTCCTCT<u>GGCGGAGGGGGATCCGGCGGCG</u>

<u>GAGGATCTGGCGGAGGTGGAAGTGGGGGAGGCGGATCT</u>CATGTGCAGCTGGTGG

AAAGCGGAGGCGGCCTGGTGCAGCCTGGGGGATCTCTGAGACTGTCTTGTGCCGCCA

GCGGCTTCTCCCTGACCGATTATGGCGTGCACTGGGTGCGACAGGCCCCTGGCAAAG

GACTGGAATGGCTGGGAGTGATTTGGAGTGGCGGAGGCACCGCCTACAACACCGCCC

TGATCTCCCGGTTCACCATCAGCCGGGACAACTCCAAGAACACCCTGTACCTGCAGAT

GAACTCCCTGCGGGCCGAGGACACCGCTGTGTACTACTGCGCCAGACGGGGCTCCTA

-continued

CCCCTACAACTACTTCGACGCTTGGGGCTGCGGCACCCTCGTGACAGTGTCTAGC<u>GG</u>
<u>AGGGGGAGGTTCTGGGGGCGGAGGTTCAGGTGGTGGTGGTTCCGGGGGTGGTGGCT</u>
<u>CTGGTGGCGGTGGTTCTGGCGGTGGCGGATCT</u>CAGGCTGTCGTGACCCAGGAACCCA
GCCTGACTGTGTCTCCTGGCGGAACCGTGACCCTGACCTGCGGATCTTCTACCGGCG
CTGTGACCGCCAGCAACTACGCCAATTGGGTGCAGCAGAAACCTGGACAGTGCCCTA
GAGGCCTGATCGGCGGCCACAACAACAGACCTCCAGGCGTGCCAGCCCGGTTCTCTG
GATCTCTGCTGGGCGGAAAGGCCGCTCTGACACTGCTGGGTGCTCAGCCTGAGGACG
AGGCCGAGTACTACTGTGCCCTGTGGTACTCCGACCACTGGGTCATCGGAGGCGGGA
CCAAGCTGACCGTGCTGGGA(ACACCCCTGGGAGACACCACACATACT)AGTGGGA
GGCACGGCGACGAAGATACCTACTATCTGCAGGTGAGGGGACGGGAGAACT
TCGAAATCCTGATGAAGCTGAAAGAGTCCCTGGAACTGATGGAGCTGGTGC
CCCAGCCTCTGGTCGACAGCTACAGACAGCAGCAGCAGCTGCTGCAGAGGC
CAGGAGGGTCAGGAGGAGCACCGCACCATCATCATCACCAT

HER2 (HL DS) HNRNPC BiDE(LL) polypeptide (hu4D5-scFv,
huC825-scFv, huHNRNPC-tet, <u>GS linker</u>, (IgG3 spacer))
SEQ ID NO: 89
EVQLVESGGGLVQPGGSLRLSCAASGFNIKDTYIHWVRQAPGKCLEWVARIYPTNG
YTRYADSVKGRFTISADTSKNTAYLQMNSLRAEDTAVYYCSRWGGDGFYAMDYW
GQGTLVTVSS<u>GGGGSGGGGSGGGGSGGGGSGGGGSGGGGS</u>DIQMTQSPSSLSASVG
DRVTITCRASQDVNTAVAWYQQKPGKAPKLLIYSASFLYSGVPSRFSGSRSGTDFTLT
ISSLQPEDFATYYCQQHYTTPPTFGQCTKVEIKR<u>GGGGSGGGGSGGGGSGGGGS</u>HVQ
LVESGGGLVQPGGSLRLSCAASGFSLTDYGVHWVRQAPGKGLEWLGVIWSGGGTAYNTA
LISRFTISRDNSKNTLYLQMNSLRAEDTAVYYCARRGSYPYNYFDAWGCGTLVTVSS<u>GGGGS</u>
<u>GGGGSGGGGSGGGGSGGGGSGGGGS</u>QAVVTQEPSLTVSPGGTVTLTCGSSTGAVTASNY
ANWVQQKPGQCPRGLIGGHNNRPPGVPARFSGSLLGGKAALTLLGAQPEDEAEYYCALW
YSDHWVIGGGTKLTVLG(TPLGDTTHT)SGQAIKKELTQIKQKVDSLLENLEKIEKEG
GSGGAPHHHHHH HER2 (HL DS) HNRNPC BiDE(LL) cDNA (hu4D5-scFv,
huC825-scFv, huHNRNPC-tet, <u>GS linker</u>, (IgG3 spacer))
SEQ ID NO: 90
GAAGTGCAGCTGGTCGAATCCGGGGGGGGCCTGGTGCAGCCTGGAGGGTCACTGAG
ACTGTCCTGTGCCGCATCTGGGTTCAATATCAAGGACACCTACATCCACTGGGTGCGG
CAGGCACCTGGCAAGtGtCTGGAGTGGGTGGCAAGGATCTATCCAACCAACGGCTACA
CACGGTATGCCGACTCCGTGAAGGGCCGGTTCACCATCTCCGCCGATACCTCTAAGAA
CACAGCCTACCTGCAGATGAATTCTCTGAGGGCCGAGGATACAGCCGTGTACTATTGC
AGCCGCTGGGGAGGCGACGGCTTCTACGCTATGGACTATTGGGGCCAGGGCACCCTG
GTGACAGTGAGCTCT<u>GGCGGCGGCGGATCCGGAGGAGGAGGCAGCGGCGGAGGA</u>
<u>GGCTCCGGAGGAGGCGGCTCTGGCGGCGGCGGCAGCGGCGGCGGCGGCTCC</u>GAC
ATCCAGATGACCCAGTCCCCATCTAGCCTGAGCGCCTCCGTGGGCGACAGGGTGACC
ATCACATGCCGCGCCAGCCAGGATGTGAATACAGCCGTGGCCTGGTACCAGCAGAAG
CCAGGCAAGGCCCCCAAGCTGCTGATCTACTCTGCCAGCTTCCTGTATAGCGGAGTGC
CATCCCGGTTTTCCGGCAGCCGGAGCGGCACCGACTTCACCCTGACAATCTCCTCTCT
GCAGCCTGAGGATTTTGCCACATACTATTGTCAGCAGCACTATACCACACCCCCTACAT -continued TCGGACAGTGTACAAAGGTCGAGATCAAACGCGG<u>CGGAGGGGATCCGGCGGCGGA</u>

<u>GGATCTGCGGAGGTGGAAGTGGGGGAGGCGGATCT</u>CATGTGCAGCTGGTGGAAA

GCGGAGGCGGCCTGGTGCAGCCTGGGGATCTCTGAGACTGTCTTGTGCCGCCAGC

GGCTTCTCCCTGACCGATTATGGCGTGCACTGGGTGCGACAGGCCCCTGGCAAGGA

CTGGAATGGCTGGGAGTGATTTGGAGTGGCGGAGGCACCGCCTACAACACCGCCCTG

ATCTCCCGGTTCACCATCAGCCGGGACAACTCCAAGAACACCCTGTACCTGCAGATGA

ACTCCCTGCGGGCCGAGGACACCGCTGTGTACTACTGCGCCAGACGGGGCTCCTACC

CCTACAACTACTTCGACGCTTGGGGCTGCGGCACCCTCGTGACAGTGTCTAGC<u>GGAG</u>

<u>GGGGAGGTTCTGGGGGCGGAGGTTCAGGTGGTGGTGGTTCCGGGGGTGGTGGCTCT</u>

<u>GGTGGCGGTGGTTCTGGCGGTGGCGGATCT</u>CAGGCTGTCGTGACCCAGGAACCCAG

CCTGACTGTGTCTCCTGGCGGAACCGTGACCCTGACCTGCGGATCTTCTACCGGCGC

TGTGACCGCCAGCAACTACGCCAATTGGGTGCAGCAGAAACCTGGACAGTGCCCTAG

AGGCCTGATCGGCGGCCACAACAACAGACCTCCAGGCGTGCCAGCCCGGTTCTCTGG

ATCTCTGCTGGGCGGAAAGGCCGCTCTGACACTGCTGGGTGCTCAGCCTGAGGACGA

GGCCGAGTACTACTGTGCCCTGTGGTACTCCGACCACTGGGTCATCGGAGGCGGGAC

CAAGCTGACCGTGCTGGGA(ACACCCCTGGGAGACACCACACATACT)AGTGGGCA

GGCCATCAAGAAGGAGCTGACCCAGATCAAGCAGAAGGTGGACAGCCTGCT

GGAGAACCTGGAGAAGATCGAGAAGGAGGGAGGGTCAGGAGGAGCACCGCA

CCATCATCATCACCAT

HER2 (HL) HNRNPC BiDE(LL) polypeptide (hu4D5-scFv,
huC825-scFv, huHNRNPC-tet, <u>GS linker</u>, (IgG3 spacer))
SEQ ID NO: 91

*EVQLVESGGGLVQPGGSLRLSCAASGFNIKDTYIHWVRQAPGKGLEWVARIYPTNG*

*YTRYADSVKGRFTISADTSKNTAYLQMNSLRAEDTAVYYCSRWGGDGFYAMDYW*

*GQGTLVTVSS*<u>GGGGSGGGGSGGGGSGGGGSGGGGSGGGGS</u>*DIQMTQSPSSLSASVG*

*DRVTITCRASQDVNTAVAWYQQKPGKAPKLLIYSASFLYSGVPSRFSGSRSGTDFTLT*

*ISSLQPEDFATYYCQQHYTTPPTFGQGTKVEIKR*<u>GGGGSGGGGSGGGGSGGGGS</u>*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*<u>GGGGS</u>

<u>GGGGSGGGGSGGGGSGGGGSGGGGS</u>*QAVVTQEPSLTVSPGGTVTLTCGSSTGAVTASNY*

*ANWVQQKPGQCPRGLIGGHNNRPPGVPARFSGSLLGGKAALTLLGAQPEDEAEYYCALW*

*YSDHWVIGGGTKLTVLG*(TPLGDTTHT)SGQAIKKELTQIKQKVDSLLENLEKIEKEG

GSGGAPHHHHHH

HER2 (HL) HNRNPC BiDE(LL) cDNA (hu4D5-scFv,
huC825-scFv, huHNRNPC-tet, <u>GS linker</u>, (IgG3 spacer))
SEQ ID NO: 92

*GAAGTGCAGCTGGTCGAATCCGGGGGGGCCTGGTGCAGCCTGGAGGGTCACTGAG*

*ACTGTCCTGTGCCGCATCTGGGTTCAATATCAAGGACACCTACATCCACTGGGTGCGG*

*CAGGCACCTGGCAAGGGACTGGAGTGGGTGGCAAGGATCTATCCAACCAACGGCTAC*

*ACACGGTATGCCGACTCCGTGAAGGGCCGGTTCACCATCTCCGCCGATACCTCTAAGA*

*ACACAGCCTACCTGCAGATGAATTCTCTGAGGGCCGAGGATACAGCCGTGTACTATTG*

*CAGCCGCTGGGGAGGCGACGGCTTCTACGCTATGGACTATTGGGGCCAGGGCACCCT*

*GGTGACAGTGAGCTCT*<u>GGCGGCGGCGGATCCGGAGGAGGAGGCAGCGGCGGAGG</u>

<u>AGGCTCCGGAGGAGGCGGCTCTGGCGGCGGCGGCAGCGGCGGCGGCGGCTCCGA</u>

-continued

CATCCAGATGACCCAGTCCCCATCTAGCCTGAGCGCCTCCGTGGGCGACAGGGTGAC

CATCACATGCCGCGCCAGCCAGGATGTGAATACAGCCGTGGCCTGGTACCAGCAGAA

GCCAGGCAAGGCCCCCAAGCTGCTGATCTACTCTGCCAGCTTCCTGTATAGCGGAGTG

CCATCCCGGTTTTCCGGCAGCCGGAGCGGCACCGACTTCACCCTGACAATCTCCTCTC

TGCAGCCTGAGGATTTTGCCACATAGTATTGTCAGCAGCACTATACCACACCCCTACA

TTCGACAGGGGACAAAGGTCGAGATCAAACGC<u>GGCGGAGGGGGATCCGGCGGCG</u>

<u>GAGGATCTGGCGGAGGTGGAAGTGGGGGAGGCGGATCT</u>CATGTGCAGCTGGTGG

AAAGCGGAGGCGGCCTGGTGCAGCCTGGGGGATCTCTGAGACTGTCTTGTGCCGCCA

GCGGCTTCTCCCTGACCGATTATGGCGTGCACTGGGTGCGACAGGCCCCTGGCAAAG

GACTGGAATGGCTGGGAGTGATTTGGAGTGGCGGAGGCACCGCCTACAACACCGCCC

TGATCTCCCGGTTCACCATCAGCCGGGACAACTCCAAGAACACCCTGTACCTGCAGAT

GAACTCCCTGCGGGCCGAGGACACCGCTGTGTACTACTGCGCCAGAGGGGCTCCTA

CCCCTACAACTACTTCGACGCTTGGGGCTGCGGCACCCTCGTGACAGTGTCTAGC<u>GG</u>

<u>AGGGGGAGGTTCTGGGGGCGGAGGTTCAGGTGGTGGTGGTTCCGGGGGTGGTGGCT</u>

<u>CTGGTGGCGGTGGTTCTGGCGGTGGCGGATCT</u>CAGGCTGTCGTGACCCAGGAACCCA

GCCTGACTGTGTCTCCTGGCGGAACCGTGACCCTGACCTGCGGATCTTCTACCGGCG

CTGTGACCGCCAGCAACTACGCCAATTGGGTGCAGCAGAAACCTGGACAGTGCCCTA

GAGGCCTGATCGGCGGCCACAACAACAGACCTCCAGGCGTGCCAGCCCGGTTCTCTG

GATCTCTGCTGGGCGGAAAGGCCGCTCTGACACTGCTGGGTGCTCAGCCTGAGGACG

AGGCCGAGTACTACTGTGCCCTGTGGTACTCCGACCACTGGGTCATCGGAGGCGGGA

CCAAGCTGACCGTGCTGGGA(ACACCCCTGGGAGACACCACACATACT)

AGTGGGCAGGCCATCAAGAAGGAGCTGACCCAGATCAAGCAGAAGGTGGAC

AGCCTGCTGGAGAACCTGGAGAAGATCGAGAAGGAGGGAGGGTCAGGAGGA

GCACCGCACCATCATCATCACCAT

HER2 (LH DS) HNRNPC BiDE(LL) polypeptide (hu4D5-scFv,
huC825-scFv, huHNRNPC-tet, <u>GS linker</u>, (IgG3 spacer))
SEQ ID NO: 93

DIQMTQSPSSLSASVGDRVTITCRASQDVNTAVAWYQQKPGKAPKLLIYSASFLYSG

VPSRFSGSRSGTDFTLTISSLQPEDFATYYCQQHYTTPPTFGQCTKVEIKR<u>GGGGSGG</u>

<u>GGSGGGGSGGGGSGGGGSGGGGS</u>EVQLVESGGGLVQPGGSLRLSCAASGFNIKDTY

IHWVRQAPGKCLEWVARIYPTNGYTRYADSVKGRFTISADTSKNTAYLQMNSLRAE

DTAVYYCSRWGGDGFYAMDYWGQGTLVTVSS<u>GGGGSGGGGSGGGGSGGGGS</u>HVQ

LVESGGGLVQPGGSLRLSCAASGFSLTDYGVHWVRQAPGKGLEWLGVIWSGGGTAYNTA

LISRFTISRDNSKNTLYLQMNSLRAEDTAVYYCARRGSYPYNYFDAWGCGTLVTVSS<u>GGGGS</u>

<u>GGGGSGGGGSGGGGSGGGGSGGGGS</u>QAVVTQEPSLTVSPGGTVTLTCGSSTGAVTASNY

ANWVQQKPGQCPRGLIGGHNNRPPGVPARFSGSLLGGKAALTLLGAQPEDEAEYYCALW

YSDHWVIGGGTKLTVLG(TPLGDTTHT)SGQAIKKELTQIKQKVDSLLENLEKIEKEG

GSGGAPHHHHHH

HER2 (LHDS) HNRNPC BiDE(LL) cDNA (hu4D5-scFv,
huC825-scFv, huHNRNPC-tet, <u>GS linker</u>, (IgG3 spacer))
SEQ ID NO: 94

GATATTCAGATGACTCAGTCCCCTAGTTCACTGTCTGCCTCAGTCGGAGATCGGGTCA

CTATCACTTGTCGGGCTTCTCAGGATGTGAACACCGCCGTGGCCTGGTACCAGCAGAA

-continued

```
GCCAGGCAAGGCCCCCAAGCTGCTGATCTACTCTGCCAGCTTCCTGTATTCCGGAGTG
CCATCTCGGTTTTCCGGCAGCCGGAGCGGCACCGACTTCACCCTGACAATCAGCTCC
CTGCAGCCTGAGGATTTTGCCACATACTATTGCCAGCAGCACTATACCACACCCCCTAC
CTTCGGCCAgtGCACAAAGGTGGAGATCAAGAGGGGAGGAGGAGGATCCGGAGGAG
GAGGCAGCGGAGGCGGCGGCTCCGGCGGCGGCGGCTCTGGCGGCGGCGGCAGC
GGAGGAGGCGGCTCCGAGGTGCAGCTGGTGGAGTCCGGCGGCGGCCTGGTGCAGC
CCGGCGGCAGCCTGCGGCTGTCCTGTGCCGCCTCTGGCTTTAACATCAAGGACACCT
ACATCCACTGGGTGAGGCAGGCACCTGGCAAGtGCCTGGAGTGGGTGGCAAGGATCT
ATCCAACCAATGGCTACACAAGATATGCCGACTCCGTGAAGGGCCGCTTTACCATCAG
CGCCGATACCTCCAAGAACACAGCCTACCTGCAGATGAATTCTCTGCGGGCCGAGGAT
ACAGCCGTGTACTATTGCTCCAGATGGGGCGGCGACGGCTTCTATGCTATGGACTATT
GGGGCAGGGAACTCTGGTCACTGTCTCCTCTGGCGGAGGGGGATCCGGCGGCGG
AGGATCTGGCGGAGGTGGAAGTGGGGGAGGCGGATCTCATGTGCAGCTGGTGGAA
AGCGGAGGCGGCCTGGTGCAGCCTGGGGGATCTCTGAGACTGTCTTGTGCCGCCAG
CGGCTTCTCCCTGACCGATTATGGCGTGCACTGGGTGCGACAGGCCCCTGGCAAAGG
ACTGGAATGGCTGGGAGTGATTTGGAGTGGCGGAGGCACCGCCTACAACACCGCCCT
GATCTCCCGGTTCACCATCAGCCGGGACAACTCCAAGAACACCCTGTACCTGCAGATG
AACTCCCTGCGGGCCGAGGACACCGCTGTGTACTACTGCGCCAGACGGGGCTCCTAC
CCCTACAACTACTTCGACGCTTGGGGCTGCGGCACCCTCGTGACAGTGTCTAGCGGA
GGGGGAGGTTCTGGGGGCGGAGGTTCAGGTGGTGGTGGTTCCGGGGGTGGTGGCTC
TGGTGGCGGTGGTTCTGGCGGTGGCGGATCTCAGGCTGTCGTGACCCAGGAACCCAG
CCTGACTGTGTCTCCTGGCGGAACCGTGACCCTGACCTGCGGATCTTCTACCGGCGC
TGTGACCGCCAGCAACTACGCCAATTGGGTGCAGCAGAAACCTGGACAGTGCCCTAG
AGGCCTGATCGGCGGCCACAACAACAGACCTCCAGGCGTGCCAGCCCGGTTCTCTGG
ATCTCTGCTGGGCGGAAAGGCCGCTCTGACACTGCTGGGTGCTCAGCCTGAGGACGA
GGCCGAGTACTACTGTGCCCTGTGGTACTCCGACCACTGGGTCATCGGAGGCGGGAC
CAAGCTGACCGTGCTGGGA(ACACCCCTGGGAGACACCACACATACT)AGTGGGCA
GGCCATCAAGAAGGAGCTGACCCAGATCAAGCAGAAGGTGGACAGCCTGCT
GGAGAACCTGGAGAAGATCGAGAAGGAGGGAGGGTCAGGAGGAGCACCGCA
CCATCATCATCACCAT
```

HER2 (LH) HNRNPC BiDE(LL) polypeptide (hu4D5-scFv, huC825-scFv, huHNRNPC-tet, GS linker, (IgG3 spacer))

SEQ ID NO: 95

```
DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKRGGGGSGG
GGSGGGGSGGGGSGGGGSGGGGSEVQLVESGGGLVQPGGSLRLSCAASGFNIKDTY
IHWVRQAPGKGLEWVARIYPTNGYTRYADSVKGRFTISADTSKNTAYLQMNSLRAE
DTAVYYCSRWGGDGFYAMDYWGQGTLVTVSSGGGGSGGGGSGGGGSGGGGSHVQ
LVESGGGLVQPGGSLRLSCAASGFSLTDYGVHWVRQAPGKGLEWLGVIWSGGGTAYNTA
LISRFTISRDNSKNTLYLQMNSLRAEDTAVYYCARRGSYPYNYFDAWGCGTLVTVSSGGGGS
GGGGSGGGGSGGGGSGGGGSQAVVTQEPSLTVSPGGTVTLTCGSSTGAVTASNY
ANWVQQKPGQCPRGLIGGHNNRPPGVPARFSGSLLGGKAALTLLGAQPEDEAEYYCALW
```

-continued

```
YSDHWVIGGGTKLTVLG(TPLGDTTHT)SGQAIKKELTQIKQKVDSLLENLEKIEKEG

GSGGAPHHHHHH

HER2 (LH) HNRNPC BiDE(LL) cDNA (hu4D5-scFv,
huC825-scFv, huHNRNPC-tet, GS linker, (IgG3 spacer))
                                                SEQ ID NO: 96
GATATTCAGATGACTCAGTCCCCTAGTTCACTGTCTGCCTCAGTCGGAGATCGGGTCA

CTATCACTTGTCGGGCTTCTCAGGATGTGAACACCGCCGTGGCCTGGTACCAGCAGAA

GCCAGGCAAGGCCCCCAAGCTGCTGATCTACTCTGCCAGCTTCCTGTATTCCGGAGTG

CCATCTCGGTTTTCCGGCAGCCGGAGCGGCACCGACTTCACCCTGACAATCAGCTCC

CTGCAGCCTGAGGATTTTGCCACATACTATTGCCAGCAGCACTATACCACACCCCCTAC

CTTCGGCCAGGGCACAAAGGTGGAGATCAAGAGGGGAGGAGGAGGATCCGGAGGA

GGAGGCAGCGGAGGCGGCGGCTCCGGCGGCGGCGGCTCTGGCGGCGGCGGCAG

CGGAGGAGGCGGCTCCGAGGTGCAGCTGGTGGAGTCCGGCGGCGGCCTGGTGCAG

CCCGGCGGCAGCCTGCGGCTGTCCTGTGCCGCCTCTGGCTTTAACATCAAGGACACC

TACATCCACTGGGTGAGGCAGGCACCTGGCAAGGGCCTGGAGTGGGTGGCAAGGATC

TATCCAACCAATGGCTACACAAGATATGCCGACTCCGTGAAGGGCCGCTTTACCATCA

GCGCCGATACCTCCAAGAACACAGCCTACCTGCAGATGAATTCTCTGCGGGCCGAGG

ATACAGCCGTGTACTATTGCTCCAGATGGGGCGGCGACGGCTTCTATGCTATGGACTA

TTGGGGGCAGGGAACTCTGGTCACTGTCTCCTCGGCGGAGGGGATCCGGCGGCG

GAGGATCTGGCGGAGGTGGAAGTGGGGGAGGCGGATCTCATGTGCAGCTGGTGG

AAAGCGGAGGCGGCCTGGTGCAGCCTGGGGATCTCTGAGACTGTCTTGTGCCGCCA

GCGGCTTCTCCCTGACCGATTATGGCGTGCACTGGGTGCGACAGGCCCCTGGCAAAG

GACTGGAATGGCTGGGAGTGATTTGGAGTGGCGGAGGCACCGCCTACAACACCGCCC

TGATCTCCCGGTTCACCATCAGCCGGGACAACTCCAAGAACACCCTGTACCTGCAGAT

GAACTCCCTGCGGGCCGAGGACACCGCTGTGTACTACTGCGCCAGACGGGGCTCCTA

CCCCTACAACTACTTCGACGCTTGGGGCTGCGGCACCCTCGTGACAGTGTCTAGCGG

AGGGGGAGGTTCTGGGGGCGGAGGTTCAGGTGGTGGTGGTTCCGGGGGTGGTGGCT

CTGGTGGCGGTGGTTCTGGCGGTGGCGGATCTCAGGCTGTCGTGACCCAGGAACCCA

GCCTGACTGTGTCTCCTGGCGGAACCGTGACCCTGACCTGCGGATCTTCTACCGGCG

CTGTGACCGCCAGCAACTACGCCAATTGGGTGCAGCAGAAACCTGGACAGTGCCCTA

GAGGCCTGATCGGCGGCCACAACAACAGACCTCCAGGCGTGCCAGCCCGGTTCTCTG

GATCTCTGCTGGGCGGAAAGGCCGCTCTGACACTGCTGGGTGCTCAGCCTGAGGACG

AGGCCGAGTACTACTGTGCCCTGTGGTACTCCGACCACTGGGTCATCGGAGGCGGGA

CCAAGCTGACCGTGCTGGGA(ACACCCCTGGGAGACACCACACATACT)AGTGGGC

AGGCCATCAAGAAGGAGCTGACCCAGATCAAGCAGAAGGTGGACAGCCTGC

TGGAGAACCTGGAGAAGATCGAGAAGGAGGGAGGGTCAGGAGGAGCACCGC

ACCATCATCATCACCAT
```

Figure 13A:
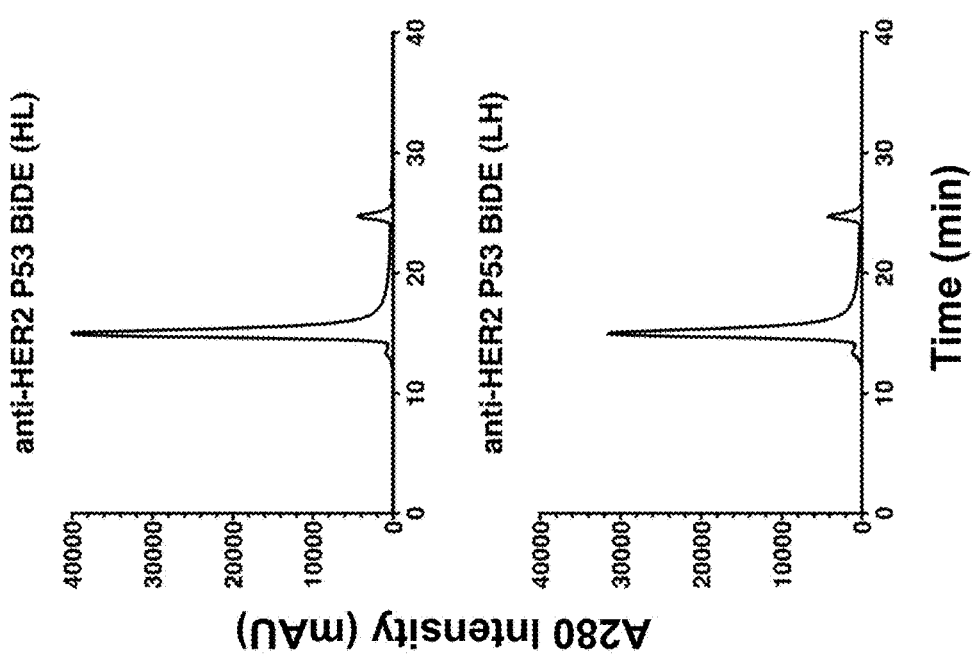
FIG. 13A and FIG. 13B depict in vitro analysis of an exemplary anti-HER2 SADA construct.

Exemplary anti-HER2 SADA-BiDE constructs of the present example exhibit tetrameric self-assembly, similar to SADA-BiDEs described above. Specifically, FIG. 13A shows SEC-HPLC chromatograms of two different scFv variants of anti-HER2 P53-BiDE constructs with an anti-HER2 scFv in a HL orientation in the upper graph and with an anti-HER2 scFv in a LH orientation in the lower graph. As shown, anti-HER2 P53-BiDE proteins are exceptionally pure after single-step affinity purification and retains a size of ~200 kDa (~16 min), which corresponds to the tetramerized form.

Figure 13B:
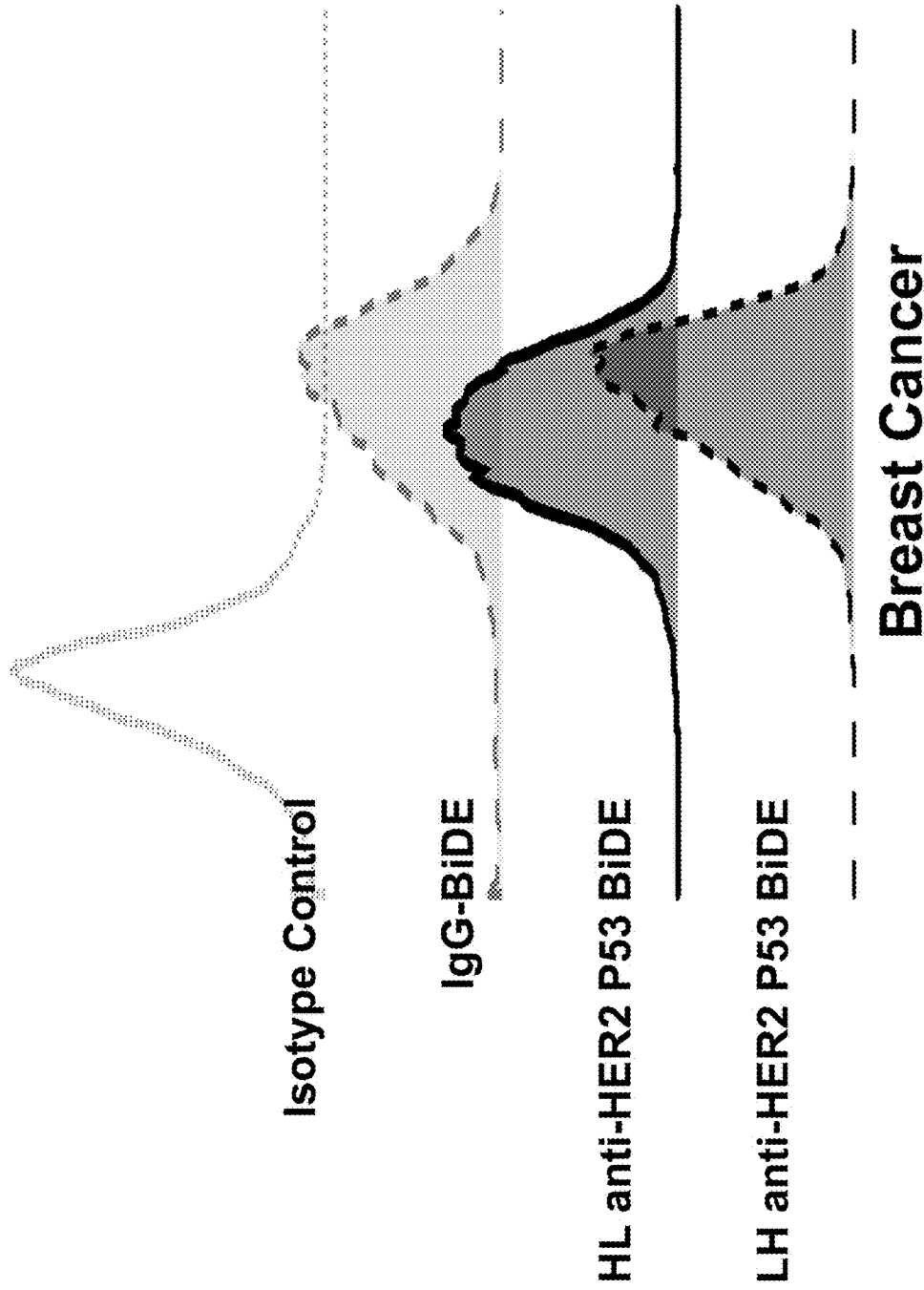

Moreover, exemplary anti-HER2 SADA-BiDE constructs have comparable binding characteristics to other SADA-BiDEs. FIG. 13B depicts the results of a FACS analysis on a HER2(+) cell line HCC1954 (breast cancer) using a fluorescently labeled $^{175}$Lu-Bn-DOTA conjugate for detection. HER2/BnDOTA binding capacity of these exemplary anti-HER2 BiDEs (Black solid and dashed, filled) is comparable to that of IgG-BiDE (grey dashed, filled) suggesting strong tumor antigen and payload binding.

Accordingly, this example confirms, that pairing of various targeting and/or antigen binding portions with a SADA domains retains binding and other beneficial characteristics of SADA constructs. These data support that SADA constructs with various targeting domains can be useful.

Example 13—Exemplary Conjugate with a hnRNPC SADA Domain

This example confirms that a HNRNPC tetramerization domain can act as a SADA domain and self-assemble to form tetrameric proteins. Specifically, this example shows in vitro analyses of an exemplary bispecific antibody based conjugate with a HNRNPC SADA domain, a HNRNPC-BiDE. Provided below are an exemplary polypeptide sequence (SEQ ID NO: 97) and corresponding nucleotide sequence (SEQ ID NO: 98) for an exemplary HNRNPC-BiDE construct.

```
GD2 HNRNPC BiDE(LL) polypeptide (hu3F8-scFv,
huC825-scFv, huHNRNPC-tet, GS linker,
(IgG3 spacer))
                                        SEQ ID NO: 97
EIVMTQTPATLSVSAGERVTITCKASQSVSNDVTWYQQKPGQAPRLLIY

SASNRYSGVPARFSGSGYGTEFTFTISSVQSEDFAVYFCQQDYSSFGCG

TKLEIKRGGGGSGGGGSGGGGSGGGGSGGGGSGGGGSQVQLVESGPGVV

QPGRSLRISCAVSGFSVTNYGVHWVRQPPGKCLEWLGVIWAGGITNYNS

AFMSRLTISKDNSKNTVYLQMNSLRAEDTAMYYCASRGGHYGYALDYWG

QGTLVTVSSGGGGSGGGGSGGGGSGGGGSHVQLVESGGGLVQPGGSLRL

SCAASGFSLTDYGVHWVRQAPGKGLEWLGVIWSGGGTAYNTALISRFTI

SRDNSKNTLYLQMNSLRAEDTAVYYCARRGSYPYNYFDAWGCGTLVTVS

SGGGGSGGGGSGGGGSGGGGSGGGGSGGGGSQAVVTQEPSLTVSPGGTV

TLTCGSSTGAVTASNYANWVQQKPGQCPRGLIGGHNNRPPGVPARFSGS

LLGGKAALTLLGAQPEDEAEYYCALWYSDHWVIGGGTKLTVLG(TPLGD

TTHT)SGQAIKKELTQIKQKVDSLLENLEKIEKEGGSGGAPHHHHHH

GD2 HNRNPC BiDE(LL) cDNA (hu3F8-scFv,
huC825-scFv, huHNRNPC-tet, GS linker,
(IgG3 spacer))
                                        SEQ ID NO: 98
GAGATCGTGATGACCCAGACACCCGCAACACTGAGCGTGTCTGCCGGCG

AAAGGGTCACTATTACCTGCAAGGCCAGTCAGTCAGTGTCCAACGACGT

GACTTGGTACCAGCAGAAACCAGGCCAGGCTCCCCGGCTGCTGATCTAC

AGCGCATCTAATAGATATAGCGGAGTGCCTGCTCGCTTCAGTGGTTCAG

GCTATGGAACTGAGTTCACCTTCACCATTTCCAGCGTGCAGTCCGAAGA

CTTCGCAGTGTACTTTTGCCAGCAGGATTATTCTAGTTTTGGGTGTGGT

ACAAAGCTGGAGATCAAAAGGGGAGGAGGAGGTAGTGGCGGAGGAGGTT

CAGGCGGAGGGGTAGCGGCGGAGGGGGTTCTGGCGGCGGCGGTAGTGG

CGGCGGAGGTAGCCAGGTGCAGCTGGTCGAATCCGGCCCTGGAGTGGTC

CAGCCAGGCAGGTCTCTGCGGATCAGTTGCGCCGTGTCCGGATTCAGCG
```

```
                          -continued
TCACCAACTACGGAGTGCACTGGGTCAGACAGCCACCTGGCAAGTGTCT

GGAGTGGCTGGGAGTGATCTGGGCAGGAGGAATCACAAACTACAACTCA

GCTTTTATGTCCCGCCTGACTATTAGCAAGGACAACTCTAAAAATACCG

TGTATCTGCAGATGAATTCTCTGCGAGCCGAAGATACCGCTATGTACTA

TTGTGCATCCCGTGGGGGTCATTACGGCTATGCCCTGGATTATTGGGGG

CAGGGTACCCTGGTGACAGTCTCATCCGGCGGAGGGGGATCCGGCGGCG

GAGGATCTGGCGGAGGTGGAAGTGGGGGAGGCGGATCTCATGTGCAGCT

GGTGGAAAGCGGAGGCGGCCTGGTGCAGCCTGGGGGATCTCTGAGACTG

TCTTGTGCCGCCAGCGGCTTCTCCCTGACCGATTATGGCGTGCACTGGG

TGCGACAGGCCCCTGGCAAAGGACTGGAATGGCTGGGAGTGATTTGGAG

TGGCGGAGGCACCGCCTACAACACCGCCCTGATCTCCCGGTTCACCATC

AGCCGGGACAACTCCAAGAACACCCTGTACCTGCAGATGAACTCCCTGC

GGGCCGAGGACACCGCTGTGTACTACTGCGCCAGACGGGGCTCCTACCC

CTACAACTACTTCGACGCTTGGGGCTGCGGCACCCTCGTGACAGTGTCT

AGCGGAGGGGGAGGTTCTGGGGGCGGAGGTTCAGGTGGTGGTGGTTCCG

GGGGTGGTGGCTCTGGTGGCGGTGGTTCTGGCGGTGGCGGATCTCAGGC

TGTCGTGACCCAGGAACCCAGCCTGACTGTGTCTCCTGGCGGAACCGTG

ACCCTGACCTGCGGATCTTCTACCGGCGCTGTGACCGCCAGCAACTACG

CCAATTGGGTGCAGCAGAAACCTGGACAGTGCCCTAGAGGCCTGATCGG

CGGCCACAACAACAGACCTCCAGGCGTGCCAGCCCGGTTCTCTGGATCT

CTGCTGGGCGGAAAGGCCGCTCTGACACTGCTGGGTGCTCAGCCTGAGG

ACGAGGCCGAGTACTACTGTGCCCTGTGGTACTCCGACCACTGGGTCAT

CGGAGGCGGGACCAAGCTGACCGTGCTGGGA(ACACCCTGGGAGACAC

CACACATACT)AGTGGGCAGGCCATCAAGAAGGAGCTGACCCAGATCAA

GCAGAAGGTGGACAGCCTGCTGGAGAACCTGGAGAAGATCGAGAAGGAG

GGAGGGTCAGGAGGAGCACCGCACCATCATCATCACCAT
```

An exemplary HNRNPC-BiDE exhibits tetrameric self-assembly, similar to SADA-BiDEs described above. As shown in FIG. 14A, an exemplary HNRNPC-BiDE polypeptide construct forms a stable tetrameric multimer has shown by SEC-HPLC chromatogram. Single-step affinity purification of an exemplary HNRNPC-BiDE polypeptide and SEC-HPLC analysis shows a tetrameric multimer at the expected size of ~200 kDa (~16 min, upper graph), and this purity is maintained after five repeated freeze and thaw cycles (~16 min, lower graph). Thus, an exemplary HNRNPC-BiDE polypeptide shows high stability and a propensity to not form higher order aggregates. FIG. 14B shows the results of a FACS analysis on a GD2(+) cell line M14-Luc (Melanoma) using a fluorescently labeled [175]Lu-Bn-DOTA conjugate for detection. GD2/BnDOTA binding capacity of an exemplary HNRNPC-BiDE (Solid Black, filled) is compared against an IgG-BiDE (Dashed black, filled) a P63-BiDE (dotted grey, filled) or an isotype control (dashed grey, empty). An exemplary HNRNPC-BIDE shows identical binding to other anti-GD2 BiDEs, suggesting strong tumor antigen and payload binding, as expected from its multimeric state. FIG. 14C depicts normalized binding kinetics of the HNRNPC-BiDE (dotted black) against a GD2 tumor antigen using SPR, compared with the P53-(solid grey), P63-(dashed grey), or IgG-BiDEs (dashed black). Each construct was run as a concentration series across a streptavidin chip coated with biotin-GD2. The highest concentrations of each were then plotted together on a normalized Y-axis to better show the differences in koff. Data was fitted using a two-state reaction model. HNRNPC-BiDE shows a greatly improved koff rate compared with the IgG-BiDE, similar to the P53- and P63-BiDEs. These binding kinetics (Table 8) are evidence of tetrameric antigen binding.

TABLE 8

Association and dissociation kinetics of HNRNPC-BiDE

| | ka1 (1/Ms) | kd1 (1/s) | ka2 (1/s) | kd2 (1/s) | $K_D$ (M) |
|---|---|---|---|---|---|
| HNRNPC-BiDE | 6.77E+05 | 6.87E−02 | 1.12E−01 | 1.37E−03 | 1.22E−09 |

Accordingly, this example confirms, that hnRNPC functions as a SADA domain. These data confirms that different, unrelated polypeptides having characteristics of a SADA domain as described herein have similar in vitro characteristics and can confer beneficial properties to a SADA construct.

Having thus described at least several aspects and embodiments of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawing are by way of example only and the invention is described in further detail by the claims that follow.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

SEQUENCE LISTING

```
Sequence total quantity: 118
SEQ ID NO: 1              moltype = AA  length = 39
FEATURE                   Location/Qualifiers
source                    1..39
                          mol_type = protein
                          organism = Homo sapiens
SEQUENCE: 1
KPLDGEYFTL QIRGRERFEM FRELNEALEL KDAQAGKEP                          39

SEQ ID NO: 2              moltype = DNA  length = 117
FEATURE                   Location/Qualifiers
source                    1..117
                          mol_type = unassigned DNA
                          organism = Homo sapiens
SEQUENCE: 2
aaacctctgg atggcgagta ctttaccctg cagattagag gccgcgaacg attcgagatg   60
tttcgcgaac tgaatgaggc cctggaactg aaggatgctc aggcaggcaa ggagcca    117

SEQ ID NO: 3              moltype = AA  length = 57
FEATURE                   Location/Qualifiers
source                    1..57
                          mol_type = protein
                          organism = Homo sapiens
SEQUENCE: 3
RSPDDELLYL PVRGRETYEM LLKIKESLEL MQYLPQHTIE TYRQQQQQQH QHLLQKQ      57

SEQ ID NO: 4              moltype = DNA  length = 171
FEATURE                   Location/Qualifiers
```

```
source                  1..171
                        mol_type = unassigned DNA
                        organism = Homo sapiens
SEQUENCE: 4
agatcccccg acgatgagct gctgtacctg cctgtgaggg gccgggagac ctatgaaatg    60
ctgctgaaga tcaaagagag cctggaactg atgcagtacc tgccacagca caccattgaa   120
acatataggc aacaacagca gcagcagcat cagcatctgc tgcagaagca g             171

SEQ ID NO: 5            moltype = AA  length = 52
FEATURE                 Location/Qualifiers
source                  1..52
                        mol_type = protein
                        organism = Homo sapiens
SEQUENCE: 5
RHGDEDTYYL QVRGRENFEI LMKLKESLEL MELVPQPLVD SYRQQQQLLQ RP             52

SEQ ID NO: 6            moltype = DNA  length = 156
FEATURE                 Location/Qualifiers
source                  1..156
                        mol_type = unassigned DNA
                        organism = Homo sapiens
SEQUENCE: 6
aggcacggcg acgaagatac ctactatctg caggtgaggg gacgggagaa cttcgaaatc    60
ctgatgaagc tgaaagagtc cctggaactg atggagctgg tgccccagcc tctggtcgac   120
agctacagac agcagcagca gctgctgcag aggcca                             156

SEQ ID NO: 7            moltype = AA  length = 27
FEATURE                 Location/Qualifiers
source                  1..27
                        mol_type = protein
                        organism = Homo sapiens
SEQUENCE: 7
QAIKKELTQI KQKVDSLLEN LEKIEKE                                         27

SEQ ID NO: 8            moltype = DNA  length = 81
FEATURE                 Location/Qualifiers
source                  1..81
                        mol_type = unassigned DNA
                        organism = Homo sapiens
SEQUENCE: 8
caagctataa agaaggaact cacccagatt aagcaaaagg ttgactcact gttggaaaat    60
cttgagaaaa tagaaaagga a                                               81

SEQ ID NO: 9            moltype = AA  length = 54
FEATURE                 Location/Qualifiers
source                  1..54
                        mol_type = protein
                        organism = Homo sapiens
SEQUENCE: 9
STRRILGLAI ESQDAGIKTI TMLDEQKEQL NRIEEGLDQI NKDMRETEKT LTEL            54

SEQ ID NO: 10           moltype = DNA  length = 162
FEATURE                 Location/Qualifiers
source                  1..162
                        mol_type = unassigned DNA
                        organism = Homo sapiens
SEQUENCE: 10
tctacccgca ggatcttggg acttgctata gagtcacagg acgccggaat aaaaactatc    60
actatgcttg atgaacagaa ggaacaactg aatcggatta ggaaggact ggaccagatt    120
aacaaggaca tgcgagagac cgaaaaaaca ctcactgagt tg                      162

SEQ ID NO: 11           moltype = AA  length = 97
FEATURE                 Location/Qualifiers
source                  1..97
                        mol_type = protein
                        organism = Homo sapiens
SEQUENCE: 11
MCGAPSATQP ATAETQHIAD QVRSQLEEKE NKKFPVFKAV SFKSQVVAGT NYFIKVHVGD    60
EDFVHLRVFQ SLPHENKPLT LSNYQTNKAK HDELTYF                              97

SEQ ID NO: 12           moltype = DNA  length = 291
FEATURE                 Location/Qualifiers
source                  1..291
                        mol_type = unassigned DNA
                        organism = Homo sapiens
SEQUENCE: 12
atgtgcgggg cgccctccgc cacgcagccg gccaccgccg agacccagca catcgccgac    60
caggtgaggt cccagcttga agagaaagaa aacaagaagt tccctgtgtt taaggccgtg   120
tcattccaaga gccaggtggt cgcggggaca aactacttca tcaaggtgca cgtcggcgac   180
```

```
gaggacttcg tacacctgcg agtgttccaa tctctccctc atgaaaacaa gcccttgacc   240
ttatctaact accagaccaa caaagccaag catgatgagc tgacctattt c            291

SEQ ID NO: 13           moltype = AA  length = 30
FEATURE                 Location/Qualifiers
source                  1..30
                        mol_type = protein
                        organism = Homo sapiens
SEQUENCE: 13
DEISMMGRVV KVEKQVQSIE HKLDLLLGFY                                     30

SEQ ID NO: 14           moltype = DNA  length = 90
FEATURE                 Location/Qualifiers
source                  1..90
                        mol_type = unassigned DNA
                        organism = Homo sapiens
SEQUENCE: 14
gatgaaatca gcatgatggg acgcgtggtc aaggtggaga agcaggtgca gtccatcgag   60
cacaagctgg acctgctgtt gggcttctat                                    90

SEQ ID NO: 15           moltype = AA  length = 60
FEATURE                 Location/Qualifiers
source                  1..60
                        mol_type = protein
                        organism = Homo sapiens
SEQUENCE: 15
TVAEAKRQAA EDALAVINQQ EDSSESCWNC GRKASETCSG CNTARYCGSF CQHKDWEKHH    60

SEQ ID NO: 16           moltype = DNA  length = 180
FEATURE                 Location/Qualifiers
source                  1..180
                        mol_type = unassigned DNA
                        organism = Homo sapiens
SEQUENCE: 16
acggtcgccg aggccaaacg gcaggcggcg gaggacgcac tggcagttat caatcagcag   60
gaggattcaa gcgagagttg ctggaattgt ggccgtaaag cgagtgaaac ctgcagtggc  120
tgtaacacag cccgatactg tggctcattt tgccagcaca aagactggga agcaccat    180

SEQ ID NO: 17           moltype = AA  length = 559
FEATURE                 Location/Qualifiers
REGION                  1..559
                        note = Description of Artificial Sequence: Synthetic
                         polypeptide
source                  1..559
                        mol_type = protein
                        organism = synthetic construct
SEQUENCE: 17
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS  120
QVQLVESGPG VVQPGRSLRI SCAVSGFSVT NYGVHWVRQP PGKCLEWLGV IWAGGITNYN  180
SAFMSRLTIS KDNSKNTVYL QMNSLRAEDT AMYYCASRGG HYGYALDYWG QGTLVTVSSG  240
GGGSGGGGSG GGGSGGGGSH VQLVESGGGL VQPGGSLRLS CAASGFSLTD YGVHWVRQAP  300
GKGLEWLGVI WSGGGTAYNT ALISRFTISR DNSKNTLYLQ MNSLRAEDTA VYYCARRGSY  360
PYNYFDAWGC GTLVTVSSGG GGSGGGGSGG GGSQAVVTQE PSLTVSPGGT VTLTCGSSTG  420
AVTASNYANW VQQKPGQCPR GLIGGHNNRP PGVPARFSGS LLGGKAALTL LGAQPEDEAE  480
YYCALWYSDH WVIGGGTKLT VLGTPLGDTT HTSGKPLDGE YFTLQIRGRE RFEMFRELNE  540
ALELKDAQAG KEPGGSGGA                                                559

SEQ ID NO: 18           moltype = DNA  length = 1677
FEATURE                 Location/Qualifiers
misc_feature            1..1677
                        note = Description of Artificial Sequence: Synthetic
                         polynucleotide
source                  1..1677
                        mol_type = other DNA
                        organism = synthetic construct
SEQUENCE: 18
gaaatcgtca tgactcagac tcccgcaacc ctgtcagtgt ccgctgggga acgtgtcact   60
attacctgca aggcatctca gagcgtgagc aacgacgtga cctgggggtatca gcagaagcct  120
ggccaggctc cacgactgct gatctattcc gcaagcaatc gctactccgg agtgcccgca  180
cgattctctg gaagtgggta cggtaccgag ttcactttta ccatttccag cgtgcagagc  240
gaagacttcg ctgtctattt tgccagcag gattactcta gttttggctg tggaacaaag  300
ctggagatca aaaggggagg aggaggttct ggcgaggag taggtggcgg aggggtttca  360
caggtgcagc tggtccagtc tgggccaggc gtggtccagc cagacgttc cctgaggatt  420
agctgcgccg tgagcgggtt ctctgtcaca aactacggag tgcactgggt ccgtcagcca  480
cctgcaaat gtctggagtg gctgggagtg atctgggcag gaggaatcac taactacaac  540
tctgcttta tgagtcgcct gaccatctca aggacaact ccaaaaatac agtgtacctg  600
cagatgaatt cactgcgggc agaagatacc gccatgtact attgcgcctc aggggggt  660
cattacggct atgcccctgga ctattgggc cagggaacac tggtgactgt ctcatccgga  720
```

-continued

```
ggaggaggat ccggaggagg aggtagcggc ggaggggggtt ctggcggagg gggtagtcac    780
gtgcagctgg tcgagtccgg aggagggctg gtgcagcctg gtggcagcct gcgactgtct    840
tgtgccgcta gtggcttctc actgacagat tacggcgtgc attgggtccg acaggctcca    900
gggaagggtc tggaatggct gggagtgatt tggtctggag ggggtacagc ttataacact    960
gcactgatca gtcggttcac tatcagtaga gacaactcaa agaacaccgt gtacctgcag   1020
atgaactctc tgcgggccga ggataccgct gtgtactatt gcgctaggcg gggcagttac   1080
ccttataatt actttgacgc atggggctgt ggaaccctgg tgacagtcag ctctggcgga   1140
gggggttcag gcggcggcgg ttccggcgga ggaggtagcc aggccgtggt cactcaggag   1200
ccttccctga ccgtgagccc aggaggagca gtcactctga cctgcgggag ttcaaccggt   1260
gccgtgacag cctccaacta cgctaattgg gtccagcaga agcccgggca gtgtcctaga   1320
ggtctgatcg ggggtcacaa caatcgtcca cccggagtgc cagccaggtt ctcaggctcc   1380
ctgctgggcg gaaaagcagc actgactctg ctgggcgctc agccagagga cgaagcagag   1440
tactattgcg ccctgtggta ttctgatcac tgggtcatcg ggggtggcac taagctgacc   1500
gtgctgggca caccCctggg agacaccaca catactactg gcaaacctct cgatggagag   1560
tactttaccc tgcagattag aggccgcgaa cgattcgaga tgtttcgcga actgaatgag   1620
gccctggaac tgaaggatgc tcaggcaggc aaggaaccag gcggtagcgg cggcgca      1677

SEQ ID NO: 19            moltype = AA   length = 581
FEATURE                  Location/Qualifiers
REGION                   1..581
                         note = Description of Artificial Sequence: Synthetic
                         polypeptide
source                   1..581
                         mol_type = protein
                         organism = synthetic construct
SEQUENCE: 19
EIVMTQTPAT LSVSAGERVT ITCKASQSVS NDVTWYQQKP GQAPRLLIYS ASNRYSGVPA     60
RFSGSGYGTE FTFTISSVQS EDFAVYFCQQ DYSSFGCGTK LEIKRGGGGS GGGGSGGGGS    120
GGGGSGGGGS GGGGSQVQLV ESGPGVVQPG RSLRISCAVS GFSVTNYGVH WVRQPPGKCL    180
EWLGVIWAGG ITNYNSAFMS RLTISKDNSK NTVYLQMNSL RAEDTAMYYC ASRGGHYGYA    240
LDYWGQGTLV TVSSGGGGSG GGGSGGGGSG GGGSHVQLVE SGGGLVQPGG SLRLSCAASG    300
FSLTDYGVHW VRQAPGKGLE WLGVIWSGGG TAYNTALISR FTISRDNSKN TLYLQMNSLR    360
AEDTAVYYCA RRGSYPYNYF DAWGCGTLVT VSSGGGGSGG GGSGGGGSQA VVTQEPSLTV    420
SPGGTVTLTC GSSTGAVTAS NYANWVQQKP GQCPRGLIGG HNNRPPGVPA RFSGSLLGGK    480
AALTLLGAQP EDEAEYYCAL WYSDHWVIGG GTKLTVLGTP LGDTTHTSGK PLDGEYFTLQ    540
IRGRERFEMF RELNEALELK DAQAGKEPGG SGGAPHHHHH H                        581

SEQ ID NO: 20            moltype = DNA  length = 1743
FEATURE                  Location/Qualifiers
misc_feature             1..1743
                         note = Description of Artificial Sequence: Synthetic
                         polynucleotide
source                   1..1743
                         mol_type = other DNA
                         organism = synthetic construct
SEQUENCE: 20
gagatcgtga tgacccagac accegcaaca ctgagcgtgt ctgccggcga aagggtcact     60
attacctgca aggccagtca gtcagtgtcc aacgacgtga cttggtacca gcagaaacca    120
ggccaggctc cccggctgct gatctacagc gcatctaata gatatagcgg agtgcctgct    180
cgcttcagtg gttcaggcta tggaactgag ttcaccttca ccatttccag cgtgcagtcc    240
gaagactteg cagtgtactt ttgccagcag gattattgta gttttggggtg tggtacaaag    300
ctggagatca aaaggggagg aggaggtagt ggcggaggag gttcaggcgg aggggtagc     360
ggcggagggg gttctggcgg cggcggtagt ggcggcggag gtagccaggt gcagctggtc    420
gaatccggcc ctggagtggt ccagccaggc aggtctctgc ggatcagttg cgccgtgtcc    480
ggattcagcg tcaccaacta cggagtgcac tgggtcagca agccacctgg caagtgtctg    540
gagtggctgg gagtgatctg ggcaggagga atcacaaact acaactcagc ttttatgtcc    600
cgcctgacta ttagcaagga caactctaaa aataccgtgt atctgcagat gaattctctg    660
cgagccgaag ataccgctat gtactattgt gcatcccgtg ggggtcatta cggctatgcc    720
ctggattatt ggggccaggg taccctggtg acagtctcat ccggcggagg gggatccgga    780
ggaggaggta gcggcggagg gggttctggc ggaggggggta gtcacgtgca gctggtcgga    840
tccgaggagg ggctggtgca gcctggtggc agcctgcgac tgtcttgtgc cgctagtggc    900
ttctcactga cagattacgg cgtgcattgg gtccgacagg ctccaggaa gggtctggaa    960
tggctgggag tgatttggtc tggagggggt acagcttata acactgcact gatcagtcgg   1020
ttcactatca gtagagacaa ctcaaagaac acctgcact tgcagatgaa ctctctcgg   1080
gccgaggata ccgctgtgta ctattgcgct aggcggggca gttacccta taattacttt    1140
gacgcatggg gctgtggaac cctggtgaca gtcagctctg gcgagggggg ttcaggcggc    1200
ggcggttccg gcggaggagg tagccaggcc gtggtcactc aggagccttc cctgaccgtg    1260
agcccaggag gaacagtcac tctgacctgc gggagttcaa ccggtgccgt gacagcctcc    1320
aactacgcta attgggtcca gcagaagccc gggcagtgtc ctagaggtct gatcggggggt    1380
cacaacaatc gtccacccgg agtgccagcc aggttctctg gctccctgct gggcggaaaa    1440
gcagcactga ctctgctggg cgctcagcca gaggacgaag cagagtacta ttgcgccctg    1500
tggtattctg atcactgggt catcgggggt ggcactaagc tgaccgtgct gggcacaccc    1560
ctgggagaca ccacacatac tagtgggaaa cctctggatg gcgagtactt taccctgcag    1620
attagaggcc gcgaacgatt cgagatgttt cgcgaactga atgaggccct ggaactgaag    1680
gatgctcagg caggcaagga gccaggaggg tcaggaggag caccgcacca tcatcatcac    1740
cat                                                                 1743

SEQ ID NO: 21            moltype = AA   length = 599
FEATURE                  Location/Qualifiers
```

```
REGION                    1..599
                          note = Description of Artificial Sequence: Synthetic
                             polypeptide
source                    1..599
                          mol_type = protein
                          organism = synthetic construct
SEQUENCE: 21
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
GGGGSGGGGS GGGGSQVQLV ESGPGVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGGSGGGGSG GGGSHVQLVE SGGGLVQPGG SLRLSCAASG   300
FSLTDYGVHW VRQAPGKGLE WLGVIWSGGG TAYNTALISR FTISRDNSKN TLYLQMNSLR   360
AEDTAVYYCA RRGSYPYNYF DAWGCGTLVT VSSGGGGSGG GGSGGGGSQA VVTQEPSLTV   420
SPGGTVTLTC GSSTGAVTAS NYANWVQQKP GQCPRGLIGG HNNRPPGVPA RFSGSLLGGK   480
AALTLLGAQP EDEAEYYCAL WYSDHWVIGG GTKLTVLGTP LGDTTHTSGR SPDDELLYLP   540
VRGRETYEML LKIKESLELM QYLPQHTIET YRQQQQQQHQ HLLQKQGGSG GAPHHHHHH    599

SEQ ID NO: 22             moltype = DNA    length = 1797
FEATURE                   Location/Qualifiers
misc_feature              1..1797
                          note = Description of Artificial Sequence: Synthetic
                             polynucleotide
source                    1..1797
                          mol_type = other DNA
                          organism = synthetic construct
SEQUENCE: 22
gagatcgtga tgacccagac acccgcaaca ctgagcgtgt ctgccggcga aagggtcact    60
attacctgca aggccagtca gtcagtgtcc aacgacgtga cttggtacca gcagaaacca   120
ggccaggctc cccggctgct gatctacagc gcatctaata gatatagcgg agtgcctgcc   180
cgcttcagtg gttcaggcta tggaactgag ttcaccttca ccatttccag cgtgcagtcc   240
gaagacttcg cagtgtactt ttgccagcag gattattcta gttttgggtg tggtacaaag   300
ctggagatca aaggggagg aggaggtagt ggcggaggag gttcaggcgg aggggtagc    360
ggcggagggg gttctggcgg cggcggtagt ggcggcggag gtagccaggt gcagctggtc   420
gaatccggcc ctggagtggt ccagccaggc aggtctctgc ggatcagttg cgccgtgtcc   480
ggattcagcg tcaccaacta cggagtgcac tgggtcagac agccacctgg caagtgtctg   540
gagtggctgg gagtgatctg gcaggagga atcacaaact acaactcagc ttttatgtcc   600
cgcctgacta ttagcaagga caactctaaa aataccgtgt atctgcagat gaattctctg   660
cgagccgaag ataccgctat gtactattgt gcatcccgtg gggtcatta cggctatgcc   720
ctggattatt gggggcaggg taccctggtg acagtctcat ccggaggagg aggatccgga   780
ggaggagta gcggcggagg gggttctggc ggaggggta gtcacgtgca gctggtcgag    840
tccggaggag ggctggtgca gcctggtggc agcctgcgac tgtcttgtgc cgctagtggc   900
ttctcactga cagattacgg cgtgcattga tccgacaggt cccagggaa gggtctggaa   960
tggctgggag tgatttggtc tggagggggt acagcttata acactgcact gatcagtcgg  1020
ttcactatca gtagagacaa ctcaaagaac accctgtacc tgcagatgaa ctctctgcgg  1080
gccgaggata ccgctgtgta ctattgcgct aggcggggca gttaccctta taattacttt  1140
gacgcatggg gctgtggaac cctggtgaca gtcagctctg gcggaggggg ttcaggcggc  1200
ggcggttccg gcggaggagg tagccaggcc gtggtcactc aggagccttc cctgaccgtg  1260
agcccaggag aacagtcac tctgacctgc gggagttcaa ccggtgccgt gacagcctcc  1320
aactacgcta attgggtcca gcagaagccc gggcagtgtc ctagaggtct gatcggggt   1380
cacaacaatc gtccacccgg agtgccagcc aggttctcag gctccctgct gggcggaaaa  1440
gcagcactga ctctgctggg cgctcagcca gaggacgaag cagagtacta ttgcgccctg  1500
tggtattctg atcactgggt catcggggt ggcactaagc tgaccgtgct gggcacaccc  1560
ctgggagaca ccacacatac tagtgggaga tcccccgacg atgagctgct gtacctgcct  1620
gtgaggggcc gggagaccta tgaaatgctg ctgaagatca aagagcct ggaactgatg  1680
cagtacctgc cacagcacac cattgaaaca tataggcaac aacagcagca gcagcatcag  1740
catctgctgc agaagcaggg agggtcagga ggagcaccgc accatcatca tcaccat     1797

SEQ ID NO: 23             moltype = AA    length = 594
FEATURE                   Location/Qualifiers
REGION                    1..594
                          note = Description of Artificial Sequence: Synthetic
                             polypeptide
source                    1..594
                          mol_type = protein
                          organism = synthetic construct
SEQUENCE: 23
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
GGGGSGGGGS GGGGSQVQLV ESGPGVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGGSGGGGSG GGGSHVQLVE SGGGLVQPGG SLRLSCAASG   300
FSLTDYGVHW VRQAPGKGLE WLGVIWSGGG TAYNTALISR FTISRDNSKN TLYLQMNSLR   360
AEDTAVYYCA RRGSYPYNYF DAWGCGTLVT VSSGGGGSGG GGSGGGGSQA VVTQEPSLTV   420
SPGGTVTLTC GSSTGAVTAS NYANWVQQKP GQCPRGLIGG HNNRPPGVPA RFSGSLLGGK   480
AALTLLGAQP EDEAEYYCAL WYSDHWVIGG GTKLTVLGTP LGDTTHTSGR HGDEDTYYLQ   540
VRGRENFEIL MKLKESLELM ELVPQPLVDS YRQQQQLLQR PGGSGGAPHH HHHH          594

SEQ ID NO: 24             moltype = DNA    length = 1782
```

```
FEATURE                 Location/Qualifiers
misc_feature            1..1782
                        note = Description of Artificial Sequence: Synthetic
                        polynucleotide
source                  1..1782
                        mol_type = other DNA
                        organism = synthetic construct
SEQUENCE: 24
gagatcgtga tgacccagac acccgcaaca ctgagcgtgt ctgccggcga aagggtcact    60
attacctgca aggccagtca gtcagtgtcc aacgacgtga cttggtacca gcagaaacca   120
ggccaggctc cccggctgct gatctacagc gcatctaata gatatagcgg agtgcctgct   180
cgcttcagtg gttcaggcta tggaactgag ttcaccttca ccatttccag cgtgcagtcc   240
gaagacttcg cagtgtactt ttgccagcag gattattcta gttttgggtg tggtacaaag   300
ctggagatca aaaggggagg aggaggtagt ggcggaggcg gtcaggcgg aggggtagc     360
ggcggagggg gttctggcgg cggcggtagt ggcggcggag gtagccaggt gcagctggtc   420
gaatccggcc ctggagtggt ccagccaggc aggtctctgc ggatcagttg cgccgtgtcc   480
ggattcagcg tcaccaacta cggagtgcac tgggtcagac agccacctgg caagtgtctg   540
gagtggctgg gagtgatctg ggcaggagga atcacaaact acaactcagc tttatgtcgc   600
cgcctgacta ttagcaagga caactctaaa aataccgtgt atctgcagat gaattctctg   660
cgagccgaag ataccgctat gtactattgt gcatcccgtg ggggtcatta cggctatgcc   720
ctggattatt gggggcaggg taccctggtg acagtctcat ccggaggagg aggatccgga   780
ggaggaggta gcggcggagg gggttctggc ggaggggtca gtcacgtgca gctggtcgga   840
tccggaggag ggctggtgca gcctggtggc agcctgcgac tgtcttgtgc cgctagtggc   900
ttctcactga cagattacgg cgtgcattgg gtccgacagg ctccaggaa gggtctggaa   960
tggctggag tgatttggtc tggaggggt acagcttata cactgcact gatcagtcgg    1020
ttcactatca gtagacaa ctcaaagaac accctgtacc tgcagatgaa ctctctgcgg    1080
gccgaggata ccgctgtgta ctattgcgct aggcggggca gttaccctta taattacttt   1140
gacgcatggg gctgtggaac cctggtgaca gtcagctctg gcggaggggg ttcaggcggc   1200
ggcggttccg gcgaggagg tagccaggcc gtggtcactc aggagcctt cctgaccgtg   1260
agcccaggag gaacagtcac tctgacctgc gggagttcaa cgggtgccgt gacagcctcc   1320
aactacgcta attgggtcca gcagaagccc gggcagtgtc ctagaggtct gatcgggggt   1380
cacaacaatc gtccacccgg agtgccagcc aggttctcag gctccctgct gggcggaaaa   1440
gcagcactga ctctgctggg cgctcagcca gaggacgaag cagagtacta ttgcgccctg   1500
tggtattctg atcactgggt catcggggt ggcactaagc tgaccgtgct gggcacaccc   1560
ctgggagaca ccacacatac tagtggagg cacggcgacg aagataccta ctatctgcag   1620
gtgaggggac gggagaactt cgaaatcctg atgaagctga aagagtccct ggaactgatg   1680
gagctggtgc cccagcctct ggtcgacagc tacagacagc agcagcagct gctgcagagg   1740
ccaggagggt caggaggagc accgcaccat catcatcacc at                     1782

SEQ ID NO: 25           moltype = AA  length = 566
FEATURE                 Location/Qualifiers
REGION                  1..566
                        note = Description of Artificial Sequence: Synthetic
                        polypeptide
source                  1..566
                        mol_type = protein
                        organism = synthetic construct
SEQUENCE: 25
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
QVQLVESGPG VVQPGRSLRI SCAVSGFSVT NYGVHWVRQP PGKCLEWLGV IWAGGITNYN   180
SAFMSRLTIS KDNSKNTVYL QMNSLRAEDT AMYYCASRGG HYGYALDYWG QGTLVTVSSG   240
GGGSGGGGSG GGGSGGGGSH VQLVESGGGL VQPGGSLRLS CAASGFSLTD YGVHWVRQAP   300
GKGLEWLGVI WSGGGTAYNT ALISRFTISR DNSKNTLYLQ MNSLRAEDTA VYYCARRGSY   360
PYNYFDAWGC GTLVTVSSGG GGSGGGGSGG GGSQAVVTQE PSLTVSPGGT VTLTCGSSTG   420
AVTASNYANW VQQKPGQCPR GLIGGHNNRP PGVPARFSGS LLGGKAALTL GAQPEDEAE    480
YYCALWYSDH WVIGGGTKLT VLGTPLGDTT HTSGKPLDGE YFTLQIRGRE RFEMFRELNE   540
ALELKDAQAG KEPGGSGGAP HHHHHH                                       566

SEQ ID NO: 26           moltype = DNA  length = 1698
FEATURE                 Location/Qualifiers
misc_feature            1..1698
                        note = Description of Artificial Sequence: Synthetic
                        polynucleotide
source                  1..1698
                        mol_type = other DNA
                        organism = synthetic construct
SEQUENCE: 26
gaaatcgtca tgactcagac tcccgcaacc ctgtcagtgt ccgctgggga acgtgtcact    60
attacctgca aggcatctca gagcgtgagc aacgacgtga cctggtatca gcagaagcct   120
ggccaggctc cacgactgct gatctattcc gcaagcaatc gctactccgg agtgcccgca   180
cgattctctg gaagtgggta cggtaccgag ttcactttta ccatttccag cgtgcagagc   240
gaagacttcg ctgtctattt ttgccagcag gattactcta gttttggctg tggaacaaag   300
ctggagatca aaaggggagg aggaggttct ggcggaggaa gtggtggcgg aggggttca   360
caggtcagc tggtcgaatc tgggccaggc gtggtccagc caggacgttc cctgaggatt   420
agctgcgccg tgagcgggtt ctctgtcaca aactacggag tgcactgggt ccgtcagcca   480
cctggcaaat gtctggagtg gctgggagtg atctgggcag aggaatcac taactacaac   540
tctgcttta tgagtcgcct gaccatctca aggacaact ccaaaaatac agtgtacctg    600
cagatgaatt cactgcgggc agaagatacc gccatgtact attgcgcctc cagggggggt   660
```

```
cattacggct atgccctgga ctattggggc cagggaacac tggtgactgt ctcatccgga    720
ggaggaggat ccggaggagg aggtagcggc ggagggggtt ctggcggagg gggtagtcac    780
gtgcagctgg tcgagtccgg aggagggctg gtgcagcctg gtggcagcct gcgactgtct    840
tgtgccgcta gtggcttctc actgacagat tacggcgtgc attgggtccg acaggctcca    900
gggaagggtc tggaatggct gggagtgatt tggtctggag gggtacagc ttataacact     960
gcactgatca gtcggttcac tatcagtaga gacaactcaa agaaccccct gtacctgcag   1020
atgaactctc tgcgggccga ggataccgct gtgtactatt gcgctaggcg gggcagttac   1080
ccttataatt actttgacgc atggggctgt ggaaccctgg tgacagtcag ctctggcgga   1140
gggggttcag gcggcggcgg ttccggcgga ggaggtagcc aggccgtggt cactcaggag   1200
ccttccctga ccgtgagccc aggaggaaca gtcactctga cctgcgggag ttcaaccggt   1260
gccgtgacag cctccaacta cgctaattgg gtccagcaga agcccgggca gtgtcctaga   1320
ggtctgatcg ggggtcacaa caatcgtcca cccggagtgc cagccaggtt ctcaggctcc   1380
ctgctggggcg aaaagcagc actgactctg ctgggcgctc agccagagga cgaagcgag    1440
tactattgcg ccctgtggta ttctgatcac tgggtcatcg ggggtggcac taagctgacc   1500
gtgctgggca cacccctggg agacaccaca catactagtg ggaaacctct ggatggcgag   1560
tactttaccc tgcagattag aggccgcgaa cgattcgaga tgtttcgcga actgaatgag   1620
gccctggaac tgaaggatgc tcaggcaggc aaggagccag gagggtcagg aggagcaccg   1680
caccatcatc atcaccat                                                 1698

SEQ ID NO: 27            moltype = AA  length = 584
FEATURE                  Location/Qualifiers
REGION                   1..584
                         note = Description of Artificial Sequence: Synthetic
                          polypeptide
source                   1..584
                         mol_type = protein
                         organism = synthetic construct
SEQUENCE: 27
EIVMTQTPAT LSVSAGERVT ITCKASQSVS NDVTWYQQKP GQAPRLLIYS ASNRYSGVPA   60
RFSGSGYGTE FTFTISSVQS EDFAVYFCQQ DYSSFGCGTK LEIKRGGGGS GGGGSGGGGS  120
QVQLVESGPG VVQPGRSLRI SCAVSGFSVT NYGVHWVRQP PGKCLEWLGV IWAGGITNYN  180
SAFMSRLTIS KDNSKNTVYL QMNSLRAEDT AMYYCASRGG HYGYALDYWG QGTLVTVSSG  240
GGGSGGGGSG GGGSGGGGSH VQLVESGGGL VQPGGSLRLS CAASGFSLTD YGVHWVRQAP  300
GKGLEWLGVI WSGGGTAYNT ALISRFTISR DNSKNTLYLQ MNSLRAEDTA VYYCARRGSY  360
PYNYFDAWGC GTLVTVSSGG GGSGGGGSGG GGSQAVVTQE PSLTVSPGGT VTLTCGSSTG  420
AVTASNYANW VQQKPGQCPR GLIGGHNNRP PGVPARFSGS LLGGKAALTL LGAQPEDEAE  480
YYCALWYSDH WVIGGGTKLT VLGTPLGDTT HTSGRSPDDE LLYLPVRGRE TYEMLLKIKE  540
SLELMQYLPQ HTIETYRQQQ QQQHQHLLQK QGGSGGAPHH HHHH                   584

SEQ ID NO: 28            moltype = DNA  length = 1753
FEATURE                  Location/Qualifiers
misc_feature             1..1753
                         note = Description of Artificial Sequence: Synthetic
                          polynucleotide
source                   1..1753
                         mol_type = other DNA
                         organism = synthetic construct
SEQUENCE: 28
gaaatcgtca tgactcagac tcccgcaacc ctgtcagtgt ccgctgggga acgtgtcact     60
attacctgca aggcatctca gagcgtgagc aacgacgtga cctggtatca gcagaagcct    120
ggccaggctc cacgactgct gatctattcc gcaagcaatc gctaccggg agtgcccgca    180
cgattctctg gaagtgggta cggtaccgag ttcactttta ccattccag cgtgcagagc     240
gaagacttcg ctgtctattt tgccagcag gattactcta gttttggctg tggaacaaag     300
ctggagatca aaggggagg aggaggttct ggcggaggag gtagtggcgg agggggttca    360
caggtgcagc tggtcgaatc tgggccaggc gtggtccagc caggacgttc cctgaggatt    420
agctgcgccg tgagcgggtt ctctgtcaca aactacggag tgcactgggt ccgtcagcca    480
cctggcaaat gtctggagtg gctgggagtg atctgggcag gaggaatcac taactacaac    540
tctgctttta tgagtcgcct gaccatctca aaggacaact ccaaaaatac agtgtacctg    600
cagatgaatt cactgcgggc agaagatacc gccatgtact attgcgcctc caggggggt    660
cattacggct atgccctgga ctattggggc cagggaacac tggtgactgt ctcatccgga   720
ggaggaggat ccggaggagg aggtagcggc ggagggggtt ctggcggagg gggtagtcac    780
gtgcagctgg tcgagtccgg aggagggctg gtgcagcctg gtggcagcct gcgactgtct    840
tgtgccgcta gtggcttctc actgacagat tacggcgtgc attgggtccg acaggctcca    900
gggaagggtc tggaatggct gggagtgatt tggtctggag gggtacagc ttataacact     960
gcactgatca gtcggttcac tatcagtaga gacaactcaa agaaccccct gtacctgcag   1020
atgaactctc tgcgggccga ggataccgct gtgtactatt gcgctaggcg gggcagttac   1080
ccttataatt actttgacgc atggggctgt ggaaccctgg tgacagtcag ctctggcgga   1140
gggggttcag gcggcggcgg ttccggcgga ggaggtagcc aggccgtggt cactcaggag   1200
ccttccctga ccgtgagccc aggaggaaca gtcactctga cctgcgggag ttcaaccggt   1260
gccgtgacag cctccaacta cgctaattgg gtccagcaga agcccgggca gtgtcctaga   1320
ggtctgatcg ggggtcacaa caatcgtcca cccggagtgc cagccaggtt ctcaggctcc   1380
ctgctggggcg aaaagcagc actgactctg ctgggcgctc agccagagga cgaagcgag    1440
tactattgcg ccctgtggta ttctgatcac tgggtcatcg ggggtggcac taagctgacc   1500
gtgctgggca cacccctggg agacaccaca catactagtg ggatcgatgg                1560
ctgctgtacc tgcctgtgag gggcggggag acctatgaaa tgctgctgaa gatcaaagag   1620
agcctggaac tgatgcagta cctgccacag cacaccattg aaacatatag gcaacaacag   1680
cagcagcagc atcagcatct gctgcagaag cagggaaggt caggaggagc accgcaccat   1740
catcatcacc att                                                     1753
```

```
SEQ ID NO: 29              moltype = AA   length = 579
FEATURE                    Location/Qualifiers
REGION                     1..579
                           note = Description of Artificial Sequence: Synthetic
                           polypeptide
source                     1..579
                           mol_type = protein
                           organism = synthetic construct
SEQUENCE: 29
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
QVQLVESGPG VVQPGRSLRI SCAVSGFSVT NYGVHWVRQP PGKCLEWLGV IWAGGITNYN   180
SAFMSRLTIS KDNSKNTVYL QMNSLRAEDT AMYYCASRGG HYGYALDYWG QGTLVTVSSG   240
GGGSGGGGSG GGGSGGGGSH VQLVESGGGL VQPGGSLRLS CAASGFSLTD YGVHWVRQAP   300
GKGLEWLGVI WSGGGTAYNT ALISRFTISR DNSKNTLYLQ MNSLRAEDTA VYYCARRGSY   360
PYNYFDAWGC GTLVTVSSGG GGSGGGGSGG GGSQAVVTQE PSLTVSPGGT VTLTCGSSTG   420
AVTASNYANW VQQKPGQCPR GLIGGHNNRP PGVPARFSGS LLGGKAALTL LGAQPEDEAE   480
YYCALWYSDH WVIGGGTKLT VLGTPLGDTT HTSGRHGDED TYYLQVRGRE NFEILMKLKE   540
SLELMELVPQ PLVDSYRQQQ QLLQRPGGSG GAPHHHHHH                         579

SEQ ID NO: 30              moltype = DNA   length = 1737
FEATURE                    Location/Qualifiers
misc_feature               1..1737
                           note = Description of Artificial Sequence: Synthetic
                           polynucleotide
source                     1..1737
                           mol_type = other DNA
                           organism = synthetic construct
SEQUENCE: 30
gaaatcgtca tgactcagac tcccgcaacc ctgtcagtgt ccgctgggga acgtgtcact     60
attacctgca aggcatctca gagcgtgagc aacgacgtga cctggtatca gcagaagcct   120
ggccaggctc cacgactgct gatctattcc gcaagcaatc gctactccgg agtgcccgca   180
cgattctctg gaagtgggta cggtaccgag ttcactttta ccatttccag cgtgcagagc   240
gaagacttcg ctgtctattt tgccagcag gattactgta gttttggctg tggaacaaag    300
ctggagatca aaaggggagg aggaggttct ggcggaggag gtagtggcag aggggttca    360
caggtgcagc tggtcgaatc tgggccaggc gtggtccagc caggacgttc cctgaggatt   420
agctgcgccg tgagcgggtt ctctgtcaca aactacggag tgcactgggt ccgtcagcca   480
cctggcaaat gtctggagtg gctgggagtg atctgggcag gaggaatcac taactacaac   540
tctgcttta tgagtcgcct gaccatctca aaggacaact ccaaaatac agtgtacctg    600
cagatgaatt cactgcgggc agaagatacc gccatgtact attgcgcctc caggggggt   660
cattacggct atgccctgga ctattggggc caggganac tggtgactgt ctcatccgga   720
ggaggaggat ccggaggagg aggtagcggc ggaggggggt ctggcggagg gggtagtcac   780
gtgcagctgg tcgagtccgg aggaggcgtg gtgcagcctg gtgcagcct gcgactgtct   840
tgtgccgcta gtggcttctc actgacagat tacggcgtgc attgggtccg acaggctcca   900
gggaagggtc tggaatggct gggagtgatt ggtctggag ggggtacagc ttataacact   960
gcactgatca gtcggttcac tatcagtaga gacaactcaa gaacaccct gtacctgcag  1020
atgaactctc tgcgggccga ggataccgct gtgtactatt gcgcgaggta ggcagttac  1080
ccttataatt actttgacgc atggggctgt ggaaccctgg tgacagtcag ctctggcgga  1140
gggggtcag gcgccggcgg ttccggcgga ggaggtagcc aggccgtggt cactcaggag  1200
ccttccctga ccgtgagccc aggaggaaca gtcactctga cctgcgggag ttcaaccggt  1260
gccgtgacag cctccaacta cgctaattgg gtccagcaga agcccggca gtgtcctaga  1320
ggtctgatcg ggggtcacaa caatcgtcca cccggagtgc cagccaggtt ctcaggctcc  1380
ctgctgggcg gaaaagcagc actgactctg ctgggcgctc agcagagga cgaagcagag  1440
tactattgcg ccctgtggta ttctgatcac tgggtcatcg ggggtggcac taagctgacc  1500
gtgctgggca cccctgggg agacaccaca catactagtg ggaggcacgg cgacgaagat  1560
acctactatc tgcaggtgag gggacgggag aacttcgaaa tcctgatgaa gctgaaagag  1620
tccctggaac tgatggagct ggtgcccag cctctggtcg acagctacag acagcagcag  1680
cagctgctgc agaggccagg agggtcagga ggagcaccgc accatcatca tcaccat    1737

SEQ ID NO: 31              moltype = AA   length = 596
FEATURE                    Location/Qualifiers
REGION                     1..596
                           note = Description of Artificial Sequence: Synthetic
                           polypeptide
source                     1..596
                           mol_type = protein
                           organism = synthetic construct
SEQUENCE: 31
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
GGGGSGGGGS GGGGSQVQLV ESGPVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGSGGGGS GGGSHVQLV QPGG SLRLSCAASG           300
FSLTDYGVHW VRQAPGKGLE WLGVIWSGGG TAYNTALISR FTISRDNSKN TLYLQMNSLR   360
AEDTAVYYCA RRGSYPYNYF DAWGCGTLVT VSSGGGGSGG GGSGGGGSGG GGSGGGGSGG   420
GGSQAVVTQE PSLTVSPGGT VTLTCGSSTG AVTASNYANW VQQKPGQCPR GLIGGHNNRP   480
PGVPARFSGS LLGGKAALTL LGAQPEDEAE YYCALWYSDH WVIGGGTKLT VLGTPLGDTT   540
HTSGKPLDGE YFTLQIRGRE RFEMFRELNE ALELKDAQAG KEPGGSGGAP HHHHHH      596
```

SEQ ID NO: 32           moltype = DNA   length = 1788
FEATURE                 Location/Qualifiers
misc_feature            1..1788
                        note = Description of Artificial Sequence: Synthetic
                        polynucleotide
source                  1..1788
                        mol_type = other DNA
                        organism = synthetic construct
SEQUENCE: 32
gagatcgtga tgacccagac acccgcaaca ctgagcgtgt ctgccggcga aagggtcact   60
attacctgca aggccagtca gtcagtgtcc aacgacgtga cttggtacca gcagaaacca  120
ggccaggctc cccggctgct gatctacagc gcatctaata gatatagcgg agtgcctgct  180
cgcttcagtg gttcaggcta tggaactgag ttccttca ccatttccag cgtgcagtcc  240
gaagacttcg cagtgtactt ttgccagcag gattattcta gttttgggtg tggtacaaag  300
ctggagatca aaaggggagg aggaggtagt ggcggaggag gttcaggcgg aggggtagc  360
ggcggagggg gttctggcgg cggcggtagt ggcggcggag gtagccaggt gcagctggtc  420
gaatccggcc ctggagtggt ccagccaggc aggtctctgc ggatcagttg cgccgtgtcc  480
ggattcagcg tcaccaacta cggagtgcac tgggtcagac agccacctgg caagtgtctg  540
gagtggctgg gagtgatctg ggcaggagga atcacaaact acaactcagc tttatgtcc  600
cgcctgacta ttagcaagga caactctaaa aataccgtgt atctgcagat gaattctctg  660
cgagccgaag ataccgctat gtactattgt gcatcccgtg ggggtcatta cggctatgcc  720
ctggattatt ggggccaggg taccctggtg acagtctcat ccggcggagg ggatccggc  780
ggcggaggat ctggcggagg tggaagtggg ggaggcggat ctcatgtgca gctggtggaa  840
agcggaggcg gcctggtgca gcctggggga tctctgagac tgtcttgtgc cgccagcggc  900
ttctccctga ccgattatgg cgtgcactgg gtgcacaggg ccctggcaa aggactgaa  960
tggctgggag tgatttggag tggcggaggc accgcctaca acaccgcctt gatctccgg 1020
ttcaccatca gccggaacaa ctccaagaac accctgtacc tgcagatgaa ctccctgcgg 1080
gccgaggaca ccgctgtgta ctactgcgcc agacgggggct cctacccta caactacttc 1140
gacgcttggg gctgcggcac cctcgtgaca gtgtctagcg gagggggagg ttctgggggc 1200
ggaggttcag gtgtggtga ttccgggggt ggtggctctg gtgccggtgg ttctggcggt 1260
ggcggatctc aggctgtcgt gacccaggaa cccagcctga ctgtgtctcc tggcggaacc 1320
gtgaccctga cctgcggatc ttctaccggc gctgtgaccg ccagcaacta cgccaattgg 1380
gtgcagcaga aacctggaca gtgccctaga ggcctgatcg gcggccacaa caacagacct 1440
ccaggcgtgc cagccccggtt ctctggatct ctgctgggcg gaaaggccgc tctgacactg 1500
ctgggtgctc agcctgagga cgaggccgag tactactgtg ccctgtggta ctccgaccac 1560
tgggtcatcg gaggcgggac caagctgacc gtgctgggaa cacccctggg agacaccaca 1620
catactagtg ggaaacctct ggatggcgag tactttaccc tgcagattag aggccgcgaa 1680
cgattcgaga tgtttcgcga actgaatgag gccctgaac tgaaggatgc tcaggcaggc 1740
aaggagccag gagggtcagg aggagcaccg caccatcatc atcaccat 1788

SEQ ID NO: 33           moltype = AA   length = 614
FEATURE                 Location/Qualifiers
REGION                  1..614
                        note = Description of Artificial Sequence: Synthetic
                        polypeptide
source                  1..614
                        mol_type = protein
                        organism = synthetic construct
SEQUENCE: 33
EIVMTQTPAT LSVSAGERVT ITCKASQSVS NDVTWYQQKP GQAPRLLIYS ASNRYSGVPA   60
RFSGSGYGTE FTFTISSVQS EDFAVYFCQQ DYSSFGCGTK LEIKRGGGGS GGGGSGGGGS  120
GGGGSGGGGS GGGGSQVQLV ESGPGVVQPG RSLRISCAVS GFSVTNYGVH WVRQPPGKCL  180
EWLGVIWAGG ITNYNSAFMS RLTISKDNSK NTVYLQMNSL RAEDTAMYYC ASRGGHYGYA  240
LDYWGQGTLV TVSSGGGGSG GGGSGGGGSG GGSHVQLVE SGGGLVQPGG SLRLSCAASG  300
FSLTDYGVHW VRQAPGKGLE WLGVIWSGGG TAYNTALISR FTISRDNSKN TLYLQMNSLR  360
AEDTAVYYCA RRGSYPYNYF DAWGCGTLVT VSSGGGGSGG GGSGGGGSGG GSGGGGSGG  420
GGSQAVVTQE PSLTVSPGGT VTLTCGSSTG AVTASNYANW VQQKPGQCPR GLIGGHNNRP  480
PGVPARFSGS LLGGKAALTL LGAQPEDEAE YYCALWYSDH WVIGGGTKLT VLGTPLGDTT  540
HTSGRSPDDE LLYLPVRGRE TYEMLLKIKE SLELMQYLPQ HTIETYRQQQ QQHQHLLQK  600
QGGSGGAPHH HHHH                                                    614

SEQ ID NO: 34           moltype = DNA   length = 1842
FEATURE                 Location/Qualifiers
misc_feature            1..1842
                        note = Description of Artificial Sequence: Synthetic
                        polynucleotide
source                  1..1842
                        mol_type = other DNA
                        organism = synthetic construct
SEQUENCE: 34
gagatcgtga tgacccagac acccgcaaca ctgagcgtgt ctgccggcga aagggtcact   60
attacctgca aggccagtca gtcagtgtcc aacgacgtga cttggtacca gcagaaacca  120
ggccaggctc cccggctgct gatctacagc gcatctaata gatatagcgg agtgcctgct  180
cgcttcagtg gttcaggcta tggaactgag ttcaccttca ccatttccag cgtgcagtcc  240
gaagacttcg cagtgtactt ttgccagcag gattattcta gttttgggtg tggtacaaag  300
ctggagatca aaaggggagg aggaggtagt ggcggaggag gttcaggcgg aggggtagc  360
ggcggagggg gttctggcgg cggcggtagt ggcggcggag gtagccaggt gcagctggtc  420
gaatccggcc ctggagtggt ccagccaggc aggtctctgc ggatcagttg cgccgtgtcc  480
ggattcagcg tcaccaacta cggagtgcac tgggtcagac agccacctgg caagtgtctg  540

```
gagtggctgg gagtgatctg ggcaggagga atcacaaact acaactcagc ttttatgtcc    600
cgcctgacta ttagcaagga caactctaaa aataccgtgt atctgcagat gaattctctg    660
cgagccgaag ataccgctat gtactattgt gcatcccgtg ggggtcatta cggctatgcc    720
ctggattatt gggggcaggg taccctggtg acagtctcat ccggaggagg aggatccgga    780
ggaggaggta gcggcggagg gggttctggc ggaggggta  gtcatgtgca gctggtggaa    840
agcggaggcg gcctggtgca gcctggggga tctctgagac tgtcttgtgc cgccagcggc    900
ttctccctga ccgattatgg cgtgcactgg gtgcgacagg cccctggcaa aggactggaa    960
tggctgggag tgatttggag tggcggaggc accgcctaca caccgccct gatctcccgg    1020
ttcaccatca gccgggacaa ctccaagaac accctgtacc tgcagatgaa ctccctgcgg    1080
gccgaggaca ccgctgtgta ctactgcgcc agacggggct cctaccccta caactacttc    1140
gacgcttggg gctgcggcac cctcgtgaca gtgtctagcg gaggggagg  ttctgggggc    1200
ggaggttcag gtggtggtgg ttccgggggt ggtggctctg gtggcggtgg ttctggcggt    1260
ggcggatctc aggctgtcgt gacccaggaa cccagcctga ctgtgtctcc tggcggaacc    1320
gtgaccctga cctgcggatc ttctaccggc gctgtgaccg ccagcaacta cgccaattgg    1380
gtgcagcaga aacctggaca gtgccctaga ggcctgatcg gcggccacaa caacagacct    1440
ccaggcgtgc cagcccggtt ctctggatct ctgctgggcg gaaaggccgc tctgacactg    1500
ctgggtgctc agcctgagga cgaggccgag tactactgtg ccctgtggta ctccgaccac    1560
tgggtcatcg gaggcgggac caagctgacc gtgctgggaa caccactg                1620
catactagtg ggagatcccc cgacgatgag ctgctgtacc tgcctgtgag gggccgggag    1680
acctatgaaa tgctgctgaa gatcaaagag agcctggaac tgatgcagta cctgccacag    1740
cacaccattg aaacatatag gcaacaacag cagcagcagc atcagcatct gctgcagaag    1800
cagggagggt caggaggagc accgcaccat catcatcacc at                       1842

SEQ ID NO: 35          moltype = AA  length = 609
FEATURE                Location/Qualifiers
REGION                 1..609
                       note = Description of Artificial Sequence: Synthetic
                         polypeptide
source                 1..609
                       mol_type = protein
                       organism = synthetic construct
SEQUENCE: 35
EIVMTQTPAT LSVSAGERVT ITCKASQSVS NDVTWYQQKP GQAPRLLIYS ASNRYSGVPA     60
RFSGSGYGTE FTFTISSVQS EDFAVYFCQQ DYSSFGCGTK LEIKRGGGGS GGGGSGGGGS    120
GGGGSGGGGS GGGGSQVQLV ESGPGVVQPG RSLRISCAVS GFSVTNYGVH WVRQPPGKCL    180
EWLGVIWAGG ITNYNSAFMS RLTISKDNSK NTVYLQMNSL RAEDTAMYYC ASRGGHYGYA    240
LDYWGQGTLV TVSSGGGGSG GGGSGGGGSG GGGSHVQLVE SGGGLVQPGG SLRLSCAASG    300
FSLTDYGVHW VRQAPGKGLE WLGVIWSGGG TAYNTALISR FTISRDNSKN TLYLQMNSLR    360
AEDTAVYYCA RRGSYPYNYF DAWGCGTLVT VSSGGGGSGG GGSGGGGSGG GGSGGGGSGG    420
GGSQAVVTQE PSLTVSPGGT VTLTCGSSTG AVTASNYANW VQQKPGQCPR GLIGGHNNRP    480
PGVPARFSGS LLGGKAALTL LGAQPEDEAE YYCALWYSDH WVIGGGTKLT VLGTPLGDTT    540
HTSGRHGDED TYYLQVRGRE NFEILMKLKE SLELMELVPQ PLVDSYRQQQ QLLQRPGGGS    600
GAPHHHHHH                                                            609

SEQ ID NO: 36          moltype = DNA  length = 1827
FEATURE                Location/Qualifiers
misc_feature           1..1827
                       note = Description of Artificial Sequence: Synthetic
                         polynucleotide
source                 1..1827
                       mol_type = other DNA
                       organism = synthetic construct
SEQUENCE: 36
gagatcgtga tgacccagac acccgcaaca ctgagcgtgt ctgccggcga aagggtcact     60
attacctgca aggccagtca gtcagtgtcc aacgacgtga cttggtacca gcagaaacca    120
ggccaggctc cccggctgct gatctacagc gcatctaata gatatagcgg agtgcctgct    180
cgcttcagtg gttcaggcta tggaactgag ttcaccttca ccatttccag cgtgcagtcc    240
gaagacttcg cagtgtactt ttgccagcag gattattcta gttttgggtg tggtacaaag    300
ctggagatca aaggggagg  aggaggtagt ggcggaggag gttcaggcgg aggggtagc     360
ggcggagggg gttctggcgg cggcggtagt ggcggcggag gtagccaggt gcagctggtc    420
gaatccggcc ctggagtggt ccagccaggc aggtctctgc ggatcagttg cgccgtgtcc    480
ggattcagcg tcaccaacta cggagtgcac tgggtcagac agccacctgg caagtgtctg    540
gagtggctgg gagtgatctg ggcaggagga atcacaaact acaactcagc ttttatgtcc    600
cgcctgacta ttagcaagga caactctaaa aataccgtgt atctgcagat gaattctctg    660
cgagccgaag ataccgctat gtactattgt gcatcccgtg ggggtcatta cggctatgcc    720
ctggattatt gggggcaggg taccctggtg acagtctcat ccggaggagg aggatccgga    780
ggaggaggta gcggcggagg gggttctggc ggaggggta  gtcatgtgca gctggtggaa    840
agcggaggcg gcctggtgca gcctggggga tctctgagac tgtcttgtgc cgccagcggc    900
ttctccctga ccgattatgg cgtgcactgg gtgcgacagg cccctggcaa aggactggaa    960
tggctgggag tgatttggag tggcggaggc accgcctaca caccgccct gatctcccgg    1020
ttcaccatca gccgggacaa ctccaagaac accctgtacc tgcagatgaa ctccctgcgg    1080
gccgaggaca ccgctgtgta ctactgcgcc agacggggct cctaccccta caactacttc    1140
gacgcttggg gctgcggcac cctcgtgaca gtgtctagcg gaggggagg  ttctgggggc    1200
ggaggttcag gtggtggtgg ttccgggggt ggtggctctg gtggcggtgg ttctggcggt    1260
ggcggatctc aggctgtcgt gacccaggaa cccagcctga ctgtgtctcc tggcggaacc    1320
gtgaccctga cctgcggatc ttctaccggc gctgtgaccg ccagcaacta cgccaattgg    1380
gtgcagcaga aacctggaca gtgccctaga ggcctgatcg gcggccacaa caacagacct    1440
ccaggcgtgc cagcccggtt ctctggatct ctgctgggcg gaaaggccgc tctgacactg    1500
ctgggtgctc agcctgagga cgaggccgag tactactgtg ccctgtggta ctccgaccac    1560
```

```
tgggtcatcg gaggcgggac caagctgacc gtgctgggaa caccCctggg agacaccaca  1620
catactagtg ggaggcacgg cgacgaagat acctactatc tgcaggtgag gggacgggag  1680
aacttcgaaa tcctgatgaa gctgaaagag tccctggaac tgatggagct ggtgcccag   1740
cctctggtcg acagctacag acagcagcag cagctgctgc agaggccagg agggtcagga  1800
ggagcaccgc accatcatca tcaccat                                      1827
```

```
SEQ ID NO: 37            moltype = AA  length = 559
FEATURE                  Location/Qualifiers
REGION                   1..559
                         note = Description of Artificial Sequence: Synthetic
                           polypeptide
source                   1..559
                         mol_type = protein
                         organism = synthetic construct
SEQUENCE: 37
EIVMTQTPAT LSVSAGERVT ITCKASQSVS NDVTWYQQKP GQAPRLLIYS ASNRYSGVPA   60
RFSGSGYGTE FTFTISSVQS EDFAVYFCQQ DYSSFGCGTK LEIKRGGGGS GGGGSGGGGS  120
QVQLVESGPG VVQPGRSLRI SCAVSGFSVT NYGVHWVRQP PGKCLEWLGV IWAGGITNYN  180
SAFMSRLTIS KDNSKNTVYL QMNSLRAEDT AMYYCASRGG HYGYALDYWG QGTLVTVSSG  240
GGGSGGGGSG GGGSGGGGSH VKLQESGPGL VQPSQSLSLT CTVSGFSLTD YGVHWVRQSP  300
GKGLEWLGVI WSGGGTAYNT ALISRLNIYR DNSKNQVFLE MNSLQAEDTA MYYCARRGSY  360
PYNYFDAWGC GTTVTVSSGG GGSGGGGSGG GGSQAVVIQE SALTTPPGET VTLTCGSSTG  420
AVTASNYANW VQEKPDHCFT GLIGGHNNRP PGVPARFSGS LIGDKAALTI AGTQTEDEAI  480
YFCALWYSDH WVIGGGTRLT VLGTPLGDTT HTSGKPLDGE YFTLQIRGRE RFEMFRELNE  540
ALELKDAQAG KEPGGSGGA                                               559
```

```
SEQ ID NO: 38            moltype = DNA  length = 1677
FEATURE                  Location/Qualifiers
misc_feature             1..1677
                         note = Description of Artificial Sequence: Synthetic
                           polynucleotide
source                   1..1677
                         mol_type = other DNA
                         organism = synthetic construct
SEQUENCE: 38
gaaatcgtca tgactcagac tcccgcaacc ctgtcagtgt ccgctgggga acgtgtcact   60
attacctgca aggcatctca gagcgtgagc aacgacgtga cctggtatca gcagaagcct  120
ggccaggctc cacgactgct gatctattcc gcaagcaatc gctactccgg agtgcccgca  180
cgattctctg gaagtgggta cggtaccgag ttcactttta ccatttccag cgtgcagagc  240
gaagacttcg ctgtctattt tgccagcag gattactcta gttttggctg tggaacaaag  300
ctggagatca aaggggagg aggaggttct ggcggaggag gtagtggcgg aggggttca   360
caggtgcagc tggtcgaatc tgggccaggc gtggtccagc caggacgttc cctgaggatt  420
agctgcgcg tgagcgggtt ctctgtcaca aactacggga tgcactggcc cgtcagcca   480
cctggcaaat gtctggagtg gctgggagtg atctgggcag gaggaatcac taactacaac  540
tctgctttta tgagtcgcct gaccatctca aaggacaact ccaaaaatac agtgtacctg  600
cagatgaatt cactgcgggc agaagatacc gccatgtact attgcgcctc caggggggt  660
cattacggct atgccctgga ctattgggc cagggaaccc tggtgactgt ctcatccgga  720
ggaggaggat ccggaggagg aggtagcggc ggaggggtt ctgcggagg gggtagtcac  780
gtgaagctgc aggaaagcgg ccctggactg gtgcagcctt cccagtctct gtccctgacc  840
tgcaccgtgt ccggcttctc cctgaccgat tacggcgtgc actgggtgcg acagtctcca  900
ggcaaggcc tggaatggct gggagtgatt tggagcggtg gcggaaccgc ctacaacgcc  960
gccctgatct cccggctgaa catctaccgg gacaactcca agaaccaggt gttcctggaa 1020
atgaactccc tgcaggcaga ggacaccgcc atgtactact cgccagacg gggctcctac 1080
ccctacaact acttcgacgc ttggggctgc ggcaccaccg tgacagtgtc tagcggaggt 1140
ggtggatctg ggggcggagg tagcggaggg ggaggttctc aggctgtcgt gatccaggaa 1200
tctgccctga ccaccccccc tggcgagaga gtgacactga cctgcggatc ttccaccggc 1260
gctgtgaccg cctccaacta cgccaactgg gtgcaggaaa agcccgacca ctgcttcacc 1320
ggcctgatcg gcggccacaa caacagacct ccaggcgtgc cagcccggtt ctccggctct 1380
ctgatcggag ataaggccgc cctgacaatc gccggcaccc agacagagga cgaggctatc 1440
tacttctgcg ccctgtggta cagcgaccac tgggtcatcg gcggaggcac cagactgacc 1500
gtgctgggaa caccctggg agacaccaca catactagtg gcaaacctct ggatggagag 1560
tactttaccc tgcagattag aggccgcaa cgattcgaga tgtttcgcga actgaatgag 1620
gccctggaac tgaaggatgc tcaggcaggc aaggaaccag cggtagcgg cggcgca     1677
```

```
SEQ ID NO: 39            moltype = AA  length = 581
FEATURE                  Location/Qualifiers
REGION                   1..581
                         note = Description of Artificial Sequence: Synthetic
                           polypeptide
source                   1..581
                         mol_type = protein
                         organism = synthetic construct
SEQUENCE: 39
EIVMTQTPAT LSVSAGERVT ITCKASQSVS NDVTWYQQKP GQAPRLLIYS ASNRYSGVPA   60
RFSGSGYGTE FTFTISSVQS EDFAVYFCQQ DYSSFGCGTK LEIKRGGGGS GGGGSGGGGS  120
GGGGSGGGGS GGGGSQVQLV ESGPGVVQPG RSLRISCAVS GFSVTNYGVH WVRQPPGKCL  180
EWLGVIWAGG ITNYNSAFMS RLTISKDNSK NTVYLQMNSL RAEDTAMYYC ASRGGHYGYA  240
LDYWGQGTLV TVSSGGGGSG GGGSGGGGSG GGHVKLQE SGPGLVQPSQ SLSLTCTVSG    300
FSLTDYGVHW VRQSPGKGLE WLGVIWSGGG TAYNTALISR LNIYRDNSKN QVFLEMNSLQ  360
```

```
AEDTAMYYCA RRGSYPYNYF DAWGCGTTVT VSSGGGGSGG GGSGGGGSQA VVIQESALTT   420
PPGETVTLTC GSSTGAVTAS NYANWVQEKP DHCFTGLIGG HNNRPPGVPA RFSGSLIGDK   480
AALTIAGTQT EDEAIYFCAL WYSDHWVIGG GTRLTVLGTP LGDTTHTSGK PLDGEYFTLQ   540
IRGRERFEMF RELNEALELK DAQAGKEPGG SGGAPHHHHH H                      581

SEQ ID NO: 40           moltype = DNA   length = 1743
FEATURE                 Location/Qualifiers
misc_feature            1..1743
                        note = Description of Artificial Sequence: Synthetic
                         polynucleotide
source                  1..1743
                        mol_type = other DNA
                        organism = synthetic construct
SEQUENCE: 40
gagatcgtga tgacccagac acccgcaaca ctgagcgtgt ctgccggcga aagggtcact   60
attacctgca aggccagtca gtcagtgtcc aacgacgtga cttggtacca gcagaaacca   120
ggccaggctc cccggctgct gatctacagc gcatctaata gatatagcgg agtgcctgct   180
cgcttcagtg gttcaggcta tggaactgag ttcaccttca ccatttccag cgtgcagtcc   240
gaagacttcg cagtgtactt ttgccagcag gattattcta gttttgggtg tggtacaaag   300
ctggagatca aaaggggagg aggaggtagt ggcggaggag gttcaggcgg aggggggtagc   360
ggcggagggg gttctggcgg cggcggtagt ggcggcggag gtagccaggt gcagctggtc   420
gaatccggcc ctggagtggt ccagccaggc aggtctctgc ggatcagttg cgccgtgtcc   480
ggattcagcg tcaccaacta cggagtgcac tgggtcagac agccacctgg caagtgtctg   540
gagtggctgg gagtgatctg ggcaggagga atcacaaact acaactcagc ttttatgtcc   600
cgcctgacta ttagcaagga caactctaaa ataccgtgt atctgcagat gaattctctg   660
cgagccgaag ataccgctat gtactattgt gcatcccgtg gtggtcatta cggctatgcc   720
ctggattatt gggggcaggg taccctggtg acagtctcat ccggcggagg gggatccgga   780
ggaggagta gcggcggagg gggttctggc ggaggggta gtcacgtgaa gctgcaggaa   840
agcggccctg gactggtgca gccttccag tctctgtccc tgacctgcac cgtgtccggc   900
ttctccctga ccgattacgg cgtgcactgg gtgcgacagt ctccaggagg gggcctggaa   960
tggctgggag tgatttggag cggtggcgga accgcctaca acaccgccct gatctcccgg  1020
ctgaacatct accgggacaa ctccaagaac caggtgttcc tggaaatgaa ctccctgcag  1080
gcagaggaca ccgccatgta ctactgcgcc agacgggggct cctaccccta caactacttc  1140
gacgcttggg gctgcggcac caccgtgaca gtgtctagcg gaggtggtgg atctggggc  1200
ggaggtagcg gaggggagg ttctcaggct gtcgtgatcc aggaatctgc cctgaccacc  1260
cccctggcg agacagtgac actgacctgc ggatcttcca ccggcgctgt gaccgcctcc  1320
aactacgcca actgggtgca ggaaaagccc gaccactgct tcaccggcct gatcggcggc  1380
cacaacaaca gacctccagg cgtgccagcc cggttcccg gctctctgat cggagataag  1440
gccgccctga caatcgccgg caccccagaca gaggacgagg ctatctactt ctgcgccctg  1500
tggtacagcg accactgggt catcggcgga ggcaccagag tgaccgtgct gggaacaccc  1560
ctgggagaca ccacacatac tagtgggaaa cctctggatg gcgagtactt taccctgcag  1620
attagaggc gcaacgatt cgagatgttt cgcgaactga atgaggccct ggaactgaag  1680
gatgctcagg caggcaagga gccaggaggg tcaggaggag caccgcacca tcatcatcac  1740
cat                                                                1743

SEQ ID NO: 41           moltype = AA   length = 599
FEATURE                 Location/Qualifiers
REGION                  1..599
                        note = Description of Artificial Sequence: Synthetic
                         polypeptide
source                  1..599
                        mol_type = protein
                        organism = synthetic construct
SEQUENCE: 41
EIVMTQTPAT LSVSAGERVT ITCKASQSVS NDVTWYQQKP GQAPRLLIYS ASNRYSGVPA   60
RFSGSGYGTE FTFTISSVQS EDFAVYFCQQ DYSSFGCGTK LEIKRGGGGS GGGGSGGGGS   120
GGGGSGGGGS GGGGSQVQLV ESGPGVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGGSGGGGS GGGSHVKLQE SGPGLVQPSQ SLSLTCTVSG   300
FSLTDYGVHW VRQSPGKGLE WLGVIWSGGG TAYNTALISR LNIYRDNSKN QVFLEMNSLQ   360
AEDTAMYYCA RRGSYPYNYF DAWGCGTTVT VSSGGGGSGG GGSGGGGSQA VVIQESALTT   420
PPGETVTLTC GSSTGAVTAS NYANWVQEKP DHCFTGLIGG HNNRPPGVPA RFSGSLIGDK   480
AALTIAGTQT EDEAIYFCAL WYSDHWVIGG GTRLTVLGTP LGDTTHTSGR SPDDELLYLP   540
VRGRETYEML LKIKESLELM QYLPQHTIET YRQQQQQQHQ HLLQKQGGSG GAPHHHHHH   599

SEQ ID NO: 42           moltype = DNA   length = 1798
FEATURE                 Location/Qualifiers
misc_feature            1..1798
                        note = Description of Artificial Sequence: Synthetic
                         polynucleotide
source                  1..1798
                        mol_type = other DNA
                        organism = synthetic construct
SEQUENCE: 42
gagatcgtga tgacccagac acccgcaaca ctgagcgtgt ctgccggcga aagggtcact   60
attacctgca aggccagtca gtcagtgtcc aacgacgtga cttggtacca gcagaaacca   120
ggccaggctc cccggctgct gatctacagc gcatctaata gatatagcgg agtgcctgct   180
cgcttcagtg gttcaggcta tggaactgag ttcaccttca ccatttccag cgtgcagtcc   240
gaagacttcg cagtgtactt ttgccagcag gattattcta gttttgggtg tggtacaaag   300
```

```
ctggagatca aaaggggagg aggaggtagt ggcggaggag gttcaggcgg aggggggtagc    360
ggcggagggg gttctggcgg cggcggtagt ggcggcggag gtagccaggt gcagctggtc    420
gaatccggcc ctggagtggt ccagccaggc aggtctctgc ggatcagttg cgccgtgtcc    480
ggattcagcg tcaccaacta cggagtgcac tgggtcagac agccacctgg caagtgtctg    540
gagtggctgg gagtgatctg ggcaggagga atcacaaact acaactcagc ttttatgtcc    600
cgcctgacta ttagcaagga caactctaaa aataccgtgt atctgcagat gaattctctg    660
cgagccgaag ataccgctat gtactattgt gcatcccgtg ggggtcatta cggctatgcc    720
ctggattatt gggggcaggg taccctggtg acagtctcat ccggaggagg aggatccgga    780
ggaggaggta gcggcggagg gggttctggc ggagggggta gtcacgtgaa gctgcaggaa    840
agcggccctg gactggtgca gccttcccag tctctgtccc tgacctgcac cgtgtccggc    900
ttctccctga ccgattacgg cgtgcactgg gtgcgacagt ctccaggcaa gggcctggaa    960
tggctgggag tgatttggag cggtggcgga accgcctaca acaccgccct gatctcccgg   1020
ctgaacatct accgggacaa ctccaagaac caggtgttcc tggaaatgaa ctccctgcag   1080
gcagaggaca ccgccatgta ctactgcgcc agacggggcc cctaccccta caactacttc   1140
gacgcttggg gctgcggcac caccgtgaca gtgtctagcg gaggtggtgg atctggggc    1200
ggaggtagcg gagggggagg ttctcaggct gtcgtgatcc aggaatctgc cctgaccacc   1260
cccccctggcg agacagtgac actgacctgc ggatcttcca ccggcgctgt gaccgcctcc   1320
aactacgcca actgggtgca ggaaaagccc gaccactgct tcaccggcct gatcggcggc   1380
cacaacaaca gacctccagg cgtgccagcc cggttctccg gctctctgat cggagataag   1440
gccgccctga caatcgccgg cacccagaca gaggacgagg ctatctactt ctgcgccctg   1500
tggtacagcg accactgggt catcggcgga ggcaccagac tgaccgtgct gggaacaccc   1560
ctgggagaca ccacacatac tagtgggaga tcccccgacg atgagctgct gtacctgcct   1620
gtgaggggcc gggagaccta tgaaatgctg ctgaagatca agagagcct ggaactgatg    1680
cagtacctgc cacagcacac cattgaaaca tataggcaac aacagcagca gcagcatcag   1740
catctgctgc agaagcaggg agggtcagga ggagcaccgc accatcatca tcaccatt    1798

SEQ ID NO: 43           moltype = AA   length = 594
FEATURE                 Location/Qualifiers
REGION                  1..594
                        note = Description of Artificial Sequence: Synthetic
                          polypeptide
source                  1..594
                        mol_type = protein
                        organism = synthetic construct
SEQUENCE: 43
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
GGGGSGGGGS GGGGSQVQLV ESGPGVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGGSGGGGSG GGSHVKLQE SGPGLVQPSQ SLSLTCTVSG    300
FSLTDYGVHW VRQSPGKGLE WLGVIWSGGG TAYNTALISR LNIYRDNSKN QVFLEMNSLQ   360
AEDTAMYYCA RRGSYPYNYF DAWGCGTTVT VSSGGGGSGG GGSGGGGSQA VVIQESALTT   420
PPGETVTLTC GSSTGAVTAS NYANWVQEKP DHCFTGLIGG HNNRPPGVPA RFSGSLIGDK   480
AALTIAGTQT EDEAIYFCAL WYSDHWVIGG GTRLTVLGTP LGDTTHTSGR HGDEDTYYLQ   540
VRGRENFEIL MKLKESLELM ELVPQPLVDS YRQQQQLLQR PGGSGGAPHH HHHH          594

SEQ ID NO: 44           moltype = DNA   length = 1782
FEATURE                 Location/Qualifiers
misc_feature            1..1782
                        note = Description of Artificial Sequence: Synthetic
                          polynucleotide
source                  1..1782
                        mol_type = other DNA
                        organism = synthetic construct
SEQUENCE: 44
gagatcgtga tgacccagac acccgcaaca ctgagcgtgt ctgccggcga aagggtcact     60
attacctgca aggccagtca gtcagtgtcc aacgacgtga cttggtacca gcagaaacca    120
ggccaggctc cccggctgct gatctacagc gcatctaata gatatagcgg agtgcctgct    180
cgcttcagtg gttcaggcta tggaactgag ttcaccttca ccatttccag cgtgcagtcc    240
gaagacttcg cagtgtactt ttgccagcag gattattcta gttttgggtg tggtacaaag    300
ctggagatca aaaggggagg aggaggtagt ggcggaggag gttcaggcgg aggggggtagc   360
ggcggagggg gttctggcgg cggcggtagt ggcggcggag gtagccaggt gcagctggtc    420
gaatccggcc ctggagtggt ccagccaggc aggtctctgc ggatcagttg cgccgtgtcc    480
ggattcagcg tcaccaacta cggagtgcac tgggtcagac agccacctgg caagtgtctg    540
gagtggctgg gagtgatctg ggcaggagga atcacaaact acaactcagc ttttatgtcc    600
cgcctgacta ttagcaagga caactctaaa aataccgtgt atctgcagat gaattctctg    660
cgagccgaag ataccgctat gtactattgt gcatcccgtg ggggtcatta cggctatgcc    720
ctggattatt gggggcaggg taccctggtg acagtctcat ccggaggagg aggatccgga    780
ggaggaggta gcggcggagg gggttctggc ggagggggta gtcacgtgaa gctgcaggaa    840
agcggccctg gactggtgca gccttcccag tctctgtccc tgacctgcac cgtgtccggc    900
ttctccctga ccgattacgg cgtgcactgg gtgcgacagt ctccaggcaa gggcctggaa    960
tggctgggag tgatttggag cggtggcgga accgcctaca acaccgccct gatctcccgg   1020
ctgaacatct accgggacaa ctccaagaac caggtgttcc tggaaatgaa ctccctgcag   1080
gcagaggaca ccgccatgta ctactgcgcc agacggggcc cctaccccta caactacttc   1140
gacgcttggg gctgcggcac caccgtgaca gtgtctagcg gaggtggtgg atctggggc    1200
ggaggtagcg gagggggagg ttctcaggct gtcgtgatcc aggaatctgc cctgaccacc   1260
cccccctggcg agacagtgac actgacctgc ggatcttcca ccggcgctgt gaccgcctcc   1320
aactacgcca actgggtgca ggaaaagccc gaccactgct tcaccggcct gatcggcggc   1380
cacaacaaca gacctccagg cgtgccagcc cggttctccg gctctctgat cggagataag   1440
```

```
gccgccctga caatcgccgg cacccagaca gaggacgagg ctatctactt ctgcgccctg  1500
tggtacagcg accactgggt catcggcgga ggcaccagac tgaccgtgct gggaacaccc  1560
ctggagacac ccacacatac tagtgggagg cacggcgacg aagataccta ctatctgcag  1620
gtgaggggac gggagaactt cgaaatcctg atgaagctga aagagtccct ggaactgatg  1680
gagctggtgc cccagcctct ggtcgacagc tacagacagc agcagcagct gctgcagagg  1740
ccaggagggt caggaggagc accgcaccat catcatcacc at                     1782

SEQ ID NO: 45           moltype = AA  length = 566
FEATURE                 Location/Qualifiers
REGION                  1..566
                        note = Description of Artificial Sequence: Synthetic
                        polypeptide
source                  1..566
                        mol_type = protein
                        organism = synthetic construct
SEQUENCE: 45
EIVMTQTPAT LSVSAGERVT ITCKASQSVS NDVTWYQQKP GQAPRLLIYS ASNRYSGVPA   60
RFSGSGYGTE FTFTISSVQS EDFAVYFCQQ DYSSFGCGTK LEIKRGGGGS GGGGSGGGGS  120
QVQLVESGPG VVQPGRSLRI SCAVSGFSVT NYGVHWVRQP PGKCLEWLGV IWAGGITNYN  180
SAFMSRLTIS KDNSKNTVYL QMNSLRAEDT AMYYCASRGG HYGYALDYWG QGTLVTSSGG  240
GGGSGGGGSG GGGSGGGGSH VKLQESGPGL VQPSQSLSLT CTVSGFSLTD YGVHWVRQSP  300
GKGLEWLGVI WSGGGTAYNT ALISRLNIYR DNSKNQVFLE MNSLQAEDTA MYYCARRGSY  360
PYNYFDAWGC GTTVTSSGGG GGSGGGGSGG GGSQAVVIQE SALTTPPGET VTLTCGSSTG  420
AVTASNYANW VQEKPDHCFT GLIGGHNNRP PGVPARFSGS LIGDKAALTI AGTQTEDEAI  480
YFCALWYSDH WVIGGGTRLT VLGTPLGDTT HTSGKPLDGE YFTLQIRGRE RFEMFRELNE  540
ALELKDAQAG KEPGGSGGAP HHHHHH                                      566

SEQ ID NO: 46           moltype = DNA  length = 1698
FEATURE                 Location/Qualifiers
misc_feature            1..1698
                        note = Description of Artificial Sequence: Synthetic
                        polynucleotide
source                  1..1698
                        mol_type = other DNA
                        organism = synthetic construct
SEQUENCE: 46
gaaatcgtca tgactcagac tcccgcaacc ctgtcagtgt ccgctgggga acgtgtcact   60
attacctgca aggcatctca gagcgtgagc aacgacgtga cctggtatca gcagaagcct  120
ggccaggctc cacgactgct gatctattcc gcaagcaatc gctactccgg agtgcccgca  180
cgattctctg gaagtgggta cggtaccgag ttcactttta ccatttccag cgtgcagagc  240
gaagacttcg ctgtctattt ttgccagcag gattactcta gttttggctg tggaacaaag  300
ctggagatca aaggggagg aggaggttct ggcggaggag gtagtggcgg aggggggttca  360
caggtgcagc tggtcgaatc tgggccaggc gtggtccagc caggacgttc cctgaggatt  420
agctgcgccg tgagcgggtt ctctgtcaca aactacggag tgcactgggt ccgtcagcca  480
cctggcaaat gtctggagtg gctgggagtg atctgggcag aggaatcac taactacaac  540
tctgctttta tgagtcgcct gaccatctca aaggacaact ccaaaaatac agtgtacctg  600
cagatgaatt cactgcgggc agaagatacc gccatgtact attgcgcctc caggggggt  660
cattacggct atgccctgga ctattgggc cagggaacac tggtgactgt ctcatccgga  720
ggaggaggat ccggaggagg aggtagcggc ggagggggtt ctgcggaggg ggtagtcac  780
gtgaagctgc aggaaagcgg ccctggactg gtgcagcctt cccagtctct gtccctgacc  840
tgcaccgtgt ccggcttctc cctgaccgat tacggcgtgc actgggtgcg acagtctcca  900
ggcaagggcc tggaatggct gggagtgatt tggagcggtg gcggaaccgc ctacaacacc  960
gccctgatct cccggctgaa catctaccgg gacaactcca agaaccaggt gttcctggaa  1020
atgaactccc tgcaggcaga ggacaccgcc atgtactact cgccagacg gggctcctac  1080
ccctacaact acttcgacgc ttggggctgc ggcaccacgtg tgacagtctc cagcggaggt  1140
ggtggatctg gggcggagg tagcggaggg ggaggttctc aggctgtcgt gatccaggaa  1200
tctgccctga ccacccccc tggcgagaca gtgacactga cctgcggatc ttccaccggc  1260
gctgtgaccc cctccaacta cgccaactgg gtgcaggaaa agcccgacca ctgcttcacc  1320
ggcctgatcg gcggccacaa caacagacct ccaggcgtgc cagccggtt ctccggctct  1380
ctgatcggag ataaggccgc cctgacaatc gccggcaccc agacagagga cgaggctatc  1440
tacttctgcg ccctgtggta cagcgaccac tgggtcatcg gcggaggcac cagactgacc  1500
gtgctgggaa caccctgggg agacaccaca catactagtg ggaaacctct ggatggcgag  1560
tactttaccc tgcagattag aggccgcgaa cgattcgaga tgtttcgcga actgaatgag  1620
gccctggaac tgaaggatgc tcaggcaggc aaggagccag agggtcagg aggagcaccg  1680
caccatcatc atcaccat                                               1698

SEQ ID NO: 47           moltype = AA  length = 584
FEATURE                 Location/Qualifiers
REGION                  1..584
                        note = Description of Artificial Sequence: Synthetic
                        polypeptide
source                  1..584
                        mol_type = protein
                        organism = synthetic construct
SEQUENCE: 47
EIVMTQTPAT LSVSAGERVT ITCKASQSVS NDVTWYQQKP GQAPRLLIYS ASNRYSGVPA   60
RFSGSGYGTE FTFTISSVQS EDFAVYFCQQ DYSSFGCGTK LEIKRGGGGS GGGGSGGGGS  120
QVQLVESGPG VVQPGRSLRI SCAVSGFSVT NYGVHWVRQP PGKCLEWLGV IWAGGITNYN  180
SAFMSRLTIS KDNSKNTVYL QMNSLRAEDT AMYYCASRGG HYGYALDYWG QGTLVTSSGG  240
```

```
GGGSGGGGSG GGGSGGGGSH VKLQESGPGL VQPSQSLSLT CTVSGFSLTD YGVHWVRQSP   300
GKGLEWLGVI WSGGGTAYNT ALISRLNIYR DNSKNQVFLE MNSLQAEDTA MYYCARRGSY   360
PYNYFDAWGC GTTVTVSSGG GGSGGGGSGG GGSQAVVIQE SALTTPPGET VTLTCGSSTG   420
AVTASNYANW VQEKPDHCFT GLIGGHNNRP PGVPARFSGS LIGDKAALTI AGTQTEDEAI   480
YFCALWYSDH WVIGGGTRLT VLGTPLGDTT HTSGRSPDDE LLYLPVRGRE TYEMLLKIKE   540
SLELMQYLPQ HTIETYRQQQ QQQHQHLLQK QGGSGGAPHH HHHH                   584

SEQ ID NO: 48           moltype = DNA   length = 1753
FEATURE                 Location/Qualifiers
misc_feature            1..1753
                        note = Description of Artificial Sequence: Synthetic
                        polynucleotide
source                  1..1753
                        mol_type = other DNA
                        organism = synthetic construct
SEQUENCE: 48
gaaatcgtca tgactcagac tcccgcaacc ctgtcagtgt ccgctgggga acgtgtcact     60
attacctgca aggcatctca gagcgtgagc aacgacgtga cctggtatca gcagaagcct   120
ggccaggctc cacgactgct gatctattcc gcaagcaatc gctactccgg agtgcccgca   180
cgattctctg gaagtgggta cggtaccgag ttcacttttta ccatttccag cgtgcagagc   240
gaagacttcg ctgtctattt tgccagcag gattactcta gttttggctg tggaacaaag   300
ctggagatca aaaggggagg aggaggttct ggcggaggtg gtagtggcgg aggggggttca   360
caggtgcagc tggtcgaatc tgggccaggc gtggtccagc caggacgttc cctgaggatt   420
agctgcgccg tgagcgggtt ctctgtcaca aactacggag tgcactgggt ccgtcagcca   480
cctggcaaat gtctggagtg gctgggagtg atctgggcag gaggaatcac taactacaac   540
tctgcttta tgagtcgcct gaccatctca aaggacaact ccaaaaatac agtgtacctg   600
cagatgaatt cactgcgggc agaagatacc gccatgtact attgcgcctc caggggggt   660
cattacggct atgccctgga ctattgggc cagggaacac tggtgactgt ctcatccgga   720
ggaggaggat ccggaggagg aggtagcggc ggagggggtt ctggcggagg ggtagtcac   780
gtgaagctgc aggaaagcgg ccctggactg gtgcagcctt cccagtctct gtccctgacc   840
tgcaccgtgt ccggcttctc cctgaccgat tacggcgtgc actgggtgcg acagtctcca   900
ggcaagggcc tggaatggct gggagtgatt tggagcggtg gcggaaccgc ctacaacacc   960
gccctgatct cccggctgaa catctaccgg gacaactcca agaaccaggt gttcctggaa  1020
atgaactccc tgcaggcaga ggacaccgcc atgtactact gcgccagacg gggctcctac  1080
ccctacaact acttcgacgc ttggggctgc ggcaccaccg tgacagtgtc tagcggaggt  1140
ggtggatctg ggggcggagg tagcggaggg ggaggttctc aggctgtcgt gatccaggaa  1200
tctgccctga ccacccccc tggcgagaca gtgacactga cctgcggatc ttccaccggc  1260
gctgtgaccg cctccaacta cgccaactgg gtgcaggaaa agcccgacca ctgcttcacc  1320
ggcctgatcg gcggccacaa caacagacct ccaggcgtgc cagcccggtt ctccggctct  1380
ctgatcggag ataaggccgc cctgacaatc gccggcaccc agacagagga cgaggctatc  1440
tacttctgcg ccctgtggta cagcgaccac tgggtcatcg gcgaggcac agactgacc    1500
gtgctgggaa caccctggg agacaccaca catactagtg gagatcccc cgacgatgag   1560
ctgctgtacc tgcctgtgag gggccgggag acctatgaaa tgctgctgaa gatcaaagag  1620
agcctggaac tgatgcagta cctgccacag cacaccattg aaacatatag gcaacaacag  1680
cagcagcagc atcagcatct gctgcagaag cagggaggt caggaggagc accgcaccat  1740
catcatcacc att                                                    1753

SEQ ID NO: 49           moltype = AA   length = 579
FEATURE                 Location/Qualifiers
REGION                  1..579
                        note = Description of Artificial Sequence: Synthetic
                        polypeptide
source                  1..579
                        mol_type = protein
                        organism = synthetic construct
SEQUENCE: 49
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
QVQLVESGPG VVQPGRSLRI SCAVSGFSVT NYGVHWVRQP PGKGLEWLGV IWAGGITNYN   180
SAFMSRLTIS KDNSKNTVYL QMNSLRAEDT AMYYCASRGG HYGYALDYWG QGTLVTVSSG   240
GGGSGGGGSG GGGSGGGGSH VKLQESGPGL VQPSQSLSLT CTVSGFSLTD YGVHWVRQSP   300
GKGLEWLGVI WSGGGTAYNT ALISRLNIYR DNSKNQVFLE MNSLQAEDTA MYYCARRGSY   360
PYNYFDAWGC GTTVTVSSGG GGSGGGGSGG GGSQAVVIQE SALTTPPGET VTLTCGSSTG   420
AVTASNYANW VQEKPDHCFT GLIGGHNNRP PGVPARFSGS LIGDKAALTI AGTQTEDEAI   480
YFCALWYSDH WVIGGGTRLT VLGTPLGDTT HTSGRHGDED TYYLQVRGRE NFEILMKLKE   540
SLELMELVPQ PLVDSYRQQQ QLLQRPGGSG GAPHHHHHH                          579

SEQ ID NO: 50           moltype = DNA   length = 1737
FEATURE                 Location/Qualifiers
misc_feature            1..1737
                        note = Description of Artificial Sequence: Synthetic
                        polynucleotide
source                  1..1737
                        mol_type = other DNA
                        organism = synthetic construct
SEQUENCE: 50
gaaatcgtca tgactcagac tcccgcaacc ctgtcagtgt ccgctgggga acgtgtcact     60
attacctgca aggcatctca gagcgtgagc aacgacgtga cctggtatca gcagaagcct   120
ggccaggctc cacgactgct gatctattcc gcaagcaatc gctactccgg agtgcccgca   180
```

```
cgattctctg gaagtgggta cggtaccgag ttcactttta ccatttccag cgtgcagagc    240
gaagacttcg ctgtctattt ttgccagcag gattactcta gttttggctg tggaacaaag    300
ctggagatca aaaggggagg aggaggttct ggcggaggag gtagtggcgg aggggggttca   360
caggtgcagc tggtcgaatc tgggccaggc gtggtccagc caggacgttc cctgaggatt    420
agctgcgccg tgagcgggtt ctctgtcaca aactacggag tgcactggtt ccgtcagcca    480
cctggcaaat gtctggagtg gctgggagtg atctgggcag gagaatcac taactacaac    540
tctgctttta tgagtcgcct gaccatctca aaggacaact ccaaaaatac agtgtacctg    600
cagatgaatt cactgcgggc agaagatacc gccatgtact attgcgcctc cagggggggt   660
cattacggct atgccctgga ctattgggca cagggaacac tggtgactgt ctcatccgga    720
ggaggaggat ccggaggagg aggtagcggc ggaggggtt ctggcggagg gggtagtcac    780
gtgaagctgc aggaaagcgg ccctggactg gtgcagcctt cccagtctct gtccctgacc    840
tgcaccgtgt ccggcttctc cctgaccgat acggcgtgc actgggtgcg acagtctcca    900
ggcaagggcc tggaatggct gggagtgatt tggagcggtg gcgaaccgc ctacaacacc    960
gccctgatct cccggctgaa catctaccgg gacaactcca agaaccaggt gttcctggaa   1020
atgaactccc tgcaggcaga ggacaccgcc atgtactact cgccagacg gggctcctac   1080
ccctacaact acttcgacgc ttggggctgc ggcaccaccg tgacagtgtc tagcggaggt   1140
ggtggatctg ggggcggagg tagcggaggg ggaggttctc aggctgtcgt gatccaggaa   1200
tctgccctga ccacccccc tggcgagaca gtgacactga cctgcggatc ttccaccggt   1260
gctgtgaccg cctccaacta cgccaactgg gtgcaggaaa agcccgacca ctgcttcacc   1320
ggcctgatcg gcggccacaa caacagacct ccaggcgtgc cagcccggtt ctccggctct   1380
ctgatcggag ataaggccgc cctgacaatc gccggcaccc agacagagga cgaggctatc   1440
tacttctgcg ccctgtggta cagcgaccac tgggtcggag ggcac cagactgacc         1500
gtgctgggaa cacccctggg agacaccaca catactagtg gaggcacgg cgacgaagat   1560
acctactatc tgcaggtgag gggacgggag aacttcgaaa tcctgatgaa gctgaaagag   1620
tccctggaac tgatggagct ggtgcccag cctctggtcg acagctacag acagcagcag   1680
cagctgctgc agaggccagg agggtcagga ggagcaccgc accatcatca tcaccat     1737

SEQ ID NO: 51          moltype = AA   length = 596
FEATURE                Location/Qualifiers
REGION                 1..596
                       note = Description of Artificial Sequence: Synthetic
                        polypeptide
source                 1..596
                       mol_type = protein
                       organism = synthetic construct
SEQUENCE: 51
EIVMTQTPAT LSVSAGERVT ITCKASQSVS NDVTWYQQKP GQAPRLLIYS ASNRYSGVPA     60
RFSGSGYGTE FTFTISSVQS EDFAVYFCQQ DYSSFGCGTK LEIKRGGGGS GGGGSGGGGS   120
GGGGSGGGGS GGGGSQVQLV ESGPGVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGGSGGGGSG GGGSHVKLQE SGPGLVQPSQ SLSLTCTVSG   300
FSLTDYGVHW VRQSPGKGLE WLGVIWSGGG TAYNTALISR LNIYRDNSKN QVFLEMNSLQ   360
AEDTAMYYCA RRGSYPYNYF DAWGCGTTVT VSSGGGGSGG GGSGGGGSGG GGSGGGGSGG   420
GGSQAVVIQE SALTTPPGET VTLTCGSSTG AVTASNYANW VQEKPDHCFT GLIGGHNNRP   480
PGVPARFSGS LIGDKAALTI AGTQTEDEAI YFCALWYSDH WVIGGGTRLT VLGTPLGDTT   540
HTSGKPLDGE YFTLQIRGRE RFEMFRELNE ALELKDAQAG KEPGGSGGAP HHHHHH       596

SEQ ID NO: 52          moltype = DNA   length = 1788
FEATURE                Location/Qualifiers
misc_feature           1..1788
                       note = Description of Artificial Sequence: Synthetic
                        polynucleotide
source                 1..1788
                       mol_type = other DNA
                       organism = synthetic construct
SEQUENCE: 52
gagatcgtga tgacccagac acccgcaaca ctgagcgtgt ctgccggcga aagggtcact     60
attacctgca aggccagtca gtcagtgtcc aacgacgtga cttggtacca gcagaaacca   120
ggccaggctc cccggctgct gatctacagc gcatctaata gatatagcgg agtgcctgct   180
cgcttcagtg gttcaggcta tggaactgag ttcaccttca ccatttccag cgtgcagtcc   240
gaagacttcg cagtgtactt ttgccagcag gattattcta gttttggtg tggtacaaag    300
ctggagatca aaggggagg aggaggtagt ggcggaggag gttcaggcgg aggggtagc    360
ggcggagggg gttctggcgg cggcgtagt ggcggcggag gtagccaggt gcagctggtc    420
gaatccggcc ctgagtggt ccagccaggc aggtctctgc ggatcagttg cgccgtgtc    480
ggattcagcg tcaccaacta cggagtgcac tgggtcagac agccaccctgg caagtgtctg   540
gagtggctgg gagtgatctg gcagaggga tcacaaact acaactcagc ttttatgtcc    600
cgcctgacta ttagcaagga caactctaaa ataccgtgt atctgcagat gaattctctg    660
cgagccgaag ataccgctat gtactattgt gcatcccgtg ggggtcatta cggctatgcc    720
ctggattatt ggggccagtg taccctggtg acagtctcat ccggcggagg tggatccggc    780
ggcgaggat ctggcggagg tggaagtggg ggaggcggat ctcacgtgaa gctgcaggaa    840
agcggccctg gactggtgca gccttccag tctctgtccc tgacctgcac cgtgtccggc    900
ttctcctga ccgattacgg cgtgcactgg gtgcgacagt ctccaggcaa gggcctgaa    960
tggctgggag tgatttggag cggtggcgga accgcctaca acaccgccct gatctcccgg   1020
ctgaacatct accgggacaa ctccaagaac caggtgttcc tggaaatgaa ctccctgcag   1080
gcagaggaca ccgccatgta ctactgcgcc agacgggct cctacccta caactacttc   1140
gacgcttggg gctgcggcac caccgtgaca gtgtctagcg gaggtggtgg atctgggggc   1200
ggaggtagcg gaggggagg ttctggaggt ggtggatctg ggggcggagg tagcggaggg   1260
ggaggttctc aggctgtcgt gatccaggaa tctgccctga ccacccccc tggcgagaca   1320
gtgacactga cctgcggatc ttccaccggc gctgtgaccg cctccaacta cgccaactgg   1380
```

```
gtgcaggaaa agcccgacca ctgcttcacc ggcctgatcg gcggccacaa caacagacct   1440
ccaggcgtgc cagcccggtt ctccggctct ctgatcggag ataaggccgc cctgacaatc   1500
gccggcaccc agacagagga cgaggctatc tacttctgcg ccctgtggta cagcgaccac   1560
tgggtcatcg gcgcgaggcac cagactgacc gtgctgggaa cacccctggg agacaccaca   1620
catactagtg ggaaacctct ggatggcgag tactttaccc tgcagattag aggccgcgaa   1680
cgattcgaga tgtttcgcga actgaatgag gccctggaac tgaaggatgc tcaggcaggc   1740
aaggagccag gagggtcagg aggagcaccg caccatcatc atcaccat              1788
```

```
SEQ ID NO: 53           moltype = AA   length = 614
FEATURE                 Location/Qualifiers
REGION                  1..614
                        note = Description of Artificial Sequence: Synthetic
                        polypeptide
source                  1..614
                        mol_type = protein
                        organism = synthetic construct
SEQUENCE: 53
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
GGGGSGGGGS GGGGSQVQLV ESGPGVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGGSGGGGSG GGGSHVKLQE SGPGLVQPSQ SLSLTCTVSG   300
FSLTDYGVHW VRQSPGKGLE WLGVIWSGGG TAYNTALISR LNIYRDNSKN QVFLEMNSLQ   360
AEDTAMYYCA RRGSYPYNYF DAWGCGTTVT VSSGGGGSGG GGSGGGGSGG GGSGGGGSGG   420
GGSQAVVIQE SALTTPPGET VTLTCGSSTG AVTASNYANW VQEKPDHCFT GLIGGHNNRP   480
PGVPARFSGS LIGDKAALTI AGTQTEDEAI YFCALWYSDH WVIGGGTRLT VLGTPLGDTT   540
HTSGRSPDDE LLYLPVRGRE TYEMLLKIKE SLELMQYLPQ HTIETYRQQQ QQQHQHLLQK   600
QGGSGGAPHH HHHH                                                    614
```

```
SEQ ID NO: 54           moltype = DNA   length = 1842
FEATURE                 Location/Qualifiers
misc_feature            1..1842
                        note = Description of Artificial Sequence: Synthetic
                        polynucleotide
source                  1..1842
                        mol_type = other DNA
                        organism = synthetic construct
SEQUENCE: 54
gagatcgtga tgacccagac acccgcaaca ctgagcgtgt ctgccggcga aagggtcact     60
attacctgca aggccagtca gtcagtgtcc aacgacgtga cttggtacca gcagaaacca   120
ggccaggctc cccggctgct gatctacagc gcatctaata gatatagcgg agtgcctgct   180
cgcttcagtg gttcaggcta tggaactgag ttcaccttca ccatttccag cgtgcagtcc   240
gaagacttcg cagtgtactt ttgccagcag gattattgta gtttttggtg tggtacaaag   300
ctggagatca aaaggggagg aggaggtagt ggcggaggag gttcaggcgg aggggggtagc   360
ggcggagggg gttctggcgg cggcggtagt ggcggcggag gtagccaggt gcagctggtc   420
gaatccggcc ctggagtggt ccagccaggc aggtctctgc ggatcagttg cgccgtgtcc   480
ggattcagcg tcaccaacta cggagtgcac tgggtcagac agccacctgg caagtgctg    540
gagtggctgg gagtgatctg gcaggaggaa atcacaaact acaactcagc tttatgtcc    600
cgcctgacta ttagcaagga caactctaaa aataccgtgt atctgcagat gaattctctg   660
cgagccgaag ataccgctat gtactattgt gcatcccgtg ggggtcatta cggctatgcc   720
ctggattatt gggggcaggg taccctggtg acagtctcat ccggaggagg aggatccgga   780
ggaggaggta gcggcggagg ggttctggcc ggaggggggta gtcacggtgaa gctgcaggaa   840
agcggccctg gactggtgca gccttccag tctctgtccc tgacctgcac cgtgtccggc   900
ttctcccctga ccgattacgg cgtgcactgg gtgcgacagt ctccaggcaa gggcctggaa   960
tggctgggag tgatttggag cggtggcgga accgcctaca acaccgccct gatctcccgg  1020
ctgaacatct accgggacaa ctccaagaac caggtgttcc tggaaatgaa ctccctgcag  1080
gcagagacca ccgccatgta ctactgcgcc agacggccta cctacccta caactactgg  1140
gacgcttggg gctgcggcac caccgtgaca gtgtctagcg gaggtggtgg atctgggggc  1200
ggaggtagcg gaggggggagg ttctggaggt ggtggatctg ggggcggagg tagcggaggg  1260
ggaggttctc aggctgtcgt gatccaggaa tctgccctga ccaccccccc tggcgagaca  1320
gtgacactga cctgcggatc ttccaccggc gctgtgaccg cctccaacta cgccaactgg  1380
gtgcaggaaa agcccgacca ctgcttcacc ggcctgatcg gcggccacaa caacagacct  1440
ccaggcgtgc cagcccggtt ctccggctct ctgatcggag ataaggccgc cctgacaatc  1500
gccggcaccc agacagagga cgaggctatc tacttctgcg ccctgtggta cagcgaccac  1560
tgggtcatcg gcgcgaggcac cagactgacc gtgctgggaa cacccctggg agacaccaca  1620
catactagtg ggagatcccc cgacgatgag ctgctgtacc tgcctgtgag gggccgggag  1680
acctatgaaa tgctgctgaa gatcaaagag agcctggaac tgatgcagta cctgccacag  1740
cacaccattg aaacatatag gcaacaacag cagcagcagc atcagcatct gctgcagaag  1800
cagggagggt caggaggagc accgcaccat catcatcacc at                      1842
```

```
SEQ ID NO: 55           moltype = AA   length = 609
FEATURE                 Location/Qualifiers
REGION                  1..609
                        note = Description of Artificial Sequence: Synthetic
                        polypeptide
source                  1..609
                        mol_type = protein
                        organism = synthetic construct
```

```
SEQUENCE: 55
EIVMTQTPAT LSVSAGERVT ITCKASQSVS NDVTWYQQKP GQAPRLLIYS ASNRYSGVPA    60
RFSGSGYGTE FTFTISSVQS EDFAVYFCQQ DYSSFGCGTK LEIKRGGGGS GGGGSGGGGS   120
GGGGSGGGGS GGGGSQVQLV ESGPGVVQPG RSLRISCAVS GFSVTNYGVH WVRQPPGKCL   180
EWLGVIWAGG ITNYNSAFMS RLTISKDNSK NTVYLQMNSL RAEDTAMYYC ASRGGHYGYA   240
LDYWGQGTLV TVSSGGGGSG GGGSGGGGSG GGGSHVKLQE SGPGLVQPSQ SLSLTCTVSG   300
FSLTDYGVHW VRQSPGKGLE WLGVIWSGGG TAYNTALISR LNIYRDNSKN QVFLEMNSLQ   360
AEDTAMYYCA RRGSYPYNYF DAWGCGTTVT VSSGGGGSGG GGSGGGGSGG GGSGGGGSGG   420
GGSQAVVIQE SALTTPPGET VTLTCGSSTG AVTASNYANW VQEKPDHCFT GLIGGHNNRP   480
PGVPARFSGS LIGDKAALTI AGTQTEDEAI YFCALWYSDH WVIGGGTRLT VLGTPLGDTT   540
HTSGRHGDED TYYLQVRGRE NFEILMKLKE SLELMELVPQ PLVDSYRQQQ QLLQRPGGSG   600
GAPHHHHHH                                                          609

SEQ ID NO: 56           moltype = DNA  length = 1827
FEATURE                 Location/Qualifiers
misc_feature            1..1827
                        note = Description of Artificial Sequence: Synthetic
                        polynucleotide
source                  1..1827
                        mol_type = other DNA
                        organism = synthetic construct
SEQUENCE: 56
gagatcgtga tgacccagac acccgcaaca ctgagcgtgt ctgccggcga aagggtcact    60
attacctgca aggccagtca gtcagtgtcc aacgacgtga cttggtacca gcagaaacca   120
ggccaggctc cccggctgct gatctacagc gcatctaata gatatagcgg agtgcctgct   180
cgcttcagtg gttcaggcta tggaactgag ttcaccttca ccatttccag cgtgcagtcc   240
gaagacttcg cagtgtactt ttgccagcag gattattcta gttttgggtg tggtacaaag   300
ctggagatca aaaggggagg aggaggtagt ggcggaggag gttcaggcgg aggggggtagc   360
ggcggagggg gttctggcgg cggcggtagt ggcggcggag gtagccaggt gcagctggtc   420
gaatccggcc ctggagtggt ccagccaggc aggtctctgc ggatcagttg cgccgtgtcc   480
ggattcagcg tcaccaacta cggagtgcac tgggtcagac agccacctgg caagtgtctg   540
gagtggctgg gagtgatctg gcaggagga atcacaaact acaactcagc ttttatgtcc   600
cgcctgacta ttagcaagga caactctaaa aataccgtgt atctgcagat gaattctctg   660
cgagccgaag ataccgctat gtactattgt gcatcccgtg gggggtcatta cggctatgcc   720
ctggattatt gggggcaggg taccctggtg acagtctcat ccggaggagg aggatccgga   780
ggaggaggta gcggcggagg gggttctggc ggaggggggta gtcacgtgaa gctgcaggaa   840
agcggccctg gactggtgca gccttcccag tctctgtccc tgacctgcac cgtgtccggc   900
ttctccctga ccgattacgg cgtgcactgg gtgcgacagt ctccaggcaa gggcctggaa   960
tggctgggag tgatttggag cggtggcgga accgcctaca acacgcccct gatctcccgg  1020
ctgaacatct accgggacaa ctccaagaac caggtgttcc tggaaatgaa ctccctgcag  1080
gcagaggaca ccgccatgta ctactgcgcc agacgggggct cctaccccta caactacttc  1140
gacgcttggg gctgcggcac caccgtgaca gtgtctagcg gaggtggtgg atctgggggc  1200
ggaggtagcg gagggggagg ttctggaggt ggtggatctg gaggtagcgg aggtagcgga  1260
ggaggttctc aggctgtcgt gatccaggaa tctgccctga ccacccccc tggcgagaca  1320
gtgacactga cctgcggatc ttccaccggc gctgtgaccg cctccaacta cgccaactgg  1380
gtgcaggaaa agcccgacca ctgcttcacc ggcctgatcg gcgccacaa caacagacct  1440
ccaggcgtgc cagccgggtt ctccggctct ctgatcggag ataaggccgc cctgacaatc  1500
gccggcaccc agacagagga cgaggctatc tacttctgcg ccctgtggta cagcgaccac  1560
tgggtcatcg gcgcaggcac cagactgacc gtgctgggaa cacccctggg agacaccaca  1620
catactagtg gaggcacgg cgacgaagat acctactatc tgcaggtgag gggacgggag  1680
aacttcgaaa tcctgatgaa gctgaaagag tcccctggaa ctgatggagct ggtgcccag  1740
cctctggtcg acagcagcag cagctgctgc agaggccagg agggtcagga  1800
ggagcaccgc accatcatca tcaccat                                     1827

SEQ ID NO: 57           moltype = AA  length = 128
FEATURE                 Location/Qualifiers
REGION                  1..128
                        note = Description of Artificial Sequence: Synthetic
                        polypeptide
source                  1..128
                        mol_type = protein
                        organism = synthetic construct
SEQUENCE: 57
ITCPPPMSVE HADIWVKSYS LYSRERYICN SGFKRKAGTS SLTECVLNKA TNVAHWTTPS    60
LKCIRTPLGD TTHTSGKPLD GEYFTLQIRG RERFEMFREL NEALELKDAQ AGKEPGGSGG   120
APHHHHHH                                                           128

SEQ ID NO: 58           moltype = DNA  length = 384
FEATURE                 Location/Qualifiers
misc_feature            1..384
                        note = Description of Artificial Sequence: Synthetic
                        polynucleotide
source                  1..384
                        mol_type = other DNA
                        organism = synthetic construct
SEQUENCE: 58
atcacctgtc ctccacccat gtctgtggaa cacgccgaca tctgggtcaa gtcctactcc    60
ctgtactcca gagagcggta catctgcaac tccggcttca gcggaaggc cggcacctct   120
agcctgaccg agtgcgtgct gaacaaggcc accaacgtgc ccactggac cacccatcc   180
```

```
ctgaagtgca tcagaacacc cctgggtgac accacacata ctagtgggaa acctctggat    240
ggcgagtact ttaccctgca gattagaggc cgcgaacgat tcgagatgtt tcgcgaactg    300
aatgaggccc tggaactgaa ggatgctcag gcaggcaagg agccaggagg gtcaggagga    360
gcaccgcacc atcatcatca ccat                                           384

SEQ ID NO: 59           moltype = AA   length = 146
FEATURE                 Location/Qualifiers
REGION                  1..146
                        note = Description of Artificial Sequence: Synthetic
                         polypeptide
source                  1..146
                        mol_type = protein
                        organism = synthetic construct
SEQUENCE: 59
ITCPPPMSVE HADIWVKSYS LYSRERYICN SGFKRKAGTS SLTECVLNKA TNVAHWTTPS     60
LKCIRTPLGD TTHTSGRSPD DELLYLPVRG RETYEMLLKI KESLELMQYL PQHTIETYRQ    120
QQQQQHQHLL QKQGGSGGAP HHHHHH                                         146

SEQ ID NO: 60           moltype = DNA   length = 438
FEATURE                 Location/Qualifiers
misc_feature            1..438
                        note = Description of Artificial Sequence: Synthetic
                         polynucleotide
source                  1..438
                        mol_type = other DNA
                        organism = synthetic construct
SEQUENCE: 60
atcacctgtc ctccacccat gtctgtggaa cacgccgaca tctgggtcaa gtcctactcc     60
ctgtactcca gagagcggta catctgcaac tccggcttca gcggaaggc cggcacctct    120
agcctgaccg agtgcgtgct gaacaaggcc accaacgtgg cccactggac caccccatcc   180
ctgaagtgca tcagaacacc cctgggtgac accacacata ctagtgggag atccccgac    240
gatgagctgc tgtacctgcc tgtgagggc cgggagacct atgaaatgct gctgaagatc    300
aaagagagcc tggaactgat gcagtacctg ccacagcaca ccattgaaac atataggcaa    360
caacagcagc agcagcatca gcatctgctg cagaagcagg aggggtcagg aggagcaccg    420
caccatcatc atcaccat                                                  438

SEQ ID NO: 61           moltype = AA   length = 141
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 61
ITCPPPMSVE HADIWVKSYS LYSRERYICN SGFKRKAGTS SLTECVLNKA TNVAHWTTPS     60
LKCIRTPLGD TTHTSGRHGD EDTYYLQVRG RENFEILMKL KESLELMELV PQPLVDSYRQ    120
QQQLLQRPGG SGGAPHHHHH H                                              141

SEQ ID NO: 62           moltype = DNA   length = 423
FEATURE                 Location/Qualifiers
misc_feature            1..423
                        note = Description of Artificial Sequence: Synthetic
                         polynucleotide
source                  1..423
                        mol_type = other DNA
                        organism = synthetic construct
SEQUENCE: 62
atcacctgtc ctccacccat gtctgtggaa cacgccgaca tctgggtcaa gtcctactcc     60
ctgtactcca gagagcggta catctgcaac tccggcttca gcggaaggc cggcacctct    120
agcctgaccg agtgcgtgct gaacaaggcc accaacgtgg cccactggac caccccatcc   180
ctgaagtgca tcagaacacc cctgggtgac accacacata ctagtgggag cacggcgac    240
gaagatacct actatctgca ggtgagggga cgggagaact tcgaaatcct gatgaagctg    300
aaagagtccc tggaactgat ggagctggtg ccccagcctc tggtcgacag ctacagacag    360
cagcagcagc tgctgcagag gccaggaggg tcaggaggag caccgcacca tcatcatcac    420
cat                                                                  423

SEQ ID NO: 63           moltype = AA   length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 63
NWVNVISDLK KIEDLIQSMH IDATLYTESD VHPSCKVTAM KCFLLELQVI SLESGDASIH     60
DTVENLIILA NNSLSSNGNV TESGCKECEE LEEKNIKEFL QSFVHIVQMF INTS          114
```

```
SEQ ID NO: 64            moltype = DNA  length = 390
FEATURE                  Location/Qualifiers
misc_feature             1..390
                         note = Description of Artificial Sequence: Synthetic
                         polynucleotide
source                   1..390
                         mol_type = other DNA
                         organism = synthetic construct
SEQUENCE: 64
atgggctggt cctgcatcat cctgtttctg gtggctaccg ccaccggcaa ctgggtcaac   60
gtgatctccg aactgaagaa gatcgaggac ctgatccagt ccatgcacat cgacgccacc  120
ctgtacaccg agtccgacgt gcacccctcc tgcaaagtga ccgccatgaa gtgctttctg  180
ctggaactgc aagtgatctc cctggaatcc ggcgacgcct ccatccacga caccgtggaa  240
aatctgatca tcctggccaa caactccctg tcctccaacg gcaacgtgac cgagagcggc  300
tgcaaagagt gcgaggaact ggaagagaag aacatcaaag agtttctgca gtccttcgtg  360
cacatcgtgc agatgttcat caacaccagc                                    390

SEQ ID NO: 65            moltype = AA   length = 600
FEATURE                  Location/Qualifiers
REGION                   1..600
                         note = Description of Artificial Sequence: Synthetic
                         polypeptide
source                   1..600
                         mol_type = protein
                         organism = synthetic construct
SEQUENCE: 65
EVQLVESGGG LVQPGGSLRL SCAASGFNIK DTYIHWVRQA PGKCLEWVAR IYPTNGYTRY   60
ADSVKGRFTI SADTSKNTAY LQMNSLRAED TAVYYCSRWG GDGFYAMDYW GQGTLVTVSS  120
GGGGSGGGGS GGGGSGGGGS GGGGSGGGGS DIQMTQSPSS LSASVGDRVT ITCRASQDVN  180
TAVAWYQQKP GKAPKLLIYS ASFLYSGVPS RFSGSRSGTD FTLTISSLQP EDFATYYCQQ  240
HYTTPPTFGQ CTKVEIKRGG GGSGGGGSGG GGSGGGGSHV QLVESGGGLV QPGGSLRLSC  300
AASGFSLTDY GVHWVRQAPG KGLEWLGVIW SGGGTAYNTA LISRFTISRD NSKNTLYLQM  360
NSLRAEDTAV YYCARRGSYP YNYFDAWGCG TLVTVSSGGG GSGGGGSGGG GSGGGGSGGG  420
GSGGGGSQAV VTQEPSLTVS PGGTVTLTCG SSTGAVTASN YANWVQQKPG QCPRGLIGGH  480
NNRPPGVPAR FSGSLLGGKA ALTLLGAQPE DEAEYYCALW YSDHWVIGGG TKLTVLGTPL  540
GDTTHTSGKP LDGEYFTLQI RGRERFEMFR ELNEALELKD AQAGKEPGGS GGAPHHHHHH  600

SEQ ID NO: 66            moltype = DNA  length = 1800
FEATURE                  Location/Qualifiers
misc_feature             1..1800
                         note = Description of Artificial Sequence: Synthetic
                         polynucleotide
source                   1..1800
                         mol_type = other DNA
                         organism = synthetic construct
SEQUENCE: 66
gaagtgcagc tggtcgaatc cggggggggc ctggtgcagc ctggagggtc actgagactg   60
tcctgtgccg catctgggtt caatatcaag gacacctaca tccactgggt gcggcaggca  120
cctggcaagt gtctggagtg ggtggcaagg atctatccaa ccaacggcta cacacggtat  180
gccgactccg tgaagggccg gttcaccatc tccgccgata cctctaagaa cacagcctac  240
ctgcagatga attctctgag ggccgaggat acagccgtgt actattgcag ccgctgggga  300
ggcgacggct tctacgctat ggactattgg ggccagggca ccctggtgac agtgagctct  360
ggcggcggcg gatccggagg aggaggcagc ggcggaggag gctccggagg aggcggctct  420
ggcggcggcg gcagcggcgg cggcggctcc gacatccaga tgacccagtc ccatctagc   480
ctgagcgcct ccgtgggcga cagggtgacc atcacatgcc gcgccagcca ggatgtgaat  540
acagccgtgg cctggtacca gcagaagcca ggcaaggccc caagctgct gatctactct  600
gccagcttcc tgtatagcgg agtgccatcc cggttttccg gcagccggag cggcaccgac  660
ttcaccctga caatctcctc tctgcagcct gaggattttg ccacatacta ttgtcagcag  720
cactatacca cccccacta attcggacag tgtacaaagg tcgagatcaa acgcggcgga  780
ggggatccg gcggcggagg atctggcgga ggtggaagtg gggaggcgg atctcatgtg  840
cagctggtgg aaagcggagg cggcctggtg cagcctgggg gatctctgag actgtcttgt  900
gccgccagcg gcttctccct gaccgattat ggcgtgcact gggtgcgaca ggcccctggc  960
aaaggactgg aatggctggg agtgatttgg agtggcggag gcaccgccta caacaccgcc 1020
ctgatctccc ggttcaccat cagccgggac aactccaaga acaccctgta cctgcagatg 1080
aactccctgc gggccgagga caccgctgtg tactactgcg ccagacgggg ctcctacccc 1140
tacaactact cgacgcttg ggctgcggc accctcgtga cagtgtctag cggagggga 1200
ggttctgggg gcggaggttc aggtggtggt ggttccgggg tggtggctc tggtggcggt 1260
ggttctggcg gtggcggatc tcaggctgtc gtgacccagg aacccagcct gactgtgtct 1320
cctggcggaa ccgtgaccct gacctgcgga tcttctacag cgctgtgac ccagcagcaac 1380
tacgccaatt gggtgcagca gaaacctgga cagtgcccta gaggcctgat cggcggccac 1440
aacaacagac ctccaggcgt gccagcccgg ttctctggat ctctgctggg cggaaaggcc 1500
gctctgacac tgctgggtgc tcagcctgag acgaggccg agtactactg tgccctgtgg 1560
tactccgacc actgggtcat cggaggcggg accaagctga ccgtgctggg aacacccctg 1620
ggagacacca cacactagtg gggaaacct ctggatgcg agtactttac cctgcagatt 1680
agaggccgcg aacgattcga gatgtttcgc gaactgaatg aggccctgga actgaaggat 1740
gctcaggcag gcaaggagcc aggagggtca ggaggagcac cgcaccatca tcatccacat 1800

SEQ ID NO: 67            moltype = AA   length = 600
FEATURE                  Location/Qualifiers
```

```
REGION                   1..600
                         note = Description of Artificial Sequence: Synthetic
                          polypeptide
source                   1..600
                         mol_type = protein
                         organism = synthetic construct
SEQUENCE: 67
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
GGGGSGGGGS GGGGSGGGGS GGGGSGGGGS DIQMTQSPSS LSASVGDRVT ITCRASQDVN   180
TAVAWYQQKP GKAPKLLIYS ASFLYSGVPS RFSGSRSGTD FTLTISSLQP EDFATYYCQQ   240
HYTTPPTFGQ GTKVEIKRGG GGSGGGGSGG GGSGGGGSHV QLVESGGGLV QPGGSRLRLSC  300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGKP LDGEYFTLQI RGRERFEMFR ELNEALELKD AQAGKEPGGS GGAPHHHHHH   600

SEQ ID NO: 68            moltype = DNA  length = 1800
FEATURE                  Location/Qualifiers
misc_feature             1..1800
                         note = Description of Artificial Sequence: Synthetic
                          polynucleotide
source                   1..1800
                         mol_type = other DNA
                         organism = synthetic construct
SEQUENCE: 68
gaagtgcagc tggtcgaatc cggggggggc ctggtgcagc tggaggggtc actgagactg     60
tcctgtgccg catctgggtt caatatcaag gacacctaca tccactgggt gcggcaggca   120
cctggcaagg gactggagtg ggtggcaagg atctatccaa ccaacggcta cacacggtat   180
gccgactccg tgaagggccg gttcaccatc tccgccgata cctctaagaa cacagcctac   240
ctgcagatga attctctgag ggccgaggat acagccgtgt actattgcag ccgctgggga   300
ggcgacggct tctacgctat ggactattgg gccagggca cctgtgac agtgagctct   360
ggcggcggcg gatccggagg aggaggcagc ggcgaggag gctccggagg aggcggctcc   420
ggcggcggcg gcagcggcgg cggcggctcc gacatccaga tgacccagtc ccctatctagc   480
ctgagcgcct ccgtgggcga cagggtgacc atcacatgcc cgccagcca ggatgtgaat   540
acagccgtgg cctggtacca gcagaagcca ggcaaggccc ccaagctgct gatctactct   600
gccagcttcc tgtatagcgg agtgccatcc cggttttccg gcagcggag cggcaccgac   660
ttcaccctga caatctcctc tctgcagcct gaggattttg ccacatacta ttgtcagcag   720
cactatacca caccccctac attcggacag gggacaaagg tcgagatcaa acgcggcgga   780
gggggatccg gcggcggagg atctggcgga ggtggaagtg ggggaggcgg atctcatgtg   840
cagctggtgg aaagcggagg cggcctggtg cagcctgggg gatctctgag actgtcttgt   900
gccgccagcg gcttctcccct gaccgattat ggcgtgcact ggtgcgcaca ggccccctgg   960
aaaggactgg aatggctggg agtgatttgg agtggcggag gcaccgccta caacaccgcc  1020
ctgatctccc ggttcaccat cagccggac aactccaaga acaccctgta cctgcagatg  1080
aactccctgc gggccgagga caccgctgtg tactactgcg ccagacgggg ctcctacccc  1140
tacaactact tcgacgcttg gggctgcggc accctgtga ggagggggaa  1200
ggttctgggg gcggaggttc aggtggtggt ggttccgggg gtggtggctc tggtggcggt  1260
ggttctggcg gtggcggatc tcaggctgtc gtgacccagg aacccagcct gactgtgtct  1320
cctggcggaa ccgtgaccct gacctgcgga tcttctaccg gcgctgtgac cgccagcaac  1380
tacgccaatt gggtgcagca gaaacctgga cagtgcccta gaggcctgat cggcggccac  1440
aacaacagac ctccaggcgt gccagcccgg ttctctggat ctctgctggg cggaaaggcc  1500
gctctgacac tgctggtgc tcagcctgag gacgaggccg agtactactg tgccctgtgg  1560
tactccgacc actgggtcat cggaggcggg accaagctga ccgtgctggg aacacccctg  1620
ggagacacca cacatactag tgggaaacct ctggatgccg agtactttac cctgcagatt  1680
agaggccgcg aacgattcga gatgtttcgc gaactgaatg aggcctgga actgaaggat  1740
gctcaggcag gcaaggagcc aggagggtca ggaggagcac cgcaccatca tcatcaccat  1800

SEQ ID NO: 69            moltype = AA  length = 600
FEATURE                  Location/Qualifiers
REGION                   1..600
                         note = Description of Artificial Sequence: Synthetic
                          polypeptide
source                   1..600
                         mol_type = protein
                         organism = synthetic construct
SEQUENCE: 69
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ CTKVEIKRGG GGSGGGGSGG   120
GGSGGGGSGG GGSGGGGSEV QLVESGGGLV QPGGSRLRLSC AASGFNIKDT YIHWVRQAPG   180
KCLEWVARIY PTNGYTRYAD SVKGRFTISA DTSKNTAYLQ MNSLRAEDTA VYYCSRWGGD   240
GFYAMDYWGQ GTLVTVSSGG GGSGGGGSGG GGSGGGGSHV QLVESGGGLV QPGGSRLRLSC  300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGKP LDGEYFTLQI RGRERFEMFR ELNEALELKD AQAGKEPGGS GGAPHHHHHH   600

SEQ ID NO: 70            moltype = DNA  length = 1800
```

```
FEATURE                 Location/Qualifiers
misc_feature            1..1800
                        note = Description of Artificial Sequence: Synthetic
                         polynucleotide
source                  1..1800
                        mol_type = other DNA
                        organism = synthetic construct
SEQUENCE: 70
gatattcaga tgactcagtc ccctagttca ctgtctgcct cagtcggaga tcgggtcact    60
atcacttgtc gggcttctca ggatgtgaac accgccgtgg cctggtacca gcagaagcca   120
ggcaaggccc ccaagctgct gatctactct gccagcttcc tgtattccgg agtgccatct   180
cggttttccg gcagccggag cggcaccgac ttcaccctga caatcagctc cctgcagcct   240
gaggattttg ccacatacta ttgccagcag cactatacca caccccctac cttcggccag   300
tgcacaaagg tggagatcaa gaggggagga ggaggatccg gaggaggagg cagcggaggc   360
ggcggctccg gcggcggcgg ctctggcggc ggcggcagcg gaggaggcgg ctccgaggtg   420
cagctggtgg agtccggcgg cggcctggtg cagcccggcg gcagcctgcg gctgtcctgt   480
gccgcctctg gctttaacat caaggacacc tacatccact gggtgaggca ggcacctggc   540
aagtgcctgg agtgggtggc aaggatctat ccaaccaatg gctacacaag atatgccgac   600
tccgtgaagg gccgctttac catcagcgcc gatacctcca agaacacagc ctacctgcag   660
atgaattctc tgcgggccga ggatacagcc gtgtactatt gctccagatg gggcggcgac   720
ggcttctatg ctatggacta ttgggggcag ggaactctgg tcactgtctc ctctggcgga   780
gggggatccg gcggcggagg atctggcgga ggtggaagtg gaggaggcgg atctcatgtg   840
cagctggtgg aaagcggagg cggcctggtg cagcctgggg gatctctgag actgtcttgt   900
gccgccagcg gcttctccct gaccgattat ggcgtgcact gggtgcgaca ggcccctggc   960
aaaggactga atggctgggg agtgatttgg agtggcggag gcaccgccta caacaccgcc  1020
ctgatctccc ggttcaccat cagccgggac aactccaaga acacactgta cctgcagatg  1080
aactccctgc gggccgagga caccgctgtg tactactgcg ccagacgggg ctcctacccc  1140
tacaactact cgacgcttg gggctgcggc accctcgtga cagtgtctag cggaggggga  1200
ggttctgggg gcggaggttc aggtggtggt ggttccgggg tggtggctc tggtggcggt  1260
ggttctgggg gtggcggatc tcaggctgtc gtgacccagg aacccagcct gactgtgtct  1320
cctggcggaa ccgtgaccct gacctgcgga tcttctaccg gcgctgtgac cgccagcaac  1380
tacgccaatt gggtgcagca gaaacctgga cagtgcccta gaggcctgat cggcggccac  1440
aacaacagac tccaggcgt gccagcccgg ttctctggat ctctgctggg cggaaaggcc  1500
gctctgacac tgctgggtgc tcagctgag acgaggccg agtactactg tgccctgtgg  1560
tactccgacc actgggtcat cggaggcggg accaagctga ccgtgctggg aaccccctg  1620
ggagacacca cacatactag tgggaaacct ctggatggcg agtactttac cctgcagatt  1680
agaggccgcg aacgattcga gatgtttcgc gaactgaatg aggccctgga actgaaggat  1740
gctcaggcag gcaaggagcc aggagggtca ggaggagcac cgcaccatca tcatcaccat  1800

SEQ ID NO: 71           moltype = AA  length = 600
FEATURE                 Location/Qualifiers
REGION                  1..600
                        note = Description of Artificial Sequence: Synthetic
                         polypeptide
source                  1..600
                        mol_type = protein
                        organism = synthetic construct
SEQUENCE: 71
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRGG GGSGGGGSGG   120
GGSGGGGSGG GGSGGGGSEV QLVESGGGLV QPGGSLRLSC AASGFNIKDT YIHWVRQAPG   180
KGLEWVARIY PTNGYTRYAD SVKGRFTISA DTSKNTAYLQ MNSLRAEDTA VYYCSRWGGD   240
GFYAMDYWGQ GTLVTVSSGG GGSGGGGSGG GGSGGGGSHV QLVESGGGLV QPGGSLRLSC   300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGKP LDGEYFTLQI RGRERFEMFR ELNEALELKD AQAGKEPGGS GGAPHHHHHH   600

SEQ ID NO: 72           moltype = DNA  length = 1800
FEATURE                 Location/Qualifiers
misc_feature            1..1800
                        note = Description of Artificial Sequence: Synthetic
                         polynucleotide
source                  1..1800
                        mol_type = other DNA
                        organism = synthetic construct
SEQUENCE: 72
gatattcaga tgactcagtc ccctagttca ctgtctgcct cagtcggaga tcgggtcact    60
atcacttgtc gggcttctca ggatgtgaac accgccgtgg cctggtacca gcagaagcca   120
ggcaaggccc ccaagctgct gatctactct gccagcttcc tgtattccgg agtgccatct   180
cggttttccg gcagccggag cggcaccgac ttcaccctga caatcagctc cctgcagcct   240
gaggattttg ccacatacta ttgccagcag cactatacca caccccctac cttcggccag   300
ggcacaaagg tggagatcaa gaggggagga ggaggatccg gaggaggagg cagcggaggc   360
ggcggctccg gcggcggcgg ctctggcggc ggcggcagcg gaggaggcgg ctccgaggtg   420
cagctggtgg agtccggcgg cggcctggtg cagcccggcg gcagcctgcg gctgtcctgt   480
gccgcctctg gctttaacat caaggacacc tacatccact gggtgaggca ggcacctggc   540
aagggcctgg agtgggtggc aaggatctat ccaaccaatg gctacacaag atatgccgac   600
tccgtgaagg gccgctttac catcagcgcc gatacctcca agaacacagc ctacctgcag   660
```

```
atgaattctc tgcgggccga ggatacagcc gtgtactatt gctccagatg gggcggcgac    720
ggcttctatg ctatggacta ttgggggcag ggaactctgg tcactgtctc ctctggcgga    780
gggggatccg gcggcggagg atctggcgga ggtggaagtg ggggaggcgg atctcatgtg    840
cagctggtgt aaagcggagg cggcctggtg cagcctgggg gatctctgag actgtcttgt    900
gccgccagcg gcttctccct gaccgattat ggcgtgcact gggtgcgaca ggccctggc    960
aaaggactgg aatggctggg agtgatttgg agtggcggag gcaccgccta caacaccgcc   1020
ctgatctccc ggttcaccat cagccgggac aactccaaga cacccctgta cctgcagatg   1080
aactccctgc gggccgagga caccgctgtg tactactgcg ccagacgggg ctcctacccc   1140
tacaactact tcgacgcttg gggctgcggc accctcgtga cagtgtctag cggagggga    1200
ggttctgggg gcggaggttc aggtggtggt ggttccgggg gtggtggctc tggtggcggt   1260
ggttctggcg gtgcggatc tcaggctgtc gtgacccagg aacccagcct gactgtgtct   1320
cctggcggaa ccgtgaccct gacctgcgga tcttctaccg gcgctgtgac cgccagcaac   1380
tacgccaatt gggtgcagca gaaacctgga cagtgcccta gaggcctgat cggcggccac   1440
aacaacagac ctccaggcgt gccagcccgg ttctctggat ctctgctggg cggaaaggcc   1500
gctctgacac tgctgggtgc tcagcctgag gacgaggccg agtactactg tgccctgtgg   1560
tactccgacc actgggtcat cggaggcggg accaagctga ccgtgctggg aacacccctg   1620
ggagacacca cacatactag tgggaaacct ctggatggcg agtactttac cctgcagatt   1680
agaggccgcg aacgattcga gatgtttcgc gaactgaatg aggcccctgga actgaaggat   1740
gctcaggcag caaggagcc aggagggtca ggaggagcac cgcaccatca tcatccat    1800

SEQ ID NO: 73        moltype = AA  length = 618
FEATURE              Location/Qualifiers
REGION               1..618
                     note = Description of Artificial Sequence: Synthetic
                     polypeptide
source               1..618
                     mol_type = protein
                     organism = synthetic construct
SEQUENCE: 73
EVQLVESGGG LVQPGGSLRL SCAASGFNIK DTYIHWVRQA PGKCLEWVAR IYPTNGYTRY     60
ADSVKGRFTI SADTSKNTAY LQMNSLRAED TAVYYCSRWG GDGFYAMDYW GQGTLVTVSS    120
GGGGSGGGGS GGGGSGGGGS GGGGSGGGGS DIQMTQSPSS LSASVGDRVT ITCRASQDVN    180
TAVAWYQQKP GKAPKLLIYS ASFLYSGVPS RFSGSRSGTD FTLTISSLQP EDFATYYCQQ    240
HYTTPPTFGQ CTKVEIKRGG GGSGGGGSGG GGSGGGGSHV QLVESGGGLV QPGGSLRLSC    300
AASGFSLTDY GVHWVRQAPG KGLEWLGVIW SGGGTAYNTA LISRFTISRD NSKNTLYLQM    360
NSLRAEDTAV YYCARRGSYP YNYFDAWGCG TLVTVSSGGG GSGGGGSGGG GSGGGGSGGG    420
GSGGGGSQAV VTQEPSLTVS PGGTVTLTCG SSTGAVTASN YANWVQQKPG QCPRGLIGGH    480
NNRPPGVPAR FSGSLLGGKA ALTLLGAQPE DEAEYYCALW YSDHWVIGGG TKLTVLGTPL    540
GDTTHTSGRS PDDELLYLPV RGRETYEMLL KIKESLELMQ YLPQHTIETY RQQQQQQHQH    600
LLQKQGGSGG APHHHHHH                                                  618

SEQ ID NO: 74        moltype = DNA  length = 1854
FEATURE              Location/Qualifiers
misc_feature         1..1854
                     note = Description of Artificial Sequence: Synthetic
                     polynucleotide
source               1..1854
                     mol_type = other DNA
                     organism = synthetic construct
SEQUENCE: 74
gaagtgcagc tggtcgaatc cggggggggc ctggtgcagc ctggagggtc actgagactg     60
tcctgtgccg catctgggtt caatatcaag gacacctaca tccactgggt gcggcaggca    120
cctggcaagt gtctggagtg ggtggcaagg atctatccaa ccaacggcta cacacggtat    180
gccgactccg tgaagggccg gttcaccatc tccgccgata cctctaagaa cacagcctac    240
ctgcagatga attctctgag ggccgaggat acagccgtgt actattgcag ccgctgggga    300
ggcgacggct tctacgctat ggactattgg ggccagggca ccctggtgac agtgagctct    360
ggcggcggcg gatccggagg aggaggcagc ggcggaggag gctccggagg aggcggctct    420
ggcggcggcg gcagcggcgg cggcggctcc gacatccaga tgacccagtc cccatctagc    480
ctgagcgcct ccgtgggcga cagggtgacc atcacatgcc gcgccagcca ggatgtgaat    540
acagccgtgg cctggtacca gcagaagcca ggcaagccca ccaagctgct gatctactct    600
gccagcttcc tgtatagcgg agtgccatcc cggttttccg gcagccgag cggcaccgac    660
ttcaccctga caatctcctc tctgcagcct gaggattttg ccacatacta ttgtcagcag    720
cactatacca caccccctac attcggacag tgtacaaagg tcgagatcaa acgcggcgga    780
gggggatccg gcggcggagg atctggcgga ggtggaagtg ggggaggcgg atctcatgtg    840
cagctggtgg aaagcggagg cggcctggtg cagcctgggg gatctctgag actgtcttgt    900
gccgccagcg gcttctccct gaccgattat ggcgtgcact gggtgcgaca ggcccctggc    960
aaaggactgg aatggctggg agtgatttgg agtggcggag gcaccgccta caacaccgcc   1020
ctgatctccc ggttcaccat cagccgggac aactccaaga cacccctgta cctgcagatg   1080
aactccctgc gggccgagga caccgctgtg tactactgcg ccagacgggg ctcctacccc   1140
tacaactact tcgacgcttg gggctgcggc accctcgtga cagtgtctag cggagggga   1200
ggttctgggg gcggaggttc aggtggtggt ggttccgggg gtggtggctc tggtggcggt   1260
ggttctggcg gtgcggatc tcaggctgtc gtgacccagg aacccagcct gactgtgtct   1320
cctggcggaa ccgtgaccct gacctgcgga tcttctaccg gcgctgtgac cgccagcaac   1380
tacgccaatt gggtgcagca gaaacctgga cagtgcccta gaggcctgat cggcggccac   1440
aacaacagac ctccaggcgt gccagcccgg ttctctggat ctctgctggg cggaaaggcc   1500
gctctgacac tgctgggtgc tcagcctgag gacgaggccg agtactactg tgccctgtgg   1560
tactccgacc actgggtcat cggaggcggg accaagctga ccgtgctggg aacacccctg   1620
ggagacacca cacatactag tgggagatcc ccgacgatg agctgctgta cctgcctgtg   1680
aggggccggg agacctatga aatgctgctg aagatcaaag agagcctgga actgatgcag   1740
```

```
tacctgccac agcacaccat tgaaacatat aggcaacaac agcagcagca gcatcagcat   1800
ctgctgcaga agcagggagg gtcaggagga gcaccgcacc atcatcatca ccat         1854

SEQ ID NO: 75           moltype = AA  length = 618
FEATURE                 Location/Qualifiers
REGION                  1..618
                        note = Description of Artificial Sequence: Synthetic
                        polypeptide
source                  1..618
                        mol_type = protein
                        organism = synthetic construct
SEQUENCE: 75
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
GGGGSGGGGS GGGGSGGGGS GGGGSGGGGS DIQMTQSPSS LSASVGDRVT ITCRASQDVN   180
TAVAWYQQKP GKAPKLLIYS ASFLYSGVPS RFSGSRSGTD FTLTISSLQP EDFATYYCQQ   240
HYTTPPTFGQ GTKVEIKRGG GGSGGGGSGG GGSGGGGSHV QLVESGGGLV QPGGSLRLSC   300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGRS PDDELLYLPV RGRETYEMLL KIKESLELMQ YLPQHTIETY RQQQQQQHQH   600
LLQKQGGSGG APHHHHHH                                                618

SEQ ID NO: 76           moltype = DNA  length = 1854
FEATURE                 Location/Qualifiers
misc_feature            1..1854
                        note = Description of Artificial Sequence: Synthetic
                        polynucleotide
source                  1..1854
                        mol_type = other DNA
                        organism = synthetic construct
SEQUENCE: 76
gaagtgcagc tggtcgaatc cggggggggc ctggtgcagc ctggagggtc actgagactg     60
tcctgtgccg catctgggtt caatatcaag gacacctaca tccactgggt gcggcaggca    120
cctggcaagg gactggagtg ggtggcaagg atctatccaa ccaacggcta cacacgtat     180
gccgactccg tgaagggccg gttcaccatc tccgccgata cctctaagaa cacagcctac    240
ctgcagatga attctctgag ggccgaggat acagccgtgt actattgcag ccgctgggga    300
ggcgacggct tctacgctat ggactattgg ggccagggca cccttgtgac agtgagctct    360
ggcggcggcg gatccggagg aggaggcagc ggcggaggag gctccggagg aggcggctct    420
ggcggcggcg gcagcggcgg cggcggctcc gacatccaga tgacccagtc cccatctagc    480
ctgagcgcct ccgtgggcga cagggtgacc atcacatgcc gcgccagcca ggatgtgaat    540
acagcgtgg cctggtacca gcagaagcca ggcaaggccc ccaagctgct gatctactct    600
gccagcttcc tgtatagcgg agtgccatcc cggttttccg gcagccggag cggcaccgac    660
ttcaccctga caatcctcc tctgcagcct gaggattttg ccacatacta ttgtcagcag    720
cactatacca caccccctac attcggacag gggacaaagg tcgagatcaa acgcggcgga    780
ggggatccg gcggcggagg atctggcgga ggtggaagtg ggggaggcgg atctcatgtg    840
cagctggtgg aaagcggagg cggcctggtg cagcctgggg gatctctgag actgtcttgt    900
gccgccagcg gcttctccct gaccgattat ggcgtgcact gggtgcgaca ggcccctggc    960
aaaggactgg aatggctggg agtgatttgg agtggcggag gcaccgccta caacaccgcc   1020
ctgatctccc ggttcaccat cagccggac aactccaaga acaccctgta cctgcagatg    1080
aactccctgc gggccgagga caccgctgtg tactactgcg ccagacgggg ctcctacccc   1140
tacaactact cgacgcttg gggctgcggc accctcgtga cagtgtctag cggagggggga   1200
ggttctgggg gcggaggttc aggtggtggt ggttccgggg gtggtggctc tggtggcggt   1260
ggttctggcg gtggcggatc tcaggctgtc gtgacccagg aacccagcct gactgtgtct   1320
cctggcggaa ccgtgaccct gacctgcgga tcttctaccg gcgctgtgac cgccagcaac   1380
tacgccaatt gggtgcagca gaaacctgga cagtgcccta gaggcctgat cggcggccac   1440
aacaacagac tccaggcgt gccagcccgg ttctctggat ctctgctggg cggaaaggcc   1500
gctctgacac tgctgggtgc tcagccgag acgaggccg agtactactg tgccctgtgg   1560
tactctgacc actgggtcat cggaggcggg accaagctga ccgtgctggg aacacccctg    1620
ggagacacca cacatactag tgggagatcc cccgacgatg agctgctgta cctgcctgtg   1680
aggggccggg agacctatga aatgctgctg aagatcaaag agagcctgga actgatgcag   1740
tacctgccac agcacaccat tgaaacatat aggcaacaac agcagcagca gcatcagcat   1800
ctgctgcaga agcagggagg gtcaggagga gcaccgcacc atcatcatca ccat         1854

SEQ ID NO: 77           moltype = AA  length = 618
FEATURE                 Location/Qualifiers
REGION                  1..618
                        note = Description of Artificial Sequence: Synthetic
                        polypeptide
source                  1..618
                        mol_type = protein
                        organism = synthetic construct
SEQUENCE: 77
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRGG GGSGGGGSGG   120
GGSGGGGSGG GGSGGGGSEV QLVESGGGLV QPGGSLRLSC AASGFNIKDT YIHWVRQAPG   180
KGLEWVARIY PTNGYTRYAD SVKGRFTISA DTSKNTAYLQ MNSLRAEDTA VYYCSRWGGD   240
GFYAMDYWGQ GTLVTVSSGG GGSGGGGSGG GGSGGGGSHV QLVESGGGLV QPGGSLRLSC   300
```

```
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGRS PDDELLYLPV RGRETYEMLL KIKESLELMQ YLPQHTIETY RQQQQQQHQH   600
LLQKQGGSGG APHHHHHH                                                618

SEQ ID NO: 78           moltype = DNA  length = 1854
FEATURE                 Location/Qualifiers
misc_feature            1..1854
                        note = Description of Artificial Sequence: Synthetic
                        polynucleotide
source                  1..1854
                        mol_type = other DNA
                        organism = synthetic construct
SEQUENCE: 78
gatattcaga tgactcagtc ccctagttca ctgtctgcct cagtcggaga tcgggtcact    60
atcacttgtc gggcttctca ggatgtgaac accgccgtgg cctgctacca gcagaagcca   120
ggcaaggccc ccaagctgct gatctactct gccagcttcc tgtattccgg agtgccatct   180
cggttttccg gcagccggag cggcaccgac ttcaccctga caatcagctc cctgcagcct   240
gaggattttg ccacatacta ttgccagcag cactatacca cccccctac cttcggccag    300
tgcacaaagg tggagatcaa gaggggagga ggaggatccg gaggaggagg cagcggaggc   360
ggcggctccg gcggcggcgg ctctggcggc ggcggcagcg gaggaggcgg ctccgaggtg   420
cagctggtgg agtccggcgg cggcctggtg cagcccggcg gcagcctgcg gctgtcctgt   480
gccgcctctg gctttaacat caaggacacc tacatccact gggtgaggca ggcacctggc   540
aagtgcctgg agtgggtggc aaggatctat ccaaccaatg gctacacaag atatgccgac   600
tccgtgaagg gccgctttac catcagcgcc gatacctcca agaacacagc ctacctgcag   660
atgaattctc tgcgggccga ggatacagcc gtgtactatt gctccagatg gggcggcgac   720
ggcttctatg ctatggacta ttgggggcag ggaactctgg tcactgtctc ctctggcgga   780
ggggggatccg gcggcggagg atctggcgga ggtggaagtg gaggaggcgg atctcatggc   840
cagctggtgg aaagcggagg cggcctggtg cagcctgggg gatctctgag actgtcttgt   900
gccgccagcg gcttctccct gaccgattat ggcgtgcact gggtgcgaca ggcccctggc   960
aaaggactgg aatggctggg agtgatttgg agtggcggag gcaccgccta acaccgcc   1020
ctgatctccc ggttcaccat cagccggac aactccaaga caccctgta cctgcagatg    1080
aactccctgc gggccgagga caccgctgtg tactactgcg ccagacgggg ctcctacccc   1140
tacaactact cgacgccttg gggctgcggc accctcgtga cagtgtctag cggagggga    1200
ggttctgggg gcggaggttc aggtggtggt ggttccgggg tggtggctc tggtggcggt    1260
ggttctggcg gtggcggatc tcaggctgtc gtgacccagg aacccagcct gactgtgtct   1320
cctggcggaa ccgtgaccct gacctgcgga tcttctaccg gcgctgtgac cgccagcaac   1380
tacgccaatt gggtgcagca gaaacctgga cagtgcccta gaggcctgat cggcggccac   1440
aacaacagac ctccaggcgt gccagccgcg ttctctggat ctctgctggg cggaaaggcc   1500
gctctgacac tgctgggtgc tcagcctgag gacgaggccg agtactactg tgccctgtgg   1560
tactccgacc actgggtcat cggaggcggg accaagctga ccgtgctggg aacacccctg   1620
ggagacacca cacatactag tgggagatcc ccgacgatg agctgctgta cctgcctgtg    1680
aggggccggg agacctatga aatgctgctg aagatcaaag agagcctgga actgatgcag   1740
tacctgccac agcacaccat tgaaacatat aggcaacaac agcagcagca gcatcagcat   1800
ctgctgcaga agcagggagg gtcaggagga gcaccgcacc atcatcatca ccat           1854

SEQ ID NO: 79           moltype = AA  length = 618
FEATURE                 Location/Qualifiers
REGION                  1..618
                        note = Description of Artificial Sequence: Synthetic
                        polypeptide
source                  1..618
                        mol_type = protein
                        organism = synthetic construct
SEQUENCE: 79
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRGG GGSGGGGSGG   120
GGSGGGGSGG GGSGGGGSEV QLVESGGGLV QPGGSLRLSC AASGFNIKDT YIHWVRQAPG   180
KGLEWVARIY PTNGYTRYAD SVKGRFTISA DTSKNTAYLQ MNSLRAEDTA VYYCSRWGGD   240
GFYAMDYWGQ GTLVTVSSGG GGSGGGGSGG GGSGGGGSHV QLVESGGGLV QPGGSLRLSC   300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGRS PDDELLYLPV RGRETYEMLL KIKESLELMQ YLPQHTIETY RQQQQQQHQH   600
LLQKQGGSGG APHHHHHH                                                618

SEQ ID NO: 80           moltype = DNA  length = 1854
FEATURE                 Location/Qualifiers
misc_feature            1..1854
                        note = Description of Artificial Sequence: Synthetic
                        polynucleotide
source                  1..1854
                        mol_type = other DNA
                        organism = synthetic construct
```

-continued

```
SEQUENCE: 80
gatattcaga tgactcagtc ccctagttca ctgtctgcct cagtcggaga tcgggtcact   60
atcacttgtc gggcttctca ggatgtgaac accgccgtgg cctggtacca gcagaagcca  120
ggcaaggccc ccaagctgct gatctactct gccagcttcc tgtattccgg agtgccatct  180
cggttttccg gcagccggag cggcaccgac ttcaccctga caatcagctc cctgcagcct  240
gaggattttg ccacatacta ttgccagcag cactatacca cacccctac cttcggccaa   300
ggcacaaagg tggagatcaa gaggggagga ggaggatccg gaggaggagg cagcggaggc  360
ggcggctccg gcggcggcgg ctctggcgg ggcggcagcg gaggaggcgg ctccgaggtg   420
cagctggtgg agtccggcgg cggcctggtg cagcccggcg gcagcctgcg gctgtcctgt  480
gccgcctctg gctttaacat caaggacacc tacatccact gggtgaggca ggcacctgg   540
aagggcctgg agtgggtggc aaggatctat ccaaccaatg gctacacaag atatgccgac  600
tccgtgaagg gccgctttac catcagcgcc gatacctcca gaacacagc ctacctgcag   660
atgaattctc tgcgggccga ggatacagcc gtgtactatt gctccagatg gggcggcgac  720
ggcttctatg ctatggacta ttggggccag ggaactctgg tcactgtctc ctctggcgga  780
gggggatccg gcggcggagg atctggcgga ggtggaagtg ggggaggcgg atctcatgtg  840
cagctggtgg aaagcggagg cggcctggtg cagcctgggg gatctctgag actgtcttgt  900
gccgccagcg gcttctccct gaccgattat ggcgtgcact gggtgcgaca ggcccctggc  960
aaaggactgg aatggctggg agtgatttgg agtggcggag gcaccgccta caacaccgcc 1020
ctgatctccc ggttcaccat cagccggac aactccaaga acaccctgta cctgcagatg  1080
aactccctgc gggccgagga caccgctgtg tactactgcg ccagacgggg ctcctacccc 1140
tacaactact cgacgcttg gggctgcggc accctcgtga cagtgtctag cggaggggga  1200
ggttctgggg gcggaggttc aggtggtggt ggttccgggg tggctc tggtggcggt    1260
ggttctggcg gtggcggatc tcaggctgtc gtgacccagg aacccagcct gactgtgtct  1320
cctggcggaa ccgtgaccct gacctgcgga tcttctaccg gcgctgtgac cgccagcaac  1380
tacgccaatt gggtgcagca gaaacctgga cagtgcccta gaggcctgat cggcggccac  1440
aacaacagac ctccaggcgt gccagcccgc ttctctggat ctctgctggg cggaaaggcc  1500
gctctgacac tgctgggtgc tcagcctgag gacgaggcc agtactactg tgccctgtgg   1560
tactccgacc actgggtcat cggaggcggc accaagctga ccgtgctggg aacacccctg  1620
ggagacacca cacatactag tgggagatcc ccgacgatg agctgctgta cctgcctgtg   1680
aggggccggg agacctatga aatgctgctg aagatcaaag agagcctgga actgatgcag  1740
tacctgccac agcacaccat tgaaacatat aggcaacaac agcagcagca gcatcagcat  1800
ctgctgcaga agcagggagg gtcaggagga gcaccgcacc atcatcatca ccat        1854

SEQ ID NO: 81            moltype = AA  length = 613
FEATURE                  Location/Qualifiers
REGION                   1..613
                         note = Description of Artificial Sequence: Synthetic
                         polypeptide
source                   1..613
                         mol_type = protein
                         organism = synthetic construct
SEQUENCE: 81
EVQLVESGGG LVQPGGSLRL SCAASGFNIK DTYIHWVRQA PGKCLEWVAR IYPTNGYTRY   60
ADSVKGRFTI SADTSKNTAY LQMNSLRAED TAVYYCSRWG GDGFYAMDYW GQGTLVTVSS  120
GGGGSGGGGS GGGGSGGGGS GGGGSGGGGS DIQMTQSPSS LSASVGDRVT ITCRASQDVN  180
TAVAWYQQKP GKAPKLLIYS ASFLYSGVPS RFSGSRSGTD FTLTISSLQP EDFATYYCQQ  240
HYTTPPTFGQ CTKVEIKRGG GSGGGGSGG GGSGGGSHV QLVESGGGLV QPGGSLRLSC   300
AASGFSLTDY GVHWVRQAPG KGLEWLGVIW SGGGTAYNTA LISRFTISRD NSKNTLYLQM  360
NSLRAEDTAV YYCARRGSYP YNYFDAWGCG TLVTVSSGGG GSGGGGSGGG GSGGGGSGGG  420
GSGGGGSQAV VTQEPSLTVS PGGTVTLTCG SSTGAVTASN YANWVQQKPG QCPRGLIGGH  480
NNRPPGVPAR FSGSLLGGKA ALTLLGAQPE DEAEYYCALW YSDHWVIGGG TKLTVLGTPL  540
GDTTHTSGRH GDEDTYYLQV RGRENFEILM KLKESLELME LVPQPLVDSY RQQQQLLQRP  600
GGSGGAPHHH HHH                                                    613

SEQ ID NO: 82            moltype = DNA  length = 1839
FEATURE                  Location/Qualifiers
misc_feature             1..1839
                         note = Description of Artificial Sequence: Synthetic
                         polynucleotide
source                   1..1839
                         mol_type = other DNA
                         organism = synthetic construct
SEQUENCE: 82
gaagtgcagc tggtcgaatc cggggggggc ctggtgcagc ctggagggtc actgagactg   60
tcctgtgccg catctgggtt caatatcaag gacacctaca tccactgggt gcggcaggca  120
cctggcaagt gtctgagtg gtggcaagg atctatccaa ccaacggcta cacacgtat    180
gccgactccg tgaagggccg gttcaccatc tccgccgata cctctaagaa cacagccac   240
ctgcagatga attctctgag ggccgaggat acagccgtgt actattgcag ccgctgggga  300
ggcgacggct tctacgctat ggactattgg ggccagggca cctgtgac agtgagtct     360
ggcggcggcg gatccggagg aggaggcagc ggcggaggag gctccggagg aggcggctct  420
ggcggcggcg gcagcggcgg cggcggctcc gacatccaga tgacccagtc cccatctagc  480
ctgagcgcct ccgtgggcga cagggtgacc atcacatgcc gcgccagcca ggatgtgaat  540
acagccgtgg cctggtacca gcagaagcca ggcaaggccc ccaagctgct gatctactct  600
gccagcttcc tgtatagcgg agtgccatcc cggttttccg gcagccggag cggcaccgac  660
ttcaccctga caatctccc tctgcagcct gaggattttg ccacatacta ttgtcagcag  720
cactatacca cacccctac attcggacag tgtacaaagg tcgagatcaa acgcggcgga  780
ggggatccg gcggcggagg atctggcgga ggtggaagtg ggggaggcgg atctcatgtg  840
cagctggtgg aaagcggagg cggcctggtg cagcctgggg gatctctgag actgtcttgt  900
gccgccagcg gcttctccct gaccgattat ggcgtgcact gggtgcgaca ggcccctggc  960
```

```
aaaggactgg aatggctggg agtgatttgg agtggcggag gcaccgccta caacaccgcc   1020
ctgatctccc ggttcaccat cagccgggac aactccaaga acaccctgta cctgcagatg   1080
aactccctgc gggccgagga caccgctgtg tactactgcg ccagacgggg ctcctacccc   1140
tacaactact tcgacgcttg gggctgcggc accctcgtga cagtgtctag cggaggggga   1200
ggttctgggg gcggaggttc aggtggtggt ggttccgggg gtggtggctc tggtggcggt   1260
ggttctggcg gtggcggatc tcaggctgtc gtgacccagg aacccagcct gactgtgtct   1320
cctggcggaa ccgtgaccct gacctgcgga tcttctaccg cgctgtgac cgccagcaac   1380
tacgccaatt gggtgcagca gaaacctgga cagtgcccta gaggcctgat cggcggccac   1440
aacaacagac ctccaggcgt gccagcccgg ttctctggat ctctgctggg cggaaaggcc   1500
gctctgacac tgctgggtgc tcagcctgag gacgaggccg agtactactg tgccctgtgg   1560
tactccgacc actgggtcat cggaggcggg accaagctga ccgtgctggg aacacccctg   1620
ggagacacca cacatactag tgggaggcac ggcgacgaag atacctacta tctgcaggtg   1680
aggggacggg agaacttcga aatcctgatg aagctgaaag agtccctgga actgatggag   1740
ctggtgcccc agcctctggt cgacagctac agacagcagc agcagctgct gcagaggcca   1800
ggagggtcag gaggagcacc gcaccatcat catcaccat                          1839

SEQ ID NO: 83           moltype = AA  length = 613
FEATURE                 Location/Qualifiers
REGION                  1..613
                        note = Description of Artificial Sequence: Synthetic
                        polypeptide
source                  1..613
                        mol_type = protein
                        organism = synthetic construct
SEQUENCE: 83
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
GGGGSGGGGS GGGGSGGGGS GGGGSGGGGS DIQMTQSPSS LSASVGDRVT ITCRASQDVN   180
TAVAWYQQKP GKAPKLLIYS ASFLYSGVPS RFSGSRSGTD FTLTISSLQP EDFATYYCQQ   240
HYTTPPTFGQ GTKVEIKRGG GGSGGGGSGG GGSGGGGSHV QLVESGGGLV QPGGSLRLSC   300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGRH GDEDTYYLQV RGRENFEILM KLKESLELME LVPQPLVDSY RQQQQLLQRP   600
GGSGGAPHHH HHH                                                      613

SEQ ID NO: 84           moltype = DNA  length = 1839
FEATURE                 Location/Qualifiers
misc_feature            1..1839
                        note = Description of Artificial Sequence: Synthetic
                        polynucleotide
source                  1..1839
                        mol_type = other DNA
                        organism = synthetic construct
SEQUENCE: 84
gaagtgcagc tggtcgaatc cggggggggc ctggtgcagc ctggagggtc actgagactg    60
tcctgtgccg catctgggtt caatatcaag gacacctaca tccactgggt gcggcaggca   120
cctggcaagg gactggagtg ggtggcaagg atctatccaa ccaacggcta cacacggtat   180
gccgactccg tgaagggccg gttcaccatc tccgccgata cctctaagaa cacagcctac   240
ctgcagatga attctctgag ggccgaggat acagccgtgt actattgcag ccgctgggga   300
ggcgacggct tctacgctat ggactattgg ggccagggca ccctggtgac agtgagctct   360
ggcggcggcg gatccggagg aggaggcagc ggcggaggag gctccggagg aggcggctct   420
ggcggcggcg gcagcggcgg cggcggctcc gacatccaga tgacccagtc ccatctagc    480
ctgagcgcct ccgtgggcga cagggtgacc atcacatgcc gcgccagcca ggatgtgaat   540
acagccgtgg cctggtacca gcagaagcca ggcaaggccc caagctgct gatctactct   600
gccagcttcc tgtatagcgg agtgccatcc cggttttccg gcagccggag cggcaccgac   660
ttcaccctga caatctcctc tctgcagcct gaggattttg ccacatacta ttgtcagcag   720
cactatacca caccccctac attcggacag gggacaaagg tcgagatcaa acgcggcgga   780
gggggatccg gcggcggagg atctggcgga ggtgaagtg ggggaggcgg atctcatgtg   840
cagctggtga aaagcggagg cggcctggtg cagcctgggg gatctctgag actgtcttgt   900
gccgccagcg gcttctcct gaccgattat ggcgtgcact gggtgcgaca ggcccctggc   960
aaaggactgg aatggctggg agtgatttgg agtggcggag gcaccgccta caacaccgcc   1020
ctgatctccc ggttcaccat cagccgggac aactccaaga acaccctgta cctgcagatg   1080
aactccctgc gggccgagga caccgctgtg tactactgcg ccagacgggg ctcctacccc   1140
tacaactact tcgacgcttg gggctgcggc accctcgtga cagtgtctag cggaggggga   1200
ggttctgggg gcggaggttc aggtggtggt ggttccgggg gtggtggctc tggtggcggt   1260
ggttctggcg gtggcggatc tcaggctgtc gtgacccagg aacccagcct gactgtgtct   1320
cctggcggaa ccgtgaccct gacctgcgga tcttctaccg cgctgtgac cgccagcaac   1380
tacgccaatt gggtgcagca gaaacctgga cagtgcccta gaggcctgat cggcggccac   1440
aacaacagac ctccaggcgt gccagcccgg ttctctggat ctctgctggg cggaaaggcc   1500
gctctgacac tgctgggtgc tcagcctgag gacgaggccg agtactactg tgccctgtgg   1560
tactccgacc actgggtcat cggaggcggg accaagctga ccgtgctggg aacacccctg   1620
ggagacacca cacatactag tgggaggcac ggcgacgaag atacctacta tctgcaggtg   1680
aggggacggg agaacttcga aatcctgatg aagctgaaag agtccctgga actgatggag   1740
ctggtgcccc agcctctggt cgacagctac agacagcagc agcagctgct gcagaggcca   1800
ggagggtcag gaggagcacc gcaccatcat catcaccat                          1839

SEQ ID NO: 85           moltype = AA  length = 613
```

```
FEATURE            Location/Qualifiers
REGION             1..613
                   note = Description of Artificial Sequence: Synthetic
                    polypeptide
source             1..613
                   mol_type = protein
                   organism = synthetic construct
SEQUENCE: 85
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ CTKVEIKRGG GGSGGGGSGG  120
GGSGGGGSGG GGSGGGGSEV QLVESGGGLV QPGGSLRLSC AASGFNIKDT YIHWVRQAPG  180
KCLEWVARIY PTNGYTRYAD SVKGRFTISA DTSKNTAYLQ MNSLRAEDTA VYYCSRWGGD  240
GFYAMDYWGQ GTLVTVSSGG GGSGGGGSGG GGSGGGGSHV QLVESGGGLV QPGGSLRLSC  300
AASGFSLTDY GVHWVRQAPG KGLEWLGVIW SGGGTAYNTA LISRFTISRD NSKNTLYLQM  360
NSLRAEDTAV YYCARRGSYP YNYFDAWGCG TLVTVSSGGG GSGGGGSGGG GSGGGGSGGG  420
GSGGGGSQAV VTQEPSLTVS PGGTVTLTCG SSTGAVTASN YANWVQQKPG QCPRGLIGGH  480
NNRPPGVPAR FSGSLLGGKA ALTLLGAQPE DEAEYYCALW YSDHWVIGGG TKLTVLGTPL  540
GDTTHTSGRH GDEDTYYLQV RGRENFEILM KLKESLELME LVPQPLVDSY RQQQQLLQRP  600
GGSGGAPHHH HHH                                                    613

SEQ ID NO: 86      moltype = DNA  length = 1839
FEATURE            Location/Qualifiers
misc_feature       1..1839
                   note = Description of Artificial Sequence: Synthetic
                    polynucleotide
source             1..1839
                   mol_type = other DNA
                   organism = synthetic construct
SEQUENCE: 86
gatattcaga tgactcagtc ccctagttca ctgtctgcct cagtcggaga tcgggtcact   60
atcacttgtc gggcttctca ggatgtgaac accgccgtgg cctggtacca gcagaagcca  120
ggcaaggccc ccaagctgct gatctactct gccagcttcc tgtattccgg agtgccatct  180
cggttttccg gcagccggag cggcaccgac ttcaccctga caatcagctc cctgcagcct  240
gaggattttg ccacatacta ttgccagcag cactatacca caccccctac cttcggccag  300
tgcacaaagg tggagatcaa gagggggagga ggaggatccg gaggaggagg cagcggaggc  360
ggcggctccg gcggcggcgg ctctggcggc ggcggcagcg gaggaggcgg ctccgaggtg  420
cagctggtga gtccggcgg cggcctggtg cagcccggcg gcagcctgcg gctgtcctgt  480
gccgcctctg gctttaacat caaggacacc tacatccact gggtgaggca ggcacctggc  540
aagtgcctgg agtgggtggc aaggatctat ccaaccaatg gctacacaag atatgccgac  600
tccgtgaagg gccgctttac catcagcgcc gatacctcca gaacacagc ctacctgcag  660
atgaattctc tgcgggccga ggatacagcc gtgtactatt gctccagatg gggcggcgac  720
ggcttctatg ctatggacta ttggggggcag ggaactctgg tcactgtctc ctctggcgga  780
gggggatccg gcggcggagg atctggcgga ggtggaaggtg gggaggcgg atctcatgtg  840
cagctggtgg aaagcggagg cggcctggtg cagcctgggg gatctctgag actgtcttgt  900
gccgccagcg gcttctccct gaccgattat ggcgtgcact gggtgcgaca ggcccctggc  960
aaaggactgg aatggctggg agtgatttgg agtggcggag gcaccgccta caacaccgcc 1020
ctgatctccc ggttcaccat cagccgggac aactccaaga acaccctgta cctgcagatg 1080
aactccctgc gggccgagga caccgctgtg tactactgcg ccagacgggg ctcctacccc 1140
tacaactact cgacgcttg gggctgcggg accctcgtga cagtgtctag cggagggga 1200
ggttctgggg gcggaggttc aggtggtggt ggttccgggg tggtggctc tggtggcggt 1260
ggttctggcg gtggcggatc tcaggctgtc gtgacccagg aacccagcct gactgtgtct 1320
cctggcggaa ccgtgaccct gacctgcgga tcttctaccg gcgctgtgac cgccagcaac 1380
tacgccaatt gggtgcagca gaaacctgga cagtgcccta gaggcctgat cggcggccac 1440
aacaacagac tctccaggcgt gccagccgg ttctctggat ctctgctggg cggaaaggcc 1500
gctctgacac tgctggggtgc tcagcctgag gacgaggccg agtactactg tgccctgtgg 1560
tactccgacc actgggtcat cggaggcggg accaagctga ccgtgctggg aacacccctg 1620
ggagacacca cacatactag tgggaggcac ggcgacgaag atacctacta tctgcaggtg 1680
aggggacggg agaacttcga aatcctgatg aagctgaaag agtccctgga actgatggag 1740
ctggtgcccc agcctctggt cgacagctac agacagcagc agcagctgct gcagaggcca 1800
ggagggtcag gaggagcacc gcaccatcat catcaccat                         1839

SEQ ID NO: 87      moltype = AA  length = 613
FEATURE            Location/Qualifiers
REGION             1..613
                   note = Description of Artificial Sequence: Synthetic
                    polypeptide
source             1..613
                   mol_type = protein
                   organism = synthetic construct
SEQUENCE: 87
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ GTKVEIKRGG GGSGGGGSGG  120
GGSGGGGSGG GGSGGGGSEV QLVESGGGLV QPGGSLRLSC AASGFNIKDT YIHWVRQAPG  180
KGLEWVARIY PTNGYTRYAD SVKGRFTISA DTSKNTAYLQ MNSLRAEDTA VYYCSRWGGD  240
GFYAMDYWGQ GTLVTVSSGG GGSGGGGSGG GGSGGGGSHV QLVESGGGLV QPGGSLRLSC  300
AASGFSLTDY GVHWVRQAPG KGLEWLGVIW SGGGTAYNTA LISRFTISRD NSKNTLYLQM  360
NSLRAEDTAV YYCARRGSYP YNYFDAWGCG TLVTVSSGGG GSGGGGSGGG GSGGGGSGGG  420
GSGGGGSQAV VTQEPSLTVS PGGTVTLTCG SSTGAVTASN YANWVQQKPG QCPRGLIGGH  480
NNRPPGVPAR FSGSLLGGKA ALTLLGAQPE DEAEYYCALW YSDHWVIGGG TKLTVLGTPL  540
```

```
GDTTHTSGRH GDEDTYYLQV RGRENFEILM KLKESLELME LVPQPLVDSY RQQQQLLQRP    600
GGSGGAPHHH HHH                                                      613

SEQ ID NO: 88           moltype = DNA   length = 1839
FEATURE                 Location/Qualifiers
misc_feature            1..1839
                        note = Description of Artificial Sequence: Synthetic
                        polynucleotide
source                  1..1839
                        mol_type = other DNA
                        organism = synthetic construct
SEQUENCE: 88
gatattcaga tgactcagtc ccctagttca ctgtctgcct cagtcggaga tcgggtcact    60
atcacttgtc gggcttctca ggatgtgaac accgccgtgg cctggtacca gcagaagcca   120
ggcaaggccc ccaagctgct gatctactct gccagcttcc tgtattccgg agtgccatct   180
cggttttccg gcagccggag cggcaccgac ttcaccctga caatcagctc cctgcagcct   240
gaggattttg ccacatacta ttgccagcag cactatacca cccccctac cttcggccag    300
ggcacaaagg tggagatcaa ggggggagga ggaggatccg gaggaggagg cagcggaggc   360
ggcggctccg gcggcggcgg ctctggcggc ggcggcagcg gaggaggcgg ctccgaggtg   420
cagctggtgg agtccggcgg cggcctggtg cagcccggcg gcagcctgcg gctgtcctgt   480
gccgcctctg gctttaacat caaggacacc tacatccact gggtgaggca ggcacctggc   540
aagggcctgg agtgggtggc aaggatctat ccaaccaacg gctacacaag atatgccgac   600
tccgtgaagg gccgctttac catcagcgcc gataccccca gaacacagc ctacctgcag    660
atgaattctc tgcggccga ggatacagcc gtgtactatt gctccagatg gggcggcgac    720
ggcttctatg ctatggacta ttgggggcag ggaactctgg tcactgtctc ctctggcgga   780
ggggatccg gcggcggagg atctggcgga ggtggaagtg gaggaggcgg atctcatgg     840
cagctggtgg aaagcggagg cggcctggtg cagcctgggg gatctctgag actgtcttgt   900
gccgccagcg gcttctccct gaccgattat ggcgtgcact gggtgcgaca ggcccctggc   960
aaaggactgg aatggctggg agtgatttgg agtggcggag gcaccgccta caacaccgcc  1020
ctgatctccc ggttcaccat cagccggac aactccaaga cacccctgta cctgcagatg   1080
aactccctgc gggccgagga caccgctgtg tactactgcg ccagacgggg ctcctacccc  1140
tacaactact cgacgcttg gggctgcggc accctcgtga cagtgtctag cggagggggga  1200
ggttctgggg gcggaggttc aggtggtggt ggttccgggg gtggtggctc tggtggcggt   1260
ggttctggcg gtggcggatc tcaggctgtc gtgacccagg aacccagcct gactgtgtct   1320
cctgcggaa ccgtgacct gacctgcgga tcttctaccg gcgctgtgac cgccagcaac    1380
tacgccaatt gggtgcagca gaaacctgga cagtgcccta gaggcctgat cggcggccac   1440
aacaacagac tccaggcgt gccagcccgg ttctctggat ctctgctggg cggaaaggcc   1500
gctctgacac tgctgggtgc tcagcctgag gacgaggcca gtactactg tgccctgtgg    1560
tactccgacc actgggtcat cggaggcggg accaagctga ccgtgctggg aaccccctg   1620
ggagacacca cacatactag tgggaggcac ggcgacgaag atacctacta tctgcaggtg  1680
aggggacggg agaacttcga aatcctgatg aagctgaaag agtccctgga actgatggag   1740
ctggtgcccc agcctctggt cgacagctac agacagcagc agcagctgct gcagaggcca   1800
ggagggtcag gaggagcacc gcaccatcat catcaccat                          1839

SEQ ID NO: 89           moltype = AA   length = 588
FEATURE                 Location/Qualifiers
REGION                  1..588
                        note = Description of Artificial Sequence: Synthetic
                        polypeptide
source                  1..588
                        mol_type = protein
                        organism = synthetic construct
SEQUENCE: 89
EVQLVESGGG LVQPGGSLRL SCAASGFNIK DTYIHWVRQA PGKCLEWVAR IYPTNGYTRY    60
ADSVKGRFTI SADTSKNTAY LQMNSLRAED TAVYYCSRWG GDGFYAMDYW GQGTLVTVSS   120
GGGGSGGGGS GGGGSGGGGS GGGGSGGGGS DIQMTQSPSS LSASVGDRVT ITCRASQDVN   180
TAVAWYQQKP GKAPKLLIYS ASFLYSGVPS RFSGSRSGTD FTLTISSLQP EDFATYYCQQ   240
HYTTPPTFGQ CTKVEIKRGG GGSGGGGSGG GGSGGGGSHV QLVESGGGLV QPGGSLRLSC   300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSGGG   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGQA IKKELTQIKQ KVDSLLENLE KIEKEGGSGG APHHHHHH                588

SEQ ID NO: 90           moltype = DNA   length = 1764
FEATURE                 Location/Qualifiers
misc_feature            1..1764
                        note = Description of Artificial Sequence: Synthetic
                        polynucleotide
source                  1..1764
                        mol_type = other DNA
                        organism = synthetic construct
SEQUENCE: 90
gaagtgcagc tggtcgaatc cggggggggc ctggtgcagc tggagggtc actgagactg     60
tcctgtgccg catctggtt caatatcaag acacctaca tccactgggt gcggcaggca    120
cctggcaagt gtctggagtg ggtggcaagg atctatccaa ccaacggcta cacacggtat   180
gccgactccg tgaagggccg gttcaccatc tccgccgata cctctaagaa cacagcctac   240
ctgcagatga attctctgag ggccgaggat acagccgtgt actattgcag ccgctgggga   300
ggcgacggct ctacgctat ggactattgg ggccagggca ccctggtgac agtgagctct    360
```

-continued

```
ggcggcggcg gatccggagg aggaggcagc ggcggaggag gctccggagg aggcggctct    420
ggcggcggcg gcagcggcgg cggcggctcc gacatccaga tgacccagtc cccatctagc    480
ctgagcgcct ccgtgggcga cagggtgacc atcacatgcc gcgccagcca ggatgtgaat    540
acagccgtgg cctggtacca gcagaagcca ggcaaggccc ccaagctgct gatctactct    600
gccagcttcc tgtatagcgg agtgccatcc cggttttccg gcagccggag cggcaccgac    660
ttcaccctga caatctcctc tctgcagcct gaggattttg ccacatacta ttgtcagcag    720
cactatacca caccccctac attcggacag tgtacaaagg tcgagatcaa acgcggcgga    780
gggggatccg gcggcggagg atctggcgga ggtggaagtg ggggaggcgg atctcatgtg    840
cagctggtgg aaagcggagg cggcctggtg cagcctgggg gatctctgag actgtcttgt    900
gccgccagcg gcttctccct gaccgattat ggcgtgcact gggtgcgaca ggcccctggc    960
aaaggactgg aatggctggg agtgatttgg agtggcggag gcaccgccta caacaccgcc    1020
ctgatctccc ggttcaccat cagccggac aactccaaga cacccgtata cctgcagatg    1080
aactccctgc gggccgagga caccgctgtg tactactgcg ccagacgggg ctcctacccc    1140
tacaactact tcgacgcttg gggctgcggc accctcgtga cagtgtctag cggaggggga    1200
ggttctgggg gcggaggttc aggtggtggt ggttccgggg gtggtggctc tggtggcggt    1260
ggttctggcg gtggcggatc tcaggctgtc gtgacccagg aacccagcct gactgtgtct    1320
cctggcggaa ccgtgaccct gacctgcgga tcttctaccg gcgctgtgac cgccagcaac    1380
tacgccaatt gggtgcagca gaaacctgga cagtgcccta gaggcctgat cggcggccac    1440
aacaacagac ctccaggcgt gccagcccgg ttctctggat ctctgctggg cggaaaggcc    1500
gctctgacac tgctgggtgc tcagcctgag gacgaggccg agtactactg tgccctgtgg    1560
tactccgacc actgggtcat cggaggcggg accaagctga ccgtgctggg aacacccctg    1620
ggagacacca cacatactag tgggcaggcc atcaagaagg agctgaccca gatcaagcag    1680
aaggtggaca gcctgctgga gaacctggag aagatcgaga aggaggagg gtcaggagga    1740
gcaccgcacc atcatcatca ccat                                           1764
```

| SEQ ID NO: 91 | moltype = AA length = 588 |
|---|---|
| FEATURE | Location/Qualifiers |
| REGION | 1..588 |
| | note = Description of Artificial Sequence: Synthetic polypeptide |
| source | 1..588 |
| | mol_type = protein |
| | organism = synthetic construct |

SEQUENCE: 91
```
EVQLVESGGG LVQPGGSLRL SCAASGFNIK DTYIHWVRQA PGKGLEWVAR IYPTNGYTRY     60
ADSVKGRFTI SADTSKNTAY LQMNSLRAED TAVYYCSRWG DGDFYAMDYW GQGTLVTVSS    120
GGGGSGGGGS GGGGSGGGGS GGGGSGGGGS DIQMTQSPSS LSASVGDRVT ITCRASQDVN    180
TAVAWYQQKP GKAPKLLIYS ASFLYSGVPS RFSGSRSGTD FTLTISSLQP EDFATYYCQQ    240
HYTTPPTFGQ GTKVEIKRGG GSGGGGSGG GGSGGGGSHV QLVESGGGLV QPGGSLRLSC    300
AASGFSLTDY GVHWVRQAPG KGLEWLGVIW SGGGTAYNTA LISRFTISRD NSKNTLYLQM    360
NSLRAEDTAV YYCARRGSYP YNYFDAWGCG TLVTVSSGGG GSGGGGSGGG GSGGGGSGGG    420
GSGGGGSQAV VTQEPSLTVS PGGTVTLTCG SSTGAVTASN YANWVQQKPG QCPRGLIGGH    480
NNRPPGVPAR FSGSLLGGKA ALTLLGAQPE DEAEYYCALW YSDHWVIGGG TKLTVLGTPL    540
GDTTHTSGQA IKKELTQIKQ KVDSLLENLE KIEKEGGSGG APHHHHHH                 588
```

| SEQ ID NO: 92 | moltype = DNA length = 1764 |
|---|---|
| FEATURE | Location/Qualifiers |
| misc_feature | 1..1764 |
| | note = Description of Artificial Sequence: Synthetic polynucleotide |
| source | 1..1764 |
| | mol_type = other DNA |
| | organism = synthetic construct |

SEQUENCE: 92
```
gaagtgcagc tggtcgaatc cggggggggc ctggtgcagc ctggagggtc actgagactg     60
tcctgtgccg catctgggtt caatatcaag gacacctaca tccactgggt gcggcaggca    120
cctggcaagg gactggagtg ggtggcaagg atctatccaa ccaacggcta cacacggtat    180
gccgactccg tgaagggccg gttcaccatc tccgccgata cctctaagaa cacagcctac    240
ctgcagatga attctctgag ggccgaggat acagccgtgt actattgcag ccgctgggga    300
ggcgacggct tctacgctat ggactattgg ggccagggca ccctggtgac agtgagctct    360
ggcggcggcg gatccggagg aggaggcagc ggcggaggag gctccggagg aggcggctct    420
ggcggcggcg gcagcggcgg cggcggctcc gacatccaga tgacccagtc cccatctagc    480
ctgagcgcct ccgtgggcga cagggtgacc atcacatgcc gcgccagcca ggatgtgaat    540
acagccgtgg cctggtacca gcagaagcca ggcaaggccc ccaagctgct gatctactct    600
gccagcttcc tgtatagcgg agtgccatcc cggttttccg gcagccggag cggcaccgac    660
ttcaccctga caatctcctc tctgcagcct gaggattttg ccacatacta ttgtcagcag    720
cactatacca caccccctac attcggacag gggacaaagg tcgagatcaa acgcggcgga    780
gggggatccg gcggcggagg atctggcgga ggtggaagtg ggggaggcgg atctcatgtg    840
cagctggtgg aaagcggagg cggcctggtg cagcctgggg gatctctgag actgtcttgt    900
gccgccagcg gcttctccct gaccgattat ggcgtgcact gggtgcgaca ggcccctggc    960
aaaggactgg aatggctggg agtgatttgg agtggcggag gcaccgccta caacaccgcc    1020
ctgatctccc ggttcaccat cagccggac aactccaaga cacccgtata cctgcagatg    1080
aactccctgc gggccgagga caccgctgtg tactactgcg ccagacgggg ctcctacccc    1140
tacaactact tcgacgcttg gggctgcggc accctcgtga cagtgtctag cggaggggga    1200
ggttctgggg gcggaggttc aggtggtggt ggttccgggg gtggtggctc tggtggcggt    1260
ggttctggcg gtggcggatc tcaggctgtc gtgacccagg aacccagcct gactgtgtct    1320
cctggcggaa ccgtgaccct gacctgcgga tcttctaccg gcgctgtgac cgccagcaac    1380
tacgccaatt gggtgcagca gaaacctgga cagtgcccta gaggcctgat cggcggccac    1440
aacaacagac ctccaggcgt gccagcccgg ttctctggat ctctgctggg cggaaaggcc    1500
```

-continued

```
gctctgacac tgctgggtgc tcagcctgag gacgaggccg agtactactg tgccctgtgg    1560
tactccgacc actgggtcat cggaggcggg accaagctga ccgtgctggg aacacccctg    1620
ggagacacca cacatactag tgggcaggcc atcaagaagg agctgaccca gatcaagcag    1680
aaggtggaca gcctgctgga gaacctggag aagatcgaga aggagggagg gtcaggagga    1740
gcaccgcacc atcatcatca ccat                                           1764
```

```
SEQ ID NO: 93              moltype = AA  length = 588
FEATURE                    Location/Qualifiers
REGION                     1..588
                           note = Description of Artificial Sequence: Synthetic
                             polypeptide
source                     1..588
                           mol_type = protein
                           organism = synthetic construct
SEQUENCE: 93
DIQMTQSPSS LSASVGDRVT ITCRASQDVN TAVAWYQQKP GKAPKLLIYS ASFLYSGVPS     60
RFSGSRSGTD FTLTISSLQP EDFATYYCQQ HYTTPPTFGQ CTKVEIKRGG GSGGGGSGG    120
GGSGGGGSGG GGSGGGGSEV QLVESGGGLV QPGGSLRLSC AASGFNIKDT YIHWVRQAPG   180
KCLEWVARIY PTNGYTRYAD SVKGRFTISA DTSKNTAYLQ MNSLRAEDTA VYYCSRWGGD   240
GFYAMDYWGQ GTLVTVSSGG GGSGGGGSGG GGSGGGGSHV QLVESGGGLV QPGGSLRLSC   300
AASGFSLTDY GVHWVRQAPG KGLEWLGVIW SGGGTAYNTA LISRFTISRD NSKNTLYLQM   360
NSLRAEDTAV YYCARRGSYP YNYFDAWGCG TLVTVSSGGG GSGGGGSGGG GSGGGGSQAV   420
GSGGGGSQAV VTQEPSLTVS PGGTVTLTCG SSTGAVTASN YANWVQQKPG QCPRGLIGGH   480
NNRPPGVPAR FSGSLLGGKA ALTLLGAQPE DEAEYYCALW YSDHWVIGGG TKLTVLGTPL   540
GDTTHTSGQA IKKELTQIKQ KVDSLLENLE KIEKEGGSGG APHHHHHH                588
```

```
SEQ ID NO: 94              moltype = DNA  length = 1764
FEATURE                    Location/Qualifiers
misc_feature               1..1764
                           note = Description of Artificial Sequence: Synthetic
                             polynucleotide
source                     1..1764
                           mol_type = other DNA
                           organism = synthetic construct
SEQUENCE: 94
gatattcaga tgactcagtc ccctagttca ctgtctgcct cagtcggaga tcgggtcact     60
atcacttgtc gggcttctca ggatgtgaac accgccgtgg cctggtacca gcagaagcca    120
ggcaaggccc ccaagctgct gatctactct gccagcttcc tgtattccgg agtgccatct    180
cggttttccg gcagcggag cggcaccgac ttcaccctga caatcagctc cctgcagcct    240
gaggattttg ccacatacta ttgccagcag cactatacca cccccctac cttcggccaa    300
tgcacaaagg tggagatcaa gaggggagga ggaggatccg gaggaggagg cagcggaggc    360
ggcggctccg gcggcggcgg ctctggcggc ggcggcagcg gaggaggcgg ctccgaggtg    420
cagctggtgg agtccggcgg cggcctggtg cagcccgggg gctctgtcct gtgtcctg     480
gccgcctctg gctttaacat caaggacacc tacatccact gggtgaggca ggcacctggc    540
aagtgcctgg agtgggtggc aaggatctat ccaaccaatg gctacacaag atatgccgac    600
tccgtgaagg gccgctttac catcagcgcc gatacctcca gaacacagc ctacctgcag    660
atgaattctc tgcgggccga ggatacagcc gtgtactatt gctccagatg gggcggcgac    720
ggcttctatg ctatggacta ttgggggcag gaactctggt cactgtctc ctctggcgga    780
gggggatccg gcggcggagg atctggcgga ggtggaagtg ggggaggcgg atctcatgtg    840
cagctggtgg aaagcggagg cggcctggtg cagcctgggg gatctctgag actgtcttgt    900
gccgccagcg gcttctccct gaccgattat ggcgtgcact gggtgcgaca gggtgccggc    960
aaaggactgg aatggctggg agtgatttgg agtggcggag gcaccgccta caacaccgcc   1020
ctgatctccc ggttcaccat cagccgggac aactccaaga acacccgta cctgcagatg    1080
aactccctgc gggccgagga caccgctgtg tactactgcg ccagacgggg ctcctacccc   1140
tacaactact tcgacgcttg gggctgcggc accctgtga cagtgctag cggaggggga   1200
ggttctgggg gcggaggttc aggtggtggt ggttccgggg gtggtggctc tggtggcggt    1260
ggttctggcg gtggcggatc tcaggctgtc gtgacccagg aacccagcct gactgtgtct    1320
cctggcggaa ccgtgaccct gacctgcgga tcttctaccg gcgctgtgac cgccagcaac    1380
tacgccaatt gggtgcagca gaaacctgga cagtgcccta gaggcctgat cggcggccac    1440
aacaacagac ctccaggcgt gccagcccgg ttctctggat ctctgctggg cggaaaggcc    1500
gctctgacac tgctgggtgc tcagcctgag gacgaggccg agtactactg tgccctgtgg   1560
tactccgacc actgggtcat cggaggcggg accaagctga ccgtgctggg aacacccctg    1620
ggagacacca cacatactag tgggcaggcc atcaagaagg agctgaccca gatcaagcag    1680
aaggtggaca gcctgctgga gaacctggag aagatcgaga aggagggagg gtcaggagga    1740
gcaccgcacc atcatcatca ccat                                           1764
```

```
SEQ ID NO: 95              moltype = AA  length = 588
FEATURE                    Location/Qualifiers
REGION                     1..588
                           note = Description of Artificial Sequence: Synthetic
                             polypeptide
source                     1..588
                           mol_type = protein
                           organism = synthetic construct
SEQUENCE: 95
DIQMTQSPSS LSASVGDRVT ITCRASQDVN TAVAWYQQKP GKAPKLLIYS ASFLYSGVPS     60
RFSGSRSGTD FTLTISSLQP EDFATYYCQQ HYTTPPTFGQ GTKVEIKRGG GSGGGGSGG    120
GGSGGGGSGG GGSGGGGSEV QLVESGGGLV QPGGSLRLSC AASGFNIKDT YIHWVRQAPG   180
KGLEWVARIY PTNGYTRYAD SVKGRFTISA DTSKNTAYLQ MNSLRAEDTA VYYCSRWGGD   240
```

```
GFYAMDYWGQ  GTLVTVSSGG  GGSGGGGSGG  GGSGGGGSHV  QLVESGGGLV  QPGGSLRLSC  300
AASGFSLTDY  GVHWVRQAPG  KGLEWLGVIW  SGGGTAYNTA  LISRFTISRD  NSKNTLYLQM  360
NSLRAEDTAV  YYCARRGSYP  YNYFDAWGCG  TLVTVSSGGG  GSGGGGSGGG  GSGGGGSGGG  420
GSGGGGSQAV  VTQEPSLTVS  PGGTVTLTCG  SSTGAVTASN  YANWVQQKPG  QCPRGLIGGH  480
NNRPPGVPAR  FSGSLLGGKA  ALTLLGAQPE  DEAEYYCALW  YSDHWVIGGG  TKLTVLGTPL  540
GDTTHTSGQA  IKKELTQIKQ  KVDSLLENLE  KIEKEGGSGG  APHHHHHH                588

SEQ ID NO: 96            moltype = DNA   length = 1764
FEATURE                  Location/Qualifiers
misc_feature             1..1764
                         note = Description of Artificial Sequence: Synthetic
                         polynucleotide
source                   1..1764
                         mol_type = other DNA
                         organism = synthetic construct
SEQUENCE: 96
gatattcaga tgactcagtc ccctagttca ctgtctgcct cagtcggaga tcgggtcact   60
atcacttgtc gggcttctca ggatgtgaac accgccgtgg cctggtacca gcagaagcca  120
ggcaaggccc ccaagctgct gatctactct gccagcttcc tgtattccgg agtgccatct  180
cggttttccg gcagccggag cggcaccgac ttcaccctga caatcagctc cctgcagcct  240
gaggattttg ccacatacta ttgccagcag cactatacca caccccctac cttcggccag  300
ggcacaaagg tggagatcaa gaggggagga ggaggaggcc agcggaggc  360
ggcggctccg gcggcggcgg ctctggcggc ggcggcagcg gaggaggcgg ctccgaggtg  420
cagctggtgg agtccggcgg cggcctggtg cagcccggcg gcagcctgcg gctgtcctgt  480
gccgcctctg gctttaacat caaggacacc tacatccact gggtgaggca ggcacctggc  540
aagggcctgg agtgggtggc aaggatctat ccaaccaatg gctacacaag atatgcgtat  600
tccgtgaagg gccgctttac catcagcgcc gatacctcca agaacacagc ctacctgcag  660
atgaattctc tgcgggccga ggatacagcc gtgtactatt gctccagatg gggcggcgac  720
ggcttctatg ctatggacta ttgggggcag ggaactctgg tcactgtctc ctctggcgga  780
ggggatccg gcggcggagg atctggcgga ggtggaagtg gggagggcgg atctcatgg  840
cagctggtgg aaagcggagg cggcctggtg cagcctgggg gatctctgag actgtcttgt  900
gccgccagcg gcttctccct gaccgattat ggcgtgcact gggtgcgaca ggcccctggc  960
aaaggactgg aatggctggg agtgatttgg agtggcggag caccgcctaa caccgcc   1020
ctgatctccc ggttcaccat cagccgggac aactccaaga cacccctgca cctgcagatg 1080
aactccctgc gggccgagga caccgctgtg tactactgcg ccagacgggg ctcctacccc 1140
tacaactact cgacgcttg gggctgcggc accctcgtga cagtgtctag cggaggggga 1200
ggttctgggg gcggaggttc aggtggtggt ggttccgggg tggtggctc tggtggcggt  1260
ggttctggcg gtggcggatc tcaggctgtc gtgacccagg aacccagcct gactgtgtct  1320
cctggcggaa ccgtgaccct gacctgcgga tcttctaccg gcgctgtgac cgccagcaac  1380
tacgccaatt gggtgcagca gaaacctgga cagtgcccta gaggcctgat cggcggccac  1440
aacaacagac tccaggcgt gccagcccgg ttctctggat ctctgctggg cggaaaggcc   1500
gctctgacac tgctgggtgc tcagcctgag gacgaggccg agtactactg tgccctgtgg  1560
tactccgacc actgggtcat cggaggcggg accaagctga cctgctggg aacacccctg  1620
ggagacacca cacatactag tgggcaggcc atcaagaagg agctgaccca gatcaagcag  1680
aaggtggaca gcctgctgga gaacctggag aagatcgaga aggagggagg gtcaggagga  1740
gcaccgcacc atcatcatca ccat                                         1764

SEQ ID NO: 97            moltype = AA   length = 584
FEATURE                  Location/Qualifiers
REGION                   1..584
                         note = Description of Artificial Sequence: Synthetic
                         polypeptide
source                   1..584
                         mol_type = protein
                         organism = synthetic construct
SEQUENCE: 97
EIVMTQTPAT  LSVSAGERVT  ITCKASQSVS  NDVTWYQQKP  GQAPRLLIYS  ASNRYSGVPA   60
RFSGSGYGTE  FTFTISSVQS  EDFAVYFCQQ  DYSSFGCGTK  LEIKRGGGGS  GGGGSGGGGS  120
GGGGSGGGGS  GGGGSQVQLV  ESGPGVVQPG  RSLRISCAVS  GFSVTNYGVH  WVRQPPGKCL  180
EWLGVIWAGG  ITNYNSAFMS  RLTISKDNSK  NTVYLQMNSL  RAEDTAMYYC  ASRGGHYGYA  240
LDYWGQGTLV  TVSSGGGGSG  GGGSGGGGSG  GGSHVQLVE  SGGGLVQPGG  SLRLSCAASG  300
FSLTDYGVHW  VRQAPGKGLE  WLGVIWSGGG  TAYNTALISR  FTISRDNSKN  TLYLQMNSLR  360
AEDTAVYYCA  RRGSYPYNYF  DAWGCGTLVT  VSSGGGGSGG  GGSGGGGSGG  GGSGGGGSGG  420
GGSQAVVTQE  PSLTVSPGGT  VTLTCGSSTG  AVTASNYANW  VQQKPGQCPR  GLIGGHNNRP  480
PGVPARFSGS  LLGGKAALTL  LGAQPEDEAE  YYCALWYSDH  WVIGGGTKLT  VLGTPLGDTT  540
HTSGQAIKKE  LTQIKQKVDS  LLENLEKIEK  EGGSGGAPHH  HHHH                    584

SEQ ID NO: 98            moltype = DNA   length = 1752
FEATURE                  Location/Qualifiers
misc_feature             1..1752
                         note = Description of Artificial Sequence: Synthetic
                         polynucleotide
source                   1..1752
                         mol_type = other DNA
                         organism = synthetic construct
SEQUENCE: 98
gagatcgtga tgacccagac accgcaaca ctgagcgtgt ctgccggcga aagggtcact     60
attacctgca aggccagtca gtcagtgtcc aacgacgtga cttggtacca gcagaaacca  120
ggccaggctc ccggctgct gatctacagc gcatctaata gatatagcgg agtgcctgct   180
```

```
cgcttcagtg gttcaggcta tggaactgag ttcaccttca ccatttccag cgtgcagtcc   240
gaagacttcg cagtgtactt ttgccagcag gattattcta gttttgggtg tggtacaaag   300
ctggagatca aaaggggagg aggaggtagt ggcggaggag gttcaggcgg agggggtagc   360
ggcggagggg gttctggcgg cggcggtagt ggcggcggag gtagccaggt gcagctggtc   420
gaatccggcc ctggagtggt ccagccaggc aggtctctgc ggatcagttg cgccgtgtcc   480
ggattcagcg tcaccaacta cggagtgcac tgggtcagac agccacctgg caagtgtctg   540
gagtggctgg gagtgatctg ggcaggagga atcacaaact acaactcagc ttttatgtcc   600
cgcctgacta ttagcaagga caactctaaa aataccgtgt atctgcagat gaattctctg   660
cgagccgaag ataccgctat gtactattgt gcatcccgtg ggggtcggag cggctatgcc   720
ctggattatt gggggcaggg taccctggtg acagtctcat ccggcgggag gggatccggc   780
ggcggaggat ctggcggagg tggaagtggg ggaggcggag ctcatgtgca gctggtggaa   840
agcggaggcg gcctggtgca gcctggggga tctctgagac tgtcttgtgc cgccagcggc   900
ttctccctga ccgattatgg cgtgcactgg gtgcgacagg ccctggcaa  aggactggaa   960
tgggtgggaa tgatttggag tggcggaggc accgcctaca caccgcccct gatctcccgg  1020
ttcaccatca gccgggacaa ctccaagaac accctgtacc tgcagatgaa ctccctgcgg  1080
gccgaggaca ccgctgtgta ctactgcgcc agacggggct cctacccca  caactacttc  1140
gacgcttggg gctgcggcac cctcgtgaca gtgtctagcg gaggggagg  ttctggggc   1200
ggaggttcag gtggtggtgg ttccggggt  ggtggctgg ttctggcggt  1260
ggcggatctc aggctgtcgt gacccaggaa cccagcctga ctgtgtctcc tggcggaacc  1320
gtgaccctga cctgcggatc ttctaccggc gctgtgaccg ccagcaacta cgccaattgg  1380
gtgcagcaga aacctggaca gtgccctaga ggcctgatcg gcgccacaa  caacagacct  1440
ccaggcgtgc cagcccgtt  ctctggatct ctgctgactg gaaaggccgc tctgacactg  1500
ctggtgctct agcctgagga cgaggccgag tactactgtg ccctgtggta ctccgaccac  1560
tgggtcatcg gagcgggac  caagctgacc gtgctggaa  caccctgg   agacaccaca  1620
catactagtg gcaggccat  caagaaggag ctgacccaga tcaagcagaa ggtggacagc  1680
ctgctggaga acctggagaa gatcgagaag gagggagggt caggaggagc accgcaccat  1740
catcatcacc at                                                      1752

SEQ ID NO: 99        moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 99
GGGGSGGGGS GGGGS                                                     15

SEQ ID NO: 100       moltype = AA  length = 30
FEATURE              Location/Qualifiers
REGION               1..30
                     note = Description of Artificial Sequence: Synthetic
                      polypeptide
source               1..30
                     mol_type = protein
                     organism = synthetic construct
SEQUENCE: 100
GGGGSGGGGS GGGGSGGGGS GGGGSGGGGS                                     30

SEQ ID NO: 101       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 101
GGGGS                                                                5

SEQ ID NO: 102       moltype = AA  length = 150
FEATURE              Location/Qualifiers
REGION               1..150
                     note = Description of Artificial Sequence: Synthetic
                      polypeptide
VARIANT              1..150
                     note = MISC_FEATURE - This sequence may encompass 1-30
                      GGGGS repeating units
source               1..150
                     mol_type = protein
                     organism = synthetic construct
SEQUENCE: 102
GGGGSGGGGS GGGGSGGGGS GGGGSGGGGS GGGGSGGGGS GGGGSGGGGS GGGGSGGGGS    60
GGGGSGGGGS GGGGSGGGGS GGGGSGGGGS GGGGSGGGGS GGGGSGGGGS GGGGSGGGGS   120
GGGGSGGGGS GGGGSGGGGS GGGGSGGGGS                                   150

SEQ ID NO: 103       moltype = AA  length = 5
FEATURE              Location/Qualifiers
REGION               1..5
                     note = VH-CDR1
```

```
                                   -continued
source                  1..5
                        mol_type = protein
                        organism = synthetic construct
SEQUENCE: 103
DYGVH                                                                       5

SEQ ID NO: 104          moltype = AA  length = 16
FEATURE                 Location/Qualifiers
REGION                  1..16
                        note = VH-CDR2
source                  1..16
                        mol_type = protein
                        organism = synthetic construct
SEQUENCE: 104
VIWSGGGTAY NTALIS                                                          16

SEQ ID NO: 105          moltype = AA  length = 11
FEATURE                 Location/Qualifiers
REGION                  1..11
                        note = VH-CDR3
source                  1..11
                        mol_type = protein
                        organism = synthetic construct
SEQUENCE: 105
RGSYPYNYFD A                                                               11

SEQ ID NO: 106          moltype = AA  length = 14
FEATURE                 Location/Qualifiers
REGION                  1..14
                        note = VL-CDR1
source                  1..14
                        mol_type = protein
                        organism = synthetic construct
SEQUENCE: 106
GSSTGAVTAS NYAN                                                            14

SEQ ID NO: 107          moltype = AA  length = 7
FEATURE                 Location/Qualifiers
REGION                  1..7
                        note = VL-CDR2
source                  1..7
                        mol_type = protein
                        organism = synthetic construct
SEQUENCE: 107
GHNNRPP                                                                     7

SEQ ID NO: 108          moltype = AA  length = 9
FEATURE                 Location/Qualifiers
REGION                  1..9
                        note = VH-CDR3
source                  1..9
                        mol_type = protein
                        organism = synthetic construct
SEQUENCE: 108
ALWYSDHWV                                                                   9

SEQ ID NO: 109          moltype = AA  length = 8
FEATURE                 Location/Qualifiers
REGION                  1..8
                        note = VH-CDR1
source                  1..8
                        mol_type = protein
                        organism = synthetic construct
SEQUENCE: 109
GFSVTNYG                                                                    8

SEQ ID NO: 110          moltype = AA  length = 7
FEATURE                 Location/Qualifiers
REGION                  1..7
                        note = VH-CDR2
source                  1..7
                        mol_type = protein
                        organism = synthetic construct
SEQUENCE: 110
IWAGGIT                                                                     7

SEQ ID NO: 111          moltype = AA  length = 13
FEATURE                 Location/Qualifiers
```

```
REGION                  1..13
                        note = VH-CDR3
source                  1..13
                        mol_type = protein
                        organism = synthetic construct
SEQUENCE: 111
ASRGGHYGYA LDY                                                              13

SEQ ID NO: 112          moltype = AA  length = 6
FEATURE                 Location/Qualifiers
REGION                  1..6
                        note = VL-CDR1
source                  1..6
                        mol_type = protein
                        organism = synthetic construct
SEQUENCE: 112
QSVSND                                                                       6

SEQ ID NO: 113          moltype = AA  length = 6
FEATURE                 Location/Qualifiers
REGION                  1..6
                        note = VH-CDR3
source                  1..6
                        mol_type = protein
                        organism = synthetic construct
SEQUENCE: 113
QQDYSS                                                                       6

SEQ ID NO: 114          moltype = AA  length = 8
FEATURE                 Location/Qualifiers
REGION                  1..8
                        note = VH-CDR1
source                  1..8
                        mol_type = protein
                        organism = synthetic construct
SEQUENCE: 114
GFNIKDTY                                                                     8

SEQ ID NO: 115          moltype = AA  length = 8
FEATURE                 Location/Qualifiers
REGION                  1..8
                        note = VH-CDR2
source                  1..8
                        mol_type = protein
                        organism = synthetic construct
SEQUENCE: 115
IYPTNGYT                                                                     8

SEQ ID NO: 116          moltype = AA  length = 13
FEATURE                 Location/Qualifiers
REGION                  1..13
                        note = VH-CDR3
source                  1..13
                        mol_type = protein
                        organism = synthetic construct
SEQUENCE: 116
SRWGGDGFYA MDY                                                              13

SEQ ID NO: 117          moltype = AA  length = 6
FEATURE                 Location/Qualifiers
REGION                  1..6
                        note = VL-CDR1
source                  1..6
                        mol_type = protein
                        organism = synthetic construct
SEQUENCE: 117
QDVNTA                                                                       6

SEQ ID NO: 118          moltype = AA  length = 9
FEATURE                 Location/Qualifiers
REGION                  1..9
                        note = VH-CDR3
source                  1..9
                        mol_type = protein
                        organism = synthetic construct
SEQUENCE: 118
QQHYTTPPT                                                                    9
```

The invention claimed is:

1. A method of treating or diagnosing cancer in a subject, comprising:
   a. providing a composition comprising a conjugate comprising a self-assembly disassembly (SADA) polypeptide having an amino acid sequence that is identical to a human homo-multimerizing polypeptide sequence comprising any one of SEQ ID NOs: 1, 3, 5, 7, 9, 11, 13, and 15 and having one or more multimerization dissociation constants (KD); and a bispecific antibody comprising a first scFv that binds a tumor target and a second scFv that binds a DOTA moiety comprising a radioactive payload, wherein (a) the first scFv is operably linked to the second scFv, (b) the second scFv includes a VH-CDR1 sequence comprising DYGVH (SEQ ID NO: 103), a VH-CDR2 sequence comprising VIWSGGGTAYNTALIS (SEQ ID NO: 104), a VH-CDR3 sequence comprising RGSYPYNYFDA (SEQ ID NO: 105), a VL-CDR1 sequence comprising GSSTGAVTASNYAN (SEQ ID NO: 106), a VL-CDR2 sequence comprising GHNNRPP (SEQ ID NO: 107), and a VH-CDR3 sequence comprising ALWYSDHWV (SEQ ID NO: 108); and (c) the second scFv is operably linked to the SADA polypeptide;
   b. administering the composition to a subject that is suffering from or susceptible to cancer; and
   c. administering a DOTA chelator comprising a radionuclide.

2. The method of claim 1, wherein the conjugate is constructed and arranged so that it adopts a first multimerization state and at least one additional multimerization state, wherein:
   the first multimerization state is less than about 70 kDa in size,
   at least one additional multimerization state is a homo-tetramer or a homo-multimer greater than 150 kDa in size.

3. The method of claim 1, wherein at least 90% of the conjugate in the composition is in a higher order multimerization state.

4. The method of claim 1, wherein the concentration of the conjugate in the composition is in the range selected from the group consisting of 50 nM to 1 mM, 100 nM to 500 µM, 500 nM to 400 µM, 1 µM to 300 µM, 10 µM to 200 µM, and 50 µM to 100 µM.

5. The method of claim 4, wherein the concentration of the conjugate is at least 50 nM, 100 nM, 500 nM, 1 µM, 10 µM, 50 µM, 100 µM, 200 µM, 300 µM, 400 µM, 500 µM, or 1 mM.

6. The method of claim 1, wherein step c is performed at least 30 minutes, at least 1 hour, at least 2 hours, at least 3 hours, at least 4 hours, at least 5 hours, at least 6 hours, at least 12 hours, at least 24 hours, at least 36 hours, at least 48 hours, or at least 72 hours after the administration of the conjugate in step b.

7. The method of claim 1, wherein the method does not include the administration of a clearing agent.

8. The method of claim 1, wherein the first scFv is an anti-GD2, anti-Globo H, anti-GPA33, anti-PSMA, anti-polysialic acid, anti-Lewy, anti-L1CAM, anti-HER2, anti-B7H3, anti-CD33, anti-peptide/MHC, anti-glypican3, or anti-GD3 scFv.

9. The method of claim 1, wherein the second scFv binds to the DOTA moeity of a metal-Bn-DOTA.

10. The method of claim 9, wherein the metal-Bn-DOTA comprises a radioisotope.

11. The method of claim 1, wherein the conjugate comprises the amino acid sequence selected from the group consisting of SEQ ID NOs: 17, 19, 21, 23, 25, 27, 29, 31, 33, 35, 37, 39, 41, 43, 45, 47, 49, 51, 53, 55, and 97.

* * * * *